(12) United States Patent
Fernandez Rodriguez et al.

(10) Patent No.: US 11,697,802 B2
(45) Date of Patent: Jul. 11, 2023

(54) PRODUCTION BACTERIAL CELLS AND USE THEREOF IN PRODUCTION METHODS

(71) Applicant: Eligo Bioscience, Paris (FR)

(72) Inventors: Jesus Fernandez Rodriguez, Paris (FR); Antoine Decrulle, Paris (FR); Aymeric Leveau, Paris (FR); Ines Canadas Blasco, Paris (FR); Aurélie Mathieu, Paris (FR); Thibault Carlier, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

(21) Appl. No.: 17/742,671

(22) Filed: May 12, 2022

(65) Prior Publication Data

US 2022/0364062 A1 Nov. 17, 2022

Related U.S. Application Data

(60) Provisional application No. 63/187,531, filed on May 12, 2021, provisional application No. 63/187,532, filed on May 12, 2021.

(51) Int. Cl.
 *C12N 7/00* (2006.01)
 *C12N 1/20* (2006.01)
 (Continued)

(52) U.S. Cl.
 CPC ............. *C12N 7/00* (2013.01); *C12N 1/20* (2013.01); *C12N 15/70* (2013.01); *C12N 15/74* (2013.01);
 (Continued)

(58) Field of Classification Search
 None
 See application file for complete search history.

(56) References Cited

U.S. PATENT DOCUMENTS

| 4,920,048 A | 4/1990 | Diderichsen |
| 5,691,185 A | 11/1997 | Dickely et al. |

(Continued)

FOREIGN PATENT DOCUMENTS

| WO | 94/17201 A1 | 8/1994 |
| WO | 2014/124226 A1 | 8/2014 |

(Continued)

OTHER PUBLICATIONS

Rajagopala et al. The protein interaction map of bacteriophage lambda. BMC Microbiology 2011, 11:213, 1-15.
(Continued)

*Primary Examiner* — Michelle S Horning
(74) *Attorney, Agent, or Firm* — Arrigo, Lee, Guttman & Mouta-Bellum LLP

(57) ABSTRACT

The present invention concerns a production bacterial cell for producing phage particles or phage-derived delivery vehicles, said production bacterial cell stably comprising at least one phage structural gene(s) and at least one phage DNA packaging gene(s), said phage structural gene(s) and phage DNA packaging gene(s) being derived from a first type of bacteriophage, wherein the expression of at least one of said phage structural gene(s) and/or at least one of said phage DNA packaging gene(s) in said production bacterial cell is controlled by at least one induction mechanism, and wherein said production bacterial cell is from a bacterial species or strain different from the bacterial species or strain from which said first type of bacteriophage comes and/or that said first type of bacteriophage targets.

9 Claims, 11 Drawing Sheets

Specification includes a Sequence Listing.

(51) Int. Cl.
 *C12N 15/74* (2006.01)
 *C12N 15/70* (2006.01)
(52) U.S. Cl.
 CPC ............ *C12N 2795/10322* (2013.01); *C12N 2795/10352* (2013.01); *C12N 2800/101* (2013.01); *C12N 2800/40* (2013.01)

(56) References Cited

U.S. PATENT DOCUMENTS

| | | | |
|---|---|---|---|
| 6,291,245 | B1 | 9/2001 | Kopetzki et al. |
| 6,413,768 | B1 | 7/2002 | Galen |
| 6,752,994 | B2 | 6/2004 | Jacobs, Jr. et al. |
| 10,113,163 | B2 | 10/2018 | Liu et al. |
| 2005/0186666 | A1 | 8/2005 | Schneider et al. |
| 2015/0064138 | A1 | 3/2015 | Lu et al. |
| 2015/0166980 | A1 | 6/2015 | Liu et al. |
| 2019/0160120 | A1* | 5/2019 | Haaber ............... A61K 38/162 |
| 2022/0135986 | A1 | 5/2022 | Leveau et al. |
| 2022/0135987 | A1* | 5/2022 | Leveau .................. C12N 9/22 424/199.1 |

FOREIGN PATENT DOCUMENTS

| | | |
|---|---|---|
| WO | 2017/141173 A2 | 8/2017 |
| WO | 2018/236548 A1 | 12/2018 |
| WO | 2020/181178 A1 | 9/2020 |
| WO | 2020/181180 A1 | 9/2020 |
| WO | 2020/181193 A1 | 9/2020 |
| WO | 2020/181195 A1 | 9/2020 |
| WO | 2020/181202 A1 | 9/2020 |

OTHER PUBLICATIONS

Ravin et al. The anti-immunity system of phage-plasmid N15: identification of the antirepressor gene and its control by a small processed RNA Molecular Microbiology (1999) 34(5), 980-994.
Rees and Liu. Base editing: precision chemistry on the genome and transcriptome of living cells. Nat Rev Genet. Dec. 2018 ; 19(12): 770-788. doi:10.1038/s41576-018-0059-1.
Russel and Model. Genetic Analysis of the Filamentous Bacteriophage Packaging Signal and of the Proteins That Interact with It. Journal of Virology, Aug. 1989, 63 (8), 3284-3295.
Sharon et al. Functional genetic variants revealed by massively parallel precise genome editing. Cell. Oct. 4, 2018; 175(2): 544-557.e16. doi:10.1016/j.cell.2018.08.057.
Simon et al. Retrons and their applications in genome engineering. Nucleic Acids Research, 2019, vol. 47, No. 21 11007-11019 doi: 10.1093/nar/gkz86.
Sorensen et al. A Food-Grade Cloning System for Industrial Strains of Lactococcus lactis. Applied and Environmental Microbiology, Apr. 2000, 66(4), 1253-1258.
Stanton et al. Genomic Mining of Prokaryotic Repressors for Orthogonal Logic Gates. Nat Chem Biol. Feb. 2014 ; 10(2): 99-105. doi:10.1038/nchembio.1411.
Struhl et al. Functional genetic expression of eukaryotic DNA in *Escherichia coli.* Proc. Natl. Acad. Sci. May 1976. 73 (5), 1471-1475.
Tomida et al. Pan-Genome and Comparative Genome Analyses of Propionibacterium acnes Reveal Its Genomic Diversity in the Healthy and Diseased Human Skin Microbiome. mBio. 4(3), e00003-13, 1-11. doi:10.1128/mBio.00003-13.
Vo et al. CRISPR RNA-guided integrases for high-efficiency, multiplexed bacterial genome engineering. Nature Biotechnology, 2021, 39, 480-489. https://doi.org/10.1038/s41587-020-00745-y.
Wanneir et al. Improved bacterial recombineering by parallelized protein discovery. PNAS, 2020, 117(24), 13689-13698.
Wannier et al. Recombineering and MAGE. Nat Rev Methods Primers. 2021, 1-51. doi:10.1038/s43586-020-00006-x.
Weigele and Raleigh. Biosynthesis and Function of Modified Bases in Bacteria and Their Viruses. Chemical Reviews. 2016, 12655-12687.
Wu et al. The DNA site utilized by bacteriophage P22 for initiation of DNA packaging. Molecular Microbiology (2002) 45(6), 1631-1646.
Yan et al. Cas13d is a compact RNA-targeting type VI CRISPR effector positively modulated by a WYL domain-containing accessory protein. Mol Cell. Apr. 19, 2018; 70(2): 327-339.e5. doi:10.1016/j.molcel.2018.02.028.
Zhao et al. New base editors change C to A in bacteria and C to G in mammalian cells. Nat Biotechnol 2021, 39, 35-40. https://doi.org/10.1038/s41587-020-0592-2.
Abudayyeh et al RNA targeting with CRISPR-Cas13a. Nature. Oct. 12, 2017; 550(7675): 280-284. doi:10.1038/nature24049.
Anne et al. Protein Secretion in Gram-Positive Bacteria: From Multiple Pathways to Biotechnology. Current Topics in Microbiology and Immunology. Nov. 25, 2016. 267-308. DOI 10.1007/82_2016_49.
Anzalone et al. Search-and-replace genome editing without double-strand breaks or donor DNA. Nature. Dec. 2019 ; 576(7785): 149-157. doi:10.1038/s41586-019-1711-4.
Brede et al. Heterologous Production of Antimicrobial Peptides in Propionibacterium freudenreichii. Applied and Environmental Microbiology, Dec. 2005, 8077-8084. doi:10.1128/AEM.71.12.8077-8084.2005.
Brüggemann H, et al. A Janus-Faced Bacterium: Host-Beneficial and -Detrimental Roles of Cutibacterium acnes. Front. Microbiol. (2021)12:673845. 1-22. doi: 10.3389/fmicb.2021.673845.
Cambray G et al. Measurement and modeling of intrinsic transcription terminator. Nucleic Acids Research, 2013, vol. 41, No. 9 5139-5148 doi:10.1093/nar/gkt163.
Casjens et al. The pKO2 Linear Plasmid Prophage of Klebsiella oxytoca. Journal of Bacteriology, Mar. 2004, vol. 186, No. 6, 1818-1832 DOI: 10.1128/JB.186.6.1818-1832.2004.
Chen et al. Characterization of 582 natural and synthetic terminators and quantification of their design constraints. 2013. Nature Methods, vol. 10, No. 7, 659-666.
Chen et al. Precise and programmable C:G to G:C base editing in genomic DNA.2020. 1-19. https://doi.org/10.1101/2020.07.21.213827.
Chen et al. Programmable C:G to G:C genome editing with CRISPR-Cas9-directed base excision repair proteins. Nature Communications, (2021) 12:1384. 1-7. https://doi.org/10.1038/s41467-021-21559-9.
Cheng et al. Complete genomic sequences of Propionibacterium freudenreichii phages from Swiss cheese reveal greater diversity than Cutibacterium (formerly Propionibacterium) acnes phages. BMC Microbiology (2018) 18:19, 1-13 https://doi.org/10.1186/s12866-018-1159-y.
Chung and Hinkle. Bacteriophage T7 DNA Packaging II. Analysis of the DNA Sequences Required for Packaging Using a Plasmid Transduction Assay. Journal of Molecular Biology. 1990, 216, 927-938.
Costa et al. Secretion systems in Gram-negative bacteria: structural and mechanistic insights. 2015. Nature Reviews Microbiology. vol. 13, 343-359.
Cotter et al. Bacteriocins—a viable alternative to antibiotics. 2013. Nature Reviews Microbiology. vol. 11, 95-105.
Cox et al. RNA Editing with CRISPR-Cas13. Science. Nov. 24, 2017; 358(6366): 1019-1027. doi:10.1126/science.aaq0180.
Del Solar et al. Replication and Control of Circular Bacterial Plasmids. Microbiology and Molecular Biology Reviews. 1998. vol. 62, No. 2, 434-4.
Dickely et al. Isolation of Lactococcus lactis nonsense suppressors and construction of a food-grade cloning vector. Molecular Microbiology (1992), 15 (5), 839-847.
Farzadfard and Lu. Genomically Encoded Analog Memory with Precise In vivo DNA Writing in Living Cell Population. Science. Nov. 14, 2014; 346(6211): 1256272. doi:10.1126/science.1256272.

(56) References Cited

OTHER PUBLICATIONS

Fiedler and Skerra. proBA complementation of an auxotrophic E. coli strain improves plasmid stability and expression yield during fermenter production of a recombinant antibody fragment. 2001. Gene. 274, 111-118.

Fillol-Salom et al. Phage-inducible chromosomal islands are ubiquitous within the bacterial universe. The ISME Journal (2018) 12:2114-2128.

Fonfara et al. Phylogeny of Cas9 determines functional exchangeability of dual-RNA and Cas9 among orthologous type II CRISPR-Cas systems. Nucleic Acids Research, 2014, vol. 42, No. 4 2577-2590.

Gaudelli et al. Programmable base editing of A•T to G•C in genomic DNA without DNA cleavage. Nature. Nov. 23, 2017; 551(7681): 464-471. doi:10.1038/nature24644.

Gautier et al. Bacteriophages infecting dairy propionibacteria. Lait (1995) 75, 427-434.

Gautier et al. Occurrence of Propionibacterium freudenreichii Bacteriophages in Swiss Cheese. Applied and Environmental Microbiology, Jul. 1995, vol. 61, No. 7. p. 2572-2576.

Groenen and Van de Putte. Mapping of a Site for Packaging of Bacteriophage Mu DNA. Virology. 1985, 144, 520-522.

Grunewald et al. A dual-deaminase CRISPR base editor enables concurrent adenine and cytosine editing. Nat Biotechnol. Jul. 2020 ; 38(7): 861-864. doi:10.1038/s41587-020-0535-y.

Hashimoto and Fujisawa. DNA Sequences Necessary for Packaging Bacteriophage T3 DNA. Virology 1992, 187, 7, 788-795.

Henkel et al. Toxins from Bacteria. EXS. 2010 ; 100: 1-29.

Hohn. DNA sequences necessary for packaging of bacteriophage a DNA (cosmid/in vivo packaging/in vitro packaging of restriction fragments). Dec. 1983. Proc. Nati. Acad. Sci. USA vol. 80, pp. 7456-7460.

Ioannidi et al. Drag-and-drop genome insertion without DNA cleavage with CRISPR directed integrases. 2021. bioRxiv 2021.11.01.466786; doi: https://doi.org/10.1101/2021.11.01.466786.

Jinek et al. A Programmable Dual-RNA-Guided DNA Endonuclease in Adaptive Bacterial Immunity. Science. Aug. 17, 2012. vol. 337, 6096, 816-821.

Kabashima et al. The immunological anatomy of the skin. Nature Reviews Immunology. 2019. vol. 19, 19-30.

Kala et al. HNH proteins are a widespread component of phage DNA packaging machines. PNAS 2014. 111, 16, 6022-6027.

Karberg et al. Group II introns as controllable gene targeting vectors for genetic manipulation of bacteria. Nature Biotechnology. 2001, 19, 1162-1167.

Kashaf et al. Integrating cultivation and metagenomics for a multi-kingdom view of skin microbiome diversity and functions. Nature Microbiology. 2022. 7, 169-191.

Komor et al. Programmable editing of a target base in genomic DNA without double-stranded DNA cleavage. Nature. 2016. 533(7603): 420-424. doi:10.1038/nature17946.

Koonin et al. Diversity, classification and evolution of CRISPR-Cas systems. 2018. Curr Opin Microbiol. Jun. 2017 : 37: 67-78. doi:10.1016/j.mib.2017.05.008.

Krupovic et al. A classification system for virophages and satellite viruses. 2016. Arch Virology. 161:233-247.

Kues and Stahl. Replication of Plasmids in Gram-Negative Bacteria. Microbiological Reviews, Dec. 1989, 53, 5, 491-516.

Kurt et al. CRISPR C-to-G base editors for inducing targeted DNA transversions in human cells. Nat Biotechnol. Jan. 2021 ; 39(1): 41-46. doi:10.1038/s41587-020-0609-x.

Li et al. Targeted, random mutagenesis of plant genes with dual cytosine and adenine base editors. Nature Biotechnology. 2020. 38, 875-882.

Ma et al. Transposon-Associated CRISPR-Cas System: A Powerful DNA Insertion Tool. Trends in Microbiology. 2021. 29, 7, 565-586.

MacCormick et al. Construction of a food-grade host/vector system for Lactococcus lactis based on the lactose operon. FEMS Microbiology Letters 127 (1995) 105-109.

Marinelli et al. Propionibacterium acnes Bacteriophages Display Limited Genetic Diversity and Broad Killing Activity against Bacterial Skin Isolates. mBio 2012, 3(5), 1-13.

Miwa and Matsubara. Identification of sequences necessary for packaging DNA into lambda phage heads (Recombinant DNA; cosmid; Ml3 dideoxynucleotide sequencing; h cohesive end; plasmid vector). Gene, 20(1982) 261-279.

Moodley et al. The protein gp74 from the bacteriophage HK97 functions as a HNH endonuclease. Protein Science. 2012. 21, 809-818.

Mutalik et al. Precise and reliable gene expression via standard transcription and translation initiation elements. Nature Methods. 2013, 10, 4, 354-368.

Nakayama et al. The R-type pyocin of Pseudomonas aeruginosa is related to P2 phage, and the F-type is related to lambda phage. Molecular Microbiology (2000) 38(2), 213-231.

Petri and Schmieger. Isolation of fragments with pac function for phage P22 from phage LP7 DNA and comparison of packaging gene 3 sequences. Gene, 88 (1990) 47-55.

Quiles-Puchalt et al. Staphylococcal pathogenicity island DNA packaging system involving cos-site packaging and phage-encoded HNH endonucleases. PNAS. 2014. 111 (16), 6016-6021.

\* cited by examiner

PCR ORF3 with expected size ~ 1329bp based on reference BW phage genome KX620751

PCR ORF5 with expected size ~ 1036bp based on reference BW phage genome KX620751

SEQUENCE LISTING

```
<160> NUMBER OF SEQ ID NOS: 31

<210> SEQ ID NO 1
<211> LENGTH: 282
<212> TYPE: DNA
<213> ORGANISM: Artificial Sequence
<220> FEATURE:
<223> OTHER INFORMATION: primase ori from the PICI of the Escherichia
      coli strain CFT073

<400> SEQUENCE: 1
tttgttgcaa tggctgtcta ccctgtctac ctgagtaaag aaaaatacat ttaattcagt      60
acattaactt gggtagacag cctttttta ctgtctacct actatctacc ctctctacct     120
gattttacct gaatcagaca gggaggtaga tacgggtag atagtggata aaagcactct     180
accccactga aagccgcgcc attactggca tggtggccag taaggtagat aaggtagaca     240
aggggaggca caactcaaaa cttttaaac gaggggtaa aa                         282

<210> SEQ ID NO 2
<211> LENGTH: 13
<212> TYPE: DNA
<213> ORGANISM: Artificial Sequence
<220> FEATURE:
<223> OTHER INFORMATION: restriction site
<220> FEATURE:
<221> NAME/KEY: misc_feature
<222> LOCATION: (5)..(10)
<223> OTHER INFORMATION: n is a, c, g, or t

<400> SEQUENCE: 2
twcannnnnn tgg                                                        13

<210> SEQ ID NO 3
<211> LENGTH: 282
```

```
<212> TYPE: DNA
<213> ORGANISM: Artificial Sequence
<220> FEATURE:
<223> OTHER INFORMATION: Primase ori deltaGAAABCC

<400> SEQUENCE: 3
tttgttgcaa tggctgtcta ccctgtctac ctgagtaaag aaaaatacat ttaattcagt    60
acattaactt gggtagacag cctttttta ctgtctacct actatctacc ctctctacct    120
gattttacct gaatcagaca gggaggtaga tacggggtag atagtggata aaagcactct   180
accccactga aagcagcgcc attactggca tggtggccag taaggtagat aaggtagaca   240
aggggaggca caactcaaaa ctttttaaac gagggggtaa aa                      282

<210> SEQ ID NO 4
<211> LENGTH: 282
<212> TYPE: DNA
<213> ORGANISM: Artificial Sequence
<220> FEATURE:
<223> OTHER INFORMATION: Primase ori devoid of restriction sites

<400> SEQUENCE: 4
tttgttgcaa tggctgtcta ccctgtctac ctgagtaaag aaaaatacat ttaattcagt    60
atattaactt gggtagacag cctttttta ctgtctacct tctgtctacc ctctctacct    120
gattttacct gaatcagaca gggaggtaga cacggggtag acagtggata aaagcactct   180
accccactga aagcagtgcc attactggca tggttgccag taaggttgat aaggtagaca   240
aggggaggga caactcaaaa ctttttaaac gagggggtaa aa                      282

<210> SEQ ID NO 5
<211> LENGTH: 584
<212> TYPE: PRT
<213> ORGANISM: Artificial Sequence
<220> FEATURE:
<223> OTHER INFORMATION: PICI primase-helicase

<400> SEQUENCE: 5
```

Met Lys Leu Ala Pro Asn Val Lys Gln Gln Ser Arg Gly Ile Lys His
1               5                   10                  15

Lys Glu Thr Glu Val Ile Ile Phe Ala Gly Ser Asp Ala Trp Ser His
            20                  25                  30

Ala Lys Gln Trp Gln Glu His Asp Ala Arg Met Ala Gly Asp Asn Glu
        35                  40                  45

Pro Pro Val Trp Leu Gly Glu Gln Gln Leu Ser Glu Leu Asp Lys Leu
    50                  55                  60

Gln Ile Val Pro Glu Gly Arg Lys Ser Val Arg Ile Phe Arg Ala Gly
65                  70                  75                  80

Tyr Leu Ala Pro Val Met Ile Lys Ala Ile Gly Gln Lys Leu Ala Ala
                85                  90                  95

Ala Gly Val Gln Asp Ala Asn Phe Tyr Pro Asp Gly Met His Gly Gln
            100                 105                 110

Lys Val Glu Asn Trp Arg Glu Tyr Leu Ala Arg Glu Arg Gln Asn Leu
        115                 120                 125

Ser Asp Gly Leu Val Ile Glu Leu Pro Val Lys Gln Lys Ala Gln Leu
    130                 135                 140

Ser Gln Met Ala Asp Ser Glu Arg Ala Gln Leu Leu Ala Asp Arg Phe
145                 150                 155                 160

Asp Gly Val Cys Val His Pro Glu Ser Glu Ile Val His Val Trp Cys
                165                 170                 175

-continued

```
Gly Gly Val Trp Cys Pro Val Ser Thr Met Glu Leu Ser Arg Glu Met
                180                 185                 190
Val Ala Ile Tyr Ser Glu His Arg Ala Thr Phe Ser Lys Arg Val Ile
            195                 200                 205
Asn Asn Ala Val Glu Ala Leu Lys Val Ile Ala Glu Pro Met Gly Glu
        210                 215                 220
Pro Ser Gly Asp Leu Leu Pro Phe Ala Asn Gly Ala Leu Asp Leu Lys
225                 230                 235                 240
Thr Gly Glu Phe Ser Pro His Thr Pro Glu Asn Trp Ile Thr Thr His
                245                 250                 255
Asn Gly Ile Glu Tyr Thr Pro Pro Ala Pro Gly Glu Asn Ile Arg Asp
            260                 265                 270
Asn Ala Pro Asn Phe His Lys Trp Leu Glu His Ala Ala Gly Lys Asp
        275                 280                 285
Pro Arg Lys Met Met Arg Ile Cys Ala Ala Leu Tyr Met Ile Met Ala
    290                 295                 300
Asn Arg Tyr Asp Trp Gln Met Phe Ile Glu Ala Thr Gly Asp Gly Gly
305                 310                 315                 320
Ser Gly Lys Ser Thr Phe Thr His Ile Ala Ser Leu Leu Ala Gly Lys
                325                 330                 335
Gln Asn Thr Val Ser Ala Glu Met Thr Ser Leu Asp Asp Ala Gly Gly
            340                 345                 350
Arg Ala Gln Val Val Gly Ser Arg Leu Ile Val Leu Ala Asp Gln Pro
        355                 360                 365
Lys Tyr Thr Gly Glu Gly Thr Gly Ile Lys Lys Ile Thr Gly Gly Asp
    370                 375                 380
Pro Val Glu Ile Asn Pro Lys Tyr Glu Lys Arg Phe Thr Ala Val Ile
385                 390                 395                 400
Arg Ala Val Val Leu Ala Thr Asn Asn Asn Pro Met Ile Phe Thr Glu
                405                 410                 415
Arg Ala Gly Gly Val Ala Arg Arg Arg Val Ile Phe Arg Phe Asp Asn
            420                 425                 430
Ile Val Ser Glu Ala Glu Lys Asp Arg Glu Leu Pro Glu Lys Ile Ala
        435                 440                 445
Ala Glu Ile Pro Val Ile Ile Arg Arg Leu Leu Ala Asn Phe Ala Asp
    450                 455                 460
Pro Glu Lys Ala Arg Ala Leu Leu Ile Glu Gln Arg Asp Gly Asp Glu
465                 470                 475                 480
Ala Leu Ala Ile Lys Gln Gln Thr Asp Pro Val Ile Glu Phe Cys Gln
                485                 490                 495
Phe Leu Asn Phe Leu Glu Glu Ala Arg Gly Leu Met Met Gly Gly Gly
            500                 505                 510
Gly Asp Ser Val Lys Tyr Thr Thr Arg Asn Ser Leu Tyr Arg Val Tyr
        515                 520                 525
Leu Ala Phe Met Ala Tyr Ala Gly Arg Ser Lys Pro Leu Asn Val Asn
    530                 535                 540
Asp Phe Gly Lys Ala Met Lys Pro Ala Ala Lys Val Tyr Gly His Glu
545                 550                 555                 560
Tyr Ile Thr Arg Lys Val Lys Gly Val Thr Gln Thr Asn Ala Ile Thr
                565                 570                 575
Thr Asp Asp Cys Asp Ala Phe Leu
            580
```

<210> SEQ ID NO 6
<211> LENGTH: 1752
<212> TYPE: DNA
<213> ORGANISM: Artificial Sequence
<220> FEATURE:
<223> OTHER INFORMATION: PICI primase-helicase

<400> SEQUENCE: 6

```
atgaaactgg caccgaacgt aaaacagcag tcacgcggca taaaacacaa agaaacagaa        60
gtcattattt ttgcgggtag tgatgcctgg tcacacgcaa acaatggca ggaacatgac        120 gcgcgtatgg ccggagataa tgagcctcct gtgtggcttg gggagcagca gttatccgaa       180
ctggataagc tgcaaattgt gccggaaggc agaaaatccg tgcgcatatt cagggccgga       240
tatcttgcgc cagtaatgat aaaggcgatt ggtcagaagc tggcggcggc aggcgtacag       300
gatgcaaatt tttaccctga tggtatgcac ggtcagaagg tggagaactg cgcgaatat        360 ctggcccgtg agcgccagaa tctttctgat ggtctggtca ttgagcttcc ggtaaagcaa       420
aaggcgcaac tttcgcagat ggcggacagt gagcgcgcgc agctgcttgc cgatcgcttt       480
gatggcgttt gcgtacatcc tgaaagtgaa atcgttcacg tatggtgcgg cggggtatgg       540
tgtccggtca gcacaatgga gctgagccgc gaaatggtgg cgatctattc agagcacagg       600
gccactttca gcaagcgcgt aatcaataac gccgtggaag cgttaaaagt tattgccgaa       660
ccaatgggcg agccgtccgg cgatttgctg ccgttcgcca atggtgcgct tgacctgaaa       720
acgggggaat tttccccgca cacgccggag aactggatca ccacgcacaa cggcattgag       780
tacacgccac cagcacccgg ggagaacatc cgccgataacg cgccaaactt tcataaatgg       840
cttgagcacg cagccggaaa agacccgcgc aagatgatgc gtatatgtgc cgcgctgtac       900
atgattatgg cgaaccggta cgactggcag atgttattg aggccaccgg agacggcggg       960
agcggtaaaa gtacattcac acacatagcc agccttctgg cagggaaaca aaacacggta      1020
agcgctgaaa tgcatcgct tgatgatgct ggtgggcgtg cgcaggttgt cgggagtcgt      1080
cttatcgtcc tggcagacca gccgaaatat acaggcgaag gaacgggcat caagaaaatc      1140
acgggcggcg accccgtgga aattaacccg aaatatgaaa agcgttttac ggcggtaatc      1200
agggcggtgg tgctggcaac caataacaat ccgatgatat tcaccgaacg ggccggaggt      1260
gtggcacgtc gtcgggtgat attccggttc gataacatcg taagcgaggc agaaaaagac      1320
agggagctac cggaaaagat cgcggctgaa atccctgtca ttatccgccg cttgctggcg      1380
aactttgccg accctgaaaa ggcacgggct ttactcattg aacagcgtga cggtgatgaa      1440
gcactggcaa taaagcaaca gacggatccg gttattgagt tttgccagtt cctgaatttt      1500
ctggaggaag cacgcggcct gatgatgggc ggcggtggcg attcagtgaa gtacacgacc      1560
agaaacagcc tttaccgcgt ctatctggcg tttatggcgt acgcaggcag gagcaaaccg      1620
ctaaacgtaa atgactttgg caaggctatg aagccagccg cgaaagttta cggacatgaa      1680
tatattacgc ggaaagttaa aggagtaacg cagactaacg caataacaac agacgattgc      1740
gacgcgtttt ta                                                           1752
```

<210> SEQ ID NO 7
<211> LENGTH: 29808
<212> TYPE: DNA
<213> ORGANISM: Kappa phage

<400> SEQUENCE: 7

```
gctgttttgg ggtgcttttg aatgagtaca gggatgcgat cacctggtgg cggacgcaaa        60
```

```
tcgaataaca ctggaaatca ggttagttct ttaaccagag cggtttctcc gccggatgaa    120
ttactgggcg atatggctat cgatgcctgg aaacggacgt gcaaaattct tattaaccgt    180
ggcacgttcg aaatggaaga ttgttatttg ctgatggaat actgcaacac cgtgcagctg    240
ctgtacgacg ccaaccagga aattaaaagc gatggccttg gtgatgatac cgctgccggc    300
ggtcagaaac ttggtgcggc agtgaaggcg cgtagccgtt atatcagcga attaattcga    360
ctctccgttg tgttaaagct ggaccccaat agccgcatcc tgaagaaaca gcccggagat    420
aatgacaaat ccagcggtga gttcgacgag ttttaatttt ggtgcggccc taatgactta    480
aggatggagc atggccgcat atccaaacgt caatgtggcg aacaaatatg cgcgggatat    540
catagacggg aaaatagtcg cctgcagagc tattcggctg gcatgtcagc gccatttgga    600
cgatttaaaa aaatcactcg ataacaatta cccttaccgg ttcgacagag atttagctga    660
gcgggcctgc cggtttgttc agaaattacc gcactccagt ggcgatttgg cggggcagaa    720
attaaaactg gaaccttggc aaagttttat tttttgttcg attttggct gggtcacgaa     780 aaaggataaa aaacgccgat tcgcgaagc gtatatccgg gtagccagga aaaacgggaa     840
atcgtttttt gctgccggga ttggcaccta catgttttgc gctgatggcg aaaacagcgc    900
agaagtgtat tgcggtgcga caactatggc gcaggcgaaa aaggtcttca ccccagccag    960
gcagatggcc agccgcctgc cggcacttcg ctccagattt gatatttcgg tatggaccga   1020
cagcctgaca cgcccggatg gttccgtttt cgcacctatg gcggggaaac ccggcgatgg   1080
tgacagccca cattgcgcga tcattgacga gtatcacgaa cacgatacgg atcatatgta   1140
cgaggccatg acaatgggga tgggcgcccg ttcgcagccg ttaacgctca ttatcacgac   1200
agccggctcg tcactggagt ccccttgcta tgacaaggac aaggaagtca agaggttat    1260 cgaaggcata acccgtaatg atcgcctgtt tggcatgatt tacgaactgg atgctggcga   1320
tgactggacc gacccgaaaa acttaatcaa agctaaccca atctggacg tttcggttaa    1380 gtacagcgac ctggttgagc ttctggaagt agcgaaacag gttcctcgca aggttaacgc   1440
cttcaaaacc aaacgcctca atatttgggt atccggtaaa tccgcgttct acaacatgga   1500
gcagtggaag gctgctgaag accccaacct tgagctggct gattttgcga atgacagctg   1560
caatatcggt ctcgatctcg ccaaaaagct ggatatgaac gccgggatac ggctatttac   1620
gcgggaaatt gaaggtaaac ggcattatta ctgcatcaaa cctaaatttt gggtcccgga   1680
agacacgatc catacaaccg atccaaaact gctgaaaact gctgacaggt atcagaagtt   1740
ttatgaaatg ggcgtgctgg aagcgacgga tggagcagag gcagactatc gcgagattct   1800
ggccagtatt atcgatatgc aggacgaaaa ccgcattgac gagattgata tcgaccctgc   1860
cggcgcaaca gcacttcgcc accagttgga ggacaacgga tttaccgtag tcgatatccg   1920
gcaggattac accaatatgt caccggcgat gaaagagctt gaagcggctc tggccggtgg   1980
tcgattccac catgatggca atcccattct gacctggtgt atcagcaatg ttatcgggaa   2040
atttataccc ggtagcgatg atctcgttcg cccgacaaag ggagacaatc aaagcaaaat   2100
cgatggagct acagcgttat ttaacgccat gactcgcgca atgctgcacg aaagcagcgg   2160
cggcacatcg gtatatgatg aggaagacat agcgtgttaa tcacaattct gagtttcatt   2220
attggcctgg ccggggctgt actcatatcc gccggagcct ggttgatttt gcctgctgcc   2280
ggtcttatta cgggtgggtc aatatgtctt atctggtcat atctaactgc gcgggcggtt   2340
tcagccggtg ccaaatttaa cgggggtgaa taatgtttat cccccaaatg ttcagagggc   2400
```

```
gccagcagtc gagggatggc ctctgggaag ccatgctggg cggggttcgt tcaagccaga      2460
gcaaaactgg catcataatc acgccgaaaa ccgctctggg actttcagcg gtccgggcct      2520
gtgtcactct cctggctgag tccgtcgcgc agctgccgtg cgaactttac cggcgggata      2580
aaaatggcgg cgccagcgt gcgacggacc acccggttta tgacctgatt cactcccagc      2640
ccaacaggaa agacacctca ttcgagtatt tcgagcagca gcaggggttg ctggggcttg      2700
agggaaattg ctactcgatc atcgaacggg acggaaaagg ctacccgaaa gagctgatcc      2760
ccattaaccc gaaaaaggtc attgtgctga aagggccgga cggtatgccg tattaccaac      2820
tcccggaagt cggcgaaatt ctgccgatgc catgatgca ccatgtgaag gtcttttctc       2880
tggatggcta tatcggcagc tcccccattc agacgaacgc cgatgttctt ggactgaatt      2940
tggccgttga ggagcatgcg gcagcgacat tccggcgcgg gacaacgatg agcggagtga      3000
tagagcgtcc gagagaagcc gcgaccatta aaagccagga tgctattgat cgcctgctgg      3060
cgaaatggac cgagcgccat tccggtattc acaatatgtt ctctgtggca ctgctgcagg      3120
agggtatgag ctacaaacaa ctgtcgcagg ataacgaaaa ggcgcagctg ctacagtcgc      3180
ggcagtgggg cgtggaagag gtctgccggc tctataaaat cccgccacat atggtgcaga      3240
tgctggcgaa agcgaccaac aacaacattg agcaccaggg cctgcagttc gtgatgtata      3300
cgctgctggc atggctgaaa cgccatgagg gtgcgctgca gcgcgatctg cttctgccca      3360
gcgaacgccg cgatttgtac atcgagttca acgtttccgg gctgctgcga ggcgatcaga      3420
aatcacgcta tgaatcttat gcgctgggcc ggcagtgggg atggctatcc actaacgata      3480
tccggcgtat ggagaatctg ccgcccattg ccggcgggga taaatacctg acgccgctca      3540
atatggtcga cagtgcgaag atccttcctg gcgataaatc gccgacagca aaacagctgg      3600
ccgaaatcga aacccttctg gccagagcct gattatttcc cgccgcgcgg gatgacctgg      3660
aagacaacat gacaacgaaa ttaattaacc tgccgcacct ggcagatatg gtctttggtg      3720
tgccgcatta cgtgacgcgg caaacaatgg actccgtgaa agcggtgctc atccctcgta      3780
ttcaggggat caccgaagat accgtcattc agatggcgct aaatccggat aaatcacctg      3840
ctgctgagca ggtccagccc accggcgggg tggcggtgat ccccgttcac ggcatactcg      3900
ttccacgccg ggggcagatt acagcgatgt gctccgagct gaccagctac gagcggatac      3960 gcggcagtt gcaggcggcg ttaaacgacc cctcaatcag cgaaatcgtt ctggatatta      4020
actccggcgg cggcgcagcg gtggggtgca aggagctggc cgattacatt tatcagtctc      4080
gcgacacgaa gcccatcacg gcgattgtga actacagcgc gtactccgcc gcgtatttca      4140
tcgcatcggc ctgcagcaaa atcatcgtca gccagaccag tggcgtgggg tcgattggtg      4200
tgatcatgga gcacctcgat acgtcgaaga tggaagaaaa aatggggctg acgttcacca      4260
ccatttaccg gggagataac aaaaataacg gtacccaaca tgaaccactg agtgaagagt      4320
cgcggggtat gttccagggc atgatcgacg aaatgtacga gacgtttacg gggtcggtgg      4380
ccgaatatcg cggcctgaag cagcaggccg tcattgatac gcaggcgggg ctgtattttg      4440
gccctggcgc tgtgtctgcc ggcctggcgg atgaagtctc tgaccccag gcggcgctca      4500 atgctatcgc ggcaaagtat cagcaacccc gtcaaaaaac ctccattcag atgcaggcag      4560
ccgcgatgga cctgcaaacc aaaatgtaac ccggcgcaaa cacaaaccgc gtcaccttaa      4620
gcagccagca ggctgctttt tttatgtcta aaagagaga aataaatgc cacatattga      4680 agaattgcgt cgtcagcgtg cgggtatcaa cgaacagatt caggccctgg caaccattga      4740
cgccagcggc gtcacgctga ctgcggagca gatgacggag ttttcgaacc tgcagcagca      4800
```

```
gttcactgat atcagcgcca aaattgaacg cctggaagcc gccgaacgtg ctgcggcgct    4860
ggtcgcaaaa cccgtgaaag cgactcagca ggcccccggc attattgtta agcaggagcc    4920
gaaacagtac accggtgctg gcatgacccg actggttatg tctgtcgccg caggcgcagg    4980
gaatctgcag gacgcggcaa aattcgcttc agaagagctg aatgaccagt ccgtatcgat    5040
ggccatttcc accgcagcgg cgtccggtgg tgtgcttatt ccgcagaacc tccacagtga    5100
ggtgatcgag ctactgagcg accgaaccat cgtccgcaag ctgggtgccc gtcccgttcc    5160
gctgcctaac ggtaatatga cgctaccacg cgtggccggt ggagcaacgg caagctacac    5220
aggagaaaac aaagacgcca agacatcaga aacacgcttt gatgatgtaa aactgacggc    5280
gaaaactctg attgcgatgg tgcctatttc aatgcactg attggccgcg ccggattcaa    5340
cgtcgagcag ctggtcctgc aggatattct gaccgccatc tcagtgcgtg aggataaagc    5400
ctttatgcgc gatgacggta ccggcgatac accgattggt atgaaggcgc gcgcgacgca    5460
gtggaaccgc ctgctgccgt gggaagctga tgcagcgatc aacctgaaca cggttgacga    5520
gtacctggac aagatcattt tgatggcgat ggacggcaac agcaatatga tcagcagcgg    5580
ctggggcatg tcgaaccgta cctatatgaa gttgtttggg ctgcgtgacg caacggcaa    5640 caaagtctat ccggaaatgg ctcagggatt acttaaagga tatccggttc agcgtaccag    5700
cgcgatccct gcgaatctgg ggaccggggg taaggagact gagatttact ttgctgactt    5760
caatgatgtg gttatcgctg aagacggcaa tatgaaagtc gacttctcga aggaagcctc    5820
ttacatcgat gccgatggca ccctggtatc tgcgttttcc cgtaaccagt cgctaatccg    5880
cgttgttact gagcatgata ttggcttccg tcatccggaa ggcctggtgc tgggtaccgg    5940
cgtcctgttc taaccatcc ctcagtaaat acggcccgca tgcgggct tttccttttc    6000 aggagaatgt tatggctgtg aaaaataaag cagtggagcc ggaagaaaca ggcacacagg    6060
acaaccatgc gaccgtggtc gcacaggcag agcgtaaatc cgttgtgttc cttgggccgc    6120
accaccgtta ttcccgtgga gatatcgcgt gctttgaagg atcgcgcgcc gaagaactgg    6180
ttaagcggcg tatcgcggta tggccggagg atgccgaacg tgcgctgaaa ccgaagccgg    6240
gagacagcga ttttgatact gaaattggat gatgtgaaaa cccagctacg cctggaactg    6300
gatttcacgg agcatgacgc catgctcacg caaatggtga acgccgcgca gcggagcatc    6360
gagcgtgatt attactgcaa gctggtcacc agtgatgaag agctgcaggc actcccggag    6420
accgtccgcg gatttatcgc ggatgaagat atccggctgg ccattcagtt tctggtcagc    6480
gatgcgtatc tgaatggcca taccggacag tggctgaaaa ccgctgcggt gaggcatctt    6540 cttttcccc tgcaggagca tacgctatga gcctgaaacc gggtgatatg aactgtcgca    6600
ttgcgattag ctacgttcag tccggtcggg ggccgctggg cgaaccgcta ccggaaaagc    6660
aggttgaatc gggaaaagcg tgggcaaaac gggagctggt atcggggcgg aaagtccgca    6720
cgctggatca gcagcaggtg gtggaaacct gcctgtttac ggtctatccg ggtgtgctgg    6780
ttgatattga ctggaaaatc acgacgaaaa atctggttta taccgtccgg aatatcgacc    6840
gcaaaacaga ccggatcatt atcacggggg aggctgacgg gcggcatgat agagctggcg    6900
attaagggtg cgctgagcg catcaccggc atgaatgcgt atccgctttt actgccggac    6960
acggtccagg aaggtgcgac ctttcagcgt atctctgacc cggaaatggt ctcgggaatg    7020
ttgcgaacgg ggatcgtctc tgcccgtatc caggtgaatc tgtaccgtct cgatgattac    7080
acctcactgc tgcagctgga taaaaaaatc tggacggaac tgaagtccgt cgttcatggc    7140
```

```
cagctggagg gtatcccggt tcagtatgtg gagcgaggcg gtatccatca ggataaaaac    7200
cagctgacga atcgtcgcat tcagtatcgc ctgacccgcg atttcatcat tcactacgtg    7260
gaggactcct cgtgatccga atggaaatta aagggctgga tgagctggag cggcagttaa    7320
cggccctggg cgaaaaagtg gcgacaaagg tattgcggga tgccgggcgc gaagcgctaa    7380
aggtcgtcga ggaagatatg aagcagcatg ccggctttga cgaaacgtct gccggaccgc    7440
acatgcggga ctcaatcaaa atccgctctt ccactcgcaa gggtaaaggg aacgcggttg    7500
taacgctccg tgttggcccc agcaagcagc accatatgaa ggcgctggcg caggagtttg    7560
gcacggttaa acaggttgca gaccccttta tccgacccgc cctggattac aacctccaga    7620
ccgttttgcg cgtgttaacc gtggaaatcc gaaacggcat tgaaaacagg tagcatccgc    7680
tgccgtataa aaagagagag aaacatggct gataaaactt cacctgaata tgcgatgttg    7740
ccagcgggca ccattgtgaa atacggggag cctggcgctg ccacgtcagc gctgaaaccg    7800
ctgattaact gtaaagcgct gggtgcaatg gggcagacgg ggggctttgt cgactgcacc    7860
acgttactgg ataagcagaa acagtccatc agcgatctgc ctgacgggcc tgaaaagtcg    7920
ctgggcttta ttgatgatcc aggcaatacc gattttgccg cgctgctgaa cgcagcagag    7980
gcccgcaaga ccatccagtt atacgtcgaa ttacccaaca gcgaacagc gacgatgctc    8040 cttgcgctgt ccgggtggca gatgaatgaa atcgccgctc cggcgaatga ggtcatccag    8100
atcactgttc agggtaagca gaacaagatc acctggggaa ccgtcgctga taccagcggc    8160
gcctgattaa cttaactttt aaaccgccac cttcgggtgg cttttttattt ttaaggacta    8220 cctgtgaaag acaaagatta cctgtccacg ctgaaatccg cgttgcttaa atcggagcca    8280
accgtcatta aaaccgagtt gtttggcgcc accgtattca tccgccgcct gaccggggat    8340
tacctcatca gctacgaaga gaaaatggct gaaaccgcaa aagctggcgc agcgcgcgag    8400
gcatcggagc aagtcatcca gatcgtcatc gatgcactgg ttcagccgga tggaacggcc    8460
attccggatg agtttaaacc cacggcagcc gagctgctga aggcccatga aaaccccgaa    8520
ctgctggctg cagtggaaaa agtgaagcaa cacgcaatcg gcaagctgga ggaagcggaa    8580
aaaaactgag tgactcgccc tggctggagc tgattttctg gctggccgac cgctggggcg    8640
agcctgaccc atccaaaatt gccgcattgc cggcaaacac tctgtaccac tggcgagcct    8700
acttcctgaa acagggcact ttccgccgtc ctggcgatga aaacacgcca cctaccgaaa    8760
ccacacctgc gccatcccgg gtcgatgatg aatgcgcggc agtcatgagg gcattaatgt    8820
aatggcagac gtcgcatctt tagcggtcgg gctgcacctg aacgcagcca gttttaaatc    8880
ccagctgctg ggagcgtatg gcgatgcgga gaaccagtca cgacggttta accgtaatgc    8940
ccaggcggac gcgaaaaaga cggaggacgc ctataagaag gtcggtctgt cgatatccgg    9000
gatggccagc cggctggcgg ggctggcagg agccggtctt tccatcggta cgatcgtcac    9060
cacgtccaga caatatggac aggcattatc agacctgcag gccatcaccg gtgcgactgc    9120
tgctgaaatg aaagcgctgg atctggctgc gcaggaaatg ggacgcacga cagagtacag    9180
cgccagccag gccgccgagg cgctaaagct gatggcgtcg gctaaaccgg agcttttaaa    9240
aacgtccgat ggactgcaga aggctacgaa cagcgcgctt atcctggcgc aggccgccgg    9300
cacaacgctg cccgatgcga ccagaacgct ggcgctctcc ttaaaccagt acggggcgag    9360
cgcgcaggag gcggatcgtt atatcaacgt gctggccgcc ggcgcgaagt acggtgtcgt    9420
ggagattgtg aatacagcgg ccgccattaa aaatggtggc gtcgcagccg cacaggccgg    9480
cgttggtttt gagcagctga atgccgcgat tcaggtgctg cagagcgtg aaattaaagg    9540
```

```
cggtgaagcc ggcacggcgc tgcgtaacgt catcctgaat ctggaaaagg gcacggacaa    9600
gagtctcaag ccgtccgtgg ttggtctcag ccaggcgctg accaatctat ccgggaaaaa    9660
tctctccacg gcccaggccg taaaactgtt tggcgtggag aacctgaatg cggcgtctat    9720
cctggtccag aaccgttcaa ggcttgatga gctgaccgct tccctgaccg gtaccaaaac    9780
ggcgcatgag caggcatcca tcagggttaa caacctgaac ggcgatttgc tgggtctgag    9840
cagtgcgttt gaagggatgg tcattaagat cggccagagc agtaacgggc cactccgcag    9900
cgggattcag gttgccacgg aggcactgaa cagcctggca gacaatttca acaccgtctc    9960
cagcgtggcg ctttacagtc tgatccccgt gctatccacg aaactgaccg cagggctgcg    10020
ggagaatatc gcggcctggc gggaaagcca ggcggcggta aaagcgcggg cgcaggctga    10080
tgcggatatt gcccgcaaaa cgctggattc gacagctgcc atcctgaaac agaacgacgg    10140
tgagtttggc cactaccggc agatggagcg gacggctaaa cagtacggga tgaatatcag    10200
ttaccaagat gagtttgccc gcctcatccg acaggaaact gaacaaacca atctggccag    10260
ccaggcgaaa ctgaaactgg cggcggcaaa ccggcaattg tcgatatcag cccgcgcggc    10320
ctctgttgcg gtgggcctgg caagaggcgc cctggctttt gttggtggtc cggttggcgc    10380
ggcgacgctg gctggatctg cattactgta tttccatcaa caggcaaaag aagcccggca    10440
atcggccatt gatttaaaag atgccgtagt ggaaaccagt gaagcgctga tgcgcctctc    10500
gcttaaccag ttaaatgtga agcagttcga cctggaggat aagtacgaaa accaggtcgt    10560
gcagcgtaac cagctgatga agagattcag ggatgccgac agccgtatcg acagcctgaa    10620
agggtttgac cccttcggcc agctggaagg ggtgacaaaa ggccaggcgc gtgcacgggc    10680
ggatctcgaa agcgttaacg agggactccg caaaactgag gaaaacatta gcgtgtcag    10740 tgatgcaaaa acactggctc agctgggttt atcgggaaaa ataacctccc ttacggacga    10800
tctgaaagga gcgttaagca cgcccccccaa agagaccgga gagggaaatc cctggggcgg    10860
cgatggcggt accggcacgg ggaaaggcag taagtcccag gtcgaccagt tcaaaacgct    10920
gcggcagcaa attgaagaag cccatgcatc cagcctggcc agaattaacc tgcaggaaaa    10980
ggacagcaac agggagctgc aggaagcggc gaagaaaaat ggcgcagtg atgctgacct    11040 gcagcgcgcg ctgttaatga atgcagagaa ctaccagaaa cagcgactgg atctggccgc    11100
gcagtattcc cccgcccggg aaactctgcg aaaagagcag gaagccagcc gggacctggc    11160
tgagcttttc aaagcccgcc ttcttgatga aaaagagtac caggccgcac gaataacgct    11220
ggccagagat accgcgaaag agctgctgca ggcaaaggct gacgaaatcg cggcgcctaa    11280
actggatatc gccggtgagg ttgatccact ggtagcactc cgcaatcagt taacgcagcg    11340
gcaggctttg ctgctgtcgt actatcagag cagcgcgatc agcaaagaac agtacgaaat    11400
gctgatgaag aaggcgacga aggattctgc agattcgcaa tatcagacgt cgctggagtt    11460
atatcgatca cagggcgaat tccagagcct ggccgtcggg ttatttgaaa cggcccatga    11520
gcgctctagc aacttcctga cgagcatgtt gacgcggacg agaagcttta aggagaacat    11580
ggctgacctg ttttcctcgc tcacgcagtc ggtcataaaa aacctcgttg atatggccgc    11640
tcaggctctt gttaccagca ctatcatgca aaccatcatg ggtgtggtgg gagctggagt    11700
gagtattgca ggtggtgttt ctggagcggc tgatgtcggc gcaggaactg cgattcagaa    11760
tgcgggtaat aactttaact ttcaaatacc gggttatgcc aaaggcggtg tcttcgattc    11820
tccttcatta agtgcctaca gcaaccaggt ctacgactct ccgcagttct tcgctttcgc    11880
```

```
aaaagggggcc ggcgtatttg gcgaggccgg gccggaggcc atcatgccgc tgacgcgtgc    11940
cggtgatggt tcgctgggtg tacgcgcggt gggtggtggt cagaacgccg gcgcgtcgga    12000
agggccaaaa gtctatatca cgattgaagg cggaaacacc tcaacgcagg caccgtctgg    12060
ttttgagcag tttggccagc agatcggctc gtttgtggag aaaaaataca gggagctgat    12120
ggcgcaggat atgcgccctg cgggatggt ctggaatgca gttaaagggc aacgttgatg     12180
gctattgaga tattcacctg gagtccgcgg gttaatcccc agcagaccgt aactttcgt    12240 gtccggaagg cgcagttcgg tgacgggtat gcgcaggtat ccggcgatgg tattaacacc    12300
cgatcacagg actgggagct gagttttgtc ggtacggagg actatatccg tccgattaag    12360
cagttcttcg accgtcatgc cggcacccgc gcgtttcagt ggaccccgcc tctggaagag    12420
gtggggcttt accgctgcga acaatataaa ccggtgccgc tgggcggcgg aaattactca    12480
ctttcagcca cttttattca ggcatttaaa ccatgagcct taacgcgaat tatcagaagt    12540
tagagccagg cgatgaggtt cgtctcctgg agatcgatgg ccaggcgttt ggcctggacg    12600
aggttttgta tttccacggc tataacgtcc cccatactgc agccgaaatc ctcgccgctg    12660
acggcgacct ggataagctg cctgcgaaaa gcatctggtg gcaggggcgg gagtataaag    12720
cctggccatg tgtaatcgaa gggatcgagt catccaccac tggcagcgac gcgcagccaa    12780
cgctgcgggt agggaacatc gacgggaaaa tatccgcgct ctgtcttcat tacgacgatc    12840
tggctctggc gcgggttgtc atccacgaca cgcaaaaaca gtatctcgat gcgaagaact    12900
ttccggacgg gaatgcctca gctgatccga cgcaggagaa acggcgcctt ttcttcattg    12960
acgtaaagca ttatgaagac gatgagaagg tggaatttac tctctccagc ccgtttgccc    13020
tgcaggggat gatgatcccc actcgccagc tgcatgcgat ttgcacctgg tgtatccgca    13080
atcaataccg cagcggtaac gggtgcgact atgccggcac ccggtatttt gacaggaaca    13140
atcagccagt tgatgacccg tcgcaggatg tctgcaacgg aacgctcacg gcctgcaaat    13200
tacgtcatgt tgagaatagt gaactgccgt ttggcgggtt ccccggcacc tcattaatca    13260
ggagctgata tgcgtcagaa aacgattaag gccatccagg aacatgcggc ggcagaatat    13320
ccgcgcgagg cctgcggcct cgtcgcccag aggggccgag cggagcgtta tttcccctgc    13380
cggaacctgg ccacagagtc gaaagataat tttgtgctgg cgccggagga ttatgcggag    13440
gttgaggaat ggggaacgat caccggtatt gttcacagcc atcctgatgc caccacccag    13500
ccgagcgaac tggataaagc gcaatgcgac gcgacccttc ttccctggca tattatcagc    13560
tggccagaag gcgatctccg taccatccac ccgcgtggtg agttgccgct cctcgagcga    13620
ccattcgtgc tgggccacta cgattgctgg ggcctggtga tgagctattt tcggcaaacc    13680
cacggcatcg agctgcacga ttaccgcgtc gattatccgt ggtgggaaaa ggagtatccg    13740 gacaatttt atcaggactg ctggtatgaa tgcgggttcc gtgagtttga tggtccacca    13800
caaccgggtg atatggtgat catgcaggtg caggcggata agtggaacca cgccgggatt    13860
ctgctggaag aaaatatgct cctgcatcat ctgtatggcc atctcagcaa tcgcgtgccg    13920
tatggtggat actggatgga aaggacgatg aaaatcgtgc gacatcattc actatttaaa    13980
ggtgcctgta tattatgctc ctaattcaat ttacaggagc atgcgaatga atgagccaat    14040
cactgagcag ttatacaata aagttgtaaa tttcgttaat aaaatggatg ggagtgtgcg    14100
ctttgattat atttctaagt ccttgcgcat tcctcctgac actcttgatg aaattgtgga    14160
caggatgatt gctgatggag tcgttgttaa tacaggaacg gtaggtgaat atttaccagt    14220
aaaacatgca tcttccaaaa acactgataa agataatcga tgctgtacat ctcaaaaaaa    14280
```

```
caatgatagt agtggactaa aatttcttgt tgggagagta gcattagtta tagccataat    14340
atttttatt ataacctgct tttatgctta cagagcaccg atatcgtttg tttttctaat    14400
cccagccata atggctgcat ttgttttac aaaccaaaat catggtggag aaggtttcct    14460
agggttgagt tcaatctctg catgtttaat cttttgctc cttactaatg cgcagacacc    14520
aatatttgga gaagcatatg aattaagaaa gcagagggat gaaattaaaa atgaagttac    14580
taggaaatca aaggaagaag atcagcaaca gctaaatgat atccttaacg ccagagagca    14640
tataaaaggg atgctaaaag accccctcctc agctaaattt tttggtgaat tcattggaaa    14700
aaatggtgct atctgtggcc atgtcaacgc taaaaatagt tttggtggtt acactgggga    14760
gtctcgttac atattttctg tcaattttc tgcaatagat gaaggcacca cctccttta    14820
taaggagtgg gagagacagt gttatcttaa ttgaatggca aggataaagc atgcaagaaa    14880
ccatgacgag aatagaactg tctggagtcc tgggtaaaac ctttgggaag gttcattatc    14940
gtttaataaa gaacatcaat gaagccggag aggcattatc tgcgacgatc cctggatttg    15000
aaaggttcat gatatccagt gaggagcgtg gattgaccta tgcagtattt aaagggaata    15060
agaatatcgg gcatgatgat ttaggattcc ctgtaagtgg cgaaattatc cgcatagtcc    15120
ctgttatcat tggcagtaag aaggcaggaa ttctccaaac aatccttggt gcagttattg    15180
ttgcggcaag tgttgcctat ggttttttca cagaggattg ggctaatgcc gcgtatggta    15240
ttcaagctgg cggcgccatg atgctcggcg gcgtcgttca gatgctctcc ccacagccag    15300
ctggcctggc acgaaaagaa tccgctgaca ataaagcgtc ctacgccttt ggggcgtga    15360
cgaacactgc ctctcaggga tacccggtcc ctttgcttta tggcaaacgg cgaattggcg    15420
gcgccattat atctgccggt atttacgtag aagaccagca ataagtttta ttcagtaaac    15480
catccaattc aggccaccct tgcggtggctt tttttatggg cgtaatatgg caaataacat    15540
aattaaaggg cgcaagggtg gcggctcaaa gcagcgtaca ccgacggaac agccggatga    15600
tttacagtcc gttgcaaaag ccaaaattct gctcgcatta ggtgagggtg aatttgcagg    15660
tggtttaacc gggaaagata tttatcttga tggcaccccg cttgaaaatg ctgatggttc    15720
gcaaaacttc agtggcgtgt cctgggaatt tcgcccccggc acgcaggctc agacttatat    15780
tcagggtatt cccggtactg aaaatgaaat cagtgtagga acggaagttt ccagcaagac    15840
agcctggacc cataccttta ctaatacca gctttctgcc gttcgtgtcc gcctgaaatg    15900
gccgtccctg atgaaacagg aagatgacgg cgacgtggtg ggcaataccg tcaagtatgc    15960
gattgacctg cagaccgacg gcggcgcctg gcagacggtc ctggaaaccg ctgtcacggg    16020
taaaaccacc tccggttatg agcggagcca tcgtattgat ctgccccagg ccggcagtac    16080
ctggacgcta cgcctgcgta aaatctctcc ggatgcaaac agtgtcaaag ttggcgacgt    16140
gatgacgctg cagagctata ccgaagtgat tgacgcgaag ctgcgttatc ccaacaccgc    16200
gctgctttat atcgagttcg actccagcca gtttaatggc tccattccgc aaatttcctg    16260
tgagccgcgt gggcgcgtga ttcgtgtgcc ggataactac aatccggaaa cccgcgaata    16320
taccggcgtc tggaccggcg ggtttaaatg ggcctggacg gataaccggg cctggatcta    16380
ttacgacatt gttacagctg accgttttgg tctcggtaat cgtctgagca gcgccaatat    16440
ttcgaaatgg acgttgtacc agattgcaca gtactgcgat cagctggttc ctgacgggcg    16500
cggtggtgac ggcatggagc cgcgctatac ctgtaacgtc tacgtccagg aacgcaacga    16560
cgcttacacc gtgctgcgag actttgccgc cattttccgg ggcatgacct gctggaacgg    16620
```

```
tgagcagatt gttgtgcagg ctgatatgcc gcgtgatgtc gattttacct atacgcgcgc    16680
caatattgtc ggcaaacccc gttattcgag cagcagcagc caggttcggt acaccaacgc    16740
cctggtttcc tggtctgatc cggataatgc ttatgctgat gcgatggagc cggcgtttat    16800
cccggaactg gtttcccgct acagttttaa ccagctcgaa ctgaccgcga ttggctgtac    16860
gcgccagagc gaagcccacc gtaaggggtt gtggggcata ctgaccaaca caaagaccg    16920 ggtcgttgag tttgatgtgg ggctggacgg tcgcattcct caacccggtt atatcattgc    16980
cctggcggat gagttgctgg ccggacgggt caacggcggg cgaatcagcg cggtgaatgg    17040
ccgggtgatt actctggatc gtgatgtgga tgccaaacct ggcgaccgtc tccagctaaa    17100
cctgccatcc ggtatctcac agagccggac cattcaggct gttaacggac gccggcagat    17160
tacggtcaca acggcgtaca gtgagacacc agaacgggaa tgcgtctggg ccgttgaatc    17220
cgatgacctc ttcctgcagc agtaccgggt tacagggta aaagagaaca gcgatgcaac    17280
cctcacgatc accggcgtgg cacatgaccc ggataaattc gcccgcatcg ataccggcgc    17340
tattatcgac cagcgcccgg ttagcgtatt gccggcgggc aaccagtcac ctcctgacga    17400
tattgtcatc acatcccgct cggtcgtgaa tcagggatc agcgtcgaaa cgatgcaggt    17460
taactggtca gcggtcagcg cgctattgc ctacgaggca cagtggcgcc gtaacgacgg    17520
gaactggatt aatgtgccgc gcagctcgac cacctcgttt gaggtcagcg gcatttatgc    17580
cggtcgttac ctggttcgcg tccgtgcgat caatgcggcg gagatctcga gcggctgggc    17640
gtattccgaa gagaaaaccc tgaccggcaa ggtcggcgag ccgctggcac cgctggcgct    17700
ggcaacccgt tcgctggttc atgggtcca ggttagctgg gagttcccga ccggctccgg    17760
ggatacgctg cgcacggaac tgcagtacag caaaaaccag gacggcagtg cgccaatgcc    17820
gttatcagac gtggcctatc cggggaaaag ctatcagcag atgggcctca gtatgggcgc    17880
agaattctgg taccgggcgc gccttgtgga tcgtcttggc aatgaaagcc cgtggaccgg    17940
ctgggtccag gggatggcca gcgataactt tgatgactac tacgaaaacc tgaccgacgg    18000
gatcaaggat acggctgcct gggaggaaac gcagcgcacc attagcgaaa cgcaggaagg    18060
tatccgcaat acgcagcagg aactggagca gaccgctgaa gctctgcgta aggaagccga    18120
agaccaggcg aagcaggtca gccaggatat tgatgcatcg gcgaaaagca tcactgctga    18180
tgttgacggg aagatctccg ccgtgaataa aaccatcacg gatgagatca cctcggtcaa    18240
tgaggctctc gattctggtc tggctcaggc aaacaaaggc gttcaggagg caaaatccgc    18300
cgtcgcagat gcgaacaagc agatcgcaac tgtgaacaag tcgttgaccg acagcatcac    18360
ccaggtaaga cagtcagtca ccgatacggc tgcggaaatc aacgccacca tcgacctgga    18420
gattgccagg gtcagcaaaa cgctggccga cggcgatgcc gcattgaatg cgcagataaa    18480
gactgccgaa aatggcctga agcagtcgct gtctcaggtt aacaccacgc tgaccaatgc    18540
agtgaagcag gagaccgcgg atcgtatcgc cgatgttaac gcgaaggcgg cacaggccgc    18600
tgatgaactg ctggcggcaa cgcaggggat tgaggcgagt atcgagagcc tgtctgaggc    18660
cgtgacctct ggtgacgaaa atctggcacg ccagatctca cagattgccg ctggcacagg    18720
ggagcagttt gactctctgg aaatctggta tttcgacaaa gatgccgaag ctgacggaa    18780 agacgacaac ggctacacgc caatgagcgt caccagcgat ggctggctta agccaacaa    18840 ttcgacttca acctgtcgat cccctaacgg cctgacgatc gatgcccatg cttatcgttt    18900
cattaagatg cgcattaaaa aggttggtag cccaacctgg aatgccaaaa tgttctggat    18960
cggcgctgat gaaaccggct ggaatgctgg tcgctccgtg gttatcagtg agccggaata    19020
```

```
cgatgacaag ggtattgcga ttctgaccct gcacgacatt gagtggcggg attcgacaac    19080
gattcgtcgt ttccgcttcg atttcacaac gggccaggat gcggacaact atctgttatt    19140
tgactggatc gccgttggcc ggccagcacc cggcgccagt acggcggctc tgcaggatgt    19200
gcgcagtacg ctgagcaacg cgctgactgc cgaagcgcag gcacgcagca cgctggcggc    19260
gcagatgcgt ggctcctatg agggcagcga tctggataaa gtcacctccg gctgctgta    19320 ccaggaaaaa accgcgcgcg ttaccgccat ctcggcggaa gttaaggcca gagagtccct    19380
gcagacgcag tttaacgaca acaaagctgc tgtttctggt gaactgagtt ctctgacgac    19440
agagcagagc gcgcaggcga ccgtatcgg tggcctggaa accagcctcg ggaaaaaagc    19500
cgatgcggcc gcgctgacgt ccctgacgca gaaagttgag caacagggcg ccacgctgac    19560
atcgcagggc gccgcgttaa catcgctcac taaccgggtt ggccagacgg aaacgggcct    19620
ggctggtacg aatgaggcgc tgagcgggct gcagtctgtt gttacccagc agggcgacag    19680
gataaccagc cagggtcagt ccatcacgaa actgacgagc gatttgggca cgacaaatgc    19740
cgcgctggcg aagaaagccg aagcggctgc ggtcactgcc ttaacgcagc aggtagagca    19800
aaacgggcgg gatattcgca gcaatactga cagcatcacc agcctgtcga atcaactggt    19860
caatggccag ccgaatcgct ggtcccgtcg actctatccg gtgcagctgg ctaacgccgg    19920
gacagtcccg tcattcagcg atgttcgcgc cgtggcgcca acggtcgtgg atgaggtggc    19980
cgacgcggcc aaactggact ttacgtccgc cggcagctat ctgatcgcgc tgtattcctg    20040
ccaggtgaaa gtggtcgcag ataccaccat cacactggcg cccggcgcca gggtttttga    20100
tgataccggc gccatatttg tgaatggggt acaggtcgcc tggggtaacg ccagctggaa    20160
taccgtcagt tttgaactga agccggctg gaacaccgtt gagtttctgg tgaatcagtg    20220
gacgggccag gcgtatatca acctgggtct gaagctgtca gacaaggttg ctgagatgta    20280
ctccggtctc ggggttccg cgctggcaaa cgcagccggc gtgctcagct cgaatgtcag    20340
ccagattggc aacgatgtgg tcagcaattc gcagagtatc acccagctcc ggaatgcgct    20400
gacgcagaca gacgcgaacg tggccagcaa agcggatcag acggcgatga actcgctaac    20460
cggacgagtg gagaagacgg aatccgggct gacggctgct aacgccaaca ttacctcgct    20520
gaaatccgct gtacgggccg gaaacgcatc aggcggggat ttaattccca acccgacgtt    20580
tgacccggcg tatgaccaga tggggttcag cgtggtagcc acgacggctg aggaggtccc    20640
gccgggctgc ccgtatggtt atgcggcccg aattgccagc cgggatcacc atcctaactt    20700
tgccgcgttc ccgccacgc ttaacgatgt gattgagatc agcgcactgg ttgcctgcgg    20760
cgccggcacg gcgaatttta atctgtatgt tggcaccgcc gttcggccag atacgagcac    20820
cggtgcgcca ctcatggcgg ggggcgggaa atcaccctcc gcgacctggc agagaaccac    20880
ctggcgcttc aaggtcacgc aggcgatggt ggacaggggt tatatccgcc cgttcctgca    20940
gatctcgcag aacagcccgt atggcaccgt atggttcgtt acggactggc atatgcgaaa    21000
tgtgacagcg gcgcaaaagg ttcaggatac tgcggatgcc acgcggcgg cggttgactc    21060 tctgaccacc accgtgacgc aacagggtaa tctgctgacc tcgaccggca accggacaac    21120
ccagctggaa aacgggctgg caaccatcaa tgccgcagtg gccaaaaagg ctgatgcgac    21180
agcagtgcag gatttgacca ataccgtcac acaactgggc aacgatctga ctgctgcgaa    21240
cagcgccatc acgaaactga ccggaaatct ggcgaatacc gataaagcgc tggcgcagaa    21300
agccgatgcg actgcgctgg ccacgctcga cacgaaagtg acgcagcagg gtaaaacgct    21360
```

```
ggagagccag agcaattcgc tgacgaacct gtcgaacagt ctctcgcagg ttgcggcaga    21420
tatcgatgcc agcggtcaga taccgggtaa cctggtcgtg aatccctcgt ttgaacgtgg    21480
gctggatggc tacaccgggc ggtcaaccgc gaccagtgtg gtggaggttt ccgctcctca    21540
cagcgggacg cggcgctga aggttgatcc ggggagcgtg tctccgggc aatacatccc      21600 gtttgttcag gggcgaacct atgaaatcgg ggtgtgggtc aaggaacccg gagcgacgac    21660
ggataatggc gcggggaaca acaagttgcg gatcggtaac tctgccggcc agccggtctt    21720
tgagcgtccg tacaacagcg gcacggtggg gacaaactgg accctggttt ccggtcgctg    21780
gaaagcgacg gagacagcca gcctgccggt gacgctgagc aactatctga ttaatggcag    21840
ccgctacttc gatgattttt acgtcactga cgttaccgac cgggtggaca tcgatgccac    21900
cgccggcgcc gttaccggac tgacgagccg ggtcagcaca gcggaagggg ctatcacctc    21960
gcaaagccag cagctgacga acctgcagaa cagcctgaac acgaccaaca gcaatgtgtc    22020
gaagaaggcc gatgcaacgg cactgacttc ggtcgataac cgggtgacag aggcggaagg    22080
gaaactgacc acacagagcc agcagctgac aaatctggcg aatgtgctga cggccacccg    22140
caacgctggc gacaacctga tcccgaactt tgattttcta caggcagca ctgcctggga     22200 tattcagtat ccagccggtg tgactttgg cgatttcggg gacgggaaag cggggtccg      22260 gctgaaccgg acgactaaca ccagtccggg gatcttctcc aacaacaaca gccggtgcc     22320 gctgaatggc cagcgcaagt accgcgtggt ggtgaaggcc aaaggtgttt ccggcgcgat    22380
gagtctgctg atccgtcgcc agaacaaaat cggccagacg gacagtacgt atgaggataa    22440
aacggtcacg ctgaccactg actggcaaac catcacctgg gaaaccggat tgacggctgc    22500
cggcgcggac gggcagaact tcaaacttta ttctcatccg acaaacggtg aaatctggct    22560
cgattccgtc cggttttttg atatcaccga tgaaaccaac atcaaggcga ccagcgatgc    22620
tgtttcgtct ctgaccggga cggtgacgaa ccaggggaac accctgacat cacaggggca    22680
atccatcacg gcgctgaata acgcgctgga aggggtcaaa ggcgatgtgg cgaagaaggc    22740
tgatgcgtcg gcggtcagtt cactgaccaa ccgggttacc cagactgaaa aggatatccg    22800
tagccaggcc gacagcctga ccaggctgaa tacatcgctg aagcaacagg caacacgggg    22860
agccaatgta ctgccggacg gcagttttga atcctatgcc gtcggcgatg ttctcagtaa    22920
tgcccgcgct gttatcacca gtgaagctgc gcacagcggg accaaaagcc tgcgtgttac    22980
gcgcagtacg gagtacaacc cgaacgcgac ggataataac gatacccata tcttttctgg    23040
tatgcaggtt cgcgataatg cggtctatta cgtggaggcg tgggtaagt tgccggctgg    23100 ctcgaccgcc gatccgaccg tttatatggt gctaggattt tccttccagg attctgccaa    23160
tggctggtcg tggcctggcc tgaacgtgaa agtctccgag ttgtcggtgg acaactggac    23220
aaaggtcagt ggctatctga ccaacaaccg aaccgcactg aaacaggcaa tggtgaggat    23280
ctccatcccg aatacaccaa aagttcgcct gggtgacgcc ttcctgattg atgatctgat    23340
catcactgac gtgaccgatg cgaaagcggc gctcgatgcc gccgatgcga atgcgcaggc    23400
gctttccagt ctgtccgcgt cagtcacgca gaacgggaag aatattacgt ctcagggcag    23460
cgcgatcacg aagctgcagt cggatgtgac gcaacttggt aaggatatca gcggcaaggc    23520
cgatgccagc gcgctgacga atctgacgac ccgcgtgacg gctaccgaag gcagcctgaa    23580
atcgcaggga gacagcctga ccaacctgca gaacagcctg aacacgacta acagcaatgt    23640
ggcgaagaag gctgatgcaa cggcgctgca gagcctgcag aacaccgttg aacagcatgt    23700
cagggatctg accacgcaaa gcagcgcgct gacgaacctg gaaaacaact ttcctcccct    23760
```

```
ggccgttggc gggaccaacc ttatccgcaa tgcggacaca ctggagggat ggagcagccg   23820
ccacgccaca gagacgtatc tgggcgaccg cgtggcctac acccggctgg cgaaaggtgc   23880
atccggttat atccagctgg atgaacagac gctggatgtt accgggcgta ctgaatttgt   23940
attcagcttc tatgcgaaag gtgccctataa cggacaggaa atggcgagtt attttttataa  24000 cccgtcgaac actaccacca cggaaaccag ccaggggggtt aaggcgggg ccggtgacgg   24060 caaggcggtc acgaaactga ccaccgcatg gcgcgttac tgggtgaaat gggttattcc   24120
tgccaccagt ggcaccaaac ggctgattgc cgcgcgtctg gaaagcgcga cgtctgccga   24180
caaagaagtc tggctctgtc gccctcagct ggaaaccggg accgtgatga ctgactggtc   24240
accgagtccg gatgatgcgg ccagcggtat taccgcgaac acatcggcca ttaacagcct   24300
caccagtcgg gtgacgaatg ccgaggggca actgaccgcg cagtctcaga gcatcacgaa   24360
tctgcagaac agcctgaaca ccaccaacaa caacgtggca caaaaggcca gcgcgcagtc   24420
ggtgagtgat ctcaccagcc gggtcaccag tgcggaaggc aaaatcacct cccaggggca   24480
ggctatcacg aagctgcagg gcgatttgag cagcaccacc gataaggtca acaccaaagc   24540
ggatcagacg gcgcttaacg cgctgactgg ccgggtggag aaaaccgagg caggcctcac   24600
ggcagccaac agcaacatcg tcagcctgac ggcggcggtg aacgccggga atgctgccgg   24660
ggatgattac atcccaaacc cgtcatttga tccggcgtat gaccgcatgg gttatgacgt   24720
ggtggagacc actgctgcag gtgtgccggc tgactgcccg ttcaggtatg ccgtccggct   24780
ggccgggcga gaccatgtgc caaaaatcaa caacatcgct gtgacgccgg gcgacgttta   24840
cgaaatgtct gctctggtag cgtgtggtac cggcagcgct gactttaatt tctacatcgg   24900
tcgggccacc actgctactg gtggtattgg ggcgagagcg tccgggggaa acaccaagac   24960
caccaccgcg tggaaacgag ccacctggcg ctttactgtg ccggcagaca cgaacttcct   25020
gcgaccgttc ctgcaggtta atcagagcag cccgttcggc actgtctggt acgctgccga   25080
ctggcatatg cgtaacgtga cggcggcgaa cagtgcgcag aaaaccgcag atgcgaccgc   25140
aaaagcggtg gattcactga ccaccacggt tagccagcag ggcgatacgc tcagcagcat   25200
cggcacgcgg accacctcgc tggagaacag cctccggtcg acaaacgata cggtgagtaa   25260
aaaggctgac acgacagcgg tgacgcagct gcagggcacg gtgacgcagc aggggaatga   25320
catcgcggca gccaacagcg cgctgacaaa actcagcagc gatctggcca cgacgaatgc   25380
gaatgtgaac aaaaaagcgg acgcaagcgc gatgaacacc ctgcagaacc aggtcactga   25440
gcagggcaaa cactcagtg cgcaaggga ttctctaacg caacttagta acagcctgag   25500
ccagacggca gcggatattg acgccagcgg gaaaatgccg gcaacctca ttgtcaacgg   25560 cagttttgag cgcggcgcgg cgggctttac cggctggagc agtaccgcga cggtggccga   25620
tttacaggtt ccgcattcgg gtaacaaggc gctgaaaatg tccgccggcc agtcgaacct   25680
ggtcgggcag gaaatcagta tcacgcaggg tcgtacctac cgcatggggg tatgggcgaa   25740
gcaggacccg ggaaccacta ttaaagatgc gggtaacacg aagtttcgtg tggccgacag   25800
cactggcctg ctggtcggct caaactacgg accgtttagt tctggctggc aactggtaac   25860
gtttgactgg aaagccacga agaccacgac ggccagtttc cagctgacga ccttcctcag   25920 cgcggggggca atgtatttcg atgatttcca tgtcctcgat gttacggatg aaaaggatat   25980
cgcagctaat gccggggcca tttctcagat gaatacccgc gtcaccgctg ctgaagggggc   26040 tatcaccacc caggcgcagc agctgacgaa actcagcggc gatctggccg tcacgaatgc   26100
```

```
ggcggtcagt aagaaggccg agcaaagcgc tgtcaccggg ttgaccaccc ggatgacgtc   26160
tgccgagggt aaactggatt cgcagtcgca gcagctcacc agtctgcaga acagcctgac   26220
cacgatgaat actgagctgg gtaaaaaggc tgacacgtcc gcggtgagtt cactgaccgg   26280
tcgcgtaagc caggtggaaa acaccatcac cagccagtcg cagagcatca cgtcgctgac   26340
cagcaccatc aataccatcc gcactcaggg agctaatccg tgggttgacg gtacgtttga   26400
aagctacagc gatggccagg tgctgggcgg gaacggcaca gccgttgtgg tggcgtctca   26460
gaaattcacc ggcggtaaga gcctgaagtt gagacgggat gagaacaaca gcggcaacag   26520
tgataaacag cttggcacct ggcagtcagt ccgtgaggac gcgaagttcc ggtttgagtt   26580
ctgggccatg atgccggcgg atcaggcgcc ctcctccggg tggacaacgc tggtcggtat   26640
ccagtcgcag aatgctgccg ggcaaaatgc gtggcaggcg gcggtcactg tcagcgaagc   26700
ctctctgggc gcgcgcgata agtgggtgaa attcacgggt atcgccagta acaacggggc   26760
aggcagaaca cgcgcggtgg tctggatctc cactcgtggc gccaccggca acggtacccc   26820
tggctattca ctgtatatcg acgatctggt catcacggat gttaccgatg cgaaagcggc   26880
acaggatgcc tctgacgcga cggcgagcgc cgtgagcggc ctgacggcgc gcgtaacgga   26940
tgccgaaggg aaaatcactg cccaggcgca gcagcagaca gcactggcct cgaaagtgga   27000
taacgccaac tcccgcgtcg ataacatggc gaagacgctg agcgacagcc agagcacaca   27060
ggccagcctg aatacctcgc ttcagtcgca gattgacgcg caggcggccg ccaacatcaa   27120
aaaccagacg acgctggaca acacgattaa atcggtggcc agtatcacca gtacccagca   27180
gacgcatgca acggcactgg aggcgctggc aacgcagcag acgaccctga catccagtgt   27240
cggggatctc agcgcttccg ttcagaacac cgccaaaacc gtggcggatg tgaatggtac   27300
ggtgagttcg ctgtggtcga tgaaggttga acggttaac gggaagaatg ttggcgcggg   27360
gattacgctg ggcagcaatg gtgaaacaag cgatatgatc ctctacgctg accgcttctc   27420
gctgtttaac cgtaataatg cgacggctgt tccggtgatg gttgccgaag caatgagct   27480 gtatatcgat acggcacgta ttaaaaacag ttccctgacc tcaaccaaaa tcgcggacgg   27540
ttccatcacg aacgcgaaga tcggcaacga gatccgctcg aatgactttg ttgacgggtc   27600
acgcggctgg cgtatcgcca aggatggctc ttcgcagttc aacaacgtga tcgttcgcgg   27660
tgcggtttat gcgactgacg gctggttcca gggtacggta tatgcgaacc acatcgaggg   27720
cgacatcggg tcatttgcga tcaacatcgc tcagcaccgc acgcgcaagg tgccgaaggc   27780
tacatggcag tggtttgagc tggcccggtt ccggcggcag aatttcgacc aggtgatcaa   27840
tattcgcggt ggactcctcc agacggatag catcactatc gacggcggcg cgaaactcag   27900
agcggggatg tcctacgcgc caggggctga cggcggactg aatcctggct atctgtcgta   27960
tgcaatgctt cttcgtggca caggcgctac gtctggtggc ggcagtatgg agctaggcat   28020
tgagcttatg tatgaaacag gtggagcaac acgcctgtta acggcgcaag agtcaatgaa   28080
cgtagacaac atgtcatttg tcgtccctgc cggtactggc gacgctgttc tgcgatatgg   28140
ctgttacctg gaccgtaacg gacagatggt attaaccatc ctctcaagat tcgacgcctt   28200
cgccgcgcgc aataacaacg taattcgcgg ttcatcaacc tgataacaat atatggcccc   28260
gcaaggggcc ttttcttttt ccagggaaaa ccatccagga ggaactttat tatggcgatg   28320
tatgaagtcg gtaccgtcac gggtgccgcg tcgcaggcac gggtgacagg tgcgacaaca   28380
aaatggtcac aggaggcgct ggggatactg cccgggtcga ttctagtggt ctaccgcagc   28440
ggtagtgctg acctgtatgc gatcaaatcc gtggacagcg acacgcaact gacgctgacc   28500
```

```
cggaatatca ccaccgcatt ttccggtgcc agttacggca ttattaccgc tgaaaccgcc    28560
agcacctcgt cgtttgctaa ccagctggcc agcgcgtttg cattctggcg tagtgtagtg    28620
gagggctggt cgatggccct gaccggcagc ggcaatatca ccctgacaga cccgatcaca    28680
ggaaagcagg tgatcgtgcc ggcgatagcc gggatggcga aggcatcgga tcttaacgca    28740
ctggcaaaac tcacaggagg aaacaaactc gacggctcgc aggttataac cagcgataat    28800
gccggtttta ttctcggtaa gaactcagat ctggctctgc tcaaaaaaca ggggcaaggc    28860
gggacaattg ccgttggctc gggaacaccg ttcagggttc agcgttcaag agcgaccact    28920
gtatcaccgg cagacacctt tgatgacatc ctcgttattg atgccaacaa ccaaacgaca    28980
ctgcctggcg cgctgtctgc cggcggcaat atcgataaca cgtcgaaggg taaagtgttg    29040
acgcaggcga ttgagctctc atttagcacg ccatacatcg actttcattt taactacagc    29100
accgacgact tcaccgggcg gattatggcc actgccgccg atcaaattag tgtgcaaggt    29160
agtcattggc gagttgacag ggatcttcgt gttggtggca tggcagatat tggaggctgg    29220
acgcaatgcc gcgacgacct ttcggccaac aaaacagact ttggatcccc tgctattggt    29280
tcgttggttt caggcggaag gattcgatct cgaatgctcg ggcgcggcgg taacgttgac    29340
acctccgggg cgtggggcgg tttctatctt gaagagtacg tgggaaccga acacaggatt    29400
gtcatgtata tggacggctt cgggagaacg gacgcatggt cattccgcgc aggggggaca    29460
atctccacac ctaaaggcga cgtcctgacc actggttccg acgtgcgcct gaaaacagac    29520
ttcacacaag cgtctgaaaa cgcctcgagg cgcattgagc gcttaggggt gtgtgagtac    29580
cggatgaagg gggaaacgcg ccggaggcgt ggttttatcg ctcagcaggc tgaaaaagct    29640
gatgatctgt atactttcct cggcatcgag caggagattg atggcgaaaa atttaaggtg    29700
atgaatgtgg attacacggc aatcattgct gacctggtta cggtggcgca gggtttactg    29760
gttaaaaatc aggaactgga aaggcgtata tctgtactgg aggggatc                 29808
```

<210> SEQ ID NO 8
<211> LENGTH: 350
<212> TYPE: DNA
<213> ORGANISM: Kappa phage

<400> SEQUENCE: 8

```
cgggctaact gcccgaaaac atggggcggt tcatcgcgtc gcgccaatct gcgctgcagc     60
tattgtggcc agtccgggca taactcgaat gcctgcccac ataatgcgag cagcggtcga    120
cggcgcagcc tgaatgacga ctttacccct gactgaaccg atagcacgat ggcggcaggc    180
ggaattgatt tcaatgtgaa attattcaat gtcaagtcat tgcattgcgc gatgatgata    240
atagatatca tttgaggggg tagggggat caaatcccta accccttcg cgcttcggga    300 ctgccgcttc aggtagattt ttgcgcgtga gaataaaaa cttttttttg              350
```

<210> SEQ ID NO 9
<211> LENGTH: 4469
<212> TYPE: DNA
<213> ORGANISM: Artificial Sequence
<220> FEATURE:
<223> OTHER INFORMATION: p1866 payload

<400> SEQUENCE: 9

```
tgattataag aaggcgcccc aagcaccccc attttagcta taaaaaaacc cgccgaagcg     60
ggttttttcg aaaattgtaa ggtcacatta cgccccgcct tgccactcat cgcaatattg    120
```

```
ttgaagctca ttaagcatac ggcctacatg gaagccatca cacacggcat ggtgtacctg    180
gatcgccaga ggcattaaca ccttgtcgcc ttgcgtataa tatttaccca tagtgaaaac    240
aggggcgaag aagttgtcca tatttgctac gtttaaatca aaactggtga aactcaccca    300
gggattagca ctgacgaaaa acatattttc gataaaccct ttagggaaat atgctaaatt    360
ttcaccgtaa cacgccacat cttgtgaata atgtgcaga aactgacgga aatcatcatg     420
gtattctgac cataacgaac taaacgtttc agtctgttca tggaaaacgg tgtaacaagg    480
gtggacacta tcccaaatca ctaattcacc gtctttcatt gccatacgaa actccgggtg    540
tgcattcatc aggcgggcaa gaatgtgaat aaaggccgga taaaacttgt gcttattttt    600
ctttacggtt tttaaaaagg ccgtaatatc cagttgtacg gtttggttat aggtgcactg    660
cgcaactgac tggaatgcct caaaatgttc tttacgatgc cattgactaa tatcaactgt    720
agtatatccg gtaattttct tctccatttt agattcctta ggttgcgaaa tctcgataac    780
tcaaaaaata gtagtgatct tatttcatta tggtgaaagt tgtcttacgt gcaacatttt    840
cgcaacaagt tggtttcccg aggcctaact tttgttgcaa tggctgtcta ccctgtttta    900
tactagctca gcccttggta caatgctagc gttttcatta aagaggagaa aggaagccat    960
gagtaaaggt gaggaattat ttactggtgt tgttccgatc ttagttgagc tggacggcga   1020
tgttaacggt cataaattca gtgttcgtgg tgaaggtgaa ggcgatgcaa ccaacggtaa   1080 gctgacccctg aaattcatct gcactactgg aaaattacca gtaccctggc ctactctggt   1140
gactaccctg acctatggtg ttcagtgttt ttctcgttac cctgaccaca tgaagcaaca   1200
tgacttcttc aaatctgcaa tgccggaagg ttatgtacag gagcgcacca tttctttcaa   1260
agacgatggc acgtataaaa cccgtgcaga ggttaaattt gaaggtgaca ctctggtgaa   1320
tcgtattgaa ctgaaaggca ttgatttcaa agaggacggc aatatttag gccataaact    1380 ggaatataac ttcaactccc ataacgttta catcaccgca gacaaacaaa gaacggtat    1440 caaagctaac tttaaaattc gacataacgt tgaagatggt agcgtccagc ttgcggatca   1500
ttaccaacaa aacactccga ttggagacgc tcctgtttta ctgccggata accactacct   1560
gtccacccag tctaaactgt ctaaggatcc gaacgaaaag cgcgaccaca tggtgttatt   1620
agagttcgtt accgctagtg gtattacgca cggtatggat gaactctaca ataataatc    1680 agacagtttc acctgtttta cgttaaaacc cgcttcggcg gtttttact tttgggttta    1740 gccgaacgcc cgggctaact gcccgaaaac atggggcggt tcatcgcgtc gcgccaatct   1800
gcgctgcagt tattgtggcc agtccgggca taactcgaat gcctgcccac ataatgcgag   1860
cagcggtcga cggcgcagcc tgaatgacga ctttacccctc gactgaaccg atagcacgat   1920
ggcggcaggc ggaattgatt tcaatgtgaa attattcaat gtcaagtcat tgcattgcgc   1980
gatgatgata atagatatca tttgaggggg tagggggat caaatcccta acccctttcg   2040
cgcttcggga ctgccgcttc aggtagattt ttgcgcgtga gaaataaaaa cttttttttg   2100
gcgttcggct aaacgtgcta catttgaaga gataaattgc actgaaatct agaaatattt   2160
tatctgatta taagattat cttcttgaga tcgttttcgt ctgcgcgtaa tctcttgctc    2220
tgaaaacgaa aaaaccgcct tgcagggcgg tttttcgaag gtcctctgag ctaccaactc   2280
tttggaccga ggtaactggc ttggaggagc gcagtcgcca aaacttgtcc tttcagttta   2340
gccttatccg gcgcatgact tcaagactaa ctcctctaaa tcaattacca gtggctgctg   2400
ccagtggtgc ttttgcatgt cttttccgggt tggactcaag acgatagtta ccggataagg   2460
cgcagcggtc ggactgaacg gggggtttgt gcatacagtc cagcttggag cgaactgcct   2520
```

-continued

```
acccggaact gagtgtcagg cgtggaatga dacaaactcg gcagtaacag aggaatgaca    2580
ccggcaaacc gaaaggcagg aacaggagag cgcacgaggg agccgccagg gggaaacgcc    2640
tggtatcttt atagtcctgt caggtttcgc caccactgat ttgagcgtca gatttcgtga    2700
tgcttgtcag gggggcggag cctatggaaa aacggctttg ccgcgaccct ctcacttccc    2760
tgttaagtat cttcctggca tcttccagga aatctcagcc ccgttcgtaa gccatttccg    2820
ctcgccacag tcgaacgacc gagcgtagcg agtcagtgag cgaggaagcg gaatatatcc    2880
tgtatcacat attctgctga cgcaccgatg cagcctttt tctcctgcca catgaagcac     2940
ttcacttaca ccctcatcag tgccaacata gtaagccagt atacactccg ctagcgcaga    3000
tgtccggcgg tgcttttgcc gttacgcact actttagtca gttccgcagt accgtcaggc    3060
gctgacatag ctatttactt tgtattgcct gcaatcgaat ttctgaacta tcatatagtg    3120
gggataacgg gaaagttact atatttgcga actaacttag gcgtccacct cgaagctacc    3180
taatcacacc caacccgcgc ggggtaaata aggcactaat ccgagcttaa agcttgcgta    3240
gcacttagac acaagttaat taccaattgt ctggtagttt ggcggtatta gcgagatccc    3300
agacgcaagg cagagttaat tttaacctaa agccacaaat aagacaggtt gcacaagccc    3360
gccggaaatt aaatcttgct cacttcggta acggagtttc cctcccgcgt acttaattcc    3420
caataagaaa cgcgcccaag tcctatcagg caaaattcag ccccttcacg tcttagaacg    3480
agggtaaaaa tacaagccga ttgaacaagg gttgggggct tcaaatcgtc gtttacccca    3540
ctttacaacg gagggtaact agttcaccct atagtacgaa gcagaactat ttcgaggggc    3600
gtgcaataat cgaatcttct gcggttgact taacacgcta gggacgtgcc ctcgattcag    3660
tcgcaggtac tccgactcac actgcctcac acccagctag tcactgaccg ataaaattga    3720
cccgccctct aaggtagcga gtacgtccta aaaggcttcg gacagggcta tataggagag    3780
tttgatctcg ccccgacaac tgcaaccctc aactcccctta gataatattg ttagccgaag    3840
ttgcacgacc cgccgtccac ggactgctct tagggtgtgg cttcttaatc tgacaacgtg    3900 caaccccctat cgagggcgat tgtttctgcg aaaggggttg ccctaatagt cgcgacaatt    3960
ggcccttgta ggggtgaaac cacttagttt cgcgccgtag tcctaaaggc ccacctattg    4020
actttgtttc gggtagcact aggaatctta acaatttgaa tttggacttg ttttagggcc    4080
gttattcgag ggcaatcgga gctaacttca agactacttc tttgttgaat actaaatagt    4140
gcaaaggtcg tgtttcctca aggatactcc gctaacaata taggattcca atcagattca    4200
gcactggctg tacgggtgtt acggtgaggt tttcgggttt acggctggaa gctagcacgg    4260
taggaagcct ttcaatcaca aagcaaaagg gccgtcgaag gcccacaaga tacgaaagct    4320
ctcgaagcct tatccttgaa cgatccacct atttaggcag ttacgcacaa agctaccca     4380 ataatccgtg acaggcacaa tatcacggaa caaaggcgaa aactctcgta cacggttagg    4440
ttttcgctag gaagaataaa cctctatct                                      4469
```

<210> SEQ ID NO 10
<211> LENGTH: 363
<212> TYPE: DNA
<213> ORGANISM: Artificial Sequence
<220> FEATURE:
<223> OTHER INFORMATION: Candidate HNH protein ORF

<400> SEQUENCE: 10

```
atgccagccc ggtctaaacg tccatgccgc caccgggggt gtccggcgat aaccaacgac      60
```
cccagcggtt actgcgatgc tcaccggcag caacatgctg gcgacggctg gcgcaactac    120
cagggcggga aaagccggca tgaaaggggc tacggtcgcc cctgggaaat ccgccgcgcc    180
agaatcctcc agcgcgataa atatctatgc caaaactgcc ggcgtcatgg catcgccacc    240
aaagcgacca gcgtcgacca catcataccc aaagcgcgtg gcggtacaga cgacgattcc    300
aatctggagt cgttgtgctg gccctgccat agagcgaaaa cagcaacaga gagaacccga    360
tga                                                                 363

```
<210> SEQ ID NO 11
<211> LENGTH: 120
<212> TYPE: PRT
<213> ORGANISM: Artificial Sequence
<220> FEATURE:
<223> OTHER INFORMATION: Candidate HNH protein

<400> SEQUENCE: 11
```

Met Pro Ala Arg Ser Lys Arg Pro Cys Arg His Arg Gly Cys Pro Ala
1               5                   10                  15

Ile Thr Asn Asp Pro Ser Gly Tyr Cys Asp Ala His Arg Gln Gln His
            20                  25                  30

Ala Gly Asp Gly Trp Arg Asn Tyr Gln Gly Gly Lys Ser Arg His Glu
        35                  40                  45

Arg Gly Tyr Gly Arg Pro Trp Glu Ile Arg Arg Ala Arg Ile Leu Gln
    50                  55                  60

Arg Asp Lys Tyr Leu Cys Gln Asn Cys Arg Arg His Gly Ile Ala Thr
65                  70                  75                  80

Lys Ala Thr Ser Val Asp His Ile Ile Pro Lys Ala Arg Gly Gly Thr
                85                  90                  95

Asp Asp Asp Ser Asn Leu Glu Ser Leu Cys Trp Pro Cys His Arg Ala
            100                 105                 110

Lys Thr Ala Thr Glu Arg Thr Arg
        115                 120

```
<210> SEQ ID NO 12
<211> LENGTH: 4269
<212> TYPE: DNA
<213> ORGANISM: Artificial Sequence
<220> FEATURE:
<223> OTHER INFORMATION: p1869 plasmid

<400> SEQUENCE: 12
```
tcagatcctt ccgtatttag ccagtatgtt ctctagtgtg gttcgttgtt tttgcgtgag     60
ccatgagaac gaaccattga gatcatactt actttgcatg tcactcaaaa attttgcctc    120
aaaactggtg agctgaattt tgcagttaa agcatcgtgt agtgttttc ttagtccgtt      180 acgtaggtag gaatctgatg taatggttgt tggtattttg tcaccattca ttttatctg    240 gttgttctca agtccggtta cgagatccat tgtctatct agttcaactt ggaaaatcaa    300
cgtatcagtc gggcggcctc gcttatcaac caccaatttc atattgctgt aagtgtttaa    360
atctttactt attggtttca aaacccattg gttaagcctt ttaaactcat ggtagttatt    420
ttcaagcatt aacatgaact taaattcatc aaggctaatc tctatatttg ccttgtgagt    480
tttcttttgt gttagttctt ttaataacca ctcataaatc ctcatagagt atttgttttc    540
aaaagactta acatgttcca gattatattt tatgaatttt tttaactgga aaagataagg    600
caatatctct tcactaaaaa ctaattctaa ttttttcgctt gagaacttgg catagtttgt    660
ccactggaaa atctcaaagc ctttaaccaa aggattcctg atttccacag ttctcgtcat    720

```
cagctctctg gttgctttag ctaatacacc ataagcattt tccctactga tgttcatcat      780
ctgagcgtat tggttataag tgaacgatac cgtccgttct ttccttgtag ggttttcaat      840
cgtggggttg agtagtgcca cacagcataa aattagcttg gtttcatgct ccgttaagtc      900
atagcgacta atcgctagtt catttgcttt gaaaacaact aattcagaca tacatctcaa      960
ttggtctagg tgattttaat cactatacca attgagatgg gctagtcaat gataattact     1020
agtccttttc ctttgagttg tgggtatctg taaattctgc tagaccttg  ctggaaaact     1080 tgtaaattct gctagaccct ctgtaaattc cgctagacct tgtgtgttt  tttttgttta     1140 tattcaagtg gttataattt atagaataaa gaaagaataa aaaagataaa aagaataga      1200 tcccagccct gtgtataact cactacttta gtcagttccg cagtattaca aaaggatgtc     1260
gcaaacgctg tttgctcctc tacaaaacag accttaaaac cctaaaggct taagtagcac     1320
cctcgcaagc tcggttgcgg ccgcaatcgg gcaaatcgct gaatattcct tttgtctccg     1380
accatcaggc acctgagtcg ctgtcttttt cgtgacattc agttcgctgc gctcacggct     1440
ctggcagtga atgggggtaa atggcactac aggcgccttt tatggattca tgcaaggaaa     1500
ctacccataa tacaagaaaa gcccgtcacg ggcttctcag ggcgttttat ggcgggtctg     1560
ctatgtggtg ctatctgact ttttgctgtt cagcagttcc tgccctctga ttttccagtc     1620
tgaccacttc ggattatccc gtgacaggtc attcagactg gctaatgcac ccagtaaggc     1680
agcggtatca tcaacggggt ctgacgctca gtggaacgaa aactcacgtt aagggatttt     1740
ggtcatgaga ttatcaaaaa ggatcttcac ctagatcctt ttaaattaaa aatgaagttt     1800
taaatcaatc taaagtatat atgagtaaac ttggtctgac agttacgttt ccacaaccaa     1860
ttaaccaatt ctgatttaga aaactcatc  gagcatcaaa tgaaactgca atttattcat     1920
atcaggatta tcaataccat attttgaaa  agccgtttc  tgtaatgaag gagaaaactc     1980
accgaggcag ttccatagga tggcaagatc ctggtatcgg tctgcgattc cgactcgtcc     2040
aacatcaata caacctatta atttcccctc gtcaaaaata aggttatcaa gtgagaaatc     2100
accatgagtg acgactgaat ccggtgagaa tggcaaaagc ttatgcattt ctttccagac     2160
ttgttcaaca ggccagccat tacgctcgtc atcaaaatca ctcgcatcaa ccaaaccgtt     2220
attcattcgt gattgcgcct gagcgagacg aaatacgcga tcgctgttaa aaggacaatt     2280
acaaacagga atcgaatgca accggcgcag gaacactgcc agcgcatcaa caatatttc      2340 acctgaatca ggatattctt ctaatacctg gaatgctgtt ttcccgggga tcgcagtggt     2400
gagtaaccat gcatcatcag gagtacggat aaaatgcttg atggtcggaa gaggcataaa     2460
ttccgtcagc cagtttagtc tgaccatctc atctgtaaca tcattggcaa cgctaccttt     2520
gccatgtttc agaaacaact ctggcgcatc gggcttccca tacaatcgat agattgtcgc     2580
acctgattgc ccgacattat cgcgagccca tttatacccca tataaatcag catccatgtt     2640
ggaatttaat cgcggcctcg agcaagacgt tcccgttga  atatggctca taacaccccct    2700 tgtattactg tttatgtaag cagacagttt tattgttcat gatgatatat ttttatcttg     2760
tgcaatgtaa catcagagat tttgagacac aacgtggctt tccctgcagg atttcggagg     2820
cctgcgttat cccctgattc tgtggataac cgtattaccg cctttgagtg agctgatacc     2880
gctcgccgca gccgaacgcc gactagtgga ttttacggct agctcagtcc taggtacaat     2940
gctagcgaat tcattaaaga ggagaaaggt acccatggca cgtaccccga gccgtagcag     3000
cattggtagc ctgcgtagtc cgcatacccca taaagcaatt ctgaccagca ccattgaaat     3060
```

| | |
|---|---|
| cctgaaagaa tgtggttata gcggtctgag cattgaaagc gttgcacgtc gtgccggtgc | 3120 |
| aagcaaaccg accatttatc gttggtggac aataaagca gcactgattg ccgaagtgta | 3180 |
| tgaaaatgaa agcgaacagg tgcgtaaatt ccggatctg ggtagcttta aagccgatct | 3240 |
| ggattttctg ctgcgtaatc tgtggaaagt ttggcgtgaa accatttgtg gtgaagcatt | 3300 |
| tcgttgtgtt attgcagaag cacagctgga ccctgcaacc ctgacccagc tgaaagatca | 3360 |
| gtttatggaa cgtcgtcgtg agatgccgaa aaaactggtt gaaaatgcca ttagcaatgg | 3420 |
| tgaactgccg aaagatacca tcgtgaact gctgctggat atgattttg gttttgttg | 3480 |
| gtatcgcctg ctgaccgaac agctgaccgt gaacaggat attgaagaat ttaccttcct | 3540 |
| gctaattaat ggtgtttgtc cgggtacaca gcgttaacta gggcccatac ccccaattat | 3600 |
| tgaaggccgc taacgcggcc ttttttgtt tctggtctgc ccgacgtacg gtgaatctga | 3660 |
| ttcgttacca attgacatga tacgaaacgt accgtatcgt taaggttcag aacgtatcac | 3720 |
| tggtgacgta catgccagcc cggtctaaac gtccatgccg ccaccggggg tgtccggcga | 3780 |
| taaccaacga ccccagcggt tactgcgatg ctcaccggca gcaacatgct ggcgacggct | 3840 |
| ggcgcaacta ccagggcggg aaaagccggc atgaaagggg ctacggtcgc ccctgggaaa | 3900 |
| tccgccgcgc cagaatcctc cagcgcgata aatatctatg ccaaaactgc cggcgtcatg | 3960 |
| gcatcgccac caaagcgacc agcgtcgacc acatcatacc caaagcgcgt ggcggtacag | 4020 |
| acgacgattc caatctggag tcgttgtgct ggccctgcca tagagcgaaa acagcaacag | 4080 |
| agagaacccg atgatgacgc atcctcacga taatatccgg gtaggacgaa caataaggcc | 4140 |
| gcaaatcgcg gccttttta ttgataacaa aaggacagtt ttccctttga tatgtaacgg | 4200 |
| tgaacagttg ttctactttt gtttgttagt cttgatgctt cactgataga tacaagagcc | 4260 |
| ataagaacc | 4269 |

<210> SEQ ID NO 13
<211> LENGTH: 1189
<212> TYPE: DNA
<213> ORGANISM: Kappa phage

<400> SEQUENCE: 13

| | |
|---|---|
| ataatttcaa aattgaatac gttgatggcg cttttgaccgt tctggagacg gatggccagt | 60 |
| cacggatgaa tgaagccgta catggcatcc attttgagca tgtccagggc ggacgccccc | 120 |
| tgctgaaact gacgattgcg catgatattg ccccggcctc gaccccggcc ccggctgctg | 180 |
| cgtcggctca ggaaccttta gagggtgagc tggtacagga gcaacaatcc ccgctgcctg | 240 |
| gcggtcgccg ttcccgccat cgccgtggag gtaagcaatg atgtatcaac gcacggatct | 300 |
| gacgctctcc atgttctatg catccagcgc tgatgcagac gggaacaaag tggctacgtt | 360 |
| gacgatgcag gtaattgcgg cagaggttgg tgccgtccag accagtcaac tgctatgcat | 420 |
| caccgatagc gcgaagaaaa aaacgtatac cgtgggcgag caatctatca gtaatggttc | 480 |
| cgatccgttg ctggtcgcga ttgagaatta ctggcgccaa agtacggatg tcgtggttaa | 540 |
| aggactgatc gccgaggtga ccgatttcat cgcaggaat atcaactcag tgagcacctg | 600 |
| gatcggccag tttgggatga aggtatttga gaatcagcca ttagctgagc ggctgccaga | 660 |
| aagcgtgcta caggctgatg gtagctccgc tacagcgaca gggtcctgac agcaggcatt | 720 |
| acaacaggcg ctcacagagc gcctgtgata atggctgaat gcttcaccag cgcggcgttt | 780 |
| tatgggagat catgatgagt tacaccagct gtacttattg cggttcacgt ctccatacgc | 840 |
| gggctaactg cccgaaaaca tggggcggtt catcgcgtcg cgccaatctg cgctgcagct | 900 |

```
attgtggcca gtccgggcat aactcgaatg cctgcccaca taatgcgagc agcggtcgac      960
ggcgcagcct gaatgacgac tttaccctcg actgaaccga tagcacgatg gcggcaggcg     1020
gaattgattt caatgtgaaa ttattcaatg tcaagtcatt gcattgcgcg atgatgataa     1080
tagatatcat ttgaggggggt agggggggatc aaatccctaa ccccctttcgc gcttcgggac    1140 tgccgcttca ggtagatttt tgcgcgtgag aaataaaaac tttttttttg              1189
```

<210> SEQ ID NO 14
<211> LENGTH: 5308
<212> TYPE: DNA
<213> ORGANISM: Artificial Sequence
<220> FEATURE:
<223> OTHER INFORMATION: p1867 plasmid

<400> SEQUENCE: 14

```
tgattataag aaggcgcccc aagcacccccc attttagcta taaaaaaacc cgccgaagcg       60
ggttttttcg aaaattgtaa ggtcacatta cgccccgcct tgccactcat cgcaatattg      120
ttgaagctca ttaagcatac ggcctacatg gaagccatca cacacggcat ggtgtacctg      180
gatcgccaga ggcattaaca ccttgtcgcc ttgcgtataa tatttacccca tagtgaaaac      240 aggggcgaag aagttgtcca tatttgctac gtttaaatca aaactggtga aactcaccca      300
gggattagca ctgacgaaaa acatattttc gataaacct ttagggaaat atgctaaatt      360
ttcaccgtaa cacgccacat cttgtgaata aatgtgcaga aactgacgga aatcatcatg      420
gtattctgac cataacgaac taaacgtttc agtctgttca tggaaaacgg tgtaacaagg      480
gtggacacta tcccaaatca ctaattcacc gtctttcatt gccatacgaa actccgggtg      540
tgcattcatc aggcgggcaa gaatgtgaat aaaggccgga taaaacttgt gcttattttt      600
ctttacggtt tttaaaaagg ccgtaatatc cagttgtacg gtttggttat aggtgcactg      660
cgcaactgac tggaatgcct caaaatgttc tttacgatgc cattgactaa tatcaactgt      720
agtatatccg gtaattttct tctccatttt agattcctta ggttgcgaaa tctcgataac      780
tcaaaaaata gtagtgatct tatttcatta tggtgaaagt tgtcttacgt gcaacatttt      840
cgcaacaagt tggtttcccg aggcctaact tttgttgcaa tggctgtcta ccctgtttta      900
tactagctca gcccttggta caatgctagc gttttcatta agaggagaa aggaagccat      960 gagtaaaggt gaggaattat ttactggtgt tgttccgatc ttagttgagc tggacggcga     1020
tgttaacggt cataaattca gtgttcgtgg tgaaggtgaa ggcgatgcaa ccaacggtaa     1080 gctgacccctg aaattcatct gcactactgg aaaattacca gtaccctggc ctactctggt     1140
gactaccctg acctatggtg ttcagtgttt ttctcgttac cctgaccaca tgaagcaaca     1200
tgacttcttc aaatctgcaa tgccggaagg ttatgtacag gagcgcacca tttctttcaa     1260
agacgatggc acgtataaaa cccgtgcaga ggttaaattt gaaggtgaca ctctggtgaa     1320
tcgtattgaa ctgaaaggca ttgatttcaa agaggacggc aatattttag gccataaact     1380
ggaatataac ttcaactccc ataacgttta catcaccgca gacaaacaaa agaacggtat     1440
caaagctaac tttaaaattc gacataacgt tgaagatggt agcgtccagc ttgcggatca     1500
ttaccaacaa aacactccga ttggagacgc tcctgtttta ctgccggata accactacct     1560
gtccacccag tctaaactgt ctaaggatcc gaacgaaaag cgcgaccaca tggtgttatt     1620
agagttcgtt accgctagtg gtattacgca cggtatggat gaactctaca ataataatc      1680 agacagtttc acctgtttta cgttaaaacc cgcttcggcg ggttttttact tttgggttta    1740
```

```
gccgaacgcc ataatttcaa aattgaatac gttgatggcg ctttgaccgt tctggagacg      1800
gatggccagt cacggatgaa tgaagccgta catggcatcc attttgagca tgtccagggc      1860
ggacgccccc tgctgaaact gacgattgcg catgatattg ccccggcctc gaccccggcc      1920
ccggctgctg cgtcggctca ggaaccttta gagggtgagc tggtacagga gcaacaatcc      1980
ccgctgcctg gcggtcgccg ttcccgccat cgccgtggag gtaagcaatg atgtatcaac      2040
gcacggatct gacgctctcc atgttctatg catccagcgc tgatgcagac gggaacaaag      2100
tggctacgtt gacgatgcag gtaattgcgg cagaggttgg tgccgtccag accagtcaac      2160
tgctatgcat caccgatagc gcgaagaaaa aaacgtatac cgtgggcgag caatctatca      2220
gtaatggttc cgatccgttg ctggtcgcga ttgagaatta ctggcgccag agtacggatg      2280
tcgtggttaa aggactgatc gccgaggtga ccgatttcat cgcagggaat atcaactcag      2340
tgagcacctg gatcggccag tttgggatga aggtatttga gaatcagcca ttagctgagc      2400
ggctgccaga aagcgtgcta caggctgatg gtagctccgc tacagcgaca gggtcctgac      2460
agcaggcatt acaacaggcg ctcacagagc gcctgtgata atggctgaat gcttcaccag      2520
cgcggcgttt tatgggagat catgatgagt tacaccagct gtacttattg cggttcacgt      2580
ctccatacgc gggctaactg cccgaaaaca tggggcggtt catcgcgtcg cgccaatctg      2640
cgctgcagct attgtggcca gtccgggcat aactcgaatg cctgcccaca taatgcgagc      2700
agcggtcgac ggcgcagcct gaatgacgac tttaccctcg actgaaccga tagcacgatg      2760
gcggcaggcg gaattgattt caatgtgaaa ttattcaatg tcaagtcatt gcattgcgcg      2820
atgatgataa tagatatcat ttgaggcggt aggggggatc aaatccctaa cccctttcgc      2880
gcttcgggac tgccgcttca ggtagatttt tgcgcgtgag aaataaaaac ttttttttgg      2940
cgttcggcta aacgtgctac atttgaagag ataaattgca ctgaaatcta gaaatatttt      3000
atctgattaa taagattatc ttcttgagat cgttttcgtc tgcgcgtaat ctcttgctct      3060
gaaaacgaaa aaaccgcctt gcagggcggt ttttcgaagg tcctctgagc taccaactct      3120
ttggaccgag gtaactggct tggaggagcg cagtcgccaa acttgtcctt tcagtttag       3180 ccttatccgg cgcatgactt caagactaac tcctctaaat caattaccag tggctgctgc      3240
cagtggtgct tttgcatgtc tttccgggtt ggactcaaga cgatagttac cggataaggc      3300
gcagcggtcg gactgaacgg gggtttgtg catacagtcc agcttggagc gaactgccta       3360
cccggaactg agtgtcaggc gtggaatgag acaaactcgg cagtaacaga ggaatgacac      3420
cggcaaaccg aaaggcagga acaggagagc gcacgaggga ccgccaggg ggaaacgcct       3480 ggtatcttta tagtcctgtc aggtttcgcc accactgatt tgagcgtcag atttcgtgat      3540
gcttgtcagg ggggcggagc ctatggaaaa acggctttgc cgcgaccctc tcacttccct      3600
gttaagtatc ttcctggcat cttccaggaa atctcagccc cgttcgtaag ccatttccgc      3660
tcgccacagt cgaacgaccg agcgtagcga gtcagtgagc gaggaagcgg aatatatcct      3720
gtatcacata ttctgctgac gcaccgatgc agcctttttt ctcctgccac atgaagcact      3780
tcacttacac cctcatcagt gccaacatag taagccagta tacactccgc tagcgcagat      3840
gtccggcggt gcttttgccg ttacgcacta ctttagtcag ttccgcagta ccgtcaggcg      3900
ctgacatagc tatttacttt gtattgcctg caatcgaatt tctgaactat catatagtgg      3960
ggataacggg aaagttacta tatttgcgaa ctaacttagg cgtccacctc gaagctacct      4020
aatcacaccc aacccgcgcg gggtaaataa ggcactaatc cgagctttaaa gcttgcgtag      4080 cacttagaca caagttaatt accaattgtc tggtagtttg gcggtattag cgagatccca      4140
```

-continued

```
gacgcaaggc agagttaatt ttaacctaaa gccacaaata agacaggttg cacaagcccg    4200
ccggaaatta atcttgctc acttcggtaa cggagtttcc ctcccgcgta cttaattccc    4260
aataagaaac gcgcccaagt cctatcaggc aaaattcagc cccttcacgt cttagaacga    4320
gggtaaaaat acaagccgat tgaacaaggg ttgggggctt caaatcgtcg tttaccccac    4380
tttacaacgg agggtaacta gttcacccta tagtacgaag cagaactatt tcgaggggcg    4440
tgcaataatc gaatcttctg cggttgactt aacacgctag ggacgtgccc tcgattcagt    4500
cgcaggtact ccgactcaca ctgcctcaca cccagctagt cactgaccga taaaattgac    4560 ccgcccctcta aggtagcgag tacgtcctaa aaggcttcgg acagggctat ataggagagt    4620
ttgatctcgc cccgacaact gcaaccctca actcccttag ataatattgt tagccgaagt    4680
tgcacgaccc gccgtccacg gactgctctt agggtgtggc ttcttaatct gacaacgtgc    4740 aaccctatc gagggcgatt gtttctgcga aagggttgc cctaatagtc gcgacaattg    4800
gcccttgtag gggtgaaacc acttagtttc gcgccgtagt cctaaaggcc cacctattga    4860
ctttgtttcg ggtagcacta ggaatcttaa caatttgaat ttggacttgt tttaggggcg    4920
ttattcgagg gcaatcggag ctaacttcaa gactacttct ttgttgaata ctaaatagtg    4980
caaaggtcgt gtttcctcaa ggatactccg ctaacaatat aggattccaa tcagattcag    5040
cactggctgt acgggtgtta cggtgaggtt tcgggttta cggctggaag ctagcacggt    5100
aggaagcctt tcaatcacaa agcaaaaggg ccgtcgaagg cccacaagat acgaaagctc    5160
tcgaagcctt atccttgaac gatccaccta tttaggcagt tacgcacaaa agctacccaa    5220
taatccgtga caggcacaat atcacggaac aaaggcgaaa actctcgtac acggttaggt    5280
tttcgctagg aagaataaac ctctatct                                       5308
```

<210> SEQ ID NO 15
<211> LENGTH: 234
<212> TYPE: DNA
<213> ORGANISM: Artificial Sequence
<220> FEATURE:
<223> OTHER INFORMATION: predicted ORF

<400> SEQUENCE: 15

```
atgcttcacc agcgcggcgt tttatgggag atcatgatga gttacaccag ctgtacttat     60
tgcggttcac gtctccatac gcgggctaac tgcccgaaaa catggggcgg ttcatcgcgt    120
cgcgccaatc tgcgctgcag ctattgtggc cagtccgggc ataactcgaa tgcctgccca    180
cataatgcga gcagcggtcg acggcgcagc ctgaatgacg actttacccct cgac         234
```

<210> SEQ ID NO 16
<211> LENGTH: 78
<212> TYPE: PRT
<213> ORGANISM: Artificial Sequence
<220> FEATURE:
<223> OTHER INFORMATION: Predicted protein with 2 Zn fingers

<400> SEQUENCE: 16

```
Met Leu His Gln Arg Gly Val Leu Trp Glu Ile Met Met Ser Tyr Thr
1               5                   10                  15

Ser Cys Thr Tyr Cys Gly Ser Arg Leu His Thr Arg Ala Asn Cys Pro
            20                  25                  30

Lys Thr Trp Gly Gly Ser Ser Arg Arg Ala Asn Leu Arg Cys Ser Tyr
        35                  40                  45

Cys Gly Gln Ser Gly His Asn Ser Asn Ala Cys Pro His Asn Ala Ser
```

Ser Gly Arg Arg Arg Ser Leu Asn Asp Asp Phe Thr Leu Asp
65              70                  75

<210> SEQ ID NO 17
<211> LENGTH: 209
<212> TYPE: DNA
<213> ORGANISM: Artificial Sequence
<220> FEATURE:
<223> OTHER INFORMATION: Short cos site

<400> SEQUENCE: 17

| | | |
|---|---|---|
| tttaccctcg actgaaccga tagcacgatg gcggcaggcg gaattgattt caatgtgaaa | 60 |
| ttattcaatg tcaagtcatt gcattgcgcg atgatgataa tagatatcat ttgaggggt | 120 |
| agggggatc aaatccctaa ccccttcgc gcttcgggac tgccgcttca ggtagatttt | 180 |
| tgcgcgtgag aaataaaaac tttttttg | 209 |

<210> SEQ ID NO 18
<211> LENGTH: 4330
<212> TYPE: DNA
<213> ORGANISM: Artificial Sequence
<220> FEATURE:
<223> OTHER INFORMATION: p1868 payload

<400> SEQUENCE: 18

| | |
|---|---|
| tgattataag aaggcgcccc aagcaccccc attttagcta taaaaaaacc cgccgaagcg | 60 |
| ggttttttcg aaaattgtaa ggtcacatta cgccccgcct tgccactcat cgcaatattg | 120 |
| ttgaagctca ttaagcatac ggcctacatg gaagccatca cacacggcat ggtgtacctg | 180 |
| gatcgccaga ggcattaaca ccttgtcgcc ttgcgtataa tatttaccca tagtgaaaac | 240 |
| aggggcgaag aagttgtcca tatttgctac gtttaaatca aaactggtga aactcaccca | 300 |
| gggattagca ctgacgaaaa acatattttc gataaacct ttagggaaat atgctaaatt | 360 |
| ttcaccgtaa cacgccacat cttgtgaata aatgtgcaga aactgacgga aatcatcatg | 420 |
| gtattctgac cataacgaac taaacgtttc agtctgttca tggaaaacgg tgtaacaagg | 480 |
| gtggacacta tcccaaatca ctaattcacc gtctttcatt gccatacgaa actccgggtg | 540 |
| tgcattcatc aggcgggcaa gaatgtgaat aaaggccgga taaaacttgt gcttattttt | 600 |
| ctttacggtt tttaaaaagg ccgtaatatc cagttgtacg gtttggttat aggtgcactg | 660 |
| cgcaactgac tggaatgcct caaaatgttc tttacgatgc cattgactaa tatcaactgt | 720 |
| agtatatccg gtaattttct tctccatttt agattcctta ggttgcgaaa tctcgataac | 780 |
| tcaaaaaata gtagtgatct tatttcatta tggtgaaagt tgtcttacgt gcaacatttt | 840 |
| cgcaacaagt tggtttcccg aggcctaact tttgttgcaa tggctgtcta ccctgtttta | 900 |
| tactagctca gcccttggta caatgctagc gttttcatta agaggagaa aggaagccat | 960 |
| gagtaaaggt gaggaattat ttactggtgt tgttccgatc ttagttgagc tggacggcga | 1020 |
| tgttaacggt cataaattca gtgttcgtgg tgaaggtgaa ggcgatgcaa ccaacggtaa | 1080 |
| gctgaccctg aaattcatct gcactactgg aaaattacca gtaccctggc ctactctggt | 1140 |
| gactaccctg acctatggtg ttcagtgttt ttctcgttac cctgaccaca tgaagcaaca | 1200 |
| tgacttcttc aaatctgcaa tgccggaagg ttatgtacag gagcgcacca tttctttcaa | 1260 |
| agacgatggc acgtataaaa cccgtgcaga ggttaaattt gaaggtgaca ctctggtgaa | 1320 |
| tcgtattgaa ctgaaaggca ttgatttcaa agaggacggc aatatttag gccataaact | 1380 |

```
ggaatataac ttcaactccc ataacgttta catcaccgca gacaaacaaa agaacggtat    1440
caaagctaac tttaaaattc gacataacgt tgaagatggt agcgtccagc ttgcggatca    1500
ttaccaacaa aacactccga ttggagacgc tcctgtttta ctgccggata accactacct    1560
gtccacccag tctaaactgt ctaaggatcc gaacgaaaag cgcgaccaca tggtgttatt    1620
agagttcgtt accgctagtg gtattacgca cggtatggat gaactctaca aataataatc    1680
agacagtttc acctgtttta cgttaaaacc cgcttcggcg gttttttact tttgggttta    1740
gccgaacgcc cgtttaccct cgactgaacc gatagcacga tggcggcagg cggaattgat    1800
ttcaatgtga aattattcaa tgtcaagtca ttgcattgcg cgatgatgat aatagatatc    1860
atttgagggg gtagggggga tcaaatccct aaccccttc gcgcttcggg actgccgctt     1920
caggtagatt tttgcgcgtg agaaataaaa acttttttt ggcgttcggc taaacgtgct      1980
acatttgaag agataaattg cactgaaatc tagaaatatt ttatctgatt aataagatta    2040
tcttcttgag atcgttttcg tctgcgcgta atctcttgct ctgaaaacga aaaaaccgcc    2100
ttgcagggcg gttttcgaa ggtcctctga gctaccaact ctttggaccg aggtaactgg      2160
cttggaggag cgcagtcgcc aaaacttgtc ctttcagttt agccttatcc ggcgcatgac    2220
ttcaagacta actcctctaa atcaattacc agtggctgct gccagtggtg cttttgcatg    2280
tctttccggg ttggactcaa gacgatagtt accggataag gcgcagcggt cggactgaac    2340 gggggggtttg tgcatacagt ccagcttgga gcgaactgcc tacccggaac tgagtgtcag    2400
gcgtggaatg agacaaactc ggcagtaaca gaggaatgac accggcaaac cgaaaggcag    2460
gaacaggaga gcgcacgagg gagccgccag ggggaaacgc ctggtatctt tatagtcctg    2520
tcaggtttcg ccaccactga tttgagcgtc agatttcgtg atgcttgtca ggggggcgga    2580
gcctatggaa aaacggcttt gccgcgaccc tctcacttcc ctgttaagta tcttcctggc    2640
atcttccagg aaatctcagc cccgttcgta agccatttcc gctcgccaca gtcgaacgac    2700
cgagcgtagc gagtcagtga gcgaggaagc ggaatatatc ctgtatcaca tattctgctg    2760
acgcaccgat gcagcctttt ttctcctgcc acatgaagca cttcacttac accctcatca    2820
gtgccaacat agtaagccag tatacactcc gctagcgcag atgtccggcg gtgcttttgc    2880
cgttacgcac tactttagtc agttccgcag taccgtcagg cgctgacata gctatttact    2940
ttgtattgcc tgcaatcgaa tttctgaact atcatatagt ggggataacg ggaaagttac    3000
tatatttgcg aactaactta ggcgtccacc tcgaagctac ctaatcacac ccaacccgcg    3060
cggggtaaat aaggcactaa tccgagctta aagcttgcgt agcacttaga cacaagttaa    3120
ttaccaattg tctggtagtt tggcggtatt agcgagatcc cagacgcaag gcagagttaa    3180
ttttaaccta aagccacaaa taagacaggt tgcacaagcc cgccggaaat taaatcttgc    3240
tcacttcggt aacggagttt ccctcccgcg tacttaattc ccaataagaa acgcgcccaa    3300
gtcctatcag gcaaaattca gccccttcac gtcttagaac gagggtaaaa atacaagccg    3360
attgaacaag ggttgggggc ttcaaatcgt cgtttacccc actttacaac ggagggtaac    3420
tagttcaccc tatagtacga agcagaacta tttcgagggg cgtgcaataa tcgaatcttc    3480
tgcggttgac ttaacacgct agggacgtgc cctcgattca gtcgcaggta ctccgactca    3540
cactgcctca cacccagcta gtcactgacc gataaaattg acccgccctc taaggtagcg    3600
agtacgtcct aaaaggcttc ggacagggct atataggaga gtttgatctc gccccgacaa    3660 ctgcaacccct caactccctt agataatatt gttagccgaa gttgcacgac ccgccgtcca    3720
cggactgctc ttagggtgtg gcttcttaat ctgacaacgt gcaaccccta tcgagggcga    3780
```

| | |
|---|---|
| ttgtttctgc gaaagggggtt gccctaatag tcgcgacaat tggcccttgt aggggtgaaa | 3840 |
| ccacttagtt tcgcgccgta gtcctaaagg cccacctatt gactttgttt cgggtagcac | 3900 |
| taggaatctt aacaatttga atttggactt gttttagggg cgttattcga gggcaatcgg | 3960 |
| agctaacttc aagactactt ctttgttgaa tactaaatag tgcaaaggtc gtgtttcctc | 4020 |
| aaggatactc cgctaacaat ataggattcc aatcagattc agcactggct gtacgggtgt | 4080 |
| tacggtgagg ttttcgggtt tacggctgga agctagcacg gtaggaagcc tttcaatcac | 4140 |
| aaagcaaaag ggccgtcgaa ggcccacaag atacgaaagc tctcgaagcc ttatccttga | 4200 |
| acgatccacc tatttaggca gttacgcaca aagctaccc aataatccgt gacaggcaca | 4260 |
| atatcacgga acaaaggcga aaactctcgt acacggttag gttttcgcta ggaagaataa | 4320 |
| acctctatct | 4330 |

<210> SEQ ID NO 19
<211> LENGTH: 5264
<212> TYPE: DNA
<213> ORGANISM: Artificial Sequence
<220> FEATURE:
<223> OTHER INFORMATION: p1872 plasmid

<400> SEQUENCE: 19

| | |
|---|---|
| tcagatcctt ccgtatttag ccagtatgtt ctctagtgtg gttcgttgtt tttgcgtgag | 60 |
| ccatgagaac gaaccattga gatcatactt actttgcatg tcactcaaaa attttgcctc | 120 |
| aaaactggtg agctgaattt ttgcagttaa agcatcgtgt agtgtttttc ttagtccgtt | 180 |
| acgtaggtag gaatctgatg taatggttgt tggtattttg tcaccattca tttttatctg | 240 |
| gttgttctca agttcggtta cgagatccat ttgtctatct agttcaactt ggaaaatcaa | 300 |
| cgtatcagtc gggcggcctc gcttatcaac caccaatttc atattgctgt aagtgtttaa | 360 |
| atctttactt attggtttca aacccattg gttaagcctt ttaaactcat ggtagttatt | 420 |
| ttcaagcatt aacatgaact taaattcatc aaggctaatc tctatatttg ccttgtgagt | 480 |
| tttcttttgt gttagttctt ttaataacca ctcataaatc ctcatagagt atttgttttc | 540 |
| aaaagactta acatgttcca gattatattt tatgaatttt tttaactgga aaagataagg | 600 |
| caatatctct tcactaaaaa ctaattctaa ttttttcgctt gagaacttgg catagtttgt | 660 |
| ccactggaaa atctcaaagc ctttaaccaa aggattcctg atttccacag ttctcgtcat | 720 |
| cagctctctg gttgctttag ctaatacacc ataagcattt ccctactga tgttcatcat | 780 |
| ctgagcgtat tggttataag tgaacgatac cgtccgttct ttccttgtag ggttttcaat | 840 |
| cgtggggttg agtagtgcca cacagcataa aattagcttg gtttcatgct ccgttaagtc | 900 |
| atagcgacta atcgctagtt catttgcttt gaaacaact aattcagaca tacatctcaa | 960 |
| ttggtctagg tgattttaat cactatacca attgagatgg gctagtcaat gataattact | 1020 |
| agtccttttc ctttgagttg tgggtatctg taaattctgc tagaccttttg ctggaaaact | 1080 |
| tgtaaattct gctagaccct ctgtaaattc cgctagacct tgtgtgttt ttttttgttta | 1140 |
| tattcaagtg gttataattt atagaataaa gaaagaataa aaaagataa aagaataga | 1200 |
| tcccagccct gtgtataact cactacttta gtcagttccg cagtattaca aaaggatgtc | 1260 |
| gcaaacgctg tttgctcctc tacaaaacag accttaaaac cctaaaggct taagtagcac | 1320 |
| cctcgcaagc tcggttgcgg ccgcaatcgg gcaaatcgct gaatattcct tttgtctccg | 1380 |
| accatcaggc acctgagtcg ctgtcttttt cgtgacattc agttcgctgc gctcacggct | 1440 |

```
ctggcagtga atggggggtaa atggcactac aggcgccttt tatggattca tgcaaggaaa      1500
ctacccataa tacaagaaaa gcccgtcacg ggcttctcag ggcgttttat ggcgggtctg      1560
ctatgtggtg ctatctgact ttttgctgtt cagcagttcc tgccctctga ttttccagtc      1620
tgaccacttc ggattatccc gtgacaggtc attcagactg gctaatgcac ccagtaaggc      1680
agcggtatca tcaacggggt ctgacgctca gtggaacgaa aactcacgtt aagggatttt      1740
ggtcatgaga ttatcaaaaa ggatcttcac ctagatcctt ttaaattaaa aatgaagttt      1800
taaatcaatc taaagtatat atgagtaaac ttggtctgac agttacgttt ccacaaccaa      1860
ttaaccaatt ctgatttaga aaaactcatc gagcatcaaa tgaaactgca atttattcat      1920
atcaggatta tcaataccat attttttgaaa aagccgtttc tgtaatgaag gagaaaactc      1980
accgaggcag ttccatagga tggcaagatc ctggtatcgg tctgcgattc cgactcgtcc      2040
aacatcaata caacctatta atttcccctc gtcaaaaata aggttatcaa gtgagaaatc      2100
accatgagtg acgactgaat ccggtgagaa tggcaaaagc ttatgcattt ctttccagac      2160
ttgttcaaca ggccagccat tacgctcgtc atcaaaatca ctcgcatcaa ccaaaccgtt      2220
attcattcgt gattgcgcct gagcgagacg aaatacgcga tcgctgttaa aaggacaatt      2280
acaaacagga atcgaatgca accggcgcag gaacactgcc agcgcatcaa caatattttc      2340
acctgaatca ggatattctt ctaatacctg gaatgctgtt ttcccgggga tcgcagtggt      2400
gagtaaccat gcatcatcag gagtacggat aaaatgcttg atggtcggaa gaggcataaa      2460
ttccgtcagc cagtttagtc tgaccatctc atctgtaaca tcattggcaa cgctaccttt      2520
gccatgtttc agaaacaact ctggcgcatc gggcttccca tacaatcgat agattgtcgc      2580
acctgattgc ccgacattat cgcgagccca tttataccca tataaatcag catccatgtt      2640
ggaatttaat cgcggcctcg agcaagacgt ttcccgttga atatggctca taacacccct      2700
tgtattactg tttatgtaag cagacagttt tattgttcat gatgatatat ttttatcttg      2760
tgcaatgtaa catcagagat tttgagacac aacgtggctt tccctgcagg atttcggagg      2820
cctgcgttat cccctgattc tgtggataac cgtattaccg cctttgagtg agctgatacc      2880
gctcgccgca gccgaacgcc gactagtgga ttttacggct agctcagtcc taggtacaat      2940
gctagcgaat tcattaaaga ggagaaaggt acccatggca cgtaccccga gccgtagcag      3000
cattggtagc ctgcgtagtc cgcatacccca taaagcaatt ctgaccagca ccattgaaat      3060
cctgaaagaa tgtggttata gcggtctgag cattgaaagc gttgcacgtc gtgccggtgc      3120
aagcaaaccg accattttatc gttggtggac caataaagca gcactgattg ccgaagtgta      3180
tgaaaatgaa agcgaacagg tgcgtaaatt tccggatctg ggtagcttta aagccgatct      3240
ggattttctg ctgcgtaatc tgtggaaagt ttggcgtgaa accatttgtg gtgaagcatt      3300
tcgttgtgtt attgcagaag cacagctgga ccctgcaacc ctgacccagc tgaaagatca      3360
gtttatggaa cgtcgtcgtg agatgccgaa aaaactggtt gaaaatgcca ttagcaatgg      3420
tgaactgccg aaagatacca atcgtgaact gctgctggat atgatttttg gttttgttg      3480 gtatcgcctg ctgaccgaac agctgaccgt tgaacaggat attgaagaat taccttcct      3540 gctaattaat ggtgttgtc cgggtacaca gcgttaacta gggcccatac ccccaattat      3600
tgaaggccgc taacgcggcc ttttttttgtt tctggtctgc ccgacgtacg gtgaatctga      3660
ttcgttacca attgacatga tacgaaaacgt accgtatcgt taaggttcag aacgtatcac      3720
tggtgacgta catgccagcc cggtctaaac gtccatgccg ccaccggggg tgtccggcga      3780
taaccaacga ccccagcggt tactgcgatg ctcaccggca gcaacatgct ggcgacggct      3840
```

```
ggcgcaacta ccagggcggg aaaagccggc atgaaagggg ctacggtcgc cctgggaaa      3900 tccgccgcgc cagaatcctc cagcgcgata aatatctatg ccaaaactgc cggcgtcatg     3960
gcatcgccac caaagcgacc agcgtcgacc acatcatacc caaagcgcgt ggcggtacag     4020
acgacgattc caatctggag tcgttgtgct ggccctgcca tagagcgaaa acagcaacag     4080
agagaacccg atgaataatt tcaaaattga atacgttgat ggcgctttga ccgttctgga     4140
gacggatggc cagtcacgga tgaatgaagc cgtacatggc atccattttg agcatgtcca     4200 ggcggacgc cccctgctga aactgacgat tgcgcatgat attgccccgg cctcgacccc      4260
ggccccggct gctgcgtcgg ctcaggaacc tttagagggt gagctggtac aggagcaaca     4320
atccccgctg cctggcggtc gccgttcccg ccatcgccgt ggaggtaagc aatgatgtat     4380
caacgcacgg atctgacgct ctccatgttc tatgcatcca gcgctgatgc agacgggaac     4440
aaagtggcta cgttgacgat gcaggtaatt gcggcagagg ttggtgccgt ccagaccagt     4500
caactgctat gcatcaccga tagcgcgaag aaaaaaacgt ataccgtggg cgagcaatct     4560
atcagtaatg gttccgatcc gttgctggtc gcgattgaga attactggcg ccagagtacg     4620
gatgtcgtgg ttaaaggact gatcgccgag gtgaccgatt tcatcgcagg gaatatcaac     4680
tcagtgagca cctggatcgg ccagtttggg atgaaggtat ttgagaatca gccattagct     4740
gagcggctgc cagaaagcgt gctacaggct gatggtagct ccgctacagc gacagggtcc     4800
tgacagcagg cattacaaca ggcgctcaca gagcgcctgt gataatggct gaatgcttca     4860
ccagcgcggc gttttatggg agatcatgat gagttacacc agctgtactt attgcggttc     4920
acgtctccat acgcgggcta actgcccgaa acatggggc ggttcatcgc gtcgcgccaa      4980
tctgcgctgc agctattgtg gccagtccgg gcataactcg aatgcctgcc cacataatgc     5040
gagcagcggt cgacggcgca gcctgaatga cgactttacc ctcgactgat gacgcatcct     5100
cacgataata tccgggtagg acgaacaata aggccgcaaa tcgcggcctt ttttattgat     5160
aacaaaagga cagttttccc tttgatatgt aacggtgaac agttgttcta cttttgtttg     5220
ttagtcttga tgcttcactg atagatacaa gagccataag aacc                     5264
```

<210> SEQ ID NO 20
<211> LENGTH: 20
<212> TYPE: DNA
<213> ORGANISM: Artificial Sequence
<220> FEATURE:
<223> OTHER INFORMATION: AD1334 primer

<400> SEQUENCE: 20
ggacctccca ccattccaag                                                  20

<210> SEQ ID NO 21
<211> LENGTH: 20
<212> TYPE: DNA
<213> ORGANISM: Artificial Sequence
<220> FEATURE:
<223> OTHER INFORMATION: p1335 primer

<400> SEQUENCE: 21
acggcgatgt tcaggttctt                                                  20

<210> SEQ ID NO 22
<211> LENGTH: 20
<212> TYPE: DNA
<213> ORGANISM: Artificial Sequence
<220> FEATURE:

<223> OTHER INFORMATION: AD1336 primer

<400> SEQUENCE: 22
ggcgaaagaa gacctggtca                                         20

<210> SEQ ID NO 23
<211> LENGTH: 20
<212> TYPE: DNA
<213> ORGANISM: Artificial Sequence
<220> FEATURE:
<223> OTHER INFORMATION: AD1337 primer

<400> SEQUENCE: 23
tagccggcga aatggatgtt                                         20

<210> SEQ ID NO 24
<211> LENGTH: 20
<212> TYPE: DNA
<213> ORGANISM: Artificial Sequence
<220> FEATURE:
<223> OTHER INFORMATION: AD1322 primer

<400> SEQUENCE: 24
catcagaccg cattcgcttg                                         20

<210> SEQ ID NO 25
<211> LENGTH: 20
<212> TYPE: DNA
<213> ORGANISM: Artificial Sequence
<220> FEATURE:
<223> OTHER INFORMATION: AD1323 primer

<400> SEQUENCE: 25
ggacgaagat gtggaagcca                                         20

<210> SEQ ID NO 26
<211> LENGTH: 32767
<212> TYPE: DNA
<213> ORGANISM: BW4 phage

<400> SEQUENCE: 26
agcgatatct ccccgggttt ttccacaggg tgtccgccca gggcgtcgct gtcgagctca      60
cagcgcacgc tgaacgcccg ccagcactcg aggcgatccg aacagcctcg ctccgagtgc     120
gtcgggcctg tgtggatcgc tcatgagttt cgtaacaagc ccctagccac agcccgattc     180
agatagaata ggagcatgga agggcagtgc ggatggtgcg gtcgggcatt cgatcgtgcc     240
cggacgggtc gcccgcgacg cttctgctcg gcccgctgtc gggtcgccgc gtcccggtgt     300
gcgatcccgc tggccatgag gtcccgcact gcgtgggtcc gctgcgacgg caagcgcccc     360
atcaccctgg ctggcgctcc ggcctcatcc acggacccgg gcacatggtc tggctggtcg     420
caggtgcgac gcgccacggc cggcgatggc ttcgggacca tgctcggtga cgggctgggg     480
tgctgggatc tcgaccactt cgacgatcag ggcgcccggg ccttcatcga ccggatcgat     540
aagccgatca tcttcgccga gcggtcggtg tcggggcatg gcttccacat cttcgtccgg     600
actgacgagg cccccggacg ccgcaccgga acatcgagt tctactcacg ccatcggttc      660
atcagggtca caggagacca gttcgtctga agaagggggt gcgccatggc tgcacaggtc     720
agggccgtgg accccgatga gcgcccaccc gcccgcaagc gggccaagac catcacccag     780
gccgcgaagt ccggcactga ggttgaactg ttgaggcac tgcaggctcg cgtgcccgc       840
gccgtgcagg accgtgacac tccgccgcgc gatctggcag cgctgacgaa gcggctgatg     900

```
gacatcaccc gggagctcga ggcggcccgg gtcaaggatc aggaggcggg atctgatggt    960
gccgtcaccg cagacgaaac atggcgaccg caagctctct gaggtcgcca agcacctgat   1020
ccttcctgaa gggatcgtct cgacgggctg ccggccgtg cgtgaccggt gtggcgagtg    1080
gggtgtggtc ttcgaccgtt ggcaggacgg catgggccgg gtgatcctgt cgaagcgcgg   1140
cagcggcctg ttcgccgctg tgtgggcgg ggtcggcatg tcgatcccgc gccagaccgg    1200
caagaccttc accgtcggca tgatcatcct cgggctgtgc tcgctgagcg aggagctcac   1260
ggtgctgtgg acctcccacc attccaagac gaccaccaag actttcgagt cgctgcgggg   1320 catgcccag cgtaagaagg tcgccccgtt gatccgtcag gtccgaacag gaaacggtga    1380
ccagcagatc attttcagca acggttcgag gatctacttc ggtgcccggg aacagggctt   1440
cgggcgtggc ttcgacgacg tggacatcga gatctttgac gaggcgcaga tcctgtccga   1500
gcaggccctc tccgacatgg ttcccgcggc gaatgtgagc accaatccgc tgatcatctt   1560
catgggcacc ccgccgcgtc cctcggaccc gtcggaggcg ttcgcgaacc gccgcgccga   1620
agctctggcg ggcgacgccc cggacgccgc ctggatcgaa ttcggagcgg acgagcacgc   1680
cgacccgacc agccgcgccc aatggcgtaa ggcaaaccca tcctttcctc accgcacgtc   1740
ggagacctcc attctgcgga tgaagaagat gctcgggccc gagtccttca aacgcgaggg   1800
cttgggcatc tgggatgaga cggcatcggt ccgcgcgatc ccagccgaag ggtggcgcgt   1860
cctgaccgtc aaggaaccac ccgccgacgc gatccagtcc ttcggcatca agttcgccat   1920
cgacgggagt gcggtcgccc tggcagccgc cctgaaaccc aaggacgggc cgatctatgt   1980
cgaaggaatc gagcagcgct cggcatccga cggcatcgaa tggctcgccg actacctgac   2040 gccctgtgg cgcaacacgg cccagatcgt catcgatggc aagtccggcg ccggtgccct    2100
ggttgatgcg ctgccgtg gtggcgtggc tgcgaaggtg atcctcaccc cgagcgtcgc     2160
cgacgtgatc accgcccaca gcctgactct ggaggccatc aagaccggtg gactgtcgca   2220
cctggctgac ccggagctgg atcggcaggt ccgcatcgcc acgaagcgaa agatcggggc   2280
cgccgggggc ttcggctggc aggccccga aggcgacacc gtcgcctcc tcgacgccat     2340 cacgcttgcc cactgggcgg ccctcaccac gaagcgacat cccggcagga aggcggtggc   2400
actggcatga gcctcctcgt caaccctat gcgtcgccgt ccttcttctc gtccccgtcc    2460
gtggtcggac tcggagcaga cgagcaggag ctcctggacg agctggtggc cctgtgggca   2520
cgcaagaagc cccgcaacgt gctgcgcggc ctgtaccttg acggcaagca gcagatcaag   2580
aacctgaaca tcgccgtgcc cgacgagatc gccgacagtc tccagatcgt ggtcggctgg   2640
cccgagaagg ccgtcttcgg gctatcgaac ctgtgcatgt gggatggcgt cgtcactccc   2700
acaggcgacg agaatccctt cgggcttgac gatctcctgt cggccaaccg cttcgacgtc   2760
gagatcaatg aaacgatcac ctcggccatg gcgaactccg tggccttcct gaccgtatcg   2820
gcgggcaacg tgtccatagg tgagccgccg gtggtgatca tgccgttctc cgccgaatgg   2880
gcctcagccc tgtgggaccg gcgcacccgc tcaatcaagg cgggactgac catcggcgac   2940
atcgactacc tgggccgccc caccagcctc tcgctcttca cccgcaccgc caccatcacc   3000
tgcgtggggt cccggctggg atggatgatc gaagatcgcg ccgagcacgg gctgaaccgc   3060
gtcccgatgg agccggtccc gttccgccca acccttgacc gcccttcgg gcgctcgcgg    3120 atctcgcgcc aggtgatgac catcgtggac cgcgccatgc gcgcggccct gcgcatggac   3180
atctcctcag agctgttcac cgcacccggc ctgctcctca acggaatcac cccggagcag   3240
```

-continued

```
tgggcagaga tccagaagtg gacatggaag ctcggcacgg tgcgcggcct gactcgcgac    3300
gaggatggcg agaccgcatc ggtcgagacg atcccccagc agtcgatgga accgttcatc    3360
gcgcagctgc gcgagctggc cgaggaattc gcctcagcca catccatgcc gctgtctgca    3420 ttggggtcg tccaagacaa cccctcctcg gctgacgcca tctacgcggc gaaagaagac    3480
ctggtcatcg aggccaccaa cgccaaccgg atcaccggct acgcgctatc ccgggtcttc    3540
caagacgcgg tgatgatgcg cgacggcctg accgagatgc ccgacgagct cggcggggtc    3600
gccgccaagt ggcgcaaccc ggcgatgccg tcgatcgtgt cccagtccga cgcgatggtc    3660
aagcagattt cggcgatccc cgggctggcc gctaccgacg tcgccttcga acagctcggc    3720
tattcggcgg ctgacatcgt gcggattcgt acccagatgc gccgagccca ggctgcggac    3780
ggcctgactt cgttgctggc caaaccagcc acgtcgtcaa cgcctggcgc ggagccctct    3840
cagtccgcaa gtccgacgga gccagctgca agcactccgc tgccggacct cgaaggggcc    3900
cctggtgacc gatcgtgatg acctgaacca tttccacgag gccaatgacg cgatccagcg    3960
gcgcgcaatc aacgacctga caagttttg ggcgcggctt gccaagtcag acccgaaagc    4020
cgttcgcgca gccatggact tattcgtccc ccagctcatc gcctcctacg gagagttggc    4080
cgccgaagcc gctgccgtt ggtatgagga actacgcccc gccgacaaga gaacttcca    4140 ggccgaactc gcggaccctg tgtccgacga catcatcgag gcagatgtgg ctgaggccct    4200
ggggaccagc ggcgcctggg acaccgaggc ggtgcgaggg agcctggccg atgcgatcag    4260
gcgtcagatc ttctacatgg cgcgggcgac tgtcgcacgc aacatcgctc acgacccgaa    4320
gcgtccaagg tttgcacgag ttcctcgggg cgcggtcacg tgcgcgttct gcaccatgct    4380
cgcctccagg gggtgggtgt actacaccgc gaagactgcc gggatcacac gaccctggca    4440
tcgcaagtgc gactgccaga tcgtgcctga gtggaaacgc ggcaacatcc atttcgccgg    4500
ctacgaccct gacaagatgt tcgagcagta tgccgaatcg gtcgatgcgg tggggtcgag    4560
cttcgacacg aaggcaatcc tcgccgacat gcgccgacgc catcccgaag cgctgaccga    4620
cggggtcgtc aacatgagtg aaggacaggg tccggtgacc agtgattaga cagtcggtga    4680
acggatgact acgccgtcgg cgctgcgccg ccgcctggaa tggctactgg agaaccgtga    4740
acggcttctc aggagccatg gcgagtcgga cttttgccgag atgctggatg cgcccgtca    4800 cgagcttgat gaggcccgcg agcaggcagg cctggccgcg cagtcaaacc caatctgtag    4860
caagccccgt tccaccttcg ggtgggcggg gctttgtcat gcccgcatcc gggcatccaa    4920
ttccgtccca ccgcgagggt ggggcgtcga cctggtggcg cgatgccgcc gaactaatcc    4980
ctggaagggg aaactgctat gcacaagaag ctcatgccgt gggtccgtct catcgaggcg    5040
gtcgagactc ctgctggagc cgcccccacg cccgcgatcg atccgaagga tccggcagcc    5100
aatcccacca ctgagccgaa gccggccgac gcgacgtcgg agaagcctct cggcgaggcg    5160
ggcaaggttg cgttggatcg cgagcgcgag gctcgccgca gcgccgacaa gcgcgccagt    5220
gagttggagg cccgtgtgca ccagctcgag gacgcgggca agaccgaggc ccagaagcag    5280
gccgacgaac tcaagcgcac ccagtccgag ctggagacgc tgagggcga gaaggcacgg    5340 ctggaggtgg cgtccgcgac gggcgtcccg gtcgatctgc tcgctggccc cggcgacgat    5400
ctggatgcct acgcgcaggc cctgaacgcc tggcgcgaca agcagtccga aaagccagcc    5460
gcccctgcgg tggacacccc ttccccttcg ccgtccgggg tgaccggaca gcccgtgcag    5520
ccgaaccgga cggtcgatga actcatcgcg gccgccgaga agaacggcga tctgcaaccc    5580
gcgaagcaac tcaaattgat gaagctcgac gcactgcgtc ggacgtcctg atcagaaagg    5640
```

```
caccactatg ccgggcatta ccggacaggg caccacctac aaccttccga actatgtggg    5700 ggagctttt  gcggcatctc ccgaagacac cccgctgctg tcggcgatcg ggggactgac    5760
cggcggcgag tcggtcggcg cccgccagtt cgaatggcag ggctacgacc tgcgcgacgc    5820
cgacggttcg cgccagcgcc tcgagggagc caacgccccc gacggtgagg agcgcacccg    5880
ctactccgcc tccaatgtgg tcgagatcca ccaggagtcg gtggaggtgt cctacaccaa    5940
gcaggccgca aaccgtgagc gggctaccaa cggtgccgcc acgtccagc  tggcgggctc    6000 cgtgctgccg gccgatgagc tcacctggca gatcgaccag cagctcaagc aggtcgcccg    6060
cgatgtcgag aagtccttca tcgcgggcac ctaccagctg cccaccgaca cgccaagcc     6120 gcgccgcacg cgtggcctgc tggaggcgac caccacgaac gtggccgcct cgacccacac    6180
cgcaaaggaa ctcaccgtgg aggagatcct cgacctgttc cagaaggtgt gggagaacgg    6240
cggcatccag gaagccgaga cccgcaccgt cattgtcggt gccgccctga gcggacccct    6300
gacgcgcctg ttcatcaccg acgtcaagta ccaggaagaa tcccgcaacg ttggcggtgt    6360
gaacctgcag accttcgaaa ccgacttcgg caaggcgaac atcatgctcg accgcttcat    6420
gccgagcgac accctcgtgg tcgcgtcgct ggaggacctg aagccggcct tcctcgacat    6480
ccccggcaag ggccacttct tcgccgagcc gctcgccaag accggtgcag ccgacaaggt    6540
gcagatttac ggcgaggtcg ggctgcagta cgggaaccag cgcaagcacg aaagctcac     6600 tgtcgcaccc gcaaccccccg ccaagtaatc acggatcggt ttgaggttgc ctgatgaaag   6660
tcacctcgac catcccgaac ctgactgttc tcgacctgga catccagttc gttgacggtc    6720
aggccgatgt ggacccgcat ctcgccgaga ggctgcgtcg cctcgagcct ctcggcgtgc    6780
gggtccccac agccagccgc aagccgccca cgccggtcgcg gcgtaagcag ggggtcagcc   6840
atggtcgcac ctgatccgga actgccgttc gccaccgtct ccgatatgga gaccggtgg    6900 cgttctttgt ctaaggacga gcacacgcgg gccgaggccc ttctggacga tgcgagcggg    6960
ttgatcgttg ataccctgccc gcgctgggaa caggcctcac cggccaccct gcggcgtgtg    7020
acgtgctctg tcgtgcgccg ggcgatggcc gcagacgatg aggacatcgg cgcaacctcg    7080
ctcatggaca cgacgggccc cttcaccact cagcgcgcct actcatcacc ggccggggat    7140
ctcttcttga ccaaggccga gaaggccgcg ctcggcgggg tcaccggcgc attcgagacg    7200
agccttctgg ggctgacatg aagcgctcat ggccgacacc cgtggaacgt ctccgcgagg    7260
gtccgcccga gattgaccgt gacggtgatc gattgccgg  ctccggagtg atcaccaagg    7320
atcctctccc tgatgccctg ttcgcgccgg gcggctcgca gatcctcgtc gccccggcg     7380 tggcggcagt cgtggacgaa cccacccttct actggcgcgg atcagaagtg atcgatgtgg   7440
tggccaccga caaggtccgg atagccggcc gagtctggac ccctgaagga aatcctgcgc    7500
gatggccgaa gggcgtcgtg ctcaagctca aggcccagga ggcaaagaat cgtggctaat    7560
ttccgtttcg aacccaatac gaaggcgttc accgagtggg cgcagcgcga ctgcgacgcg    7620
cacctgatcg ccggcatcac ggcctcgatg ggggccaagg cgggcgaggg tttctcgacg    7680
atggtctcca acaatggcga ccgcacccgc ggttatctcg cgacggcctc cacgaagggc    7740
cgtatgcggc aggcgcaggg gcatgtcatc gagcgggtca tcggatcgag cggcgtgtga    7800
aaccgcccga cctccacacg ctcgtcgccc accatctggc tgagctcctc gacgtgccgg    7860
tcgtctccac ccgccccgag ggagagacgc cgccgtccaa gttcgttcgg atcatctcga    7920
ccggcggagc gggccgctat ggccgggtct tccagggcat ccagctgacg atcggctcct    7980
```

```
acgcgggatc ggcggcgacc gcccgtgatc tcgcgatgca ggtggacgag gccatgaatg    8040
ggctgccggt ctcgccgttg ccggtctcca aggtcaccgg caacacccg tcggacgacc     8100 ccgatcccga cactcagcag gcccgccaca cggccaccta ccaactcacc acccttatct    8160
cttaggagtc attcatggct gtcaattccg tcaacgtgca cgtcttcggg tccgatgacg    8220
acgtgctcta cctgggcccg tcaggtctga atctgggcaa catttcgctg gaaaccgcga    8280
tcccgaagga gatgatcgac accggctggc tcactgatga cggtgtgacc ctcggcatga    8340
aggactctgt caaggccatc cagggccacc agggccacgc gaatgtgctt cagttcatgg    8400
actcgtcgga taccaccctc gaggcgaccc tcatggagtc tcagctgcag accttcctgt    8460
ggaacctcga cgcggacgct gaggacatcg acggggtcac caagatcacc gcggccagct    8520
cccgcaaggt cctcaacctg tgcgcgatct gggacacctt cgacacccag cacagcggca    8580
tccattggcg ctacgtcttc ccctcgctca ccctgggcga gcgcgatgac atcccctca    8640 aggtgggcga agccagcgct tacaagtatt cgctgggtgt gctggagaag ttcttcgtct    8700
tcaccaacgc ggcagcgatg aaggccggtg gagcatccgc caagacggtg accggtgtga    8760
agatcaccac caccgacggt gcgaccgtgg gcctcccgtc gtcgctgaag gtgggggaga    8820
aggtgtccct cgccgccgag atctcctaca gcgacggac gaaggcggtc aagcagacca    8880
atgccgtggg cctcacctgg acgtcctcg acaaggccaa ggccaccatc gatggcggcg    8940
tggtcaccgg agtctcggca ggcaaggccg acatcaccgc ctcgatcgac ggcaagactt    9000
ccgaagcgct gtcgctgacc atcaacaccg ccgcctgacc aaccctcaaa ccctccgccc    9060
cggtcgtcct ctcgcgccgg ggcggagcct tgccacaccc gcgagaggtc aacttttctg    9120
cgagaggaaa ccatcatggc cgaggccaag aagatcagcg ccgccgagaa ggcgcgccgc    9180
gagacccagt ccgcgaagga caccggcacg atcaccgaca ccaccgtgca gatcggcgat    9240
atcgagttga ccgtgcccgc cgccgtcttc gaagacgact gggaattcca ggaggcgatc    9300
ctgatggcca acgatcccga tgccaccgac gaggatcggg ccagggcaag catgacgctg    9360
ttccgtcgtc tggtcggaaa ccgccaccgc gaagtgcttg accagctgcg cgacgagtcg    9420
gggcgtgtgc cggtgtctaa ggtcaccgag accgtcaaga aggtcatgga cgcggtcaac    9480
ccaaactgat gagcctcttc cagctcctcg ccacacattg ggaggagctg gaggggagct    9540
tccaagaggc ctaccgcgtc gacctgcggg acttgtggcg tggtcggctg agcccggcgc    9600
gctgctgggt gctgctgaca caactgccac ccgggtctcg gctctggcgg atgctcggcg    9660
gccccatggc gtggggcatg gtcgagcgcg ccgtccgtga agagggctgg cgactcgcct    9720
cccagaacgc tggtaaggaa ctgcctcggc cggagccgcc tgcgccggga tggcgcgaca    9780
agcaggacga cctgcgacgc cgcgaagagc gccgtcttgc ccgcttcatg caacgccacg    9840
cagaacgcaa caactgaaca gtgcaccgtc ccgggaggtt tccatggctc tagatctcgg    9900
taccgcctgg gtgcaggtgt ctccgtcctt caggggcttc gcctccacgg tgaacaaaga    9960
ggtcggttcg gcagtgggcg gggccttcaa gtctgcggcc aaggtcggca ccaccgcgat    10020
cgccacgatc ggtgcggccg tcggtgggct ggcgctcaag ggcggcatcg accgcgccct    10080
gtcgatcgag caggcgcagg ccaagctgaa gggcctgggc cacagcgcag ggtcgatcac    10140
cgagatcatg aacgacgccc tcgcctcggt gaagggcacc gccttcggtc tgggcgatgc    10200
cgcgacggtt gccgcgtcga tgtcggctgc cggcgtcaag tcgggcgagc agatgaccgg    10260
tgtgctgaag acgttgccg acaccgccca gatttcgggg cgctcgctca ccgatatcgg    10320
tgcgatcttc gggtcggtgg cggcccgcgg caagctgcag ggcgacgaca tgctgcagct    10380
```

```
catgagctcc ggcgtgccgg tgctccaatt cctttccgac cagctcggcg tcaccaccgc   10440
cgacgtgtcg gacatggtgt ccaaggggca gatcgacttc gccactttct ccgccgccat   10500
gcagaagggt cttggtggtg cggcactggc tggcggcgaa accttcaccg gtgccatggc   10560
caacgtccgc gccgccctgt cccggctggg tgaggctgcc gccaagcctg ccctggacgg   10620
gctgcgcaat gtcttcaacg cgctgatccc ggcgattgat gccgccacaa atgcgctcaa   10680
gcccatcgcc agcgccctgg cgaaccgaat ttcgcaagca gcagaggcgg cttccgcctc   10740
gatcgggcgc ctcaccggct ccctcacgag catcacgaat ctcaatacag ggatgctcgg   10800
cgcggccttc tcatcgatgc tgccgatcat cggagcactg tcggggcagc ttggctcctt   10860
gcttggcggg atcccggtcg tcgggcaggc cttcgcaggg atcactgggc cggtgggatt   10920
ggctgccggc gtgctggtcg agatcgtggc ggcttcatcg tcgctgcgtc aggccctggg   10980
cacgctggtc ggggtcgtcg ggtctcagtt gtccggtgtg atgacgggca tcgtcgcggt   11040
gtttgccggc ttcaggtccg tgcttggtgc cgtcggtgac gttctggccc cgttcgtgga   11100
ccgtgcggcg gacgccgcca atgtggtcct gcccttgctg gggggtgcgc tgtcggctgc   11160
cggtggcatc ctgcagtctt ttgcgggttt catcgagcgc aaccatgtgg cgctctccat   11220
tcttgcgggt gcggtggttg cggccgcgac gagttggaag atctataccg gcgcgcaaga   11280
tcttgcgcgg ctggcaacga cgaagctcgg gctcgcgaca acggtcctga agggcaagct   11340
gtcatcgatg ggggcggcgt tcaagacgaa tccgttcggt gtcatcctca tggcgatctc   11400
ggcgctggtg ggggcgttct cgattgccta ccagtcctct gagacgttcc gcaacggtgt   11460 gcagggggatt ctcggctcgc tggcgccggt gttttcctcc ctgatgggga cgctgtcggg   11520
gctattccag caggtcgcgg gcgctgtcgg gccggtgctg tcgtcgatcg tctcgacgct   11580
ggcgtcggtg ttctcggcga tcggtcccgt cctgtcgcag ctgccggca ccatcggatc   11640 tgtcttctcg gcgatcggtc ccgtcctggc gtcggtcttc gggtcgatcg ggtcggttct   11700
ggcgagtgtc ttctccgggg tgatgagtgt cgtggcgccg atgctcaccg cgttgcagcc   11760
gctgttcacg cagctgtcgg cttcggcggg gcagatcggt gcggcgttcg gtcctgttgg   11820
tcaggcgctg tcgtcgtcct tccagcaggt cggtgccgcg ctggcgccgc tgctgccgat   11880
gcttggtcag cagttcgggg cgatcctgtc tcagctggct gcggccctgg ctccggtcat   11940
gggtcagttg ctggctgcgg ctgctcaggt gttgccgacg ttggcgcagg ccttcgggca   12000
ggtcgccggg gtgctgatcg ggtcgctggg tcaggctctg acccagatcg ctccgctgat   12060
aggccagctg gtgggggtgc tgatcgggtc gctgggtcag gctctgacgc agattgcccc   12120
gctggtgggc accctggtcg gggtggtcgc gcagctgttc gcccagctgg ccccttttgt   12180
gggtcagctg ctggtgcagc ttgttccggt tgtcgcggga tccttgtgg cgatcgtgcc   12240 gatcgtcggg atgctgatta gtcagctcgt tccggtgatc gtcacgctgc tccaggtgat   12300
caccccgatt atcaccatgc taatcagcgc gctggtgccg gtgatccagg tcgtgaccca   12360
gctggtgctg gcgatcatcc aggcggtgat cccgttgatc tcggcgatcc tgccggcgat   12420
ctcggcactc atctcggcgc tgctgccggt gatcgtcatg atcatccagg tggtggcgca   12480
ggtgctgcag tggctggcgc cgctgatctc caccctgatc acggcactga ttccggtgat   12540
caccacgatc atccaggtgg tcatcacggt cgtgtcgaca atttggtcgg tggtcggggc   12600
ggtcattggc tggttccagt ccacggttgt gcccatcatc ggcaccgttg ttggtgcgat   12660
cgcgaacgct ttcggttggg tgcgcgaccg tatttccgat gcctggaact ggattaagga   12720
```

```
ccgcattgtc gccccggttg tcgagtggtt ccagtccacg gtggtgccga agttcgaggc    12780
ggtgcgcgac tccgtggtgc gggccttcga gacgctgaag gatggcgttg gtcgcgcctg    12840
ggatgcgttg aaggatctcg caaagaagcc ggtcgaattc gtcgtgaaca cggtggctgc    12900
cgggttggtg cgggcctaca actgggtggc gacgaagttc ggtgccgacg aggtcaagga    12960
gcctcatgtc gagttcgcca acggcgggtt cgcgggacgt gaggccggct tcgcgtcgtc    13020
gccgatcctg tgggccgagg ccggcccgga agcctatatc ccgttggatc cggccaagcg    13080
gacacgctcg ctggggatct gggccaagac cgggcagatg ctcggcgctc tacccatggc    13140
tgacggcggg atcatcggga acatcattgg cgggatcggc aacgccgctg cggcgatcgg    13200
caatttcatc aagtcaccga tcgagtggct catgggccgg gtccgggacc tgatcgatga    13260
tgtgggcagc tcaccgttcg cccagatcgc cgcgaagatc cccggcaaga tcgccgacga    13320
tatcggcgcc tgggtcaagg aacacatggc ctccatattc ggcggcggcg gttccggatc    13380
ggaagcgttc gacggctggt ggaacgcggc tgtcgccatc aatcctgata tggccccctt    13440
caagcagatc gccgccacgg tcgcccagaa cgaatccgga ttcaacccga acgtcatgaa    13500
caactgggat tcgaacgctg cggcgggcac gccgtcgggt gggctgatgc agttcatcca    13560
gcccaccttc gaggcctaca gtggcccggg attcgacaat tggatgggtg cggtcgatca    13620
gatcctcgcc tggtggaagt acgtgaatgc ccgctatggc gggccgttca atattcccgg    13680
aattgcctcg ctggcgggtg gcggcggata tgtcggctac gccggaggca ccctgaacgc    13740
ggctgccggc acggcatggg tgggggagaa cggccccgag ctggtcgatt cggtggcgg    13800 cgagtcggtc tacaaccgct cccagattga cggtctggag gatcggatcg ctgaccggac    13860
gatttcccgg ctgcagcagc tgagggtggc gctgatcgtg gacggacatc agatgggtca    13920
ggtcatcgac ggccgcatct ccatggctgg cgctgctgca cacggatcga ggtggtgaca    13980
tggcgatcat tgcgacgcgc cgcgactggc ctgaggctcc gcaacgcttc cagtccgccg    14040
atgggcggct ggtggcggag ctggaccctg accggtgcgg agtgcgactg cgcggcaccg    14100
acctggaggc gtggagcgtc accctcaccc gtgatggcga ggtgatccac accggcgacc    14160
ccatggtcac accgggagga acaggaatcg cctacgacct gtctgcaccg ttggatgctg    14220
atgtcgtcta cgaggcgcac gcgggtgggg cggtgctcac gcaggtggcc gtccacaccg    14280
gcggcttgcc tttcgagtgg gggatggtga ccccgctggc cgaccccgac aagggcctga    14340
tgctacggac cgtcgccgac accccacgc tgggcaggtc ggcacgccag aagctgtctg    14400
cggtgccctc atcgaggctg caggcaggtg gctgggacgt ccccaccgac gcggcacagg    14460
gatggacgtg gctcgcggga ttccccgacg cctccaaagc gctcgccgag cgcgacgcga    14520
tcatggaggc cctatcgctg gggccggtct acttccggcc cgaaacctcg atcggcttcc    14580
cgcccatgtg ggcactgccc ggcgacgtgt cagcgaccaa gcagggcgac gcctggacgg    14640
tgtcgtgcac gctgacgccg atcaccgctc ccgcgaccgc cgacctgccc gcctgggcgc    14700
ccggcaacag ctatgcgcgt gtggcggcca cccggggag cctcgccgag ctcgcccgca    14760
catccaagac attcctcgag ctagtgggt tctgatgatt gaagtatcca agcgatgggc    14820
ctcctcagta ggggccggtg cacgctggtc ggtgatggtc tcctggtcct ccgacggagg    14880
ccagacctgg catgacgtgg tgcccaccgc ctgctcggtg gacgagtcta ccggccagca    14940
ggtgcggtgg aagctgtcct gcaccctgcg caaggccgac gccgagggcc tgaccgtctt    15000
cggttgcagg gcgcgcgtct tcgtgtcgat gcatcacacc gacagctggg aggagacgat    15060
ccagctcggc gaattccgca ttgacaccac ctctgacacc accctcgccg ggccgtccgg    15120
```

```
tgcgcaggtc gcggcagttc aggtgagcgg ttcgagctgg gagcagcagc tgatggactc    15180
gcggctggtt gagccgcgtg aggtgtcggg tgccgcgatc gatgtgctcg gcggcctgat    15240 ccggaggtg ctccctgacg cagagatcgt cttcgacggc gggatcgatc cgggccgcaa     15300
cattccggcg acgtggtgg agcgtgaccg gtgggccttc attgacggct cgaattcgtc     15360
ggagacgtcg gtggcgcgga tgctcggcgc ccaggtctcg accgacgcac ggggcgtgtg    15420
gcatgtggcc ccgcctccgg tgctggacgg gacggcggcg tggacgatcg aggccggcaa    15480
gggcggtgcg ctcctgtcgg cggtggccag cgaggaccgc tccacgatcc gtaacgccgt    15540
catcgcgcgc ggcgagtcaa ccgataagag cgtgccggtg ttgggtccgg tgaccgtggc    15600
tgatcacaat gcgtggtcac caaccaacgt ggacactccg gtctccaggg gcggcttcgg    15660
cacagtcccg atcttctaca cttcgagcct tttcaccgac acgacgcagg tggaggcggc    15720
agcgaaggcg atgctgcagc cgcgcctggg cgtcaaacgc accctggacc tgacaacgct    15780
cttcgaccct gccaaacgcg ccggggatgt gggtgtggtg cagaccactg atggtccggt    15840
caccgtcgtg ctcgaatcag tgtcgtgcga cctggtggcg gcgtcgatga cctgccagac    15900
gcgcggcacg accggcaccg agctgatcac gaccgaaacc acgacaacca ctggggagaa    15960
gatctcatga gtgcaccaga cattgccctg caaggactga tcggggaaga caccgagcag    16020
gtggcgcttg cccaggtgct cggcgtgggc gtcgacgggc ggtcggtgcg tgtccagcgc    16080
ggcactctca cccacgaggt ccgccggctc gatagctaca agccttcagc gggagaccgg    16140
gcgctgctgt tacggctatc tggcggcgaa tgggtgctga tcggcgccct cgcctgacct    16200
tgacgaccta acctctgaca acctgaaaag gagccctcca tggcaaccgt ctatggccct    16260
gacaaattca ccgtcccgac tggtccggac gcaccggacg tgccggcgac gatcatcacg    16320
ctgctggact cgatgcgtcc ctcgctgatc gggcatgcgt cttcgatcgc tgaccgcacc    16380
gcgaaatatg gcgggcatc cgcgtcgagc attcaggcgc cgaagggcac agtggtggtg    16440
tctgccgagc tgaacgcaat ttgggtgaaa acatcggaca cgctggatga gtgggcgacg    16500
atcattcagc actcggatga ggtggcgacc gtgtcggtgg tgtccaccca gtccgaccag    16560
gtgaccacgg tccagaagtt cacgattccc gagtcgggca tctatgcgct gtatgcatcg    16620
atgaatgacc agaacggctt ggatgtcgat gggtcgatcc gtgagataca tgttctggtg    16680
aacgggacct ggaagttcgg tgggatcttc ccggcgagca agttctggct ctggtcgggt    16740
tcgcggacga cctttctcaa taagggcgac acctatcaga tcgactttat gcaacgctca    16800 ggcgggggaga ggtccctgaa ggtaacgctg tcttatcaaa ggattttgta atggcgacgt    16860
gggattacgg gtatgcgccg gctgatgtgg tgaccgatgc ggccggggat gtgctggccg    16920
gcatcgaact gcgggtgtgg gacgccgagg tggcaggaa agccgtcgcc gtccagcagg    16980
accgtggcga cggatggaaa cccgcgtcaa gagtcctcac cgacgacgtg ggccgctacc    17040
gatttcgtgc cgaagcgggc cccacggtgt gggtggagga cgtgtcaggg cggcgctggc    17100
ggatggatgc ctggcagacg ctcggcacga tgatcgactc cgcacagagc gccaccgccg    17160
cggccgagtc ggccaactca atcgcccacg aagccatgtc agtcgcccaa caagcccaga    17220
cgtcggcgaa ggccgccgcc gactccgccg ccgccgtgca gggggttgcc ccgtccgacg    17280
cgaatgtgtc gccgatcatc accggcgggg cgaagactgc tgaggcggtg cggaaggcgg    17340
cgctggctgc tttcccgacg accgggccga cgatcttcac gcacttcttg acgcgcgacg    17400
aggccctgca tgtggcgatc tccaccgacg gtgtgacggt ggaggacacc ggcctgcggt    17460
```

```
ggaagccgaa gaacgacacc accctggggg agtgcttcgt gcgcgaccca tcggtgtgtt   17520
tctggaaggg tgcctattgg gtcgccttca cccggcccac gaagggcggg ggtgacgctt   17580
tcgggacgac caagtcgttc ggactgatga agaccacgga ctggcggacc ttccaggagc   17640
tcccgccggt cgtgatgccg agtcaatttc agcagacgtg ggcgccgcag tggttcatcg   17700
gctccgacgg ggtgccgcat atctttgtgg ccctcggcac caccaccacg cccaacgcgt   17760
acttcaccca gtatgagctg cggccgctcg atgacgcgat gacgtcctgg tcggacccgg   17820
tggtcatgtc tggactgcca gcgaattgca tcgatgtcgc ggtgatcgag gacgccggta   17880
ccttccacgc ctttccgtcc aaccagaaga cgtcaacggt cgagcagtgg acgtcaaccg   17940
ggctcaccgg cccctacacg aagctggcgg ccagcgactt tcccggtgcc ggtgtcgaag   18000
gaccccagcc agtgccgctg aagacggggcg gctggcggat ctacgtcgac aattacgcgg   18060
agaccgactc gatctatttc gccgagagca cggacttgct gcattggtcg gcgctcaggc   18120
cggtcaccct gccgatgcgt cacgtcggcg cggtcgcggt ggactccttc ggtgcgctac   18180
gcacccgcga gctgtggcag ccgaacatcc cgggcatgag ggggatgggg gcacccttct   18240
ggggcgtacc cttcgccgcg gggaacgtgc tgaaggaatt cgcgcagatc gtgtccatgc   18300
gcaccgacgg cggcggcgaa atcgatctgg caaaggcggc cacgctgggc ttcaccggca   18360
tcgattacat ctcggcgacg gctgtcgcga acgtcgagat tctgcagatc gagcccgaca   18420
ttcgcgctgt cgacagcatg atccacgcg tcgccctgcg aggaccgagt acgccgcaga   18480
tcgatacaga cgtgaaggtc gcctggcggg tgctcggctg gggcgatccg agcacgccat   18540
gagcagggac gctgacgtga ccaagcaggg atccttgcct cggcgggtct gggacatgct   18600
ggcagagccg aagtcggtga cggtcctcat gacgattgcc tacgcggcgc tcgtcgcgct   18660
cggcttctgg gcgatcgacg acgcctccac gatgggggtc cgcgacatga tgggcggcct   18720
gctcatcgct ggtggcgtgt gcgggctgat cggatgcccg tggggccagt ggtggatcga   18780
gcgcgccggt ctggtggcga tcggtgccgc tttcgcggta cacctgtctt tcgtcgtggc   18840
gatctccccg cccgacggac cgtgggaagt ggcctcggcg ctggggctgc tgcttctcgt   18900
ggcgacacgc tggatcagga tcaggacgct gccagccgac ccgacgctgc ctcggcccgg   18960
gcctccagag gcggggatg aatgaatgac ttccagacct ggatcacagt gctgggcggc   19020
gccggattcc ttggcgcgct cgtcacgctc atcaaggggc tggttgggtg gcgcaccggc   19080
aagtccggcc gcaaaatgag ggccgcccac gacgccatcg actcgctgaa tctggcgggc   19140
ttgtgggctg aagcctactg gcacgctcgc ggctattgcc gcagccacca tgaatggacc   19200
agcgattacg ccgacggcta tccaccccca cccgacgaca ccaacacccc tgactgagcc   19260
ccgccttgtg cggggctttc tcattcctca aagacttgga gacattcatg gactggacca   19320
atctgaacgc tgacgtgacg aagctgatgg gcgtgcactt caccccgga cgtgaaggca   19380 ggacgatcga caagatcgtg atccaccaca acgcggcaa cctgagcatc gaccagatct   19440
ggaatgtgtg gcagacccgt gaagcctccg cgcattatca ggtggaggcg ggtggccgta   19500
tcggccagct cgtcaacgat ttggacaccg cgtggcatgc cggcgactgg gacgccaacc   19560
tgacctcgat cggcatcgag catgccgacg actcgaccga cccgtggcat gtgtctgatg   19620
ctgccgtcga tgccggcgcg cacctggtgg ctgcactgtg tcgcggctac aaccttggcc   19680
ggccggagtg gatgcgcaac gtcttcccgc actctcagtt cacgtccacg tcgtgcccgg   19740
cgtcgctggc ccgggaccag ctcggcgact acatggggcg cgcacaagcc tacttcgatg   19800
gcgcgccggt ggctgcggtc catcagtcgg tccctgcccc cgccccagcg cccagccgtc   19860
```

```
atgtggacct gcccgcgtgg aatctccccg agggcaactt ctacggcctc gtcagcggcg   19920
gaaacgactc ccacggcggc ttctatcccg ccgagcgtcc cgctgtgagg gccatccagc   19980
tgtggctcat ccgtcacggc tacgccggcg cggtgcctga cagttgggcg gacggcatct   20040
acgagcagcc gaccgccgac gccgtgaccg ctttccagca cgccgagcgc cccaacagca   20100
cggaccggtg gggcgaggtc tgggccgacg acctggccac catggccgcc aacaactgac   20160
aaggagctga tgccaagtga tctggactct cgcattctgg aagggcgcag gcgagcgcgc   20220
catcaaaacc gccgcgcaga ccgccgtcgg cctcatgggt acctcgacgc tcatcgaaca   20280
ggtgccgtgg actgtcgtcg cctccggcac cgccatggct gtggtgctgt cgctgatcac   20340
ctcgatcggc aacgccgact tcaccgccgg cgtccccact accgccaagg gctcgaggc   20400 gacgaccgtg ggcaagacgg acaccacgcc cgtcacgcca ccggcgcgcg tcgccgaaga   20460
ggtcccagcc ggcttcgtcc cggacacggc cccggatccc gtgccgaccg tctgacctga   20520
gggggtgacg gcgaccctgc gccggatagc cactcaagca acctgagcga cacaagaccg   20580
cccactctga ccttcgcggg tcggagtggg cggcttttt gcgtctcagg ggcgcagatg   20640
atgactcgtc gtctttaatt ctagcagtac gcgttcagcg tcgccagacc atgactttct   20700
cggctgcctg gagcggcgca ccttcggggc ctttgaggta gggggcgatg tagatgagct   20760
tgcgcagtcc atgcttgggg ccgtgcgcct ggtgggtcca gtgcccgcgg accatgaacc   20820
gcacggtgag cttgtgcccg gttccgtcgt cgcggtcggt gaccacggtg cgcacgggac   20880
gcagatcgac caggggtgacg tgacggtcgg ggcgtggcgt gcggggcctg tgctcggtgc   20940
ccggggcctt gccggtgcgg gagtcgatcg tgcgccgctc ggcgacggtg ggggtgtcca   21000
tgagcacgct catcgccatc agcagcgacg cggacatgcg ggcctcgggg ctcagcgtgg   21060
catccagatc ggattcgggg cggatgagaa tcgacaggat ctcgacaagg ggaccgtcca   21120
cgtcagcgaa gccgggcgga tagtcgccca gccgccccag cagctggatc atggtgcccc   21180
caccgggagc gggaagccag gcgatggccc acacgggagg attcccctgc caggtgcggc   21240
cgccgggcag gtcgaaggtg cgcggcttgg gccccggcag gggtttggcg aagcaggcca   21300
gtccggtcgg ggtgatcagc tggctcgggc tccactcggg cacgtccagg gcagcatcca   21360
gagcgagcgc cgccatctcg ccactcaccc agaacagcga cgcattaccg agccgctcgg   21420
cactccaccc gaagccggac atcggcagtg ccttgtcgcc catggcttca gccaccgcat   21480
cagggtgggt ggcggccagt tgctccaggc gctcgtcgag gtggcgggag tcccgcacaa   21540
agcggcgacg cagcccgggc actccgcggg gtgtccacgt ccagctctcc ggggctgcca   21600
tgtcaggcga cgactcgaat gccaggctc cgccacgcct cggcggtgtg gtcgagcccc   21660 agatccacc actgggtcag cgcgtgttcc atggcgatcg tggcgcaggc cgacagctgc   21720
gaggccttgt cgcgagccga cagcaggtcg gcgctgtcgg tgccgtcggg cgtgaagtcc   21780
tgcagggcga tagtgatgtc tccgccggga agctgggaga ccgtgtcggc ggtcatgcct   21840
gcctgggtgg cgtcggcgat gatgcccagc tcgaccagcg tccagccggt gcgggccagg   21900
tcgatgcgct gggcctcgcg ccacaggtcc atctcggtgc gggtgcgtgc cgacaggctc   21960
gggggtgcgc ccacatcggc tccgcgtcgg gccatccatg cggccatgtc gtcggtgggc   22020
cgccaggtga ttgtgctggc catgaagatc ctcctcggag tggaaagtgg aaaggggagg   22080
ggccggagcc cctcccctga tggttgatgt ggtcagcgga tccaggtgaa gggctggtcg   22140
ccgatgatcg agcggaccgc gaggtcgtag ggggcctcgt cctcgctgga ctcgacatcg   22200
```

```
accgcgtcga gctcgacacc gtcgcgggtg atggtgatgg tgtcggtcgt ggtggcccga   22260
ccgtcgatca ccgtcggagt gttgatgctg gtgaactctg cggtgatgcc gaccagctcg   22320
tggtcggcga ccgcttccca gaaggcgtcc tcgtcggctt cgatggagaa gtgcacgctg   22380
gaggcgatcg tcgcaccctc ggaggtctcc tcgctgtgga gcgtgaccag ctcgtcggcg   22440
atggcgtcga ggtcatactc ggcgcgggcg tcggcgactg cacctccggc ctcgatggca   22500
tcgatgatag aggcgatggc ctcgccgcgg gtggagaagg tagtgtcggt agaatcggtc   22560
atgatcctgt cccttttcagg gtcttggcct catcggggtg cttcccggtg gggcctcttg   22620 cttttgtcctt gtgacaccca ctgtcgtcac agtgttggaa catgtcaagc cagtgggcca   22680 cctttctttta aagagatttc agcgggcgac cgcgccgcct cggacacctg ggcccagtag   22740
ccctggaggg cgcactgaat caattggttg tcaattggtt gtcaaacctg accgtcgac    22800 ggggagtgag gaggtggtac cggctgatct acgcctgaaa cagatggagc gggcgacggg   22860
aatcgaaccc gcgtgtctag cttgggaaac gggcatcgtg ctagtctggg gaccgccgaa   22920
atgacgattt caggcgtaaa ccggcctccg gtgtcttacc ctgatagctg ggtgatagca   22980
ccgaattggt tgtcagattg gttgtcagat cgccccagga ggatggtcgc attgtcacgc   23040
gcaagctacg gggacggcac ccagccgacc cggcgttccg acgggcgctg ggcagcatcg   23100
gcctatgacg gctggcaggc gaacgggaac cgccggcgcc gatgggtgta cggccgcacc   23160
caggccgaat gcaagcggaa gctgcgcgac ctgaagcggg agatctggtc agacacccag   23220
cagatgaatg tgaaccccag ggagaccgtc aagagctgga cggcatcatg gctggacgac   23280
taccgatcga ttgccagacc aacaaccttc gccaccgacg agtccatggt gcgcaactgg   23340
atcgtcccag ccatcggtgc ccggcgcctg tccgaactga cagcgcgcga cgcctcgaag   23400
ctgcaacggg tctgccgaga cggggggactg tcggcgacaa cgtctcacta tgccgggctg   23460
ctcctgcggc gcatcctgaa ggctgcccgc gcgaacggct accgcatccc cgactccgtc   23520
atgctggccc ggatcccggg catcggcgca tccaacaggt ccgccctgag cgccatccag   23580
gcggccaacc tgctctcgac ggcaaacgca cgcgacacct ggccggagcc gcccagcctt   23640
cccgacctgc cctacggggc catctcgaag ctcgcaccag cagaagcgca gaagcgtgaa   23700
caactcaaga tggagcggtt ggaatggact gccgcccaaa acacggaccc ctccaggtgg   23760
gctgccgcac tcatgcaggg acttcggtca ggagaggctc gaggcctcac gtgggatcgt   23820
gtcgatctcg ataaggggac gatcaccatt gatcgtcaac tccagcgcat caagcccgac   23880
gcggcgcttc caccgggata caaggtcacc cggctgaaag cagccactg cctcgtggca    23940 ccgaaatctc gatcagggat ccgccgcgtc ccgatcgtcc cctggatggg ccaggctctc   24000
acccgctggc gcgacataca gggcgacagc cccttcgggc tcgtgtggcc gctgcccacc   24060
ggggcgccgc ccacgcgggt ccatgacctg cgggcatggc gtggactcca gcgcgtcgcc   24120
ggggtccaca aggaggatgg aaacctctac gtcctccacg aagcacgaca ctccaccgtg   24180
tcgctgctgc ttgctgccgg ggtcccggaa tcagtggtca tcgcgatcgt cgggcatgca   24240
agcttcgcgg cgaccgagca ctacgcccac accgacctcg aagcagcacg cgccgccctc   24300
atgaaggtgc aggaccgcct cgggctggag ctcgagagct gagcatgcaa agagccgccc   24360
accggaccaa tcgcggtctg gtgggcggct cttttgcgcc ttagagcacg tccgtcacca   24420
cgcctggaag ttgctgacga cgggtgcctg gtcggtgccg gtcacgtcgc agtgaaccgt   24480
gtatttggcg gagccgacgt cggcgccgat gttgacgttc cacagatcgt cggtcttatt   24540
gagggcggcg accgaatcga cggttgagtg gaccttgatc ttaagcgatg ggtattgctt   24600
```

```
gcccaaggca tccctcgcat aggtgccaca gccagaggtt gcgccggtca tggtgagtcc   24660
agtggtcgtt gcctcgacgg gtgtgggcgt ggcggacgca gtgggcgtct tcgtggccgt   24720
cggcgtcttc gccgctttcg gagtcttgga ggctgatgat gacgatcctg atgtctgggg   24780
atcgcacgcg gtcagcgcgc cggcgaggca gagtgacgca agcagggcga tggggacgag   24840
cgccttgcgg cgcatggtgt gggtcattcg ggttccttgg ttggttggtt cacatgctgt   24900
ccacagcaac ctagccgcgg aacctgcccg cctgggggtg atgagggcaa gtggcaagaa   24960
ttacatcgat gggattctcg ccaccccctg aagagcgtgg gtggcgaggt ctacattcgt   25020
acgcatgtac gaaacatgga agcctctcgg acacggctcg atctctggtg gatcggcccg   25080
cacaatggag tgcactgaag tagcggagtg ggcagagcgt cgtgcgcgtg ggtggggctc   25140
agcgctggta tcgcgcctgc gcggcgtcca tgaagacgcc gggttcaaag tcgagcacgc   25200
gagcaagctc aaagaggagt gcgacaggga gatcccgctt gccctgctcg atcctgatga   25260
tggtggattc gctgactcca gcgagtcgag cggtctcgac ctgggttaag cccttggcgg   25320
ctcgctcggc tcgaagctgg gcggcgatcg cggcgcgaat tgcatcacgc ttgctggcct   25380
ggttctggtc catgctgtca gcatagccgc cacattggac agttttccgg tccgattggg   25440
atgctcggca cttgcatctg gccatatggc atggcaagct gtccatatgg ccagttcaga   25500
catcaacctg gaggctgcgg acatgatctc cgccgccatc gagcgaagcg acaccagtcg   25560
ggctgaagtc gccacgctga cgggaatccc gttgaccact ctgcgtcgga agctcatggg   25620
ccgatcgccc gtcaacatcg aggacatctt cctgatcgcc ggcgcgctcg ggataccgcc   25680
tgtgagtatc acgcccgacg ttctcacgag tgaagccgcc gcctagcccc caaacagaag   25740
aagcccccgc ctgctgtcac agacgggagc caaccaaagg agtttccaat gagcattcta   25800
cccttcgact accacggtca ggaagtccgg ttcatcaccg atgagtccgg cgagcctcag   25860
gtcgtcgcgt cagatctcgc gaaggccctc aactatcgga acgcacccga catgatgcgt   25920
tccatcgacc tagaggaaag gggtacgcgt ccggtgcgta cccctggcgg tgagcaggag   25980
atgctcacgc tgaccgaggc cggcatgtac caagccatcc tgcaacgcca gacaggccgg   26040
atggtcgacg tcgcccaacg agccgctgtg aagcgattcc agcattgggt tacccacgag   26100
gtgattccct cgatccgcaa gcgcggcatg tatgccactc cggatgcagt cgaggcgatg   26160
ctggccgatc cggacgttat gatccggacg ctcaccgagc tgaaggccca gcgggccagg   26220
gtggcccagc tgcagcccaa ggccgactac gttgacgcct tcgtggccga cgaggatctg   26280
cggctcctgc gcaatgtggc caagtcgatc ggagtgcagg agggcgccat tcgcgacgcc   26340
ttgctcgcac acgagtggat ctacgcggag gagtcctcgc gctggtcgaa ctctcagggc   26400
tgcaaggtca tcgagcaccg ctattcaccg cgctctgaca aggcccgata ctttcgcccg   26460
gtcccgaatc accaggcacc ccgatttaag ggcgaggtaa tgcacaccct gaaggtcact   26520
ccggcagggg ctgaggcgat ctccaagatg gcaaagcgct ggggcctcgt cgtccaggag   26580
gtggcggcat gacctcgact ctcaccggca acatcatcgc cctgctgatc gtggccggcg   26640
tgatcgtcct cgccgatgggg gtgcgccgtg aaggtcgatg acttcgacga tgtgcgcccc   26700
ctgacgcaga aggacgtcgc cgagctactc cacgcaagcg tcggttacgt gcgctcctgc   26760
cgcctggcga cgaagccgaa aggccgggtc ttcccgatgc ccggctggaa gaccgacgga   26820
aagcgctatc tgcttcccgc ttggcggttc gcgagtgggg tcgaaagctt gcccgatgcc   26880
tagcccgcgc cgcttcctaa tcctgatcgc cctgggtgcc gccgccgtcg gtttcgcgcc   26940
```

```
ctcctcaatt caatttctct tcatggccgc gcttgtgctc ggcctcacca tcacatgcct   27000
caaggagtcc aaccatgcct gacacacagc cccgtcgtgc gcgtcgtcgc acgctgtccg   27060
agatcctcgc ccccgcgccg gcgccccgca gagcggaggc aacggcatga ggccaccagc   27120
cgttgaaacc cctgatgtga aggcgccggc cacgcctgct ggttcccggc tcttcaaggc   27180
tgtccgtcct gacggcttcg acttccacag cgggactgtc cggtggctcc ctgctgatgg   27240
cgcaccgatc ccggagggcg ggtggcttgt cgagcatccg catcctggtg aggttggcag   27300
ctgggatgca gctttttatc tgtcggcgtc gtcggtggag acggactgca caggtttcca   27360
gtggcctgct ctcctcctgt ccgtggagcc cgtaggtgcc atgtggaccc ctcgccccga   27420
caaatttcct cgcaagcggg ccgcgcacgc gtggcgcgtc atagaagagc tccccgcatg   27480
gcggcttttc ggtccccagg ggcggacggt cctggacatc atcgagcaaa ccgctcatct   27540
gaccaaacgc cagatcgcgg ccctgaacag ggctctggac gccgcacggg acaccgtttg   27600
ggacgttgct tggaacgccg cgtggcacgc cgctcgggtc gctgctcggg tcgctgctcg   27660
gggcgctgct cggggcgctg ctcggtacgc cgcttgggac gctgctcggg gcgctgcttg   27720
gtacgccact tgggtcgctg ctcggggcgc tgctctcgga tggctcgtca aggacctgat   27780
ctccgtcgag gacttccgca ccctgacggg cccgtgggag caggtcatgg gtccgatcga   27840
ggtggcggca tgaaccgcac ctatttcaag gccgttaggg cggacggcac tgacttctac   27900
accggcaagg tccgctggct gcccgatgat ggcgcaccga tccctgccgg gggttgggtc   27960
gttgagcatc cgacgagcga acgcgtgggg gacgacgccc gcacctatct ctcggtttcg   28020
acggtggaaa ccgactgcgc cgggatgggc tggccgtgcc gtctcctgcg ggtcgtcccc   28080
gacggcagac aggtgagcat ccctgaaccc gtggggctgc ccagcacgag ggcctcgatc   28140
aggtggcgcg tcatcgaaga gctccccgca tggcaggcgc ttggacccca ggggcgcgag   28200
attgaggcgc tgctcggaca ggttgagagt ctcacggagg accagaccct cgaaatgtct   28260
gccgctcggg gcttcgctcg gggcttcgct cgggacgtcg cgcggttcgc cgctctggtc   28320
gcctctcggg gcggtgctct gaacgctgcc cagggcggtg ctttgggcac tgctctgaac   28380
gctgttcggg acgctgttct cggatggctc gtcaaagatt ttatctctga tgaggaattc   28440
cgcaccctcg tgggccgtg ggagcaggtc atgggtcggg tgatcgcatg atgccgatca   28500
ccaagccgtg cgcggttaag gacatgccgg agggcgagta tcactcggat ccctgcgtcg   28560
agccgtccct gtcgtccacg atggcgaaaa ccattgtttc gggtgaggct ggcccggccc   28620
gtctgcgaga gatcatgtct cacgggcagg aacataaggc cgtcttcgat tcggcagcg   28680 ccgcgcacga gaaggtgctg gacgcggcg ccggtgtcga ggtgctggat ttccctgcct   28740
ggaccacgaa ggcttcgcgt gaggcgcgtc aggccgtgtg ggatgccggc ggaactcccg   28800
tgctggcgaa ggattccgcc caggtggatg cgatggctga ggcgatcctg tccaatcctg   28860
tggcaggtga gctgttcacg cgcggggctg gttctcctga attgtcgatg ttcaccattg   28920
acgaggagac gggacgctgg cagcggggac ggctcgactt cctggcggac cgcaagacca   28980
tcgtcgactt caagacatct ggacagtccg tcgagctgcc cgactggatc aagcacagct   29040
ggcagttcgg ctaccacatc caagccgccg cctatatgga ccaggcgatc tcgctggatc   29100
tggtcgatga ggacgccatc ttcctgcatg tcgtgcagga gacgaagccg cccttcttgc   29160
tcgcgatcta tcaggtttca gctgaccagc tggccgaggg caggcgtcag atgcgtcgtg   29220
ccctggacct gtgggaccgc tgcctgaccc tcgacgaatg gccgcgatc cctgcggtga   29280 tccaactatc caagctgccc gattgggtgc acaccactga tgacgaaaag gactcctgac   29340
```

```
atgaccgaaa ccacacctag caccgacatt gaaaccaccg cccccacccc gtcgggtcg   29400 atcgcggcgg tcggctccga gacggcaggc ctgacgcttc agcagaagct cgactatgcc  29460
tctgccctgg ccgactccga gctcctgccc gccgcctaca agggcaagcc cgcgaatgtg  29520
ttggtggcga tggagtacgg cggcgagctg ggcatcggca cgctcgtcgc ggtgaaccag  29580
atcacggtga tcaacggcgg cgtctccatg gaggcgaagc tcatgatgac gctcgcccgc  29640
cgagccgggc acatcgtgcg cctgtccggc gacgacaagc aggccacctg catcatcatc  29700
cgcgccgacg atcccgggca cgaatcggtc gtcacttggg acgaggccaa ggcgaagacc  29760
gccggactgt ggggcaaggg ccactggcag aagaacccgg gcttgatgtt gaagtaccgg  29820
gcggcctcgg agaacatccg gctcacctgc cctgaggtgc tggcggggat tgtctacaca  29880
cccgaagagc tcgatgagcg caccgagcgt gcaggccggt ccacgatgcg tgtccatcag  29940
gtcgtggccg agccggagaa gaccgctgcc tacttcatga aggccctcca cctgaacggc  30000
ggccagttca aggagtttgc ccagcgcgtg ctgggacatc cgttgaagag ctgggaatcg  30060
ctggccaagg cagacaagca gcgtgtcctg ggcgctctcg ccagctggga aacagcggg   30120 gccgatccca ccactggcga ggtcctcgac gccgagccgg tcgagggcgg tgcggcatga  30180
gcaccttgcc tgcggatgct gccgagaggt ggcagcagtg ggatggcctg gcccgcacga  30240
tcctcgccct tcatctcggc ctgactgatc ttgagatggt cgagctggtg ggcgggctca  30300
tcggtgccgg ctggcatcag gatgggccgg tggagtcatg agctggcccg aggagcacca  30360
cgacgtgtgg gcgggtgtcg aggacgccat ccctgagtgg gtgagcgaca aggtggcctg  30420
ctcggtgcgg tcggatgccg attggaatgc cgacgaggac agccgcaagg ccgtggcggc  30480
ggtgaggatc tgcgagcggt gcgccttaac cgagcagtgc ctggattggg cgctggccca  30540
ccacgaggcc ggcatctggg gtgggctcac cgcctccgac cgcgagcgca tcgagcgtgg  30600
cgcgccggtg cggcgggtcc gcgagattcg tcggcgtcgc acggcggtta ggcaggtgca  30660
ggagtcatga gcgcaccact gaccaaggcc cagaaggtcg cggcggtcgt cgagcagctg  30720
ttgcgtggcg cgcgccgacac cagcacgctc ctggaggcga cggggccga ccggcccgga   30780 cgattgcggg acacccttcg ccgcgctggc cgtgacgacc tcgccgcccg gatcatcacc  30840
accgaccggg cagcccagcg cagacgggaa gtcatcgagg cggtcgagaa gctggtctgg  30900
gtggacaggg ccgacgagat cgccgccgaa ctcggctaca gctcgcgcta cggcctgcaa  30960
cagtccttgc gcggctgggg gcgtcgggac cttgccgatc agatcgtgct gacccgcgag  31020
acgcaccgcg acagggtcat cgctgacgtg aatggatcg ccggtacacg gggccccgag    31080
gatgtcgccc gggcgaccgg ataccgcaac gcggcggcgc tgcaggccgc cctgaccggg  31140
tggggccgca aggacctcgc cgaccggatc gtcggagcat cacgcaacga cacgggccgc  31200
ttccgcttca catggagggc cgcatgagcg ccaaccgctc ccgccgcgcc acgtacaacc  31260
acacggggat cttcgtccat ctgcgcgaag ccgccgagcc gtccgaacag ccaccctccg  31320
accagacatg cccagccctg catgtcatcg ccggactgac accctgggcc gaccaccagc  31380
cccgccacgc cctcggcgtc gacgggcgat gccggcactg ccacaccacc atcaaaggaa  31440
acccatgatc ttcaaagaca ccacgatcgg gccgctcgaa acacggttca cctggtcgat  31500
gaggtgcgac cgctgcggga cgccgctcga ctggctcgtc gccgcttcgt gcaagaccga  31560
gcgtagtgag gtaatcgccg tcaagttcct gagggagcgt gcccgcgatg gcgggggcct  31620
cagagagtgg ggggagctgg acctttgccc ttcatgcttc tcggtgatgg acgcatgatt  31680
```

| | |
|---|---|
| accaccacac aactcggaga agcagaccgg tggggccgtg gcctccaagt ccgctcgatc | 31740 |
| ctgtgcaacg gctgcggcat agctctggcg accgacatcg gccttcgtgg agacgccacc | 31800 |
| gccctccaag tgcaatccga cctgcacgcc cgagcacgca ccgccggctg gacacacccc | 31860 |
| gcctggcgcg tcgacctctg cccgcaatgc accaccacaa ccaaaggagc atgaccatga | 31920 |
| aggccaccca gtacgccaaa tcgaccgacc ctgaagtcat cgccaccatc gaagagaacg | 31980 |
| agctgtcacg acgggcatgg atcgacgaca ccaaggcgtg gttcggcaag acgatccgga | 32040 |
| caggaatccc gggcgccaaa ttgttcctct tttccacccg gaccgctatc aggctgttgg | 32100 |
| ggatcgtgac gtcggacgag aagaagcctg ccgggtggaa gttctgctgg cgttcacgct | 32160 |
| ctcggttcga gccacgaaag aacaatccct tgcgcgccac atgggacgca cgccggtggc | 32220 |
| aagcagcgtc gatcccaggt ctgcccgtgg ttctcacgtc ctccgtgtcg ggagagttac | 32280 |
| agagctggtt gaggatgtat ccctgccccct tcatctctag tggtgccgca tggctggacc | 32340 |
| tggagcacat gcctgaccct gacagtccgc acttcggacc gcagtggact gaagtccgtg | 32400 |
| catcgcaggc aatggcagcc aaggaagcat tgaaggacgc gtcatgagca ctccgggatc | 32460 |
| actgcgcgcc gcgctcgacc agctggacga gatcggcatc gccgaccatg tgcagtcctt | 32520 |
| ggaatgggat cgggccggcg cccgcaccac agcctggctc gagacctgcg gcgacttcgc | 32580 |
| tgcggcctgc cagtggggcg atgccgcggg cgaatgggtc acgtgggaca tcaccgacgt | 32640 |
| ggccgaggcg gacgtcagcc cccggctgcg cgtcaagcac atgcacctgc gagccaggcc | 32700 |
| ctgtgctgat gcgcccgcga aggcggtggc ggcatgagca aggcccttga cccactggat | 32760 |
| caccttc | 32767 |

<210> SEQ ID NO 27
<211> LENGTH: 29768
<212> TYPE: DNA
<213> ORGANISM: PAC7 phage

<400> SEQUENCE: 27

| | |
|---|---|
| tcgtacggct tagtgaaata cctcccttttt gttgttttat cgttttgtcg acttttttgtt | 60 |
| tggtggtgtg tgtggtgcag cctgagcttc ctgatagtcg tgattggtgt ggggagacgc | 120 |
| gtcggtggtg gtgtgtgtgg ggcgaggatc cgcgtgccgg gtttgtgtct gatgaggagt | 180 |
| ggttgtttct catggatgct gcggtgattc atgatgtggt gtggcgtgag ggtcgcgcgg | 240 |
| atttggtggc ttcgttgcgt gctcatgtga aggcttttat gggtatgttg ataggtatt | 300 |
| cggttgatgt ggcgtctggt ggccgtggtg ggggttctgc ggtagcgatg attgaccggt | 360 |
| ataggaagcg tagggggggct tgagtaggtg tctggtgttg ttgggtctca ggttcctcgt | 420 |
| caccgggtgg ctgtggcgta ttcggtgtct gctggcgggg atgctgggga gcttggtagg | 480 |
| gcttatgggt tgacgcctga tccgtggcag cagcaggtgt tggatgattg gcttgctgtg | 540 |
| ggtggtaatg gcaggcttgc ttcgggtgtg tgtggggtgt ttgttccgcg gcagaatggc | 600 |
| aagaatgcta ttttggagat tgtggagttg tttaaggcga ctattcaggg tcgccgtatt | 660 |
| ttgcatacgg ctcacgagtt gaagtcggct cgtaaggcgt ttatgcggtt gcggtcgttt | 720 |
| tttgagaatg agcggcagtt tcctgacttg tatcgtatgg tgaagtcgat tcgtgcgacg | 780 |
| aatggccagg aggctattgt gttgcatcat ccggattgtg ccacgtttga agaagtgt | 840 |
| ggttgtccgg gttgggggttc ggttgagttt gtggctcgta gccggggttc tgctcgcggg | 900 |
| tttacggttg atgatttggt gtgtgatgag gctcaggagt tgtcggatga gcagttggag | 960 |
| gctttgcttc ctaccgtgag cgctgcccccg tctggtgatc ctcagcagat tttttttggt | 1020 |

```
acgccgccgg ggccgttggc tgacgggtct gtggtgttgc gtcttcgcgg gcaggctttg    1080
tcgggtggta aacggtttgc gtggacggag ttttcgattc ctgacgagtc tgatccggat    1140
gatgtgtcgc ggcagtggcg gaagttggcg ggtgacacta atccggcgtt ggggcgccgc    1200
ctgaatttcg ggacagtctc ggatgagcat gagtcgatgt ctgctgccgg gtttgctcgg    1260
gagcggcttg gctggtggga tcgtggccag tctgcttcgt ctgtgattcc ggcggataag    1320
tgggttcagt cggctgtggt tgaggcggct ctggttggcg ggaaggtttt tggtgtctcg    1380
ttttctcgct cggggatcg tgtcgcgttg gctggtgctg gtaaaacgga ttctggtgtg    1440
catgttgagg ttattgatgg cctgtctggg acgattgttg atggtgtggg ccagctggct    1500
gattggttgg cgttgcgttg gggtgacact gaaaaggtta tggttgcagg gtctggtgcg    1560
gtgttgttgc agaaggcttt gacggatcgt ggtgttccgg gtcgtggcgt gattgtggct    1620
gatactgggg tgtatgtgga ggcgtgtcaa gccttcctgg agggtgtcag gtctgggagc    1680
gtgtctcatc ctcgtgccga ttcgaggcgt gacatgttgg atattgctgt gaggtcggct    1740
gtgcagaaga agaagggttc tgcgtggggt tggggttcct cgtttaagga tggttctgag    1800
gttcctttgg aggctgtgtc tttggcgtat cttggtgcga agatggcgaa agcgaagcgg    1860
cgtgaacggt ctggtaggaa gcgggtgtct gtggtatgaa ctcggatgag ttggctctga    1920
ttgagggcat gtacgatcgt attcaagggt tgtcttcgtg gcattgccgt attgagggct    1980
actatgaggg ctctaatcgg gtgcgtgatt tgggggttgc tattccttcg gagttgcagc    2040
gggtgcagac ggtggtgtca tggcctggga ttgcggtgga tgctttggag gagcgtctgg    2100
attggcttgg ctggactaat ggtgacggct acggtttgga tggtgtgtat gctgcgaatc    2160
ggcttgctac ggcgtcgtgt gatgttcacc ttgatgcact gattttgggg ttgtcgtttg    2220
tggcgatcat tccccaagag gatgggtcgg tgttggttcg tcctcagtcg ccgaagaatt    2280
gtactggccg ttttctgcc gatgggtctt gtttggatgc tggccttgtg gtgcagcaga    2340
cgtgtgatcc tgaggttgtt gaggcggagt tgttgcttcc tgatgtgatt gttcaggtgg    2400
agcggcgggg ttcgcgtgag tgggttgaga cgggccgtat cgagaatgtg ttgggtgcgg    2460
ttccgttggt gcctgttgtg aatcgtcgcc gtacttctag gattgatggc cgttcggaga    2520
ttacgaggtc tattagggct tacacggatg aggctgttcg cacactgttg gggcagtctg    2580
tgaatcgtga ttttatgcg tatcctcagc gttgggtgac tggcgtgagc gcggatgagt    2640
tttcgcagcc gggttgggtt ctgtcgatgg cttctgtgtg ggctgtggat aaggatgatg    2700
atggtgacac tccgaatgtg gggtcgtttc ctgtgaattc tcctacaccg tattctgatc    2760
agatgcgttt gttggcgcag ttgactgcgg gtgaggcggc tgttccggaa cgctatttcg    2820
ggtttatcac ttctaacccg ccttctgggg aggctttggc tgcggaggag tctcggcttg    2880
tgaagcgtgc tgaacgcagg cagacgtcgt ttggtcaggg ctggctgtcg gttggtttcc    2940
tggctgcccg ggcgttggat tcgagtgttg atgaggccgc gttttttggt gatgttggtt    3000
tgcgttggcg tgatgcgtcg acgccgactc gggcggctac ggctgatgct gtgacgaagc    3060
ttgtgggtgc tggtattttg cctgctgatt ctcggacggt gttggagatg ttgggttttgg    3120 atgatgtgca ggttgaggct gtgatgcgtc atcgtgccga gtcttcggat ccgttggcgg    3180
cactggctgg ggctatttcc cgtcaaacta acgaggtttg ataggcgatg gcttcgggtg    3240
ctgtgtcgag gcttgctgcg actgagtatc agcgtgaggc tgtcaggttt gctgggaagt    3300
atgcgggcta ttatgccgag ttgggtcgtt tgtggcgtgc cggcaggatg agtgacacgc    3360
```

```
agtatgtgcg tttgtgtgtg gagttggagc gtgccggcca tgacggttca gcagctatgg    3420
cgggcaaatt cgtttcagat tttcgccggt tgaatggtgt cgatcctggt ttgatcgtgt    3480
atgacgagtt tgatgctgcg gcggctttgg ctaggtcgtt ttcgactatg aagattatga    3540
atagtgaccc ggatagggcg aatgatacga ttgatgcgat ggctgcgggt gttaatcggg    3600
ctgttatgaa tgctggtcgt gacacggttg agtggtcggc gggtgcgcag ggtaggtcgt    3660
ggcgtcgggt gactgatggt gatccgtgtg ctttttgtgc catgttggct acgaggtcgg    3720
attatacgac taaagagcgg gcgcttacta ctggtcatac gcggcgtcat aagcgtgccg    3780
gtaggcgtcc gtttggttcg aagtatcatg atcattgtgg ttgtacggtg gttgaggttg    3840
ttggtccttg ggaaccgaat agggctgatg ccgagtatca gaggacgtat gagaaggctc    3900
gtgagtgggt tgatgatcat gggttgcagc agtcgtctgg caatattttg aaggctatgc    3960
gtactgttgg tggcatgaga taatttgatg tggtttccgg ttgtgtgccg ccggttatcg    4020
gtgcacaggg ttgtctcccg cacgggggtc aacaatgttg tgttgttttc cgcaaggagt    4080
gtagggttag gctatggccg atcagagtat tgaggaacag aatgttgaca atgatgttgt    4140
ggagtccgga aaggataacg gcattgttga tacagtaaaa gacgatggcg ggcaggaggt    4200
agccgacaat cagttgaaga atgaaggcga gggtaaatcg ccggggactg attggaaggc    4260
ggaggcccgt aagtgggagt ctcgtgctaa aagtaatttc gccgagttgg agaagcttcg    4320
tacatcgagt gacgattctg gatctactat tgatgagctt cgccgcaaga atgaggaact    4380
cgaagaccgg attaacgggt tgttcttga gggtgtgaag cgcgaggtgg ctgccgagtg    4440
tggcctgtcg ggtgatgcga tcgcttttct tcacggtagc gataaggagt cgcttgccga    4500
gtctgctaag gctttgaagg gtttgatcga ccatagtagt ggtggtggcg cgggtgtgcg    4560
ccgtcttgcg gggagtgccc ccgttgatga tgttaaacga cgtgagggtg tcgcgtttgt    4620
ggatgctctt gtcaataatt ctaggagatg atttatcatg gctgacgatt ttctttctgc    4680
agggaagctt gagcttcctg gttctatgat tggtgcggtt cgtgaccgtg ctatcgattc    4740
tggtgttctt gctaaactgt caccggagca gccgactatt ttcgggcctg ttaagggcgc    4800 cgttttttagt ggtgttccgc gcgctaagat tgttggcgag ggcgatgtta agccttccgc    4860
tagcgttgat gtttctgcgt ttactgcgca gcctatcaag gttgtgactc agcagcgtgt    4920
ctcggacgag tttatgtggg ctgacgccga ttaccgtctg ggtgtgcttc aggatctgat    4980
ttccccggcc ctgggtgctt ctattggtcg cgccgttgat cttattgctt ccatggtat    5040 tgatcctgct acgggtaagc ctgctgcggc tgtcaaggtg tcgctggata agacgaataa    5100
gacggttgat gccaccgatt ccgctacggc tgatcttgtt aaggctgttg gtctgattgc    5160
tggtgctggt ttgcaggttc ctaacggtgt tgctttggat ccggcgttct cgtttgctct    5220
gtcaactgag gtgtatccga agggttcgcc gcttgccggt cagccaatgt atcctgccgc    5280
cgggttcgcc ggcctggata attggcgcgg cctaaatgtt ggttcttctt cgactgtttc    5340
tggtgccccg gagatgtcgc ctgcttctgg tgttaaggct attgttggtg atttctctcg    5400
tgtccattgg gggttccagc gtaacttccc gattgagctg atcgagtatg gtgacccgga    5460
tcagacgggg cgtgacttga agggccataa tgaggttatg gttcgtgccg aggctgtgct    5520
gtatgttgcg attgagtcgc ttgattcgtt tgctgtcgtg aaggagaagg ctgccccgaa    5580
gcctaatccg ccggccggta actgattcat ttgttgcgat aatgtttatg ctgtgtgcag    5640
ggggtggtgt tgatgggtat cattttgaag cctgaggata ttgagccttt cgccgatatt    5700
cctagagaga agcttgaggc gatgattgcc gatgtggagg ctgtggctgt cagtgtcgcc    5760
```

```
ccctgtatcg ctaaaccgga tttcaaatat agggatgccg ctaaggctat tctgcgtagg   5820
gctttgttgc gctggaatga tactggcgtg tcgggtcagg tgcagtatga gtctgcgggc   5880
ccgtttgctc agactacacg gtcgaatact cctacgaatt tgttgtggcc ttctgagatt   5940
gccgcgttga agaagttgtg tgagggtgat agtggggctg gtaaggcgtt cactattaca   6000
ccgaccatga ggagtagtgt gaatcattct gaggtgtgtt ccacggtgtg gggtgagggt   6060
tgctcgtgcg ggtcgaatat taacggctat gctggcccgt tgtgggagat atgatatgac   6120
cggttttcct tacggtgaaa cggttgtgat gcttcagccg actgttcgtg tcgatgatct   6180
tggtgacaag gtgtgaggatt ggtctaagcc tgtcgagact gtgtaccata acgtggccat   6240
ctatgcttcc gtttcgcagg aggatgaggc cgcggggcgt gactcggatt atgagcattg   6300
gacactgctg ttcaagcagc ctgtcaaggc tgctggttat cggtgtcgtt ggcgtattcg   6360
gggtgttgtg tgggaggctg acgggtctcc tatggtgtgg catcatccga tgtctggctg   6420
ggatgctggt acgcaggtta atgtgaagcg taagaagggc tgatgggttg tggcacgtga   6480
tgttgatgtg aagctgaact tgccgggtat tcgtgaggtg ttgaagtctt ctggggtgca   6540
gggcatgttg gctgagcgtg gtgagcgtgt caagcgtgcg gcctcggcga atgtgggcgg   6600
taacgcttac gatagggccc agtatcgtgc cgggttgtcg tctgaggtgc aggttcaccg   6660
tgttgaggct gtggcgcgta ttggcaccac ctataaggg ggtaaaagga ttgaggctaa   6720
gcatggcacg ttggcgaggt cgattggggc tgcgtcgtga tcgtttacgg tgatcctcga   6780
atatgggcta aacgtgtgtt ggcggatgat ggttggctgt ctgatgtacc gtgcacgggt   6840
actgtgccgg atacatttga gggtgatctg atttggttgg cgttggatgg tggcccggag   6900
ttgcatgttc gtgagcgtgt ttttttgcgt gtgaatgtgt tttcggatac gccggatcgt   6960
gctatgtctt tggctcgccg ggttgaggct gtgctggctg atggtgtgga tggtgatccg   7020
gtggtgtttt gcaggcgttc gactgggcct gatttgctgg tggatggtgc acgttttgat   7080
gtgtattcgc ttttttgagct gatatgtagg cctgcggagt ctgaataagc ttattgtttt   7140
tgttttaatg taattgtttg atatttaatg ggggttgtga tggctgctac acgtaaagcg   7200
tctaatgttc gttcagcggt tactggcgac gtttatattg gtgacgcgca cgcgggtgat   7260
tctattaagg gtgtggaggc ggttccttcc gggcttacag ctttggggta tctgtctgat   7320
gacgggttta agattaagcc tgagcgtaaa acgatgatt tgaaggcttg gcagaatgcg   7380
gatgttgttc gcactgtggc tacggagtcg tctatcgaga tttctttcca gctgattgag   7440
tcgaagaagg aggttatcga actgttttgg cagtcgaagg ttactgccgg atctgattcg   7500
ggttcgttcg atatttctcc tggtgccaca acaggtgttc acgccctgtt gatggatatt   7560
gttgatggcg atcaggttat tcgctactat ttccctgagg ttgagctcat tgatcgtgac   7620
gagattaagg gcaagaatgg cgaagtgtac gggtatggtg tgacgttgaa ggcgtatcct   7680
gcccagatta ataagactgg taatgcggtg tcgggtcggg ggtggatgac ggcttttaaaa   7740 gctgatactc ctccgactcc tccgccggcc ccggttcctc cgaagcctca gccggatccg   7800
aatccgccgt ccggtaactg atacacgatt ttagggatt gttaatagat gagtgacact   7860
ggtttcacgt tgaagattgg tgatcgtagc tgggtgttgg cggatgcgga ggagacggct   7920
caggctgttc ctgcccgcgt tttccgtcgt gccgccagga ttgcccagtc ggggagtct   7980 gcggatttcg cccaggttga ggtgatgttt tctatgttgg aggctgccgc cccagctgac   8040
gcggtggagg ccctgagggg gcttcctatg gttcgtgtgg cggaggtttt ccgtgagtgg   8100
```

```
atggaataca agcctgacgg taagggtgcc tcgctggggg aatagtttgg ctccacggcc    8160
tgattgatga ttatcgtggg gccatcgaat acgatttccg caccaagttt ggtgtttctg    8220
tttatagtgt tggtggcccg cagatgtgtt ggggtgaggc tgtccggctg gctggcgtgt    8280
tgtgtaccga tacgtctagc cagttggcgg cccaccttaa tggttggcag cgcccgtttg    8340
agtggtgcga gtgggctgtg ttggacatgt tggatcatta caggtctgct aatagtgagg    8400
ggcagccgga gcctgtggcg aggccgactg atgagcgtcg ggcaaggttt acgtctgggc    8460
aggtggacga tattttggcg cgtgttcgtg ccggtggcgg ggtgtctcgc gagattgata    8520
ttatggggtg aatagtgtat gtctggtgag attgcttccg catatgtgtc gttgtatacg    8580
aagatgcctg gccttaaaag tgatgttggt aaacagttgt cgggtgttat gcctgctgag    8640
gggcagcgtt cgggtagcct gtttgctaaa ggcatgaagt tggcgcttgg tggtgcggcg    8700
atgatgggtg ccatcaatgt tgctaagaag ggcctcaagt ctatctatga tgtgactatt    8760
ggtggcggta ttgctcgcgc tatggctatt gatgaggctc aggctaaact gactggtttg    8820
ggtcacacgt cttctgatac gtcttcgatt atgaattcgg ctattgaggc tgtgactggt    8880
acgtcgtatg cgttggggga tgcggcgtct acggcggcgg cgttgtctgc ttcgggtgtg    8940
aagtctggcg gtcagatgac ggatgtgttg aagactgtcg cggatgtgtc ttatatttcg    9000
ggtaagtcgt tcaggatac gggcgctatt tttacgtctg tgatggctcg cggtaagttg    9060
cagggcgatg acatgttgca gcttacgatg gctggtgttc ctgtgctgtc tttgcttgcc    9120
aggcagacgg gtaaaacctc ggctgaggtt tcgcagatgg tgtcgaaggg gcagattgat    9180
tttgccacgt ttgcggctgc gatgaagctt ggcatgggtg gtgctgcgca ggcgtctggt    9240
aagacgtttg agggcgctat gaagaatgtt aagggcgctt gggctatttt gggtgctacg    9300
gctatgcgcg cgtttcttaa cggcctgcgg cagattttg ttgcgttgaa tccggttatt    9360
aagtctatca cggattctgt gaagccgatg tttgctgccg tcgatgctgg tatccagcgg    9420
atgatgccgt ctattttggc gtggattaac cgtatgccgg ctatgatcac gagaatgaat    9480
gcacagatgc gcgccaaggt ggagcagttg aagggcattt ttgcgagaat gcatttgcct    9540
gttcctaaag tgaatttggg tgccatgttt gctggcggca ccgcagtgtt tggtattgtt    9600
gctgcgggtg tggggaagct tgttgcaggg tttgctccgt tggcggttgc gttgaagaat    9660
ctgttgccgt cgtttggtgc tttgaggggg gccgccgggg ggcttggtgg cgtgtttcgc    9720
gccctgggtg gccctgtcgg gattgtgatc ggcttgtttg cggcaatgtt tgccacgaac    9780
gcccagttcc gtgccgctgt tatgcagctg gtggctgtgg ttggtcaggc gttgggccag    9840
attatggcag ctgtgcagcc gctgtttggt ttggttgctg gcgtggttgc caggttggcg    9900
ccggtgttcg gccagattat cggtatggtt gctggtttgg ctgcccggct ggtgcctgtt    9960
attggtatgc ttattgcccg gctggttcct gttatcaccc agattattgg tatggtaacc   10020
caggttgctg ccatgttgtt gcctatgctg atgccggtta tcaggctgt tgttgctgtg   10080
atacggcagg ttattggtgt cattatgcag ttgatacctg ttttgatgcc ggttgtgcag   10140
cagattttgg gtgctgtcat gtctgttttg ccgccgattg ttggtttgat acggtcgctg   10200
ataccggtga tcatgtcgat tatgcgtgtg tggtgcagg ttgttggtgc tgtgctacag   10260
gtggtggccc gtattattcc ggttgttatg ccgatttatg tttcggtgat tggattcatt   10320
gccaagattt atgctgcggt tatcgttttt gaggctaagg ttattggcgc tattcttcgt   10380
actattacgt ggattgtgaa tcattcagtg tctggcgtga ggtctatggg cacggccatc   10440
cagaatggct ggaatcatat taaatcgttt acgtctgcgt ttattaacgg ttttaagtcg   10500
```

```
atcatttctg gcggcgtgaa cgcggttgtg gggtttttta cgcggcttgg tttgtcggtt   10560
gcttcccatg tgaggtccgg ttttaacgct gcgaggggtg ctgtttcttc cgccatgaat   10620
gctattcgga gtgttgtgtc ttcggtggcg tctgctgttg cgggttttt cagttcgatg    10680
gcgtctcgtg ttcggaatgg tgctgtgcgc gggtttaatg tgcccggag tgcggcttct    10740
tctgctatgc atgctatggg gtccgctgtg tctagtggtg tgcatggtgt gctgggtttt   10800
ttccggaatt tgcctgacaa tattcggcgt gcgcttggta atatgggtc cctgttggtg    10860
tcggctggcc gtgatgtggt gtccggttta ggtaatggta tcaagaatgc tttgagtggc   10920
ctgttggata cggtgcgtaa tatgggttct caggttgcta atgcggcgaa gtcggtgttg   10980
ggtattcatt ccccgtctcg ggtgtttcgt gacgaggttg gccggcaggt tgttgccggt   11040
ttggctgagg gtattactgg taatgctggt ttggcgttgg atgcgatgtc gggtgtggct   11100
gggaggctgc ctgatgcggt tgatgcccgg tttggtgtgc gatcgtctgt gggttcgttt   11160
accccgtatg gcaggtatca gcgcatgaat gataagagtg ttgtggtgaa tgtgaatggg   11220
cctacttatg gggatcctgc cgagtttgcg aagcggattg agcggcagca gcgtgacgct   11280
ttgaacgcgt tggcttacgt gtgattttgg gggtgtggtg catgtttatt cctgacccgt   11340
ctgatcgttc tggtttgact gtgacttggt ctatgttgcc gttgattggt aatgatccgg   11400
agcgtgtgct tcatttgacg gattatacgg ggtcgtctcc gataatgttg ttgaatgatt   11460
cgttgcgcgg tttgggtgtt cctgaggtgg agcatttttc tcaaactcat gttggggtgc   11520
atggctcgga gtggcgcggg tttaatgtga agcctcgcga ggtgacgcta ccggtgttgg   11580
tgtcgggtgt tggcccggat ccggtgggcg gttttcgtga cggttttttg aaggcgtatg   11640
acgagttgtg gtctgctttt cctcctggcg aggtggggga gttgtctgtg aagactcctg   11700
ccggtcgtga gcgtgtgttg aagtgccggt ttgattcggt ggatgacacg tttacggtgg   11760
atccggtgaa caggggttat gcgcgttatc tgttgcattt gacggcttat gacccgtttt   11820
ggtatgggga tgagcagaag tttcgtttca gtaacgctaa gttgcaggat tggttgggtg   11880
gcggccctgt cgacggtaag ggtaccgcgt ttccggtggt gttgacgcct ggtgttggtt   11940
cgggttggga taatctgtct aataagggtg atgtgcctgc gtggcctgtg attcgtgttg   12000
aggggccgtt gtcgtcgtgg tctgtgcaga ttgatggttt gcgtgtgtcc tcggattggc   12060
cggtggagga gtatgattgg atcactattg atacggatcc tcgtaagcag tctgcgttgt   12120
tggacgggtt tgaggatgtg atggatcgtt tgaaggagtg ggagtttgcg cctatcccgc   12180
ctggcggttc tcggagtgtg aatattgaga tggttggttt gggtgccatt gttgtgtcgg   12240
tgcagtacag gttttgagg gcttggtgaa tagttgatgg ctggttttgt tccgcatgta    12300
acattgttta caccggatta tcgccgtgtg gcgcctatca attttttga gtcgttgaag    12360
ttgtcgttga agtggaatgg tttgtccact ttggagttgg tggtgtctgg tgatcattct   12420
aggcttgacg ggttgactag gccgggtgcg cggcttgtgg ttgattatgg tggtggccag   12480
attttttctg ggcctgtgcg tcgggtgcat ggtgtgggtc cgtggcgttc ttcgcgtgtg   12540
actatcacgt gtgaggatga tattcgtctg ttgtggcgta tgttgatgtg gcctgtgaat   12600
tatcgtcctg gtatggttgg tatggagtgg cgtgcggatc gggattatgc ccattattcg   12660
ggtgcggcgg agtcggtggc taagcgggtg ttgggggata atgcttggcg ttttccgtct   12720
ggtttgttta tgaacgatga tgagagtcgt ggccgctata ttaaggattt tcaggtgcgg   12780
tttcacgtgt ttgccgataa gttgttgccg gtgttgtcgt gggctcggat gactgtcacg   12840
```

```
gtgaaccagt tttgagaatgc gaagtttgat cagcgtggtt tggtgtttga ttgtgtgcct    12900
gctgtgaccc ggaaacatgt gttgactgcc gagtcgggtt cgattgtgtc gtgggagtat    12960
gtgcgtgacg ccccgaaggc gacatctgtg gtggttggtg gccgtggcga gggtaaggat    13020
cggctgtttt gtgaggatgt tgattcggcg gccgaggatg attggtttga tcgtgtcgag    13080
gtgtttaagg atgcccgtaa cacggattcc gagaaggtgt ctctcttcga tgaggctgag    13140
cgggtgttgt ccgagtcggg ggctacgtcg gggtttaaga ttgagttggc tgagtcggat    13200
gtgttgcggt ttggtcccgg caatctgatg cctggggatt tgatctatgt ggatgtgggt    13260
tctgggccta ttgcggagat tgtgcggcag attgatgtgg agtgtgtatc gcctggtgat    13320
ggttggacga aggtgactcc ggttgcgggg gattatgagg ataatccgtc ggccctgttg    13380
gctcgccgtg tggctggttt ggctgcgggt gtgcggggatt tgcaaaagtt ttagtaagtg    13440
attggggttt gttgtgggta ttgtgtgtaa agggtttgat ggtgtgttga ccgagtatga    13500
ttgggctcaa atgtctggtc tgatgggtaa tatgccgtct gtgaaggggc ctgacgattt    13560
tcgtgtcggc acgacgattc agggttctac ggtgttgtgt gagatcctgc cggggcaggc    13620
ttgggctcac ggggtgatgt gcacgtcgaa tagtgttgag acggtgacgg gtcagcttcc    13680
gggcccgggt gagactcgat acgactatgt ggtgttgtct cgggattggc aggagaatac    13740
ggccaagttg gagattgttc ccggtgggcg tgcggagcgt gccagggatg tgttgagggc    13800
tgagcctggc gtgtttcatc agcagctact ggcgactttg gtgttgtcgt ctaacgggtt    13860
gcagcagcag ttggataggc gtgctgtggc ggctagggtt gcgtttgggg agtctgctgc    13920
gtgtgatcct accctgtgg agggtgaccg tgtgatggtt ccttcggggg ctgtgtgggc    13980
taaccatgcc ggcgagtgga tgttgttgtc tcccaggatt gagacgggtt cgaagtcgat    14040
catgtttggt ggttctgctg tgtatgctta cacgatcccg tttgagcgcc agttcagtag    14100
tccgcctgtt gtggtggcgt ctatggctac ggcggctggg ggcacggcac agattgatgt    14160
gaaagcctac aatgtgactg cccaaaattt tagtttggcg tttattacga atgatggttc    14220
gaagccgaat ggtgtgcctg cggtggcgaa ttggattgct gtcggcgtgt gactgcacgg    14280
gtgttgtggc ggatggtgtg atgttggggg gctgtggtgt cgtggtttac tcctgcactg    14340
gtggcctcta tttgtaccgc gttggccacg gttttgggtt ctgttcaggc tgtcacatcc    14400
cggtctagga agcgtttacg caggctgtcg gctcaggtgg atgcgatgga agagtatacg    14460
tggggtgtgc ggcgcgaggt gcgaaggttt aacgccgggc ttcctgatga tgtggagccg    14520
atgcatcttc ctgatttgcc cgagttttg aaagatactg ttgatggtgg aggtgagtag    14580
ggttgaggga gttggaggag gagaagcggc agcgccgcaa ttttgagaag gcttcactgg    14640
tgttgttgtt tttgtcgctt gtgttgttgg cggtggttgc tgcgggtgct ttgcgtttcg    14700
gggctgtatc ctctgagcgg gattcggagc aggcgagggc ccagtcgaat ggtacggctg    14760 ccagggggttt ggctgcccgt gtgaagcagg cgtgtgcttc gggtgggtg gagtctgtgc    14820 gtcttcaccg ttctggtttg tgtgtggatg ctgtgcgtgt tgagcagcgt gttcagggtg    14880
tgccgggtcc tgccggtgag cgcggcccgc aaggcccttc aggtcctgcc ggccgggatg    14940
gtgttaatgg ttcggctggg ctggttgcc ctgttggtcc gcaaggttct ccgggtttga    15000
atggtgtgaa aggtcctgac ggcttgcctg gcgctaacgg ttcggatggc cgtgatggtg    15060
ttccaggtcg tgcaggtgct gacggtgtga acgcgttga cggcgctgat ggtcgggatg    15120
gttctgccgt tgagcgcggc ccgcaaggcc cttcaggtcc tgccgggccg caaggtcac    15180 agggtgaacg gggtgagcgt ggtcccgccg gtgcgaatgg atcggatggc catgatggta    15240
```

```
aggatgggcg ctcggtggtg tctgtgtact gttccggggg ccgcctggtt gtgaaatata    15300
gtgacggtgt ggcttccacg atatcgggtt cggcggcctg ccagggtgtg aaaccgtcgc    15360
ctctagtgac tatatcatcc cacaaataga aaggagtggc tgtgatggtg gtgtttggtg    15420
gtggtgtgtt gtgagatata ttcctgcggc gcatcattct gccggctcga atagtccggt    15480
gaatagggtt gtgattcatg cgacgtgccc ggatgtgggg tttccgtccg cctcgcgtaa    15540
aggacgggct gtgtccacgg caaactattt cgcttcccca tcgtctggtg gttcggcgca    15600
ttatgtgtgt gatattgggg agacggtgca atgcttgtcg gagtctacga ttgggtggca    15660
tgccccgccg aatccgcata gtttgggtat agagatttgc gcggatgggg gttcgcacgc    15720
ctcgttccgg gtgccgggc atgcttacac tcgtgagcag tggctggatc ctcgcgtgtg    15780
gcctgcggtt gagcgtgccg ccatcctgtg tagacgtttg tgtgacaagc atggtgttcc    15840
gaaaaggaaa ctgtctgtgg ccgatttgaa ggccggtaaa cggggtgttt gcgggcatgt    15900
ggatgttacg gatgcgtggc atcagtcgga tcatgacgat ccggggccgt ggtttccgtg    15960
ggacaaattt atggctgtgg ttaatggcca cggcggcggt tcaagtagtg aggagttgag    16020
tatggctgat gtacaagcgt tacataatca gattaaacag ttgtcggcac aggtggccca    16080
gtcggtgaat aagctgcatc acgatgttgg tgtggttcag gttcagaatg gtgatttggg    16140
taaacgtgtt gatgccttgt cgtgggtgaa gaatcctgtg acggggaagc tgtggcgcac    16200
taaggatgct ttgtggagtg tctggtatta cgtgttggag tgtcgtagcc gtcttgacag    16260
gctcgagtct gctgtcaacg atttgaaaaa gtgatggtgg tttgttgtgg gtaaacagtt    16320
ttggttaggt ttgctggagc gtgccctgaa aacttttgtt caaacgtttg ttgccgtgtt    16380
gggggttact gcgggtgtca cctatactgc ggagtcgttt cgtggtttgc cgtgggaatc    16440
cgcgctgatc acggcaacgg ttgctgctgt cctgtcggtt gctacctcgt ttggtagccc    16500
gtcgtttgtg gccggcaagc ccggcaagca gccccaggtg gatgcgggtt tggttccacc    16560
ggatgatggg ggcttggttg agccgcatat ggtggatgtg tcggatcctg gcatgatcga    16620
gccgacggat gatgcggatc ttgccggcta tgagcctcgg cgtgcagccg agtcggaggt    16680
tggcacggta gagtctactg ttgcataatt gaatatagat gtgtgcccca gcggtgctgc    16740
cacgattgtg tggtggcggc tgctggggca ctatttttgt atatgcggtg tggctatgat    16800
tcgttgctgt cgatggtgtc ttcgagcatc tgatacaggt ggaggcaggt agagatagtt    16860
tcgctggcct gatcgagaac gttccggccg ataacgtttt tgtggttgtc gcggtggcgg    16920
atgatagccc acatgatctc gtcggctgcc gcctgtaata gtttggcctg gtatgcgatt    16980
ccggcgagcc agtctagtgc ttcctggctt gtatagggc tctggtcctc gctgttgccg    17040
cgggtgttgc tgttgtttgt ggggtgtcct gcactgtcgc atagccacag gatttcgctg    17100
cactcgtcta gcgtgtcttg gtcgatagcg agatcgtcga ggctgacatt gttgacggta    17160
aggttcacgt tgtcgaggga gatgggtaca ccgtactggt tttcgacact gtcaacaatg    17220 tttttccagct gttgcatgtt ggtgggctgt tgttggacga tacggtgtat cgctgtgttg    17280
agggtggtgt aggtgatgtt gtgtgtgttg tccatggttt ttatgccatt ccttcgttat    17340
cgtctggcat gtagtatgtg ctgtttgcgt actcggttaa cgtcatcagt gtttggtctg    17400
cccactgttt cacggtttgc cgggtgactc cgagtcgttg ggcggctgtg gcgtaggttt    17460
gatcataccc gtatacttcc cggaatgctg ccaacctagc taggtgtttc ctctgtttgg    17520
atggttcaca ggtgagggtg tagtcgtcga tggctagctg tagatcgatc atggagacga    17580
```

```
tgttgttgcc gtggtgttgt ggcgcggttg gtggggtgg cattcctggc tccacggagg      17640
gtttccaggg gccgccgttc cagatccatt gggcagcttg gatgatgtcg gcggtggtgt      17700
aggttcggtt cactggtcac ccctgaaca ggtcgttggt gttgttggtg tcgaatcgtc      17760
cgacgcagtg gcagtagtcg tacatgagtt taataatgtg ttggtggtct cccaaatagg      17820
tgtttccgct gatgctgtat gtggctgtgc cgtctttcgc gatggtgtat ttggcggtga      17880
tggtttcggg gttttcggtg tcggtgatga ttgctgtggt ggtggcgcct actgtttgga      17940
gtatggtggt ttgggttccg tcgtcgatgg tggttttaac catggtgtgt gttttccctt      18000
ttgttagttg cttgtttggt tgtcggctag atgaataata tcgggtaaag gtttcggctg      18060
gtctaggtgt tgtatggttt tgttggctag ccgtttggct accctgtaac acattttggt      18120
gtagtgtttg ttgtctaggt tgtggtattg ttcccgcacc gcaatatata gcagggagtc      18180
ttggtacagg tcgtctgcac tgattgcggg gtagtgtgcg gctgttttgg tgcatgcccg      18240
gttgagtgtg cgaagatgat ggtctgtggc ccacacccac gatgcggtgg tggccaggtc      18300
ggcttttgtt ggtcgtctgc tcatggcact atttcatctc gctatctgat agttgtttgg      18360
tgttttgttg tggatagtgt agcacactag tcctgggtgg ccggtggtgc ctgtgcggtg      18420
acggaaccat gtggattcgc cttccatgga tgggcattgg atgaaggtgc gttgtccttg      18480
ctcggagatt tctaggtggt gccggtgccc ggccatgaga atattagata cggtgccgtt      18540
gtggaattct tggccgcgcc accaatcata gtgtttaccg gtgcgccatt ggtgcccgtg      18600
ggcgtgcagt atccgtgtgc ctgccacatc aacggtggtg gtcatttcgt ctcggctggg      18660
gaagtggaag tgtaggttgg ggtattggtt attgagctgg taggcttctg cgatggcccg      18720
gcagcagtcc acgtcgaatg agtcatcgta ggtggtgact cctttaccga agcgcacggc      18780
ttcaccatgt tgccggggga tggatgtgat ggtcacattt ttgcagtggt cgaattggtg      18840
gatgagttgc atcatggcca tgcgggtgag cctgatttgt tcggtgaggg gtgtttgtgt      18900
tcgccaggcg ttgttgcctc cttgtgacac gtatccttcg atcatgtcgc cgaggaaggc      18960
gatgtggact cgttcgggtt tgcctgcttg ttgccagcag tgttttgcga ctatgaggga      19020
gtgtaggtag ttgtcggcga agtgtgctgt ttctccgccg gggatgcctt tgccgatttg      19080
gaagtctcct gccccgatga cgaaggctgc ggtgctgtag tcggtgtggg tgtcttgttc      19140
gggttttggg ggtgtccatt cggctagttt atcgacgagt tcgtctaccg ggtaggggtt      19200
tgttgcgggt tggtggtcga tgattttttg tatggatcgg cctgtttctc cgttggggag      19260
tgtccattcg gagatgcgtg tgcggcgcac ggtgccgttg gctagattgt cgtcgatggt      19320
gtcgatggcg ttgtcgtggt tggctagctg tgtgagtagc cggtcaatat tgtctatcac      19380
tgggtatcct cctcttgcgg ggtggtgctg gcttgtttgc ggcgatagtc tttaataacg      19440
gtggcggaga tggggtatcc tgcctgggtg agctgttttg ctagccatga ggcggggata      19500
gacctgtcgg cgagcacgtc ggcggctttg ttgccgtagc gttgaataag ggtttcagtt      19560
ttggttgcca tgatgtccta tcggttgtgt ggtgggctgc catcctgtgc ggcagtcgcc      19620
gtcgtgtcct ggtttgcgtg tgcaccacga tacggttccg tctgtgtggt tgagtgtttt      19680
accgcacatg acgtttcgga gatgctccgg cagctggtca tcctggttgc tggtttgtgt      19740
gtcgaagagt gttttctggt tggtgaaatg ttctgacacg gtgccgttat gcacgggtag      19800
tatccatgtt ttccattgtt gttgtagcct ggtgttccag tggaattgtt tggcggcgtt      19860
ttcggcctgt tttaaggttt tgtggtagcc gactagtatg cgttgatgct gctggtctgt      19920
agggtttggg cctcgccagt attgtgccgc cacggcgtag cggttgctgt ctgtgaaggc      19980
```

-continued

```
gtcccagcag tattcgataa tgtgttgcaa catactgtct ggcaggctgt cagggttgat    20040
gttgatgttt tggtgataa tgtcacggat ggcttgccgg tttttggtgg tgggtttgaa    20100
cgagatgctc acgatagtac cggctggtcg tcttgcatga actggttgaa ggtgttgttc    20160
ccggcgtgtt gggcttgtgt tatttgttgg tcggtccagt ctgggtgttg ctgtttcaga    20220
tagtgccagt ggcacgcatt gtaggtttcg tcttgtagcc gtgtgagatg ttttcggtg    20280
atgatttgtt tccacatggc ccatgacacg tcgagccggt cgaggatttc gagggctggg    20340
atgttgaatt ggttcaggaa gaggatttcg tgggtgtagt agttttctc gtaggcgtcc    20400
catccgcttc ggtgcctgtt gggctggttt ttggggtagg cttcccggca tactttgtgt    20460
aaacgcttgg ccatgtcgtc gggtagttta atgtcggggt tggcgcggat catggatcgc    20520
atcccatcat aggtggtgcc ccaggtgtgc atgatgtagg tggggtcttc tccgtcggcc    20580
cattttctg cacagatggc gaggcggata cgcctcctgg cagcttggct ggtgttgcgc    20640
cggttgggga ttgggcacgt gtcgagggga tccatgatgt tttagtgtac ctttctggtt    20700
tcgtgttgtt gacaggtttt actgtagcac agtgtctagt gcgtgtgtca accctgtttt    20760
tccggcttga aggtaggtgt ctgtgacatc ccctagggtg aggggcacgt gcacagcttg    20820
ggggagtgcc gcctggaggg tttgggccat ctggtcgcct gcggggtctg ggtctgacca    20880
gatgtagatg tggtcgtagc cttcaaaaaa tttggtccaa aaatttgcc acgaggttgc    20940
gccgggtagg gcgacggccg accatccgca ttgttcgagg atcatggagt cgaattcgcc    21000
ttcgcaaatg tgcatttcgg ctgccggggtt ggccatggcg gccatgttgt agatggagcc    21060
tgtgtctcct gccggggtta ggtatttggg gtggttgtgg gttttgcagt cgtgcgggag    21120
tgagcagcgg aaacgcattt ttcttatttc ggctgggccg ccccaaacgg ggtacatgta    21180
tgggatggtg atgcactggt tgtagttttc gtggcctggg atggggtcat tgtcgatgta    21240
tccaaggtgg tggtagcggg ctgtttcttc gctgatgcct cttgctgaga gcaggtcgag    21300
tatgttttcg aggtgggttt cgtagcgggc tgaggctttc tggattcggc ggcgttccgc    21360
aatgttgtat gggcgtatgc tgtcgtacat ttgggttttc ttcttctaat cgttgttgta    21420
gcttggcgag tccgcctccg acaccgcatg tgtggcagta ccagacgccc ttgtcgaggt    21480
tgatgctcat ggagggctgg tggtcgtcgt ggaacgggca gagtatgtgt tgctcgttcc    21540
tggacggatt gtaccgtatc tgataatggt cgaggaggcg gcaggtgtca gaggtgtggg    21600
aggagctcgt tgagggttga taccacatag gcttcactcc atggcttgtt gcgctgtttc    21660
atcactacga gtccgatggt ggaattgttt tgtttgtttc ggtgtgtttc gtagttgcgt    21720
gcctccggc tggcttgttt cacgaattgg gctaggtgtg gttgcccggc tttcgcctcg    21780
ataatgtagg ttttatggcc ggttgtgagg atgaggtcgc cttcgtcttc gcggccgttg    21840
aggtggaggc gttcgatatt gtgtccggtg tcgcgtagct ggtggaggag tcttgtttcc    21900
cattcggctc cggcccgccg gttgcgtgcc tgctgtgtgg ccatagtttt ttagagtcct    21960
ttgtgtgttg tggtcatgtt ccagggctgt ttttcggcga gtggcccgaa gaatgtgtat    22020
tcggggtatg ctctgagtcg ttcgtatcgg gtgccgtcgg ggctggattt gcctgtgcgc    22080
tgtttgagta cggcgatgcg tgcctctgcc ggtatcgata gcccgttgcc gttatcctcg    22140
ccaccataca atgagactcc gaggatgagt tgtggttttt cggagaggcc gttttttgatt    22200
tctcgccgtg ctgcgggtg ttcgatgtcg gttccggttt tgtcggttgc gtggtgtgtg    22260
acaataatgg tggagccagt atccctgccc aatgctgtga tccattgcat ggcttcttgc    22320
```

```
tgtgcctggt agtcggattc gcagtcttga atgtccatca ggttgtcgat aacaatgagt   22380
ggtgggaagg tgttccacat ttccatgtag gcttgtaact ccatggtgat gtctgtccat   22440
gtgatgggtg actggaatga gaatgtgatg tgttggccgt ggtggatgct gtctcgatag   22500
tattctggcc cgtagtcgtc gatgttttgt tgtatttgtt gggtggtgtg ttgtgtgttg   22560
agggagatga ttcgtgtgga ggcctccag  ggtgtcatgt cccctgatat gtagagggcg   22620
ggctggttga gcatcgctgt gatgaacatg gctagccctg attttggct  gccggaccgc   22680 cccgcgatca tcaccaagtc gcccttatgg atgtgcaaat cttggttatc atatagtggt   22740
gcgagttgtg gtatgcgggg tagttcggct gcggtttggg aggctctctc gaaggatcgt   22800
tgtagagaga gcatcgggac cttaatctat ctgtctgttg gttgtgtggc tggtcagatg   22860
gagtcgatat cgatatcagc atcagcagag gctgaagtgt catctagctg accattatcg   22920
cgcttgtcta cgtattcggc aaccttatcg tagatggcgt cgtccaatgt tttgagcacg   22980
accgcgttga aaccgttttt ggtgcgcacg gtggctagtt tgaaggcctg ctcctcgcca   23040
aggtatgcct ctagttcgcg gatcatggag tgtgggcggt cgttattgcc gcgggctttc   23100
tcaataatag cgttggggat ggtttctggg gtgccgttgt tgagatcgtc tagggtgtgg   23160
aagatggtga catcagcgta gatgcggtct gcgacctgtc caccgtagcc ttcagtgttg   23220
tgctggacgt cgtgcacttt gaaggcgatg gccgtggcgt cctggtttcg ggaggggttg   23280
aagaaggtgc tgttgctgtt gttgcggtag tttgcgagtc ccataactat tgtttccttt   23340
tactgttgtg tctgttttg  ttggcttata ttggtttatc gggtgaggct gtttcgctta   23400
gtgcggaaag cgtcggaaac atcactgtta ctggtgatga tcttcttgta ctgttttaga   23460
aggtctgcta gctgtgcctt gcttgttgca ttgttgattt tgttgatgac gatggtgttt   23520
tctttggatg cgattttgtt gacgtagtct ttggctgcct ggttgtatcg gtcttggagg   23580
atgattgatg cgctcgctac gagtgttgct agatcccagt cttggacac  gtcatcgttt   23640 ttgagtccgc ctagcaggtc gatgatggcc tgttttgtct gctctgctgt gtctcctcgg   23700
atgaccgccc atggtgcagc atagtctcca ccatatttga gtgtgatcgt gagtcgatca   23760
ttgtcgatct tgtctttatc tgtcatttgg tgtccttttc tttattgtct gtttctggtg   23820
gctgtacggt ggattctacc gggtatctgt acgagttttt gccgttgacg gcccagcagg   23880
cgtctcgtac ggggcatcct ttacagagtg ttgtgacgtg ggggacgaag atgccttcgc   23940
tgattccttt cattgcttga ctgtacatgg atgatacatg ccggtaggtg ttgttgtcaa   24000
ggtcgtagag ttcggtggat gtgccttgtg tcggggactt gtcgtcgttg cggctggtgg   24060
ctggcgtcca aaacatgcct ttcgtgacat ggatgtcgtg ttggttgagc atgtaccggt   24120
atgtgtgcag ctgcatactg tcggcgggta ggcgtccggt tttgaggtcg aggatgaagg   24180
tttcgccggt gtcggtgtcg gtgaaaacac ggtcgatgta gccgactatt tttgtgtcat   24240
cgtcgaggat ggtttctacc gggtattcga tgcctggttt accgtccagg attgcggtga   24300
tgtattctgg gtggttgcgc ctccatgttt tccagcggtc cacaaaggtg gggccgtaaa   24360
ccatccacca gtcgtagtct ttcttgtgtg gtccgcctga ctcgcacatg tttttgcata   24420
ttctgccgga gggtttgatt tctgtgcctt cggattcggc gagggctacc tgggtgtcga   24480
aaatgttttt gaaggatgag agtttgtctg gcagtgcagg gtattcggcg ggattgtaca   24540
ggtgtaggtc gtattgttcg gtgatgtggt gtatggcgct tccggcgatg gtggcgtacc   24600
aggtgtggtg ttgggcgtga tagccgtggg ataggcgcca tttttctccg cattcggccc   24660
actgggtgag tgaactgtag gagatgtgtc ctgggtggct gatggttttc gggtattgtg   24720
```

```
ctagaggcat tacttgtcgc ttgtgttcca tgtgttgcgg gtgtcttggc cggcgtggtg   24780
ttgctggtag gcgaggagtg cgaggcagtg ccaggctgcg tgtgctagat gggtagccc    24840 ggattcgtgg tcgaggttgt tgccttgctg ccatgatagt agatgcctgt agagggcgtc   24900
gacactgtgg ctccacgggt atcctccggt ccagttgttg tcgccatatt tggtggcacc   24960
gtatccggct acttcgccta gggcgtgaag ggatgctggg tcgatgaggg agagcctgca   25020
gagtttcaat tcttttcggg caccgctgtt ggggtcggtg tacatgcggg tgggctcatc   25080
catggggtgt gtgctcctta agggtgggtt actggttgtt gttgtgggct agggcggcgg   25140
cgagaataat gatggcgagg gtttcggcta tcagtatggg tgttgtgatc atttggtgtc   25200
tcggggattg ttggtgagtg ttgaggcacc caggagggtg gcgagggcgc atgcggcaat   25260
aatggcgagg gctgccttgt gtggggtgcc ggttgcgtac atccatgtga tgatggcacc   25320
ttggatccag gctaggctgg tgaagaaggt ttcgtagctg tgcagctcaa tgttgttgtt   25380
gggtgtgttc atgcttgctc ctgaagaatg gtgttgatgg tttataaat gttgtacagg     25440 tcggtttcga tagataacag ttggttgatt tggtggtcga gatcaatgtc tgggttgagt   25500
gtgttgatgc gggaggcaat atcggtggct gtgcgtagtg tgccgccggt gtggtgaata   25560
atgtgtgccg tgtcggcgag tccggtggtg acggcgtagt gggataggag aggcatagcg   25620
gggatgctcc ttggcgggtt actgttgcgg gttgatgttg aggtcggtga cgtgcggtga   25680
gttttctgtt ccggtgacga ggcagtggac ggtgacgggt agtttggatg ctcccggctg   25740
gcggacggtg gcgccgtaga cgatgctgaa tgtgtcttta ccgatggttt tgtggagttg   25800
gaggtcgatg tcggggttgc cgttccagtt gacaccttgc gctgcggcct gttgttcggc   25860
tttgtggttg caggtgtgtg ctgccgtgat catggtgagt ccggtggcgg tttcttcacc   25920
ccttgcttgg gcttgcttgt gggctttggc ctgctcggct tgtagggatc gggtggcggc   25980
tgcctgccgt gccgctttct cggctttgcg ctgttgggta gtcttggggg tccatgtggt   26040
gttggctgtg gttgcctgtg gggctggctg tgaggtgagt ggcgggttgt cgtctggtgc   26100
tggcatgaat gaggcggcgg caatgatggc ggctgtgatg cctgcgatgg tgtagccgtt   26160
tttcttgttc atgttttgtg tcccctttcc ggggtgttgt tcgttgctga catggttaat   26220
actttcagcg gctgggccca ctgtcaaggc tgcgctcagt ttgtgtgagc gtttggtgtg   26280
tggctagggg ttttgtcatg taagcgtgac atgtcactac cttgcgtcca gtatccatgg   26340
cggttgcgag ccatcccttt ggcgagcatc tcgtccacag tgaggcacct gcggcgattg   26400
gggccttcct tgaccccgtg atcgcctatg cggtgcatgt ccccggcata agtgccatta   26460
aatgtttcgt ggcagactgt gcagtgttct ggtcggtatc cgatgattgt gctatcgcac   26520
ttgtggcatg tccattgcat gattggtcct tctttcgtgt tttaagcttg tgctctgagg   26580
attagagcga ctttcagccc ttgggggtag gattatatag gtcaggtatt tctaggcgat   26640
tctaggctca ttgtgtgtgg ttggggtttt atcgggcgca tagggttagc aggtggccca   26700
cattggtgcg gctcacattc cagtagagtt gcgtggcttc cttactggtg agcggcttcc   26760
actcgtcatg gctgaacacg gtgccatcgg atgcgatgaa cgtgttgggg cgtagcttgt   26820
gaagctcggc ttccacatgc tgccggtagg cttcggcgag gctctcaaaa tccatgtggt   26880
cgcaggagag gttttcgagg cgtgtcaggt cgaaaggctc cgggcagtcg tagctggctg   26940
gagtgtagag ctgggtgaag tggtcggcga tcttctgcat ggcgggttcc tttctggtgt   27000
gtggatggtt tttatcgtgt ggatgcgaca aggatggcgt ctacgtcgat catgtcgatc   27060
```

```
atgtcgttga gttcctcggc ctcattctcg gagaggtggc gccagtcggg tggcccgtat  27120
acggcgccgt cgagggtgac agtccacagg ggccggatga gtcgtatggc ttcttcgact  27180
ttggcgtggt acatgcggcg caccatatcc agatcgatgt cgtctgaatg gtttccggtg  27240
aggctgtgga ggctgagcgg gtcgatttct gtctgcctgt agaggctggt gaatgatggt  27300
gtgatgagtg tgccatccat gagtgtgctc ctttctaggg gttgttgtgg tttctagagt  27360
gtgtgggctg tgaccccaca gtcaaggcta cgctcatttg gattgagcgt ttcatatggg  27420
tgtggcatgg aatctacacc ctcatactgt gtgagatgta tcacatcccc ctggcttggt  27480
gtgcacccct caagactact ctgccgacct ggcgtggagg gtgtagccca gaaatgccgt  27540
ttaaagcttc aggggtacgc ctaggagcgc cttacagggt gggggctagg tatttatacc  27600
cccagcatat tctgatcgat tctagacgac tcccagagcc cgatacacga tcaaccatct  27660
cgacatagac catcagcccc tatcctggtt agctaagcct caactatgtg gacagtgtgg  27720
gacactgtgg gggaagaagg acacggtaca agaaagaggg gggagcatca gccttaaagc  27780
cttaagatct tagcgcttag caccgatggt cttagcagtt agcaccgagc ccttgagggg  27840
gctcggcatc agcctcatcg ggctcagctc atcaggcaca gccctgaaaa gggtacacgc  27900
catcagggaa ggcttgagag tacgaggagc cctagcgacg agtactcgaa agcctgaggg  27960
aacaccctca gtactgatga gcctagcgta ttcggaaagg acgcaagagt aaagtgtgac  28020
agctatccgg gagtgaaacc cgttccgact aggggtttca gccttaacca ccctcaaagg  28080
ttacaagact ctaagaaaat ttaagaaact tcttaggaag aaagttgtgt tcatatcccc  28140
ctaaaaacac ccaaaatagt cctcaaaccc gcctatagag ccaaacagtc aagtttgact  28200
cgtctagacg gcgtatgata ggctggacag gtagccagct ggacgcaagg ccagaaagtg  28260
ctgacgcact tcccgacctc gcttaccatc agtctaccaa acactttaaa gcttcaaggc  28320
ttagcgctaa gcccttaaga tcttaacgct tagcaccgag ccccctcaa gggctcgaca  28380
tcagtcttaa agtcttaaac actttaagta actttaaagc ttcaaggctt agcccttaag  28440
gatctaagtt actataaaag ctttaaacac ttaaagtaac tataaagctt taagagctta  28500
acatttaagg atataaataa acattaaagc tttaagtct taaagtaaat atataacctt  28560
aacacttaag ttaagtataa aaccttaaag gcttagcact taaggatata aacttaacat  28620
cagtgtttaa gacttaaaga gttaaagtaa ctattaagac ttaaaggctt ataagcttta  28680
atactttaag tagctataag actttaaaaa cctgaagtac ttaaagttaa ccatcagtct  28740
taaactttaa tattataagt attaaagctt ataagttata aaagtttta gaagagttaa  28800
agggttaact tctttacttc tcttctctct ttggttcttt ctctcttctc ttcttttctt  28860
catcagggga gaagaggaac ctttaaccgt caacgctgat ggacttttca ccgtgtgact  28920
cgtgtgcttc tggtcgcaag ctcccatcgc acactcccca cactctttca cccgtgcccc  28980
tttacggctt agcgtgttcg tcggaaggcg tacggcgtgt cacgcttaaa cccttaacac  29040
caggtaagac ttaaagtgca tattataagt agaagacttt aaaacctata aggtgttccc  29100
gcttagcccg tgttcctta acgctaggcg ctcagcgcta agatgtgaaa cgtgaacacc  29160
catccacccc cattttctctt ccgtgtcctt ctccttttga caccgctggg gggcgatgtg  29220
atatttctca catgccaggg ggtagtggag aaaacaacca ccccggaacg tttaagacac  29280
cccctcaaac gaacaaaaca gggcctagaa tcgatcagca gggcaccggt agggtattcc  29340
tacccccaga cgattcaagg ccattacagg agcaatgaga ggctcacagg ggccatggga  29400
gattgggggg cgtgatggca cacaccaacc gcacagccag ccaagcccac cggcgctggc  29460
```

-continued

| | |
|---|---|
| gggcaaggct catcacccaa gcccgacaac aaggccaaac cgaatgccca ctctgcggag | 29520 |
| tcaccatcac ctggaacacc cacgacctgc caaccagccc cgaagccgac cacatcacac | 29580 |
| ccgtcagccg gggaggactc aacaccctcg acaacgggca aatcatctgc agaacatgca | 29640 |
| acagaagcaa aggcaacaga acacaaccaa acatcaaatt ccaacaacaa accacaaaaa | 29700 |
| cattgattcc atggtgaaaa acccgccaac ccccaccggg cacacccct gcacacccgt | 29760 |
| gcaagacc | 29768 |

<210> SEQ ID NO 28
<211> LENGTH: 11979
<212> TYPE: DNA
<213> ORGANISM: Artificial Sequence
<220> FEATURE:
<223> OTHER INFORMATION: pANS514 plasmid

<400> SEQUENCE: 28

| | |
|---|---|
| catggttgcg ccatgcagca caggccaagc gtgaggccca agcacgagga ctcgcccgct | 60 |
| gcccactgtg cggcgtctgg atggactacg aggtcggcaa gcgacccaac tcggccgaag | 120 |
| cagaccacat cagaccgcat tcgcttggtg gttcagacga catcgacaac attcgcgtca | 180 |
| tttgtcgtcg ttgcaatcaa tcgcgcggaa acggcctgaa gcgaccaggg cgccaacgtc | 240 |
| agcgtccaat caagcgcatc gagctggccc aaccggcccg cagtggggca tttcctgccc | 300 |
| cgccggcatg aatggaaggg cagtgcggat ggtgcggtcg ggcattcgat cgtgcccgga | 360 |
| cgggtcgccc gcgacgcttc tgctcggccc gctgtcgggt cgccgcgtcc cggtgtgcga | 420 |
| tcccgctggc catgaggtcc cgcactgcgt gggtccgctg cgacggcaag cgccccatca | 480 |
| ccctggctgg cgctccggcc tcatccacgg acccgggcac atggtctggc tggtcgcagg | 540 |
| tgcgacgcgc cacggccggc gatggcttcg ggaccatgct cggtgacggg ctggggtgct | 600 |
| gggatctcga ccacttcgac gatcaggcg cccgggcctt catcgaccgg atcgataagc | 660 |
| cgatcatctt cgccgagcgg tcggtgtcgg ggcatggctt ccacatcttc gtccggactg | 720 |
| acgaggcccc cggacgccgc accggaaaca tcgagttcta ctcacgccat cggttcatca | 780 |
| gggtcacagg agaccagttc gtctgaaggt cgtgccgggt tgtgtctga tgaggagtgg | 840 |
| ttgtttctca tggatgctgc ggtgattcat gatgtggtgt ggcgtgaggg tcgcgcggat | 900 |
| ttggtggctt cgttgcgtgc tcatgtgaag gcttttatgg gtatgttgga taggtattcg | 960 |
| gttgatgtgg cgtctggtgg ccgtggtggg ggttctgcgg tagcgatgat tgaccggtat | 1020 |
| aggaagcgta gggggcttg agtaggtgtc tggtgttgtt gggtctcagg ttcctcgtca | 1080 |
| ccgggtggct gtggcgtatt cggtgtctgc tggcggggat gctggggagc ttggtagggc | 1140 |
| ttatggggtt acgcctgatc cgtggcagca gcaggtgttg gatgattggc ttgctgtggg | 1200 |
| tggtaatggc aggcttgctt cgggtgtgtg tggggtgttt gttccgcggc agaatggcaa | 1260 |
| gaatgctatt ttggagattg tggagttgtt taaggcgact attcagggtc gccgtatttt | 1320 |
| gcatacggct cacgagttga agtcggctcg taaggcgttt atgcggttgc ggtcgttttt | 1380 |
| tgagaatgag cggcagtttc ctgacttgta tcgtatggtg aagtcgattc gtgcgacgaa | 1440 |
| tggccaggag gctattgtgt tgcatcatcc ggattgtgcc acgtttgaga agaagtgtgg | 1500 |
| ttgtccgggt tggggttcgg ttgagtttgt ggctcgtagc cggggttctg ctcgcgggtt | 1560 |
| tacggttgat gatttggtgt gtgatgaggc tcaggagttg tcggatgagc agttggaggc | 1620 |
| tttgcttcct accgtgagcg ctgccccgtc tggtgatcct cagcagattt ttttgggtac | 1680 |

```
gccgccgggg ccgttggctg acgggtctgt ggtgttgcgt cttcgcgggc aggctttgtc    1740
gggtggtaaa cggtttgcgt ggacggagtt ttcgattcct gacgagtctg atccggatga    1800
tgtgtcgcgg cagtggcgga agttggcggg tgacactaat ccggcgttgg ggcgccgcct    1860
gaatttcggg acagtctcgg atgagcatga gtcgatgtct gctgccgggt ttgctcggga    1920
gcggcttggc tggtgggatc gtggccagtc tgcttcgtct gtgattccgg cggataagtg    1980
ggttcagtcg gctgtggttg aggcggctct ggttggcggg aaggttttg gtgtctcgtt     2040 ttctcgctcg ggggatcgtg tcgcgttggc tggtgctggt aaaacggatt ctggtgtgca    2100
tgttgaggtt attgatggcc tgtctgggac gattgttgat ggtgtgggcc agctggctga    2160
ttggttggcg ttgcgttggg gtgacactga aaaggttatg gttgcagggt ctggtgcggt    2220
gttgttgcag aaggctttga cggatcgtgg tgttccgggt cgtggcgtga ttgtggctga    2280
tactggggtg tatgtggagg cgtgtcaagc cttcctggag ggtgtcaggt ctgggagcgt    2340
gtctcatcct cgtgccgatt cgaggcgtga catgttggat attgctgtga gtcggctgt     2400 gcagaagaag aagggttctg cgtggggttg gggttcctcg tttaaggatg gttctgaggt    2460
tcctttggag gctgtgtctt ggcgtatct tggtgcgaag atggcgaaag cgaagcggcg     2520
tgaacggtct ggtaggaagc gggtgtctgt ggtatgaact cggatgagtt ggctctgatt    2580
gagggcatgt acgatcgtat tcaagggttg tcttcgtggc attgccgtat tgagggctac    2640
tatgagggct ctaatcgggt gcgtgatttg ggggttgcta ttccttcgga gttgcagcgg    2700
gtgcagacgg tggtgtcatg gcctgggatt gcggtggatg cttttgagga gcgtctggat    2760
tggcttggct ggactaatgg tgacggctac ggtttgatg tgtgtatgc tgcgaatcgg      2820 cttgctacgg cgtcgtgtga tgttcacctt gatgcactga tttttgggtt gtcgtttgtg    2880
gcgatcattc cccaagagga tgggtcggtg ttggttcgtc ctcagtcgcc gaagaattgt    2940
actggccggt tttctgccga tgggtcttgt ttggatgctg gccttgtggt gcagcagacg    3000
tgtgatcctg aggttgttga ggcggagttg ttgcttcctg atgtgattgt tcaggtggag    3060
cggcggggtt cgcgtgagtg ggttgagacg ggccgtatcg agaatgtgtt gggtgcggtt    3120
ccgttggtgc ctgttgtgaa tcgtcgccgt acttctagga ttgatggccg ttcggagatt    3180
acgaggtcta ttagggctta cacggatgag gctgttcgca cactgttggg gcagtctgtg    3240
aatcgtgatt tttatgcgta tcctcagcgt tgggtgactg gcgtgagcgc ggatgagttt    3300
tcgcagccgg gttgggttct gtcgatggct tctgtgtggg ctgtggataa ggatgatgat    3360
ggtgacactc cgaatgtggg gtcgtttcct gtgaattctc ctacaccgta ttctgatcag    3420
atgcgtttgt tggcgcagtt gactgcgggt gaggcggctg ttccggaacg ctatttcggg    3480
tttatcactt ctaacccgcc ttctggggag gctttggctg cggaggagtc tcggcttgtg    3540
aagcgtgctg aacgcaggca gacgtcgttt ggtcagggct ggctgtcggt tggtttcctg    3600
gctgcccggg cgttggattc gagtgttgat gaggccgcgt tttttggtga tgttggtttg    3660
cgttggcgtg atgcgtcgac gccgactcgg gcggctacgg ctgatgctgt gacgaagctt    3720
gtgggtgctg gtattttgcc tgctgattct cggacggtgt tggagatgtt gggtttggat    3780
gatgtgcagg ttgaggctgt gatgcgtcat cgtgccgagt cttcggatcc gttggcggca    3840
ctggctgggg ctatttcccg tcaaactaac gaggtttgat aggcgatggc ttcgggtgct    3900
gtgtcgaggc ttgctgcgac tgagtatcag cgtgaggctg tcaggtttgc tgggaagtat    3960
gcgggctatt atgccgagtt gggtcgtttg tggcgtgccg gcaggatgag tgacacgcag    4020
tatgtgcgtt tgtgtgtgga gttggagcgt gccggccatg acggttcagc agctatggcg    4080
```

```
ggcaaattcg tttcagattt tcgccggttg aatggtgtcg atcctggttt gatcgtgtat    4140
gacgagtttg atgctgcggc ggctttggct aggtcgtttt cgactatgaa gattatgaat    4200
agtgacccgg ataggcgaa  tgatacgatt gatgcgatgg ctgcgggtgt taatcgggct    4260
gttatgaatg ctggtcgtga cacggttgag tggtcggcgg gtgcgcaggg taggtcgtgg    4320
cgtcgggtga ctgatggtga tccgtgtgct ttttgtgcca tgttggctac gaggtcggat    4380
tatacgacta aagagcgggc gcttactact ggtcatacgc ggcgtcataa gcgtgccggt    4440
aggcgtccgt ttggttcgaa gtatcatgat cattgtggtt gtacggtggt tgaggttgtt    4500
ggtccttggg aaccgaatag ggctgatgcc gagtatcaga ggacgtatga gaaggctcgt    4560
gagtgggttg atgatcatgg gttgcagcag tcgtctggca atattttgaa ggctatgcgt    4620
actgttggtg gcatgagata atttgatgtg gtttccggtt gtgtgccgcc ggttatcggt    4680
gcacagggtt gtctcccgca cggggtcaa  caatgttgtg ttgttttccg caaggagtgt    4740
agggttaggc tatggccgat cagagtattg aggaacagaa tgttgacaat gatgttgtgg    4800
agtccggaaa ggataacggc attgttgata cagtaaaaga cgatggcggg caggaggtag    4860
ccgacaatca gttgaagaat gaaggcgagg gtaaatcgcc ggggactgat tggaaggcgg    4920
aggcccgtaa gtgggagtct cgtgctaaaa gtaatttcgc cgagttggag aagcttcgta    4980
catcgagtga cgattctgga tctactattg atgagcttcg ccgcaagaat gaggaactcg    5040
aagaccggat taacgggttt gttcttgagg gtgtgaagcg cgaggtggct gccgagtgtg    5100
gcctgtcggg tgatgcgatc gcttttcttc acggtagcga taaggagtcg cttgccgagt    5160
ctgctaaggc tttgaagggt ttgatcgacc atagtagtgg tggtggcgcg ggtgtgcgcc    5220
gtcttgcggg gagtgccccc gttgatgatg ttaaacgacg tgagggtgtc gcgtttgtgg    5280
atgctcttgt caataattct aggagatgat ttatcatggc tgacgatttt ctttctgcag    5340
ggaagcttga gcttcctggt tctatgattg gtgcggttcg tgaccgtgct atcgattctg    5400
gtgttcttgc taaactgtca ccggagcagc cgactatttt cgggcctgtt aagggcgccg    5460
tttttagtgg tgttccgcgc gctaagattg ttggcgaggg cgatgttaag ccttccgcta    5520
gcgttgatgt ttctgcgttt actgcgcagc ctatcaaggt tgtgactcag cagcgtgtct    5580
cggacgagtt tatgtgggct gacgccgatt accgtctggg tgtgcttcag gatctgatttt   5640 cccggccct  gggtgcttct attggtcgcg ccgttgatct tattgctttc catggtattg    5700
atcctgctac gggtaagcct gctgcggctg tcaaggtgtc gctggataag acgaataaga    5760
cggttgatgc caccgattcc gctacggctg atcttgttaa ggctgttggt ctgattgctg    5820
gtgctggttt gcaggttcct aacggtgttg ctttggatcc ggcgttctcg tttgctctgt    5880
caactgaggt gtatccgaag ggttcgccgc ttgccggtca gccaatgtat cctgccgccg    5940
ggttcgccgg cctggataat tggcgcggcc taaatgttgg ttcttcttcg actgtttctg    6000 gtgcccgga  gatgtcgcct gcttctggtg ttaaggctat tgttggtgat ttctctcgtg    6060
tccattgggg gttccagcgt aacttcccga ttgagctgat cgagtatggt gacccggatc    6120
agacggggcg tgacttgaag ggccataatg aggttatggt tcgtgccgag gctgtgctgt    6180
atgttgcgat tgagtcgctt gattcgtttg ctgtcgtgaa ggagaaggct gccccgaagc    6240
ctaatccgcc ggccggtaac tgattcattt gttgcgataa tgtttatgct gtgtgcaggg    6300
ggtggtgttg atgggtatca ttttgaagcc tgaggatatt gagcctttcg ccgatattcc    6360
tagagagaag cttgaggcga tgattgccga tgtggaggct gtggctgtca gtgtcgcccc    6420
```

```
ctgtatcgct aaaccggatt tcaaatatag ggatgccgct aaggctattc tgcgtagggc   6480
tttgttgcgc tggaatgata ctggcgtgtc gggtcaggtg cagtatgagt ctgcgggccc   6540
gtttgctcag actacacggt cgaatactcc tacgaatttg ttgtggcctt ctgagattgc   6600
cgcgttgaag aagttgtgtg agggtgatag tggggctggt aaggcgttca ctattacacc   6660
gaccatgagg agtagtgtga atcattctga ggtgtgttcc acggtgtggg gtgagggttg   6720
ctcgtgcggg tcgaatatta acggctatgc tggcccgttg tgggagatat gatatgaccg   6780
gttttcctta cggtgaaacg gttgtgatgc ttcagccgac tgttcgtgtc gatgatcttg   6840
gtgacaaggt ggaggattgg tctaagcctg tcgagactgt gtaccataac gtggccatct   6900
atgcttccgt ttcgcaggag gatgaggccg cggggcgtga ctcggattat gagcattgga   6960
cactgctgtt caagcagcct gtcaaggctg ctggttatcg gtgtcgttgg cgtattcggg   7020
gtgttgtgtg ggaggctgac gggtctccta tggtgtggca tcatccgatg tctggctggg   7080
atgctggtac gcaggttaat gtgaagcgta agaagggctg atgggttgtg gcacgtgatg   7140
ttgatgtgaa gctgaacttg ccgggtattc gtgaggtgtt gaagtcttct ggggtgcagg   7200
gcatgttggc tgagcgtggt gagcgtgtca agcgtgcggc ctcggcgaat gtgggcggta   7260
acgcttacga tagggcccag tatcgtgccg ggttgtcgtc tgaggtgcag gttcaccgtg   7320
ttgaggctgt ggcgcgtatt ggcaccacct ataagggtgg taaaaggatt gaggctaagc   7380
atggcacgtt ggcgaggtcg attggggctg cgtcgtgatc gtttacggtg atcctcgaat   7440
atgggctaaa cgtgtgttgg cggatgatgg ttggctgtct gatgtaccgt gcacgggtac   7500
tgtgccggat acatttgagg gtgatctgat ttggttggcg ttggatggtg cccggagtt   7560 gcatgttcgt gagcgtgttt ttttgcgtgt gaatgtgttt tcggatacgc cggatcgtgc   7620
tatgtctttg gctcgccggg ttgaggctgt gctggctgat ggtgtggatg tgatccggt   7680 ggtgttttgc aggcgttcga ctgggcctga tttgctggtg gatggtgcac gttttgatgt   7740
gtattcgctt tttgagctga tatgtaggcc tgcggagtct gaataagctt attgtttttg   7800
ttttaatgta attgtttgat atttaatggg ggttgtgatg gctgctacac gtaaagcgtc   7860
taatgttcgt tcagcggtta ctggcgacgt ttatattggt gacgcgcacg cgggtgattc   7920
tattaagggt gtggaggcgg ttccttccgg gcttacagct ttggggtatc tgtctgatga   7980
cgggtttaag attaagcctg agcgtaaaac ggatgatttg aaggcttggc agaatgcgga   8040
tgttgttcgc actgtggcta cggagtcgtc tatcgagatt tctttccagc tgattgagtc   8100
gaagaaggag gttatcgaac tgttttggca gtcgaaggtt actgccggat ctgattcggg   8160
ttcgttcgat atttctcctg gtgccacaac aggtgttcac gccctgttga tggatattgt   8220
tgatggcgat caggttattc gctactattt ccctgaggtt gagctcattg atcgtgacga   8280
gattaagggc aagaatggcg aagtgtacgg gtatggtgtg acgttgaagg cgtatcctgc   8340
ccagattaat aagactggta atgcggtgtc gggtcggggg tggatgacgg ctttaaaagc   8400
tgatactcct ccgactcctc cgccggcccc ggttcctccg aagcctcagc cggatccgaa   8460
tccgccgtcc ggtaactgat acacgatttt aggggattgt taatagatga gtgacactgg   8520
tttcacgttg aagattggtg atcgtagctg ggtgttggcg gatgcggagg agacggctca   8580
ggctgttcct gcccgcgttt ccgtcgtgc cgccaggatt gcccagtcgg gggagtctgc   8640
ggatttcgcc caggttgagg tgatgttttc tatgttggag ctgccgccc cagctgacgc   8700 ggtggaggcc ctgagggggc ttcctatggt tcgtgtggcg gaggttttcc gtgagtggat   8760
ggaatacaag cctgacggta agggtgcctc gctgggggaa tagtttggct ccacggcctg   8820
```

```
attgatgatt atcgtggggc catcgaatac gatttccgca ccaagtttgg tgtttctgtt    8880
tatagtgttg gtggcccgca gatgtgttgg ggtgaggctg tccggctggc tggcgtgttg    8940
tgtaccgata cgtctagcca gttggcggcc caccttaatg gttggcagcg cccgtttgag    9000
tggtgcgagt gggctgtgtt ggacatgttg gatcattaca ggtctgctaa tagtgagggg    9060
cagccggagc ctgtggcgag gccgactgat gagcgtcggg caaggtttac gtctgggcag    9120
gtggacgata ttttggcgcg tgttcgtgcc ggtggcgggg tgtctcgcga gattgatatt    9180
atggggtgaa tagtgtatgt ctggtgagat tgcttccgca tatgtgtcgt tgtatacgaa    9240
gatgcctggc cttaaaagtg atgttggtaa acagttgtcg ggtgttatgc ctgctgaggg    9300
gcagcgttcg ggtagcctgt ttgctaaagg catgaagttg gcgcttggtg gtgcggcgat    9360
gatgggtgcc atcaatgttg ctaagaaggg cctcaagtct atctatgatg tgactattgg    9420
tggcggtatt gctcgcgcta tggctattga tgaggctcag gctaaactga ctggtttggg    9480
tcacacgtct tctgatacgt cttcgattat gaattcggct attgaggctg tgactggtac    9540
gtcgtatgcg ttgggggatg cggcgtctac ggcggcggcg ttgtctgctt cgggtgtgaa    9600
gtctggcggt cagatgacgg atgtgttgaa gactgtcgcg gatgtgtctt atatttcggg    9660
taagtcgttt caggatacgg gcgctatttt tacgtctgtg atggctcgcg gtaagttgca    9720
gggcgatgac atgttgcagc ttacgatggc tggtgttcct gtgctgtctt tgcttgccag    9780
gcagacgggt aaaacctcgg ctgaggtttc gcagatggtg tcgaaggggc agattgattt    9840
tgccacgttt gcggctgcga tgaagcttgg catgggtggt gctgcgcagg cgtctggtaa    9900
gacgtttgag ggcgctatga agaatgttaa gggcgctttg ggctatttgg gtgctacggc    9960
tatggcgccg tttcttaacg gcctgcggca gattttttgtt gcgttgaatc cggttattaa   10020
gtctatcacg gattctgtga agccgatgtt tgctgccgtc gatgctggta tccagcggat   10080
gatgccgtct attttggcgt ggattaaccg tatgccggct atgatcacga gaatgaatgc   10140
acagatgcgc gccaaggtgg agcagttgaa gggcattttt gcgagaatgc atttgcctgt   10200
tcctaaagtg aatttgggtg ccatgtttgc tggcggcacc gcagtgtttg gtattgttgc   10260
tgcgggtgtg gggaagcttg ttgcagggtt tgctccgttg gcggttgcgt tgaagaatct   10320
gttgccgtcg tttggtgctt tgaggggtgc cgccgggggg cttggtggcg tgtttcgcgc   10380
cctgggtggc cctgtcggga ttgtgatcgg cttgtttgcg gcaatgtttg ccacgaacgc   10440
ccagttccgt gccgctgtta tgcagctggt ggctgtggtt ggtcaggcgt gggccagat    10500
tatgcagct gtgcagccgc tgtttggttt ggttgctggc gtggttgcca ggttggcgcc   10560
ggtgttcggc cagattatcg gtatggttgc tggtttggct gcccggctgg tgcctgttat   10620
tggtatgctt attgcccggc tggttcctgt tatcacccag attattggta tggtaaccca   10680
ggttgctgcc atgttgttgc ctatgctgat gccggttatt caggctgttg ttgctgtgat   10740
acggcaggtt attggtgtca ttatgcagtt gatacctgtt ttgatgccgg ttgtgcagca   10800
gattttgggt gctgtcatgt ctgttttgcc gccgattgtt ggtttgatac ggtcgctgat   10860
accggtgatc atgtcgatta tgcgtgtggt ggtgcaggtt gttggtgctg tgctacaggt   10920
ggtggcccgt attattccgg ttgttatgcc gatttatgtt tcggtgattg gattcattgc   10980
caagatttat gctgcggtta tcgttttttga ggctaaggtt attggcgcta ttcttcgtac   11040
tattacgtgg attgtgaatc attcagtgtc tggcgtgagg tctatgggca cggccatcca   11100
gaatggctgg aatcatatta aatcgtttac gtctgcgttt attaacggtt ttaagtcgat   11160
```

```
catttctggc ggcgtgaacg cggttgtggg gttttttacg cggcttggtt tgtcggttgc    11220
ttcccatgtg aggtccggtt ttaacgctgc gaggggtgct gtttcttccg ccatgaatgc    11280
tattcggagt gttgtgtctt cggtggcgtc tgctgttggc gggttttttca gttcgatggc   11340 gtctcgtgtt cggaatggtg ctgtgcgcgg gtttaatggt gcccggagtg cggcttcttc    11400
tgctatgcat gctatggggt ccgctgtgtc tagtggtgtg catggtgtgc tgggttttttt   11460 ccggaatttg cctgacaata ttcggcgtgc gcttggtaat atgggtccc tgttggtgtc     11520 ggctggccgt gatgtggtgt ccggtttagg taatggtatc aagaatgctt tgagtggcct    11580
gttggatacg gtgcgtaata tgggttctca ggttgctaat gcggcgaagt cggtgttggg    11640
tattcattcc ccgtctcggg tgtttcgtga cgaggttggc cggcaggttg ttgccggttt    11700
ggctgagggt attactggta atgctggttt ggcgttggat gcgatgtcgg gtgtggctgg    11760
gaggctgcct gatgcggttg atgcccggtt tggtgtgcga tcgtctgtgg gttcgtttac    11820
cccgtatggc aggtatcagc gcatgaatga taagagtgtt gtggtgaatg tgaatgggcc    11880
tacttatggg gatcctgccg agtttgcgaa gcggattgag cggcagcagc gtgacgcttt    11940
gaacgcgttg gcttacgtgt gattttgggg gtgtggtgc                          11979

<210> SEQ ID NO 29
<211> LENGTH: 83
<212> TYPE: DNA
<213> ORGANISM: Artificial Sequence
<220> FEATURE:
<223> OTHER INFORMATION: PAC7 cos of pAN594

<400> SEQUENCE: 29
acaaaaggga ggtatttcac taagccgtac gaggtcttgc acgggtgtgc aggggtgtg     60 cccggtgggg gttggcgggt ttt                                           83

<210> SEQ ID NO 30
<211> LENGTH: 4670
<212> TYPE: DNA
<213> ORGANISM: Artificial Sequence
<220> FEATURE:
<223> OTHER INFORMATION: operon of gp15-gp19+gp45

<400> SEQUENCE: 30
cgacgcggcg gtctgccgac ccggcaacga ccaactcccc gacgggcgct gacaccggcc    60
cggcagcgtg catgcgtgca tttccaccct caagaaccat tgactggcga cgcgcaggtg   120
ggagaattga actgaacgct ttgaacgcgt tggcttacgt gtgattttgg gggtgtggtg   180
catgtttatt cctgacccgt ctgatcgttc tggtttgact gtgacttggt ctatgttgcc   240
gttgattggt aatgatccgg agcgtgtgct tcatttgacg gattatacgg ggtcgtctcc   300
gataatgttg ttgaatgatt cgttgcgcgg tttgggtgtt cctgaggtgg agcatttttc   360
tcaaactcat gttggggtgc atggctcgga gtggcgcggg tttaatgtga agcctcgcga   420
ggtgacgcta ccggtgttgg tgtcgggtgt tggcccggat ccggtgggcg ttttcgtga    480 cggttttttg aaggcgtatg acgagttgtg gtctgctttt cctcctggcg aggtggggga   540
gttgtctgtg aagactcctg ccggtcgtga gcgtgtgttg aagtgccggt ttgattcggt   600
ggatgacacg tttacggtgg atccggtgaa cagggggttat gcgcgttatc tgttgcattt   660
gacggcttat gacccgtttt ggtatgggga tgagcagaag tttcgttttca gtaacgctaa   720 gttgcaggat tggttgggtg gcggcccctgt cgacggtaag ggtaccgcgt ttccggtggt   780
gttgacgcct ggtgttggtt cgggttggga taatctgtct aataaggggtg atgtgcctgc   840
```

```
gtggcctgtg attcgtgttg aggggccgtt gtcgtcgtgg tctgtgcaga ttgatggttt       900
gcgtgtgtcc tcggattggc cggtggagga gtatgattgg atcactattg atacggatcc       960
tcgtaagcag tctgcgttgt tggacgggtt tgaggatgtg atggatcgtt tgaaggagtg      1020
ggagtttgcg cctatcccgc ctggcggttc tcggagtgtg aatattgaga tggttggttt      1080
gggtgccatt gttgtgtcgg tgcagtacag gttttgagg gcttggtgaa tagttgatgg       1140
ctggttttgt tccgcatgta acattgttta caccggatta tcgccgtgtg gcgcctatca      1200
atttttttga gtcgttgaag ttgtcgttga agtggaatgg tttgtccact ttggagttgg      1260
tggtgtctgg tgatcattct aggcttgacg ggttgactag gccgggtgcg cggcttgtgg      1320
ttgattatgg tggtggccag attttttctg ggcctgtgcg tcgggtgcat ggtgtgggtc      1380
cgtggcgttc ttcgcgtgtg actatcacgt gtgaggatga tattcgtctg ttgtggcgta      1440
tgttgatgtg gcctgtgaat tatcgtcctg gtatggttgg tatggagtgg cgtgcggatc      1500
gggattatgc ccattattcg ggtgcggcgg agtcggtggc taagcgggtg ttggggata      1560 atgcttggcg ttttccgtct ggtttgttta tgaacgatga tgagagtcgt ggccgctata      1620
ttaaggattt tcaggtgcgg tttcacgtgt ttgccgataa gttgttgccg gtgttgtcgt      1680
gggctcggat gactgtcacg gtgaaccagt ttgagaatgc gaagtttgat cagcgtggtt      1740
tggtgtttga ttgtgtgcct gctgtgaccc ggaaacatgt gttgactgcc gagtcgggtt      1800
cgattgtgtc gtgggagtat gtgcgtgacg ccccgaaggc gacatctgtg gtggttggtg      1860
gccgtggcga gggtaaggat cggctgtttt tgaggatgt tgattcggcg gccgaggatg      1920
attggtttga tcgtgtcgag gtgtttaagg atgcccgtaa cacggattcc gagaaggtgt      1980
ctctcttcga tgaggctgag cgggtgttgt ccgagtcggg ggctacgtcg gggtttaaga      2040
ttgagttggc tgagtcggat gtgttgcggt ttggtcccgg caatctgatg cctggggatt      2100
tgatctatgt ggatgtgggt tctgggccta ttgcggagat tgtgcggcag attgatgtgg      2160
agtgtgtatc gcctggtgat ggttggacga aggtgactcc ggttgcgggg gattatgagg      2220
ataatccgtc ggccctgttg gctcgccgtg tggctggttt ggctgcgggt gtgcgggatt      2280
tgcaaaagtt ttagtaagtg attgggtttt gttgtggta ttgtgtgtaa agggtttgat       2340
ggtgtgttga ccgagtatga ttgggctcaa atgtctggtc tgatgggtaa tatgccgtct      2400
gtgaaggggc ctgacgattt tcgtgtcggc acgacgattc agggttctac ggtgttgtgt      2460
gagatcctgc cggggcaggc ttgggctcac ggggtgatgt gcacgtcgaa tagtgttgag      2520
acggtgacgg tcagcttcc gggcccgggt gagactcgat acgactatgt ggtgttgtct      2580
cgggattggc aggagaatac ggccaagttg gagattgttc ccggtgggcg tgcggagcgt      2640
gccagggatg tgttgagggc tgagcctggc gtgtttcatc agcagctact ggcgactttg      2700
gtgttgtcgt ctaacgggtt gcagcagcag ttggataggc gtgctgtggc ggctagggtt      2760
gcgtttgggg agtctgctgc gtgtgatcct accctgtgg agggtgaccg tgtgatggtt       2820
ccttcggggg ctgtgtgggc taaccatgcc ggcgagtgga tgttgttgtc tcccaggatt      2880
gagacgggtt cgaagtcgat catgtttggt ggttctgctg tgtatgctta cacgatcccg      2940
tttgagcgcc agttcagtag tccgcctgtt gtggtggcgt ctatggctac ggcggctggg      3000
ggcacggcac agattgatgt gaaagcctac aatgtgactg cccaaaattt tagtttggcg      3060
tttattacga atgatggttc gaagccgaat ggtgtgcctg cggtggcgaa ttggattgct      3120
gtcggcgtgt gactgcacgg gtgttgtggc ggatggtgtg atgttggggg gctgtggtgt      3180
```

-continued

| | |
|---|---|
| cgtggtttac tcctgcactg gtggcctcta tttgtaccgc gttggccacg gttttgggtt | 3240 |
| ctgttcaggc tgtcacatcc cggtctagga agcgtttacg caggctgtcg gctcaggtgg | 3300 |
| atgcgatgga agagtatacg tggggtgtgc ggcgcgaggt gcgaaggttt aacgccgggc | 3360 |
| ttcctgatga tgtggagccg atgcatcttc ctgatttgcc cgagtttttg aaagatactg | 3420 |
| ttgatggtgg aggtgagtag ggttgaggga gttggaggag gagaagcggc agcgccgcaa | 3480 |
| ttttgagaag gcttcactgg tgttgttgtt tttgtcgctt gtgttgttgg cggtggttgc | 3540 |
| tgcgggtgct ttgcgtttcg gggctgtatc ctctgagcgg gattcggagc aggcgagggc | 3600 |
| ccagtcgaat ggtacggctg ccaggggttt ggctgcccgt gtgaagcagg cgtgtgcttc | 3660 |
| gggtggggtg gagtctgtgc gtcttcaccg ttctggtttg tgtgtggatg ctgtgcgtgt | 3720 |
| tgagcagcgt gttcagggtg tgccgggtcc tgccggtgag cgcggcccgc aaggcccttc | 3780 |
| aggtcctgcc ggccgggatg tgttaatgg ttcgctgggg ctggttggcc ctgttggtcc | 3840 |
| gcaaggttct ccgggtttga atggtgtgaa aggtcctgac ggcttgcctg gcgctaacgg | 3900 |
| ttcggatggc cgtgatggtg ttccaggtcg tgcaggtgct gacggtgtga acggcgttga | 3960 |
| cggcgctgat ggtcgggatg gttctgccgg tgagcgcggc ccgcaaggcc cttcaggtcc | 4020 |
| tgccggcccg caaggtgcac agggtgaacg gggtgagcgt ggtcccgccg gtgcgaatgg | 4080 |
| atcggatggc catgatggta aggatgggcg ctcggtggtg tctgtgtact gttccggggg | 4140 |
| ccgcctggtt gtgaaatata gtgacggtgt ggcttccacg atatcgggtt cggcggcctg | 4200 |
| ccagggtgtg aaaccgtcgc ctctagtgac tatatcatcc cacaaataga ggctcacagg | 4260 |
| ggccatggga gattgggggg cgtgatggca cacaccaacc gcacagccag ccaagcccac | 4320 |
| cggcgctggc gggcaaggct catcacccaa gcccgacaac aaggccaaac cgaatgccca | 4380 |
| ctctgcggag tcaccatcac ctggaacacc cacgacctgc caaccagccc cgaagccgac | 4440 |
| cacatcacac ccgtcagccg gggaggactc aacaccctcg acaacgggca aatcatctgc | 4500 |
| agaacatgca acagaagcaa aggcaacaga acacaaccaa acatcaaatt ccaacaacaa | 4560 |
| accacaaaaa cattgattcc atggtgagga tatccacgag ctgcgttcgg ctaaacccaa | 4620 |
| aagtaaaaac ccgccgaagc gggttttaac gtaaaacagg tgaaactgac | 4670 |

<210> SEQ ID NO 31
<211> LENGTH: 1910
<212> TYPE: DNA
<213> ORGANISM: Artificial Sequence
<220> FEATURE:
<223> OTHER INFORMATION: pAN241 vector

<400> SEQUENCE: 31

| | |
|---|---|
| caagtggccc atcgaagagg acggcaccac catctcgccg gcaagctcaa aggacgtgtc | 60 |
| caggctgacg ctcacggtgc tgctgcaccc ctcgtgcgcc atcatcgtgg atccccaaga | 120 |
| ttgtccggac ggcggttgag cgcggcctga taggcgccgc agctcctgct cccgggccgc | 180 |
| cccggtcggc ggtttactcc tttcctgccg gccggggcac tcaagacaac cgggggccct | 240 |
| cgcgaaattg agggcccccg cctgattgca aggggtgcc catgaagcaa cccgggcccc | 300 |
| accaaagaat gcgggctacc ttcaaggccg acagggctg gcgagtggca tgcccacggt | 360 |
| gcgcctggca tgccaccagc acccaccttg catggctcat ggatcaggcc agcacacaca | 420 |
| cctgtgcacc cctgctgttg tcgcccacgc cacccgacgt ggagctggca ccggcaggcg | 480 |
| acgggctgtc cgtcctgtgg cccgaggtgg acggtgacgt gcagttcacc tgcatccaca | 540 |
| ccagcaccgc cacgtgcagg caggacgcac catgagcacc agtcgcaccg gcacggccac | 600 |

-continued

```
atggttgcgc catgcagcac aggccaagcg tgaggcccaa gcacgaggac tcgcccgctg      660
cccactgtgc ggcgtctgga tggactacga ggtcggcaag cgacccaact cggccgaagc      720
agaccacatc agaccgcatt cgcttggtgg ttcagacgac atcgacaaca ttcgcgtcat      780
ttgtcgtcgt tgcaatcaat cgcgcggaaa cggcctgaag cgaccagggc gccaacgtca      840
gcgtccaatc aagcgcatcg agctggccca accggcccgc agtggggcat ttcctgcccc      900
gccggcatga atggaagggc agtgcggatg gtgcggtcgg gcattcgatc gtgcccggac      960
gggtcgcccg cgacgcttct gctcggcccg ctgtcgggtc gccgcgtccc ggtgtgcgat     1020
cccgctggcc atgaggtccc gcactgcgtg ggtccgctgc gacggcaagc gccccatcac     1080
cctggctggc gctccggcct catccacgga cccgggcaca tggtctggct ggtcgcaggt     1140
gcgacgcgcc acggccggcg atggcttcgg gaccatgctc ggtgacgggc tggggtgctg     1200
ggatctcgac cacttcgacg atcagggcgc ccgggccttc atcgaccgga tcgataagcc     1260
gatcatcttc gccgagcggt cggtgtcggg gcatggcttc cacatcttcg tccggactga     1320
cgaggccccc ggacgccgca ccggaaacat cgagttctac tcacgccatc ggttcatcag     1380
ggtcacagga gaccagttcg tctgaagaag ggggtgcgcc atggctgcac aggtcagggc     1440
cgtggacccc gatgagcgcc caccgcccg caagcgggcc aagaccatca cccaggccgc     1500
gaagtccggc actgaggttg aactgttgga ggcactgcag gctcgcgtgg cccgcgccgt     1560
gcaggaccgt gacactccgc cgcgcgatct ggcagcgctg acgaagcggc tgatggacat     1620
cacccgggag ctcgaggcgg cccgggtcaa ggatcaggag gcgggatctg atggtgccgt     1680
caccgcagac gaaacatggc gaccgcaagc tctctgaggt cgccaagcac ctgatccttc     1740
ctgaagggat cgtctcgacg ggctggccgg ccgtgcgtga ccggtgtggc gagtggggtg     1800
tggtcttcga ccgttggcag gacggcatgg gccgggtgat cctgtcgaag cgcggcagcg     1860
gcctgttcgc cgctggtgtg ggcggggtcg gcatgtcgat cccgcgccag                1910
```

PRODUCTION BACTERIAL CELLS AND USE THEREOF IN PRODUCTION METHODS

CROSS REFERENCE TO RELATED APPLICATIONS

This application claims the benefit of U.S. application 63/187,531 filed May 12, 2021, and U.S. application 63/187,532 filed May 12, 2021, which are incorporated herein by reference in their entirety.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on May 12, 2022, is named EB2021-04a_sequence_listing_ST25.txt and is 193,125 bytes in size.

FIELD OF THE INVENTION

The present invention concerns bacterial cells for producing phage particles and methods using such bacterial cells.

BACKGROUND

Most current phage or phage-derived delivery vehicle production methods imply the use, as production cell, of the bacterial species or strain which is the natural host of said phages. Such methods can turn out to be dangerous when such bacterial cells are pathogenic, for example when they produce toxins. Moreover, many bacterial species cannot be easily manipulated, for instance because of their growth conditions or because there is no efficient genetic tool for those bacteria. It can also be difficult to identify a bacterial strain that only contains a prophage, since in many cases, a same bacterial strain contains several prophages, which can give rise to unwanted particles being produced or unwanted recombination events, etc., and/or to induce and/or stably maintain a prophage/phage in a given species or strain, for example.

There is thus a need for a method enabling the safe, easier and efficient production of any phage or phage-derived particle.

The present invention meets this need.

The present inventors considered that phages can be viewed as more or less large genetic circuits, the final output of which is the generation of more phage particles. To do this, no matter if the phage is lytic, temperate or chronic (for instance filamentous phages such as M13), the present inventors considered that the information encoded in their genomes can be roughly categorized depending on the function it performs:

Genes devoted to insertion/excision (for temperate phages).
Genes devoted to DNA replication, RNA transcription, etc. Indeed, some lytic phages encode their own RNA or DNA polymerases, for instance. Some genes modify the host's RNA polymerases to be able to work past terminators, and some other genes are involved in the segregation of the prophage sequence if it exists in a plasmid or linear plasmid form.
Genes devoted to packaging of the newly synthesized phage genome into the newly synthesized phage capsids: terminases and accessory proteins, ligases, etc.
Structural genes devoted to building a protein capsid for the DNA: apart from strictly structural genes, such as capsid genes, tape measure, fibers, baseplate etc, many other genes are needed to assemble the components (chaperones, proteases) as well as proteins that can be packaged inside the capsid, be it as scaffold or as pilot proteins injected into the cell (for instance, the RNA polymerase of phage N4 or some minor pilot proteins in other phages).
Genes related to defense from host's anti-phage mechanisms, degradation/modification of host's elements to complete the lytic cycle, super-exclusion mechanisms or genes that are advantageous for the host.

The DNA packaging and structural genes categories are deeply connected, since the packaging machinery recognizes the pre-assembled capsid heads and the DNA to be packaged in these heads, initiates and terminates DNA packaging.

The present inventors hypothesized that by abstracting and differentiating all the modules defined above, a system could be built that contains all excision/insertion, replication and regulation elements from one phage and encodes the packaging/structural elements for another one, since, as considered by the inventors, they could be viewed as independent genetic modules.

Treating them as independent genetic modules could also allow for the construction of a system that contains only the desired structural and/or regulatory elements of the phage to be produced under the control of a master regulatory element (an inducible repressor, for example) that may not be derived from a phage, as opposed to wild-type phages where gene expression is tightly regulated by phage elements. For instance, only the structural operon and the DNA packaging machinery of a phage could be placed under the control of a repressor that responds to a small molecule or a physical/chemical signal (LacI, AraC, PhIF, Lambda cI, etc.), triggering the production of all the elements necessary to generate pure mature phage delivery particles (phages or packaged phagemids). This "trimmed down" version of a phage genome could be stably maintained in a bacterial production strain.

SUMMARY OF THE INVENTION

The present invention arises from the unexpected finding by the inventors that it is possible, by exchanging the structural operon of an *Escherichia coli* production strain encoding a system to generate pure Lambda packaged phagemids with the structural operon of a prophage coming from a different species (such as *Klebsiella pneumoniae*), to drive the assembly and packaging of pure heterologous phagemid particles when supplemented with a plasmid containing the correct packaging signals (cos site for the *Klebsiella pneumoniae* phage). The present inventors thus here showed that phagemids can be produced structurally based on a *K. pneumoniae* prophage, but regulated and maintained in the lysogenic state by the Lambda prophage machinery in an *Escherichia coli* production strain.

The inventors also showed that the structural operon of a *P. freudenreichii* prophage can be exchanged with the structural operon of a phage of a *C. acnes* strain. With this approach, the inventors showed that it is possible, by exchanging the structural operon of a *P. freudenreichii* prophage with the structural operon of a phage of a *C. acnes* strain, to drive the assembly and packaging of pure *C. acnes* phagemids.

This approach represents a novel avenue for easier and/or safer generation of phage particles and/or phage-derived delivery vehicles, targeting bacterial cells known to be pathogenic and/or difficult to manipulate and/or inefficient to use in phage particles and/or phage-derived delivery vehicles production for any reason.

The present invention thus concerns a production bacterial cell for producing phage particles or phage-derived delivery vehicles, said production bacterial cell stably comprising at least one phage structural gene(s) and at least one phage DNA packaging gene(s), said phage structural gene(s) and phage DNA packaging gene(s) being derived from a first type of bacteriophage, wherein the expression of at least one of said phage structural gene(s) and/or at least one of said phage DNA packaging gene(s) in said production bacterial cell is controlled by at least one induction mechanism, and wherein said production bacterial cell is from a bacterial species or strain different from the bacterial species or strain from which said first type of bacteriophage comes and/or that said first type of bacteriophage targets.

The present invention also concerns a method for producing phage particles or phage-derived delivery vehicles, comprising:
(a) providing the production bacterial cell of the invention, and
(b) inducing, in said production bacterial cell, expression of said at least one of said phage structural gene(s) and phage DNA packaging gene(s), and assembly of the products expressed by said at least one phage structural gene(s) and said at least one phage DNA packaging gene(s), thereby producing phage particles or phage-derived delivery vehicles.

Another object of the invention concerns a hybrid helper phage system comprising:
(i) at least one phage DNA packaging gene(s) derived from a first type of bacteriophage,
(i') at least one phage structural gene(s) derived from said first type of bacteriophage, and
(ii) at least one gene, derived from a second type of bacteriophage, involved in phage excision/insertion, phage DNA replication, and/or phage regulation, wherein said genes (i), (i') and (ii) are comprised in a unique nucleic acid molecule or in separate nucleic acid molecules, wherein said first type of bacteriophage comes from and/or target bacterial species or strain different from the bacterial species or strain from which said second type of bacteriophage comes and/or that said second type of bacteriophage targets, and wherein said hybrid helper phage system does not comprise any expressed phage structural gene derived from said second type of bacteriophage.

DETAILED DESCRIPTION OF THE INVENTION

Production Bacterial Cell

The present invention concerns a production bacterial cell for producing phage particles or phage-derived delivery vehicles, said production bacterial cell stably comprising at least one phage structural gene(s) and at least one phage DNA packaging gene(s) derived from a first type of bacteriophage, wherein the expression of at least one of said phage structural gene(s) and at least one of said phage DNA packaging gene(s) in said production bacterial cell is controlled by an induction mechanism, and wherein said production bacterial cell is from a bacterial species or strain different from the bacterial species or strain from which said first type of bacteriophage comes and/or that said first type of bacteriophage targets.

As used herein, the term "phage particle" refers to a functional or non-functional (for example non-reproductive and/or replicative) virion.

As used herein, the term "phage-derived delivery vehicle" refers to any means that allows the transfer of a payload into a bacterium and which is derived from a bacteriophage. In the context of the invention, the term "phage-derived delivery vehicle" further encompasses bacteriophage-derived particles which do not comprise any payload but are able to target bacterial cells.

The phage-derived delivery vehicle can refer to a bacteriophage derived scaffold and can be obtained from a natural, evolved or engineered bacteriophage.

Bacterial Cell

The production bacterial cell of the invention may be of any bacterial species or strain, in particular defined below under the section "Targeted bacteria", provided that said bacterial species or strain is different from the bacterial species or strain from which said first type of bacteriophage comes and/or that said first type of bacteriophage targets.

However, the production bacterial cell is preferably a non-pathogenic bacterial cell. Still preferably, the production bacterial cell is a bacterial cell which can be easily manipulated.

By "easily manipulated" is meant herein that the bacterial cell can be cultured and/or modified using well-known techniques.

In a particular preferred embodiment, said production bacterial cell is an *E. coli* bacterial cell. Alternatively, said production bacterial cell may be a *Bacteroides* bacterial cell, more particularly a *Bacteroides thetaiotaomicron* bacterial cell, a *P. freudenreichii* bacterial cell, a *Fusobacterium* bacterial cell, or a *Streptococcus* bacterial cell. In a particular embodiment, said production bacterial cell is a *P. freudenreichii* bacterial cell.

The production bacterial cell of the invention can be obtained by any technique well-known from the skilled person, in particular by introducing into a bacterial cell, said phage structural gene(s) and phage DNA packaging gene(s) derived from a first type of bacteriophage, by any technique well-known in the art.

The production bacterial cell of the invention can typically be obtained by homologous recombination or recombineering including for example MAGE (Wannier et al. Recombineering and MAGE. *Nat Rev Methods Primers* 1, 7 (2021)), using CRISPR, TALEN, meganucleases and/or Zn-finger technologies for instance or using site specific recombination with phage integrase, PASTE (Ioannidi et al. Drag-and-drop genome insertion without DNA cleavage with CRISPR-directed integrases. Biorxiv 2021.11.01.466786 (2021) doi:10.1101/2021.11.01.466786) or Transposon-Associated CRISPR-Cas System (Ma et al. *Trends Microbiol* 29, 565-568 (2021)).

Phage DNA Packaging Genes and Phage Structural Genes

The production bacterial cell of the invention stably comprises at least one phage structural gene(s) and at least one phage DNA packaging gene(s) derived from a first type of bacteriophage.

By "stably comprise" or "stably comprising" is meant herein that the production bacterial cell retains said phage structural gene(s) and phage DNA packaging gene(s) either incorporated into its chromosome, or on an episome that is maintained in the cell typically through selection (e.g., with a nutritional, auxotrophic, or drug resistance marker). Each gene stably comprised by the production bacterial cell can independently be on a plasmid, on a helper phage, or is integrated into the production bacterial cell chromosome.

In a particular embodiment, said production bacterial cell stably comprises at least two, 3, 4, or all phage structural genes derived from said first type of bacteriophage, and at least one phage DNA packaging gene(s) derived from said first type of bacteriophage.

In a particular embodiment, said production bacterial cell stably comprises at least one phage structural gene(s) derived from said first type of bacteriophage, and at least two or all phage DNA packaging genes derived from said first type of bacteriophage.

In a particular embodiment, said production bacterial cell stably comprises at least two, 3, 4, or all phage structural genes derived from said first type of bacteriophage, and at least two or all phage DNA packaging genes derived from said first type of bacteriophage.

In a particular embodiment, said production bacterial cell stably comprises all phage structural genes derived from said first type of bacteriophage, and all phage DNA packaging genes derived from said first type of bacteriophage.

By "phage structural genes" is meant herein genes from a bacteriophage which are involved in the building of the bacteriophage protein capsid. Phage structural genes include genes encoding phage structural elements; genes encoding phage proteins involved in the assembly of the phage structural elements; and genes encoding phage proteins packaged inside the capsid as scaffold or as pilot proteins to be injected into a targeted bacterial cell.

Phage structural elements are well-known from the skilled person and depend on the type of bacteriophage from which they are derived. Phage structural elements can be proteins but also RNAs (for example some phages like phi29 from *Bacillus subtilis* encode a structural scaffold made of RNA). Phage structural elements typically include capsid proteins, tape measure proteins, fibers, baseplate proteins, tail sheath proteins, whisker proteins, decoration proteins, etc. . . .

Phage proteins involved in the assembly of the structural elements are well-known from the skilled person and depend on the type of bacteriophage from which they are derived, and optionally on the structural elements encoded by the other phage structural genes. Phage proteins involved in the assembly of the structural elements typically include phage chaperone proteins and phage proteases.

Phage proteins packaged inside the capsid as scaffold or as pilot proteins to be injected into a target host cell are well-known from the skilled person and depend on the type of bacteriophage from which they are derived. Examples of such phage proteins are RNA polymerase from phage N4 or minor pilot proteins.

As will be understood by the skilled person, the presence of a particular phage structural gene in the production bacterial cell of the invention will depend on the bacteriophage from which said phage structural genes are derived.

By "phage DNA packaging genes" is meant herein genes from a bacteriophage which are involved in the packaging of the bacteriophage genome into the bacteriophage capsid. Phage DNA packaging genes are well-known from the skilled person and include genes encoding phage terminases, genes encoding phage accessory proteins, genes encoding phage ligases, genes encoding phage exonucleases involved in DNA packaging and genes encoding phage endonucleases involved in DNA packaging.

In a particular embodiment, said production bacterial cell further stably comprises at least one gene involved in phage regulation derived from said first type of bacteriophage.

By "gene involved in phage regulation" is meant herein phage genes involved in the interaction of the phage with the host. Examples of genes involved in phage regulation include phage genes encoding master repressors, phage genes encoding anti-termination proteins, phage genes involved in super-exclusion mechanisms, phage genes involved in defense against host's anti-phage mechanisms, phage genes involved in degradation and/or modification of host's elements for example to complete the lytic cycle, and phage genes advantageous for the host.

In a particular embodiment, said production bacterial cell stably comprises phage gene(s) involved in defense against host's anti-phage mechanisms derived from said first type of bacteriophage.

In a particular embodiment, said phage structural gene(s) and phage DNA packaging gene(s) derived from said first type of bacteriophage, and optionally said gene(s) involved in phage regulation derived from said first type of bacteriophage are comprised in at least one plasmid, chromosome and/or helper phage. In a particular embodiment, said phage structural gene(s) and phage DNA packaging gene(s) derived from said first type of bacteriophage, and optionally said gene(s) involved in phage regulation derived from said first type of bacteriophage are comprised in at least two separate nucleic acid molecules, in particular at least two plasmids, chromosomes, helper phages or combinations thereof.

In a particular embodiment, said phage structural gene(s) and phage DNA packaging gene(s) derived from said first type of bacteriophage, and optionally said gene(s) involved in phage regulation derived from said first type of bacteriophage are comprised in a hybrid helper phage system as defined below.

In a particular embodiment, said phage structural gene(s) and phage DNA packaging gene(s) derived from said first type of bacteriophage, and optionally said gene(s) involved in phage regulation derived from said first type of bacteriophage are comprised in a helper phage.

Induction Mechanism

In the context of the invention, the expression of at least one of said phage structural gene(s) and/or at least one of said phage DNA packaging genes, as defined in the section "Phage DNA packaging genes, and phage structural genes" above, in said production bacterial cell is controlled by at least one induction mechanism.

In a particular embodiment, the expression of at least one of said phage structural gene(s), in particular at least two, at least three, or all said phage structural genes, in said production bacterial cell is(are) controlled by at least one induction mechanism, in particular by one induction mechanism.

In a particular embodiment, the expression of at least one of said phage DNA packaging gene(s), in particular at least two, at least three, or all said phage DNA packaging genes, in said production bacterial cell is(are) controlled by at least one induction mechanism, in particular by one induction mechanism.

In a particular embodiment, the same induction mechanism controls the expression of the at least one of said phage structural gene(s) and the at least one of said phage DNA packaging gene(s).

In an alternative embodiment, the expression of the at least one of said phage structural gene(s) and the expression of the at least one of said phage DNA packaging gene(s) are controlled by different induction mechanisms.

By "induction mechanism" is meant herein a mechanism, encoded by a gene or group of genes comprised, in particular stably comprised, in said production bacterial cell, able to induce the expression of the genes they control, in response to a given trigger.

In a particular embodiment, said induction mechanism further controls the copy number of said at least one of said phage structural gene(s) and/or said at least one of said phage DNA packaging gene(s). In other words, in a particular embodiment, said induction mechanism further controls the replication of said at least one of said phage structural gene(s) and/or of said at least one of said phage DNA packaging gene(s), in particular the replication of the nucleic acid molecule(s) carrying said at least one of said phage structural gene(s) and/or said at least one of said phage DNA packaging gene(s).

In a particular embodiment, said induction mechanism further controls the assembly of the products expressed by said at least one of said phage structural gene(s) and said at least one of said phage DNA packaging gene(s).

Examples of such induction mechanism include:
Protein repressor or activator-based induction systems responding to small molecules (for example sugars, quorum-sensing molecules, gases, synthetic molecules, peptides, amino acids, metabolites, etc), physical signals (temperature, pressure, etc.), chemical signals (osmolarity, pH, etc.), biological signals (cell density, DNA damage, etc.); these systems may be activated by a secondary protein such as an orthogonal RNA polymerase or sigma factor.
Protein degradation systems to activate or repress transcription from a promoter.
RNA-based induction systems such as aptamers responding to the signals stated above, such as RNAi, CRISPRi, toehold systems, riboswitches, etc.
One or more nucleic acids comprising at least one gene, derived from a second type of bacteriophage, involved in phage excision/insertion, phage DNA replication, and/or phage regulation.

In a particular embodiment, said induction mechanism comprises at least one gene, derived from a second type of bacteriophage, involved in phage excision/insertion, phage DNA replication, and/or phage regulation.

Therefore, in particular embodiment, said production bacterial cell further comprises at least one gene, derived from a second type of bacteriophage, involved in phage excision/insertion, phage DNA replication, and/or phage regulation.

Genes Involved in Phage Excision/Insertion, Phage DNA Replication, and/or Phage Regulation By "gene involved in phage excision/insertion" is meant herein genes from lysogenic phages involved in the excision of the phage, present as a prophage, from the genome or episome of a bacterial cell and/or the insertion of the phage, as a prophage, in the genome or episome of a bacterial cell.

By "gene involved in phage DNA replication" is meant herein genes from lysogenic or lytic phages, involved in the mechanism of replication of the phage DNA. Examples of genes involved in phage DNA replication include genes encoding DNA polymerase and genes involved in the segregation of the prophage sequence if it exists in a plasmid or linear plasmid form.

By "gene involved in phage regulation" is meant herein phage genes involved in the interaction of the phage with the host. Examples of genes involved in phage regulation include phage genes encoding master repressors, phage genes encoding anti-termination proteins, phage genes involved in super-exclusion mechanisms, phage genes involved in defense against host's anti-phage mechanisms, phage genes involved in degradation and/or modification of host's elements for example to complete the lytic cycle, and phage genes advantageous for the host.

In the context of the invention, said gene(s) involved in phage excision/insertion, phage DNA replication, and/or phage regulation, is(are) not DNA packaging gene(s) nor structural gene(s), as defined above.

In a preferred embodiment, the production bacterial cell of the invention comprises at least one gene, preferably all the genes, involved in phage excision/insertion derived from a second type of bacteriophage; at least one gene, preferably all the genes, involved in phage DNA replication derived from a second type of bacteriophage; and/or at least one gene, preferably all the genes, involved in phage regulation derived from a second bacteriophage.

In the context of the invention, said production bacterial cell does not comprise genes derived from the first type of bacteriophage which are involved in phage excision/insertion and/or phage DNA replication.

In a particular embodiment, said gene(s) involved in phage excision/insertion, phage DNA replication, and/or phage regulation derived from said second type of bacteriophage, are comprised in at least one plasmid, chromosome and/or helper phage. In a particular embodiment, said gene(s) involved in phage excision/insertion, phage DNA replication, and/or phage regulation derived from said second type of bacteriophage are comprised in at least two separate nucleic acid molecules, in particular at least two plasmids, chromosomes, helper phages or combinations thereof.

In a particular embodiment, said gene(s) involved in phage excision/insertion, phage DNA replication, and/or phage regulation derived from said second type of bacteriophage are comprised in a hybrid helper phage system as defined below.

In a particular embodiment, said gene(s) involved in phage excision/insertion, phage DNA replication, and/or phage regulation derived from said second type of bacteriophage, are comprised in a helper phage system, more particularly on the same helper phage system as said phage structural gene(s) and phage DNA packaging gene(s) derived from said first type of bacteriophage, and optionally said gene(s) involved in phage regulation derived from said first type of bacteriophage.

In the context of the invention, said second type of bacteriophage comes from and/or targets bacterial species or strain different from the bacterial species or strain from which said first type of bacteriophage comes and/or that said first type of bacteriophage targets.

In a particular embodiment, said production bacterial cell is from the same bacterial species or strain as the bacterial species or strain from which said second type of bacteriophage comes and/or that said second type of bacteriophage targets.

In a more particular embodiment, said production bacterial cell is an *E. coli* bacterial cell. In another particular embodiment, said production bacterial cell is a *P. freudenreichii* bacterial cell.

Other Elements

In a particular embodiment, the production bacterial cell of the invention further comprises at least one gene involved in phage RNA transcription.

By "gene involved in phage RNA transcription" is meant genes from temperate or lytic phages, involved in the mechanism of transcription of the phage RNA. Examples of such genes include genes encoding phage RNA polymerase and phage genes encoding proteins modifying the host's RNA polymerases, typically to be able to work past terminators.

Bacteriophage and Gene Derived from a Bacteriophage

By "gene derived from a bacteriophage" is meant herein that the sequence of the gene is obtained from a bacteriophage, said sequence being optionally modified, recoded and/or optimized compared to the sequence initially present in the bacteriophage. For example, said sequence may be recoded for codon exchange or optimization (for example some proteins of the Kappa prophage contain an amber TAG stop codon, which is not recognized by *E. coli*, and which is preferably changed to TAA or TGA) or preventing recombination.

Bacteriophages are obligate intracellular parasites that multiply inside bacteria by co-opting some or all of the host biosynthetic machinery. Bacteriophage can be found inside bacteria as a prophage whose genome is integrated in the bacterial chromosome or as a phage-plasmid whose genome is part of an extrachromosomal plasmid (such phage-plasmids are for example disclosed in Ravin et al. (1999) Molecular Microbiology 34(5):980-994). Examples of bacteriophage which can be in the form of a phage-plasmid include phages P1, N15, SSU5, P7, D6, pMCR-1-P3, IEBH, phiGIL16c, Bam35c, pBClin15, VP882, KS-14, P88, pLP39, F116, D3, phiSG1. Phage genomes come in a variety of sizes and shapes (e.g., linear or circular). Most phages range in size from 24-200 nm in diameter. Phages contain nucleic acid (i.e., genome) and proteins, and may be enveloped by a lipid membrane. Depending upon the phage, the nucleic acid genome can be either DNA or RNA, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage.

In a particular embodiment, the first type of bacteriophage is selected from the Order Caudovirales consisting of, based on the taxonomy of Krupovic et al. (Krupovic et al. Arch Virol. 2016 January; 161(1):233-47):

family Myoviridae (such as, without limitation, genus Cp220virus, Cp8virus, Ea214virus, Felixo1virus, Mooglevirus, Suspvirus, Hp1virus, P2virus, Kayvirus, P100virus, Silviavirus, Spo1virus, Tsarbombavirus, Twortvirus, Cc31virus, Jd18virus, Js98virus, Kp15virus, Moonvirus, Rb49virus, Rb69virus, S16virus, Schizot4virus, Sp18virus, T4virus, Cr3virus, Se1virus, V5virus, Abouovirus, Agatevirus, Agrican357virus, Ap22virus, Arv1virus, B4virus, Bastillevirus, Bc431virus, Bcep78virus, Bcepmuvirus, Biquartavirus, Bxz1virus, Cd119virus, Cp51virus, Cvm10virus, Eah2virus, Elvirus, Hapunavirus, Jimmervirus, Kpp10virus, M12virus, Machinavirus, Marthavirus, Msw3virus, Muvirus, Myohalovirus, Nit1virus, P1virus, Pakpunavirus, Pbunavirus, Phikzvirus, Rheph4virus, Rsl2virus, Rslunavirus, Secunda5virus, Sep1virus, Spn3virus, Svunavirus, Tg1virus, Vhmlvirus and Wphvirus)

family Podoviridae (such as, without limitation, genus Fri1virus, Kp32virus, Kp34virus, Phikmvvirus, Pradovirus, Sp6virus, T7virus, Cp1virus, P68virus, Phi29virus, Nona33virus, Pocjvirus, Tl2011virus, Bcep22virus, Bpp1virus, Cba41virus, Dfl12virus, Ea92virus, Epsilon15virus, F116virus, G7cvirus, Jwalphavirus, Kfl1virus, Kpp25virus, Lit1virus, Luz24virus, Luz7virus, N4virus, Nonanavirus, P22virus, Pagevirus, Phieco32virus, Prtbvirus, Sp58virus, Una961virus and Vp5virus)

family Siphoviridae (such as, without limitation, genus Camvirus, Likavirus, R4virus, Acadianvirus, Coopervirus, Pg1virus, Pipefishvirus, Rosebushvirus, Brujitavirus, Che9cvirus, Hawkeyevirus, Plotvirus, Jerseyvirus, K1gvirus, Sp31virus, Lmd1virus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Rogue1virus, Rtpvirus, T1virus, Tlsvirus, Ab18virus, Amigovirus, Anatolevirus, Andromedavirus, Attisvirus, Barnyardvirus, Bernal13virus, Biseptimavirus, Bronvirus, C2virus, C5virus, Cba181virus, Cbastvirus, Cecivirus, Che8virus, Chivirus, Cjw1virus, Corndogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, Lambdavirus, Laroyevirus, Liefievirus, Marvinvirus, Mudcatvirus, N15virus, Nonagvirus, Np1virus, Omegavirus, P12002virus, P12024virus, P23virus, P70virus, Pa6virus, Pamx74virus, Patiencevirus, Pbi1virus, Pepy6virus, Pfr1virus, Phic31virus, Phicbkvirus, Phietavirus, Phifelvirus, Phijl1virus, Pis4avirus, Psavirus, Psimunavirus, Rdjlvirus, Rer2virus, Sap6virus, Send513virus, Septima3virus, Seuratvirus, Sextaecvirus, Sfi11virus, Sfi21dt1virus, Sitaravirus, Sk1virus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus)

family Ackermannviridae (such as, without limitation, genus Ag3virus, Limestonevirus, Cba120virus and Vi1virus)

In a particular embodiment, the first type of bacteriophage is not part of the Order Caudovirales but from families with Unassigned order such as, without limitation, family Tectiviridae (such as genus *Alphatectivirus, Betatectivirus*), family Corticoviridae (such as genus *Corticovirus*), family Inoviridae (such as genus *Fibrovirus, Habenivirus, Inovirus, Lineavirus, Plectrovirus, Saetivirus, Vespertiliovirus*), family Cystoviridae (such as genus *Cystovirus*), family Leviviridae (such as genus *Allolevivirus, Levivirus*), family Microviridae (such as genus Alpha3microvirus, G4microvirus, Phix174microvirus, *Bdellomicrovirus, Chlamydiamicrovirus, Spiromicrovirus*) and family Plasmaviridae (such as genus *Plasmavirus*).

In a particular embodiment, the first type of bacteriophage is targeting Archea not part of the Order Caudovirales but from families with Unassigned order such as, without limitation, Ampullaviridae, FuselloViridae, Globuloviridae, Guttaviridae, Lipothrixviridae, Pleolipoviridae, Rudiviridae, Salterprovirus and Bicaudaviridae.

In a particular embodiment, the second type of bacteriophage is selected from the bacteriophages defined above, provided that said second type of bacteriophage is different from said first type of bacteriophage.

In a particular embodiment, said first type of bacteriophage comes from a first bacterial species or strain, and said second type of bacteriophage comes from a second bacterial species or strain, wherein said first and second bacterial species or strains are different.

By "bacteriophage coming from a particular bacterial species or strain" is meant herein a bacteriophage specifically targeting a particular bacterial species or strain and/or a bacteriophage hosted by a particular bacterial species or strain.

A non-exhaustive listing of bacterial genera and their known host-specific bacteria viruses is presented in the following paragraphs. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Actinomyces* can be infected by the following phages: Av-I, Av-2, Av-3, BF307, CTI, CT2, CT3, CT4, CT6, CT7, CT8 and 1281.

Bacteria of the genus *Aeromonas* can be infected by the following phages: AA-I, Aeh2, N, PMI, TP446, 3, 4, 11, 13, 29, 31, 32, 37, 43, 43-10T, 51, 54, 55R.1, 56, 56RR2, 57, 58, 59.1, 60, 63, Aehl, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aizl, AI-K-I, B, BCJAI, BCI, BC2, BLLI, BLI, BP142, BSLI, BSL2, BSI, BS3, BS8, BS15, BS18, BS22, BS26, BS28, BS31, BS104, BS105, BS106, BTB, B1715V1, C, CK-I, CoII, CorI, CP-53, CS-I, CSi, D, D, D, D5, entl, FP8, FP9, FSi, FS2, FS3, FS5, FS8, FS9, G, GH8, GT8, GV-I, GV-2, GT-4, g3, gl2, gl3, gl4, gl6, gl7, g21, g23, g24, g29, H2, kenI, KK-88, KumI, KyuI, J7W-1, LP52, (syn=LP-52), L7, MexI, MJ-1, mor2, MP-7, MPIO, MP12, MP14, MP15, NeoI, No 2, N5, N6P, PBCI, PBLA, PBPI, P2, S-a, SF2, SF6, ShaI, SiII, SP02, (syn=φSPP1), SPβ, STI, STi, SU-II, t, TbI, Tb2, Tb5, TbIO, Tb26, Tb51, Tb53, Tb55, Tb77, Tb97, Tb99, Tb560, Tb595, Td8, Td6, TdI5, TgI, Tg4, Tg6, Tg7, Tg9, TgIO, TgII, TgI3, TgI5, Tg21, TinI, Tin7, Ting, TinI3, Tm3, TocI, TogI, toll, TP-I, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, YunI, α, γ, pl I, φmed-2, φT, φμ-4, φ3T, φ75, φIO5, (syn=φIO5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), aleI, ARI, AR2, AR3, AR7, AR9, Bace-11, (syn=11), Bastille, BLI, BL2, BL3, BL4, BLS, BL6, BL8, BL9, BP124, BS28, BS80, Ch, CP-51, CP-54, D-5, darI, denI, DP-7, entI, FoSi, FoS2, FS4, FS6, FS7, G, gaII, gamma, GEI, GF-2, GSi, GT-I, GT-2, GT-3, GT-4, GT-5, GT-6, GT-7, GV-6, gI5, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No. I, N17, N19, PBSI, PKI, PMBI, PMB12, PMJI, S, SPOI, SP3, SP5, SP6, SP7, SP8, SP9, SPIO, SP-15, SP50, (syn=SP-50), SP82, SST, subI, SW, Tg8, TgI2, TgI3, TgI4, thuI, thuΛ, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (*B. megaterium*), 4 (*B. sphaericus*), AR13, BPP-IO, BS32, BS107, BI, B2, GA-I, GP-IO, GV-3, GV-5, g8, MP20, MP27, MP49, Nf, PP5, PP6, SF5, TgI8, TP-I, Versailles, φI5, φ29, 1-97, 837/IV, mï-*Bacillus* (1), BatIO, BSLIO, BSLI I, BS6, BSI I, BS16, BS23, BSIOI, BS102, gI8, morI, PBLI, SN45, thu2, thu3, TmI, Tm2, TP-20, TP21, TP52, type F, type G, type IV, HN-BacMus (3), BLE, (syn=θc), BS2, BS4, BS5, BS7, BIO, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, SPa, type 1 and μ.

Bacteria of the genus *Bacteroides* can be infected by the following phages: crAss-phage, ad I2, Baf-44, Baf-48B, Baf-64, Bf-I, Bf-52, B40-8, FI, βI, φAI, φBrOI, φBrO2, 11, 67.1, 67.3, 68.1, mt-*Bacteroides* (3), Bf42, Bf71, HN-Bdellovibrio (1) and BF-41.

Bacteria of the genus *Bordetella* can be infected by the following phages: 134 and NN-*Bordetella* (3).

Bacteria of the genus *Borrelia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=FOI), (syn=FQI), D, FP2, (syn=FP2), (syn=FD2), Fz, (syn=Fz75/13), (syn=Firenze 75/13), (syn=Fi), Fi, (syn=FI), Fim, (syn=FIm), (syn=Fim), FiU, (syn=FIU), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn-F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=Fi0), (syn=FIO), 371/XXIX, (syn=371), (syn=Fn), (syn=FI I) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phage: Chpl.

Bacteria of the genus *Clostridium* can be infected by following phages: CAKI, CA5, Ca7, CEβ, (syn=10), CEγ, CIdI, c-n71, c-203 Tox-, DEβ, (syn=ID), (syn=IDt0X+), HM3, KMI, KT, Ms, NAI, (syn=Naltox+), PA135Oe, Pfó, PL73, PL78, PL81, PI, P50, P5771, P19402, ICtOX+, 2CtOX\2D3 (syn=2Dt0X+), 3C, (syn=3Ctox+), 4C, (syn=4CtOX+), 56, III-I, NN-*Clostridium* (61), NBItOX+, αI, CAI, HMT, HM2, PFI5 P-23, P-46, Q-05, Q-oe, Q-16, Q-21, Q-26, Q-40, Q-46, S111, SA02, WA01, WA03, Wm, W523, 80, C, CA2, CA3, CPTI, CPT4, cI, c4, c5, HM7, H11/A1, H18/Ax, FWS23, Hi58ZA1, K2ZA1, K21ZS23, ML, NA2tOX; Pf2, Pf3, Pf4, S9ZS3, S41ZA1, S44ZS23, α2, 41, 112ZS23, 214/S23, 233/Ai, 234/S23, 235/S23, II-I, II-2, II-3, NN-*Clostridium* (12), CAI, FI, K, S2, 1, 5 and NN-*Clostridium* (8).

Bacteria of the genus *Corynebacterium* can be infected by the following phages: CGKI (defective), A, A2, A3, AIOI, A128, A133, A137, A139, A155, A182, B, BF, B17, B18, B51, B271, B275, B276, B277, B279, B282, C, capi, CCI, CGI, CG2, CG33, CL31, Cog, (syn=CG5), D, E, F, H, H-I, hqi, hq2, 11ZH33, Ii/31, J, K, K, (syn=Ktox"), L, L, (syn=Ltox+), M, MC-1, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ-), yI9, δ, (syn=δ'ox+), p, (syn=ptoχ-), φ9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phage: DF78, FI, F2, 1, 2, 4, 14, 41, 867, DI, SB24, 2BV, 182, 225, C2, C2F, E3, E62, DS96, H24, M35, P3, P9, SBIOI, S2, 2BII, 5, 182a, 705, 873, 881, 940, 1051, 1057, 21096C, NN-*Enterococcus* (1), PEI, FI, F3, F4, VD13, 1, 200, 235 and 341.

Bacteria of the genus *Erysipelothrix* can be infected by the following phage: NN-Eiysipelothrix (1).

Bacteria of the genus *Escherichia* can be infected by the following phages: BW73, B278, D6, D108, E, EI, E24, E41, FI-2, FI-4, FI-5, H18A, FfI8B, i, MM, Mu, (syn=mu), (syn=MuI), (syn=Mu-I), (syn=MU-I), (syn=MuI), (syn=µ), 025, PhI-5, Pk, PSP3, PI, PID, P2, P4 (defective), SI, Wφ, φK13, φR73 (defective), φI, φ2, φ7, φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FII, FI3, H, HI, H3, H8, K3, M, N, ND-2, ND-3, ND4, ND-5, ND6, ND-7, Ox-I (syn=OXI), (syn=HF), Ox-2 (syn=0x2), (syn=0X2), Ox-3, Ox-4, Ox-5, (syn=0X5), Ox-6, (syn=66F), (syn=φ66t), (syn=φ66t-)5 0111, PhI-I, RB42, RB43, RB49, RB69, S, SaI-I, SaI-2, SaI-3, SaI-4, SaI-5, SaI-6, TC23, TC45, TuII*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, αI, 1, IA, 3, (syn=Ac3), 3A, 3T+, (syn=3), (syn=MI), 5φ, (syn=φ5), 9266Q, CFO103, HK620, J, K, KIF, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, φ04-CF, φ05, φ06, φ07, φI, φI.2, φ20, φ95, φ263, φIO92, φI, φII, (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, CI, DDUP, ECI, EC2, E21, E29, FI, F26S, F27S, Hi, HK022, HK97, (syn=φHK97), HK139, HK253, HK256, K7, ND-I, no.D, PA-2, q, S2, TI, (syn=α), (syn=P28), (syn=T-I), (syn=Tx), T3C, T5, (syn=T-5), (syn=T5), UC-I, w, β4, γ2, λ (syn=lambda), (syn=φλ), φD326, φγ, φ06, φ7, φ10, φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J, 933H, O157 typing phages 1 to 16, JES-2013, 121Q, 172-1, 1720a-02, ADB-2, AKFV33, av-05, bV_EcoS_AHP42, bV_EcoS_AHP24, bC_EcoS_AHS24, bV_EcoS_AKS96, CBA120.

Bacteria of the genus *Fusobacterium* are infected by the following phage: NN-*Fusobacterium* (2), fv83-554/3, fv88-531/2, 227, fv2377, fv2527 and fv8501.

Bacteria of the genus *Haemophilus* are infected by the following phage: HPI, S2 and N3.

Bacteria of the genus *Helicobacter* are infected by the following phage: HPI and ^^-*Helicobacter* (1).

Bacteria of the genus *Klebsiella* are infected by the following phage: AIO-2, KI4B, KI6B, KI9, (syn=K19), KI14, KI15, K121, KI28, KI29, KI32, KI33, KI35, KI106B, KI171B, KI181B, KI832B, AIO-1, AO-1, AO-2, AO-3, FC3-10, K, KI1, (syn=KII), KI2, (syn=K12), KI3, (syn=K13), (syn=KI 70/11), KI4, (syn=K14), KI5, (syn=K15), KI6, (syn=K16), KI7, (syn=K17), KI8, (syn=K18), KI19, (syn=K19), KI27, (syn=K127), KI31, (syn=K131), KI35, KI171B, II, VI, IX, CI-I, KI4B, KI8, KI11, KI12, KI13, KI16, KI17, KI18, KI20, KI22, KI23, KI24, KI26, KI30, KI34, KI106B, KIi65B, KI328B, KLXI, K328, P5046, 11, 380, III, IV, VII, VIII, FC3-11, KI2B, (syn=K12B), KI25, (syn=K125), KI42B, (syn=K142), (syn=K142B), KI181B, (syn=KII 81), (syn=K1181B), KI765/!, (syn=K1765/1), KI842B, (syn=K1832B), KI937B, (syn=K1937B), LI, φ28, 7, 231, 483, 490, 632 and 864/100.

Bacteria of the genus *Lepitospira* are infected by the following phage: LEI, LE3, LE4 and ~NN-Leptospira (1).

Bacteria of the genus *Listeria* are infected by the following phage: A511, 01761, 4211, 4286, (syn=BO54), A005, A006, A020, A500, A502, A511, AI 18, A620, A640, B012, B021, B024, B025, B035, B051, B053, B054, B055, B056, BIOI, BI IO, B545, B604, B653, C707, D441, HSO47, HIOG, H8/73, H19, H21, H43, H46, H107, H108, HI IO, H163/84, H312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-*Listeria* (15).

Bacteria of the genus *Morganella* are infected by the following phage: 47.

Bacteria of the genus *Mycobacterium* are infected by the following phage: 13, AGI, ALi, ATCC 11759, A2, B.C3, BG2, BKI, BK5, *butyricum*, B-I, B5, B7, B30, B35, Clark, CI, C2, DNAIII, DSP1, D4, D29, GS4E, (syn=GS4E), GS7, (syn=GS-7), (syn=GS7), IPa, lacticola, Legendre, Leo, L5, (syn=φL-5), MC-1, MC-3, MC-4, minetti, MTPHI I, Mx4, MyF3P/59a, *phlei*, (syn=*phlei* 1), *phlei* 4, Polonus II, rabinovitschi, *smegmatis*, TM4, TM9, TMIO, TM20, Y7, YIO, φ630, IB, IF, IH, 1/1, 67, 106, 1430, BI, (syn=BoI), B24, D, D29, F-K, F-S, HP, Polonus I, Roy, RI, (syn=RI-Myb), (syn=Ri), 11, 31, 40, 50, 103a, 103b, 128, 3111-D, 3215-D and NN-*Mycobacterium* (1).

Bacteria of the genus *Neisseria* are infected by the following phage: Group I, group II and NPI.

Bacteria of the genus *Nocardia* are infected by the following phage: MNP8, NJ-L, NS-8, N5 and TtiN-*Nocardia*.

Bacteria of the genus *Proteus* are infected by the following phage: Pm5, 13vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmIO, PmI I, Pv2, πI, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* are infected by the following phage: PL25, PL26, PL37, 9211/9295, 9213/921 Ib, 9248, 7/R49, 7476/322, 7478/325, 7479, 7480, 9000/9402 and 9213/921 Ia.

Bacteria of the genus *Pseudomonas* are infected by the following phage: PfI, (syn=Pf-I), Pf2, Pf3, PP7, PRRI, 7s, im-*Pseudomonas* (1), AI-I, AI-2, B 17, B89, CB3, Col 2, Col 11, Col 18, Col 21, C154, C163, C167, C2121, E79, F8, ga, gb, H22, K1, M4, N2, Nu, PB-I, (syn=PBI), pfl6, PMN17, PPI, PPB, PsaI, PsPI, PsP2, PsP3, PsP4, PsP5, PS3, PS17, PTB80, PX4, PX7, PYOI, PYO2, PYO5, PYO6, PYO9, PYOIO, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, PIK, SLPI, SL2, S2, UNL-I, wy, Yai, Ya4, Yan, φBE, φCTX, φC17, φKZ, (syn=φKZ), φ-LT, φmu78, φNZ, φPLS-1, φST-1, φW-14, φT-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, CI-2, C5, D, gh-1, FI 16, HF, H90, K5, K6, K104, K109, K166, K267, N4, N5, O6N-25P, PE69, Pf, PPN25, PPN35, PPN89, PPN91, PP2, PP3, PP4, PP6, PP7, PPB, PP56, PP87, PPI 14, PP206, PP207, PP306, PP651, Psp231a, Pssy401, Pssy9220, psi, PTB2, PTB20, PTB42, PXI, PX3, PXIO, PX12, PX14, PYO70, PYO71, R, SH6, SH133, tf, Ya5, Ya7, φBS, φKf77, φ-MC, φmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, FIO, g, gd, ge, gξ, Hwl2, Jb 19, KFI, L°, OXN-32P, O6N-52P, PCH-I, PC13-1, PC35-1, PH2, PH51, PH93, PH132, PMW, PM13, PM57, PM61, PM62, PM63, PM69, PM105, PMI 13, PM681, PM682, PO4, PPI, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-IO, Pz, SDI, SLI, SL3, SL5, SM, φC5, φCI I, φCI I-1, φC13, φC15, φMO, φX, φO4, φI I, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), GIOI, M6, M6a, LI, PB2, PssyI5, Pssy4210, Pssy4220, PYO12, PYO34, PYO49, PYO50, PYO51, PYO52, PYO53, PYO57, PYO59, PYO200, PX2, PX5, SL4, φO3, φO6 and 1214.

Bacteria of the genus *Rickettsia* are infected by the following phage: NN-*Rickettsia*.

Bacteria of the genus *Salmonella* are infected by the following phage: b, Beccles, CT, d, Dundee, f, Fels 2, GI, GUI, GVI, GVIII, k, K, i, j, L, 01, (syn=0-1), (syn=O1), (syn=O-I), (syn=7), 02, 03, P3, P9a, PIO, Sab3, Sab5, SanIS, SanI7, SI, Taunton, ViI, (syn=ViI), 9, imSalmonella (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22aI, P22-4, P22-7, P22-11, SNT-I, SNT-2, SP6, ViIII, ViIV, ViV, ViVI, ViVII, Workshop, Sj5, ε34, 1, 37, 1(40), (syn=φI[40]), 1, 422, 2, 2.5, 3b, 4, 5, 6, 14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, GI 73, h, IRA, Jersey, MB78, P22-1, P22-3, P22-12, SabI, Sab2, Sab2, Sab4, SanI, San2, San3, San4, San6, San7, Sang, San9, SanI3, SanI4, SanI6, SanI8, SanI9, San20, San21, San22, San23, San24, San25, San26, SasLI, SasL2, SasL3, SasL4, SasL5, SIBL, SII, ViII, φ1, 1, 2, 3a, 3aI, 1010, Ym-*Salmonella* (1), N-4, SasL6 and 27.

Bacteria of the genus *Serratia* are infected by the following phage: A2P, PS20, SMB3, SMP, SMP5, SM2, V40, V56, ic, φCP-3, φCP-6, 3M, 10/Ia, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCWI, φCP6-1, φCP6-2, φCP6-5, 3T, 5, 8, 9F, 10/1, 20E, 32/6, 34B, 34CT, 34P, 37, 41, 56, 56D, 56P, 60P, 61/6, 74/6, 76/4, 101/8900, 226, 227, 228, 229F, 286, 289, 290F, 512, 764a, 2847/10, 2847/10a, L.359 and SMBI.

Bacteria of the genus *Shigella* are infected by the following phage: Fsa, (syn=a), FSD2d, (syn=D2d), (syn=W2d), FSD2E, (syn=W2e), fv, F6, f7.8, H-Sh, PES, P90, SfII, Sh, SHm, SHrv, (syn=HIV), SHvi, (syn=HVI), SHVvm, (syn=HVIII), SKγ66, (syn=gamma 66), (syn=γββ), (syn=γ66b), SKm, (syn=SIIIb)5 (syn=UI), SKw, (syn=Siva), (syn=IV), SIC™, (syn=SIVA.), (syn=IVA), SKvi, (syn=KVI), (syn=Svi), (syn=VI), SKvm, (syn=Svm), (syn=VIII), SKVIIIA, (syn=SvmA), (syn=VIIIA), STvi, STK, STx1, STxn, S66, W2, (syn=D2c), (syn=D20), φI, φIVb 3-SO-R, 8368-SO-R, F7, (syn=FS7), (syn=K29), FIO, (syn=FSIO), (syn=K31), I1, (syn=alfa), (syn=FSa), (syn=KI 8), (syn=α), I2, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO-S-R), W1, (syn=D8), (syn=FSD8), W2a, (syn=D2A), (syn=FS2a), DD-2, Sf6, FSi, (syn=FI), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssγ66), φ2, BII, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI I, P2-S0-S, SG36, (syn=SO-36/G), (syn=G36), SG3204, (syn=SO-3204/G), SG3244, (syn=SO-3244/G), SHi, (syn=HI), SHvπ, (syn=HVII), SHK, (syn=HIX), SHx1, SHxπ, (syn=HXn), SKI, KI, (syn=S1), (syn=SsI), SKVII, (syn=KVII), (syn=Svπ), (syn=SsVII), SKIX, (syn=KIX), (syn=S1x), (syn=SsIX), SKXII, (syn=KXII), (syn=Sxn), (syn=SsXII), STi, STffI, STrv, STVi, STvπ, S70, S206, U2-S0-S, 3210-SO-S, 3859-SO-S, 4020-SO-S, φ3, φ5, φ7, φ8, φ9, φIO, φI I, φI3, φI4, φI8, SHm, (syn=Hπi), SHχi, (syn=HXt) and SKxI, (syn=KXI), (syn=Sχi), (syn=SsXI), (syn=XI).

Bacteria of the genus *Staphylococcus* are infected by the following phage: A, EW, K, Ph5, Ph9, PhIO, PhI3, PI, P2, P3, P4, P8, P9, PIO, RG, SB-i, (syn=Sb-I), S3K, Twort, φSK311, φ812, 06, 40, 58, 119, 130, 131, 200, 1623, STCI, (syn=stcI), STC2, (syn=stc2), 44AHJD, 68, ACI, AC2, A6"C", A9"C", b581, CA-I, CA-2, CA-3, CA-4, CA-5, DI I, L39×35, L54a, M42, NI, N2, N3, N4, N5, N7, N8, NIO, NiI, N12, N13, N14, N16, Ph6, PhI2, PhI4, UC-18, U4, U15, SI, S2, S3, S4, S5, X2, Z1, φB5-2, φD, ω, 11, (syn=φI I), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80α, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, AIO, A13, b594n, D, HK2, N9, N15, P52, P87, SI, S6, Z4, φRE, 3A, 3B, 3C, 6, 7, 16, 21, 42B, 42C, 42E, 44, 47, 47A5 47C, 51, 54, 54×1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phage: EJ-I, NN-Streptococais (1), a, CI, FL0Ths, H39, Cp-I, Cp-5, Cp-7, Cp-9, Cp-IO, AT298, A5, aIO/JI, aIO/J2, aIO/J5, aIO/J9, A25, BTI I, b6, CAI, c20-1, c20-2, DP-I, Dp-4, DTI, ET42, eIO, FA101, FETHs, Fκ, FKKIOI, FKLIO, FKP74, FKH, FLOThs, FyIOI, fI, F10, F20140/76, g, GT-234, HB3, (syn=HB-3), HB-623, HB-746, M102, 01205, φO1205, PST, PO, PI, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, SfII 1, (syn=SFII I), (syn=φSFiIII), syn=φSFiI I), syn=φSfiI I), sfiI9, (syn=SFiI9), (syn=φSFiI9), (syn=φSfiI9), Sfi21, (syn=SFi21), (syn=φSFi21), (syn=φSfi21), ST0, STX, st2, ST2, ST4, S3, (syn=φS3), s265, φ17, φ42, φ57, φ80, φ81, φ82, φ83, φ84, φ85, φ86, φ87, φ88, φ89, φ90, φ91, φ92, φ93, φ94, φ95, φ96, φ97, φ98, φ99, φIOO, φIOI, φIO2, φ227, φ7201, ωI, ω2, ω3, ω4, ω5, ω6, ω8, ωIO, 1, 6, 9, 1OF, 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/ST16, 80/15, 80/47, 80/48, 101, 103/39, 103/40, 121/41, 121/42, 123/43, 123/44, 124/44, 337/ST17 and m*Streptococcus* (34).

Bacteria of the genus *Treponema* are infected by the following phage: NN-*Treponema* (1).

Bacteria of the genus *Vibrio* are infected by the following phage: CTXφ, fs, (syn=si), fs2, Ivpf5, VfI2, Vf33, VPIφ, VSK, v6, 493, CP-TI, ET25, kappa, K139, Labol, XN-69P, OXN-86, 06N-21P, PB-I, P147, rp-1, SE3, VA-I, (syn=VcA-I), VcA-2, VPI, VP2, VP4, VP7, VP8, VP9, VPIO, VP17, VP18, VP19, X29, (syn=29 d'Herelle), t, φHAWI-1, φHAWI-2, φHAWI-3, φHAWI-4, φHAWI-5, φHAWI-6, φHAWI-7, XHAWI-8, φHAWI-9, φHAWI-10, φHCI-1, φHC1-2, φHC1-3, φHC1-4, φHC2-1, φHC2-2, φHC2-3, φHC2-4, φHC3-1, φHC3-2, φHC3-3, φHD1S-1, φHD1S-2, φHD2S-1, φHD2S-2, φHD2S-3, φHD2S-4, φHD2S-5, φHDO-1, φHDO-2, φHDO-3, φHDO-4, φHDO-5, φHDO-6, φKL-33, φKL-34, φKL-35, φKL-36, φKWH-2, φKWH-3, φKWH-4, φMARQ-1, φMARQ-2, φMARQ-3, φMOAT-1, φO139, φPEL1A-1, φPEL1A-2, φPEL8A-1, φPEL8A-2, φPEL8A-3, φPEL8C-1, φPEL8C-2, φPEL13A-1, φPEL13B-1, φPEL13B-2, φPEL13B-3, φPEL13B-4, φPEL13B-5, φPEL13B-6, φPEL13B-7, φPEL13B-8, φPEL13B-9, φPEL13B-10, φVP143, φVP253, φ16, φI38, 1-II, 5, 13, 14, 16, 24, 32, 493, 6214, 7050, 7227, II, (syn=group II), (syn=φ2), V, VIII, ~m-*Vibrio* (13), KVP20, KVP40, nt-1, O6N-22P, P68, eI, e2, e3, e4, e5, FK, G, I, K, nt-6, NI, N2, N3, N4, N5, O6N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, I (syn=group I), Ill (syn=group III), VI, (syn=A-Saratov), VII, IX, X, HN-*Vibrio* (6), pAl, 7, 7-8, 70A-2, 71A-6, 72A-5, 72A-8, 108A-10, 109A-6, 109A-8, I IOA-1, IOA-5, 110A-7, hv-1, OXN-52P, P13, P38, P53, P65, P108, PiII, TP13 VP3, VP6, VP12, VP13, 70A-3, 70A-4, 70A-10, 72A-1, 108A-3, 109-B1, 110A-2, 149, (syn=φI49), IV, (syn=group IV), NN-*Vibrio* (22), VP5, VPII, VP15, VP16, αI, α2, α3a, α3b, 353B and HN-*Vibrio* (7).

Bacteria of the genus *Yersinia* are infected by the following phage: H, H-I, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φYerO3-12, 3, 4/01324-76, 7/F783-76, 903, 1/M6176 and Yer2AT.

In a particular embodiment, the first type of bacteriophage is selected from the group consisting of the bacteriophages listed above, and the second type of bacteriophage is selected from the group consisting of the bacteriophages listed above, said second type of bacteriophage being a type of bacteriophage different from the first type of bacteriophage.

In a particular embodiment, the first and/or the second type of bacteriophage is selected in the group consisting of *Salmonella* virus SKML39, *Shigella* virus AG3, *Dickeya* virus Limestone, *Dickeya* virus RC2014, *Escherichia* virus CBA120, *Escherichia* virus PhaxI, *Salmonella* virus 38, *Salmonella* virus Det7, *Salmonella* virus GG32, *Salmonella* virus PM10, *Salmonella* virus SFP10, *Salmonella* virus SH19, *Salmonella* virus SJ3, *Escherichia* virus ECML4, *Salmonella* virus Marshall, *Salmonella* virus Maynard, *Salmonella* virus SJ2, *Salmonella* virus STML131, *Salmonella* virus ViI, *Erwinia* virus Ea2809, *Klebsiella* virus 0507KN21, *Serratia* virus IME250, *Serratia* virus MAM1, *Campylobacter* virus CP21, *Campylobacter* virus CP220, *Campylobacter* virus CPt10, *Campylobacter* virus IBB35, *Campylobacter* virus CP81, *Campylobacter* virus CP30A, *Campylobacter* virus CPX, *Campylobacter* virus NCTC12673, *Erwinia* virus Ea214, *Erwinia* virus M7, *Escherichia* virus AYO145A, *Escherichia* virus EC6, *Escherichia* virus HY02, *Escherichia* virus JH2, *Escherichia* virus TP1, *Escherichia* virus VpaE1, *Escherichia* virus wV8, *Salmonella* virus FelixO1, *Salmonella* virus HB2014, *Salmonella* virus Mushroom, *Salmonella* virus UAB87, *Citrobacter* virus Moogle, *Citrobacter* virus Mordin, *Escherichia* virus SUSP1, *Escherichia* virus SUSP2, *Aeromonas* virus phiO18P, *Haemophilus* virus HP1, *Haemophilus* virus HP2, *Pasteurella* virus F108, *Vibrio* virus K139, *Vibrio* virus Kappa, *Burkholderia* virus phi52237, *Burkholderia* virus phiE122, *Burkholderia* virus phiE202, *Escherichia* virus 186, *Escherichia* virus P4, *Escherichia* virus P2, *Escherichia* virus Wphi, *Mannheimia* virus PHL101, *Pseudomonas* virus phiCTX, *Ralstonia* virus RSA1, *Salmonella* virus Fels2, *Salmonella* virus PsP3, *Salmonella* virus SopEphi, *Yersinia* virus L413C, *Staphylococcus* virus G1, *Staphylococcus* virus G15, *Staphylococcus* virus JD7, *Staphylococcus* virus K, *Staphylococcus* virus MCE2014, *Staphylococcus* virus P108, *Staphylococcus* virus Rodi, *Staphylococcus* virus S253, *Staphylococcus* virus S25-4, *Staphylococcus* virus SA12, *Listeria* virus A511, *Listeria* virus P100, *Staphylococcus* virus Remus, *Staphylococcus* virus SA11, *Staphylococcus* virus Stau2, *Bacillus* virus Camphawk, *Bacillus* virus SPO1, *Bacillus* virus BCP78, *Bacillus* virus TsarBomba, *Staphylococcus* virus Twort, *Enterococcus* virus phiEC24C, *Lactobacillus* virus Lb338-1, *Lactobacillus* virus LP65, *Enterobacter* virus PG7, *Escherichia* virus CC31, *Klebsiella* virus JD18, *Klebsiella* virus PKO111, *Escherichia* virus Bp7, *Escherichia* virus IME08, *Escherichia* virus JS10, *Escherichia* virus JS98, *Escherichia* virus QL01, *Escherichia* virus VR5, *Enterobacter* virus Eap3, *Klebsiella* virus KP15, *Klebsiella* virus KP27, *Klebsiella* virus Matisse, *Klebsiella* virus Miro, *Citrobacter* virus Merlin, *Citrobacter* virus Moon, *Escherichia* virus JSE, *Escherichia* virus phi1, *Escherichia* virus RB49, *Escherichia* virus HX01, *Escherichia* virus JS09, *Escherichia* virus RB69, *Shigella* virus UTAM, *Salmonella* virus S16, *Salmonella* virus STML198, *Vibrio* virus KVP40, *Vibrio* virus nt1, *Vibrio* virus ValKK3, *Escherichia* virus VR7, *Escherichia* virus VR20, *Escherichia* virus VR25, *Escherichia* virus VR26, *Shigella* virus SP18, *Escherichia* virus AR1, *Escherichia* virus C40, *Escherichia* virus E112, *Escherichia* virus ECML134, *Escherichia* virus HY01, *Escherichia* virus Ime09, *Escherichia* virus RB3, *Escherichia* virus RB14, *Escherichia* virus T4, *Shigella* virus Pss1, *Shigella* virus Shfl2, *Yersinia* virus D1, *Yersinia* virus PST, *Acinetobacter* virus 133, *Aeromonas* virus 65, *Aeromonas* virus Aeh1, *Escherichia* virus RB16, *Escherichia* virus RB32, *Escherichia* virus RB43, *Pseudomonas* virus 42, *Cronobacter* virus CR3, *Cronobacter* virus CR8, *Cronobacter* virus CR9, *Cronobacter* virus PBES02, *Pectobacterium* virus phiTE, *Cronobacter* virus GAP31, *Escherichia* virus 4MG, *Salmonella* virus SE1, *Salmonella* virus SSE121, *Escherichia* virus FFH2, *Escherichia* virus FV3, *Escherichia* virus JES2013, *Escherichia* virus V5, *Brevibacillus* virus Abouo, *Brevibacillus* virus Davies, *Bacillus* virus Agate, *Bacillus* virus Bobb, *Bacillus* virus Bp8pC, *Erwinia* virus Deimos, *Erwinia* virus Ea35-70, *Erwinia* virus RAY, *Erwinia* virus Simmy50, *Erwinia* virus SpecialG, *Acinetobacter* virus AB1, *Acinetobacter* virus AB2, *Acinetobacter* virus AbC62, *Acinetobacter* virus AP22, *Arthrobacter* virus ArV1, *Arthro-* bacter virus Trina, *Bacillus* virus AvesoBmore, *Bacillus* virus B4, *Bacillus* virus Bigbertha, *Bacillus* virus Riley, *Bacillus* virus Spock, *Bacillus* virus Troll, *Bacillus* virus Bastille, *Bacillus* virus CAM003, *Bacillus* virus Bc431, *Bacillus* virus Bcp1, *Bacillus* virus BCP82, *Bacillus* virus BM15, *Bacillus* virus Deepblue, *Bacillus* virus JBP901, *Burkholderia* virus Bcep1, *Burkholderia* virus Bcep43, *Burkholderia* virus Bcep781, *Burkholderia* virus BcepNY3, *Xanthomonas* virus OP2, *Burkholderia* virus BcepMu, *Burkholderia* virus phiE255, *Aeromonas* virus 44RR2, *Mycobacterium* virus Alice, *Mycobacterium* virus Bxz1, *Mycobacterium* virus Dandelion, *Mycobacterium* virus HyRo, *Mycobacterium* virus 13, *Mycobacterium* virus Nappy, *Mycobacterium* virus Sebata, *Clostridium* virus phiC2, *Clostridium* virus phiCD27, *Clostridium* virus phiCD119, *Bacillus* virus CP51, *Bacillus* virus JL, *Bacillus* virus Shanette, *Escherichia* virus CVM10, *Escherichia* virus ep3, *Erwinia* virus Asesino, *Erwinia* virus EaH2, *Pseudomonas* virus EL, *Halomonas* virus HAP1, *Vibrio* virus VP882, *Brevibacillus* virus Jimmer, *Brevibacillus* virus Osiris, *Pseudomonas* virus Ab03, *Pseudomonas* virus KPP10, *Pseudomonas* virus PAKP3, *Sinorhizobium* virus M7, *Sinorhizobium* virus M12, *Sinorhizobium* virus N3, *Erwinia* virus Machina, *Arthrobacter* virus Brent, *Arthrobacter* virus Jawnski, *Arthrobacter* virus Martha, *Arthrobacter* virus Sonny, *Edwardsiella* virus MSW3, *Edwardsiella* virus PEi21, *Escherichia* virus Mu, *Shigella* virus SfMu, *Halobacterium* virus phiH, *Bacillus* virus Grass, *Bacillus* virus NIT1, *Bacillus* virus SPG24, *Aeromonas* virus 43, *Escherichia* virus P1, *Pseudomonas* virus CAb1, *Pseudomonas* virus CAb02, *Pseudomonas* virus JG004, *Pseudomonas* virus PAKP1, *Pseudomonas* virus PAKP4, *Pseudomonas* virus PaP1, *Burkholderia* virus BcepF1, *Pseudomonas* virus 141, *Pseudomonas* virus Ab28, *Pseudomonas* virus DL60, *Pseudomonas* virus DL68, *Pseudomonas* virus F8, *Pseudomonas* virus JG024, *Pseudomonas* virus KPP12, *Pseudomonas* virus LBL3, *Pseudomonas* virus LMA2, *Pseudomonas* virus PB1, *Pseudomonas* virus SN, *Pseudomonas* virus PA7, *Pseudomonas* virus phiKZ, *Rhizobium* virus RHEph4, *Ralstonia* virus RSF1, *Ralstonia* virus RSL2, *Ralstonia* virus RSL1, *Aeromonas* virus 25, *Aeromonas* virus 31, *Aeromonas* virus Aes12, *Aeromonas* virus Aes508, *Aeromonas* virus AS4, *Stenotrophomonas* virus IME13, *Staphylococcus* virus IPLAC1C, *Staphylococcus* virus SEP1, *Salmonella* virus SPN3US, *Bacillus* virus 1, *Geobacillus* virus GBSV1, *Yersinia* virus R1RT, *Yersinia* virus TG1, *Bacillus* virus G, *Bacillus* virus PBS1, *Microcystis* virus Ma-LMM01, *Vibrio* virus MAR, *Vibrio* virus VHML, *Vibrio* virus VP585, *Bacillus* virus BPS13, *Bacillus* virus Hakuna, *Bacillus* virus Megatron, *Bacillus* virus WPh, *Acinetobacter* virus AB3, *Acinetobacter* virus Abp1, *Acinetobacter* virus Fri1, *Acinetobacter* virus IME200, *Acinetobacter* virus PD6A3, *Acinetobacter* virus PDAB9, *Acinetobacter* virus phiAB1, *Escherichia* virus K30, *Klebsiella* virus K5, *Klebsiella* virus K11, *Klebsiella* virus Kp1, *Klebsiella* virus KP32, *Klebsiella* virus KpV289, *Klebsiella* virus F19, *Klebsiella* virus K244, *Klebsiella* virus Kp2, *Klebsiella* virus KP34, *Klebsiella* virus KpV41, *Klebsiella* virus KpV71, *Klebsiella* virus KpV475, *Klebsiella* virus SU503, *Klebsiella* virus SU552A, *Pantoea* virus Limelight, *Pantoea* virus Limezero, *Pseudomonas* virus LKA1, *Pseudomonas* virus phiKMV, *Xanthomonas* virus f20, *Xanthomonas* virus f30, *Xylella* virus Prado, *Erwinia* virus Era103, *Escherichia* virus K5, *Escherichia* virus K1-5, *Escherichia* virus K1E, *Salmonella* virus SP6, *Escherichia* virus T7, *Kluyvera* virus Kvp1, *Pseudomonas* virus gh1, *Prochlorococcus* virus PSSP7, *Synechococcus* virus P60, *Synechococcus* virus Syn5, *Streptococcus* virus Cp1, *Streptococcus* virus Cp7, *Staphylococcus* virus 44AHJD, *Streptococcus* virus C1, *Bacillus* virus B103, *Bacillus* virus GA1, *Bacillus* virus phi29, *Kurthia* virus 6, *Actinomyces* virus Av1, *Mycoplasma* virus P1, *Escherichia* virus 24B, *Escherichia* virus 933W, *Escherichia* virus Min27, *Escherichia* virus PA28, *Escherichia* virus Stx2 II, *Shigella* virus 7502Stx, *Shigella* virus POCJ13, *Escherichia* virus 191, *Escherichia* virus PA2, *Escherichia* virus TL2011, *Shigella* virus VASD, *Burkholderia* virus Bcep22, *Burkholderia* virus Bcepil02, *Burkholderia* virus Bcepmigl, *Burkholderia* virus DC1, *Bordetella* virus BPP1, *Burkholderia* virus BcepC6B, *Cellulophaga* virus Cba41, *Cellulophaga* virus Cba172, *Dinoroseobacter* virus DFL12, *Erwinia* virus Ea9-2, *Erwinia* virus Frozen, *Escherichia* virus phiV10, *Salmonella* virus Epsilon15, *Salmonella* virus SPN1S, *Pseudomonas* virus F116, *Pseudomonas* virus H66, *Escherichia* virus APEC5, *Escherichia* virus APEC7, *Escherichia* virus Bp4, *Escherichia* virus EC1UPM, *Escherichia* virus ECBP1, *Escherichia* virus G7C, *Escherichia* virus IME11, *Shigella* virus Sb1, *Achromobacter* virus Axp3, *Achromobacter* virus JWAlpha, *Edwardsiella* virus KF1, *Pseudomonas* virus KPP25, *Pseudomonas* virus R18, *Pseudomonas* virus Ab09, *Pseudomonas* virus LIT1, *Pseudomonas* virus PA26, *Pseudomonas* virus Ab22, *Pseudomonas* virus CHU, *Pseudomonas* virus LUZ24, *Pseudomonas* virus PAA2, *Pseudomonas* virus PaP3, *Pseudomonas* virus PaP4, *Pseudomonas* virus TL, *Pseudomonas* virus KPP21, *Pseudomonas* virus LUZ7, *Escherichia* virus N4, *Salmonella* virus 9NA, *Salmonella* virus SP069, *Salmonella* virus BTP1, *Salmonella* virus HK620, *Salmonella* virus P22, *Salmonella* virus ST64T, *Shigella* virus Sf6, *Bacillus* virus Page, *Bacillus* virus Palmer, *Bacillus* virus Pascal, *Bacillus* virus Pony, *Bacillus* virus Pookie, *Escherichia* virus 172-1, *Escherichia* virus ECB2, *Escherichia* virus NJ01, *Escherichia* virus phiEco32, *Escherichia* virus Septima11, *Escherichia* virus SU10, *Brucella* virus Pr, *Brucella* virus Tb, *Escherichia* virus Pollock, *Salmonella* virus FSL SP-058, *Salmonella* virus FSL SP-076, *Helicobacter* virus 1961P, *Helicobacter* virus KHP30, *Helicobacter* virus KHP40, *Hamiltonella* virus APSE1, *Lactococcus* virus KSY1, *Phormidium* virus WMP3, *Phormidium* virus WMP4, *Pseudomonas* virus 119X, *Roseobacter* virus SIO1, *Vibrio* virus VpV262, *Vibrio* virus VC8, *Vibrio* virus VP2, *Vibrio* virus VPS, *Streptomyces* virus Amela, *Streptomyces* virus phiCAM, *Streptomyces* virus Aaronocolus, *Streptomyces* virus Caliburn, *Streptomyces* virus Danzina, *Streptomyces* virus Hydra, *Streptomyces* virus Izzy, *Streptomyces* virus Lannister, *Streptomyces* virus Lika, *Streptomyces* virus Sujidade, *Streptomyces* virus Zemlya, *Streptomyces* virus ELB20, *Streptomyces* virus R4, *Streptomyces* virus phiHau3, *Mycobacterium* virus Acadian, *Mycobacterium* virus Baee, *Mycobacterium* virus Reprobate, *Mycobacterium* virus Adawi, *Mycobacterium* virus Banel, *Mycobacterium* virus BrownCNA, *Mycobacterium* virus Chrisnmich, *Mycobacterium* virus Cooper, *Mycobacterium* virus JAMaL, *Mycobacterium* virus Nigel, *Mycobacterium* virus Stinger, *Mycobacterium* virus Vincenzo, *Mycobacterium* virus Zemanar, *Mycobacterium* virus Apizium, *Mycobacterium* virus Manad, *Mycobacterium* virus Oline, *Mycobacterium* virus Osmaximus, *Mycobacterium* virus Pg1, *Mycobacterium* virus Soto, *Mycobacterium* virus Suffolk, *Mycobacterium* virus Athena, *Mycobacterium* virus Bernardo, *Mycobacterium* virus Gadjet, *Mycobacterium* virus Pipefish, *Mycobacterium* virus Godines, *Mycobacterium* virus Rosebush, *Mycobacterium* virus Babsiella, *Mycobacterium* virus Brujita, *Mycobacterium* virus Che9c, *Mycobacterium* virus Sbash, *Mycobacterium* virus Hawkeye, *Mycobacterium* virus Plot, *Salmonella* virus AG11, *Salmonella* virus Ent1, *Salmonella* virus f18SE, *Salmonella* virus Jersey, *Salmonella* virus L13, *Salmonella* virus LSPA1, *Salmonella* virus SE2, *Salmonella* virus SETP3, *Salmonella* virus SETP7, *Salmonella* virus SETP13, *Salmonella* virus SP101, *Salmonella* virus SS3e, *Salmonella* virus wksI3, *Escherichia* virus K1G, *Escherichia* virus K1H, *Escherichia* virus K1ind1, *Escherichia* virus K1ind2, *Salmonella* virus SP31, *Leuconostoc* virus Lmd1, *Leuconostoc* virus LN03, *Leuconostoc* virus LN04, *Leuconostoc* virus LN12, *Leuconostoc* virus LN6B, *Leuconostoc* virus P793, *Leuconostoc* virus 1A4, *Leuconostoc* virus Ln8, *Leuconostoc* virus Ln9, *Leuconostoc* virus LN25, *Leuconostoc* virus LN34, *Leuconostoc* virus LNTR3, *Mycobacterium* virus Bongo, *Mycobacterium* virus Rey, *Mycobacterium* virus Butters, *Mycobacterium* virus Michelle, *Mycobacterium* virus Charlie, *Mycobacterium* virus Pipsqueaks, *Mycobacterium* virus Xeno, *Mycobacterium* virus Panchino, *Mycobacterium* virus Phrann, *Mycobacterium* virus Redi, *Mycobacterium* virus Skinnyp, *Gordonia* virus BaxterFox, *Gordonia* virus Yeezy, *Gordonia* virus Kita, *Gordonia* virus Zirinka, *Gorrdonia* virus Nymphadora, *Mycobacterium* virus Bignuz, *Mycobacterium* virus Brusacoram, *Mycobacterium* virus Donovan, *Mycobacterium* virus Fishburne, *Mycobacterium* virus Jebeks, *Mycobacterium* virus Malithi, *Mycobacterium* virus Phayonce, *Enterobacter* virus F20, *Klebsiella* virus 1513, *Klebsiella* virus KLPN1, *Klebsiella* virus KP36, *Klebsiella* virus PKP126, *Klebsiella* virus Sushi, *Escherichia* virus AHP42, *Escherichia* virus AHS24, *Escherichia* virus AKS96, *Escherichia* virus C119, *Escherichia* virus E41c, *Escherichia* virus Eb49, *Escherichia* virus Jk06, *Escherichia* virus KP26, *Escherichia* virus Rogue1, *Escherichia* virus ACGM12, *Escherichia* virus Rtp, *Escherichia* virus ADB2, *Escherichia* virus JMPW1, *Escherichia* virus JMPW2, *Escherichia* virus T1, *Shigella* virus PSf2, *Shigella* virus Shfl1, *Citrobacter* virus Stevie, *Escherichia* virus TLS, *Salmonella* virus SP126, *Cronobacter* virus Esp2949-1, *Pseudomonas* virus Ab18, *Pseudomonas* virus Ab19, *Pseudomonas* virus PaMx11, *Arthrobacter* virus Amigo, *Propionibacterium* virus Anatole, *Propionibacterium* virus B3, *Bacillus* virus Andromeda, *Bacillus* virus Blastoid, *Bacillus* virus Curly, *Bacillus* virus Eoghan, *Bacillus* virus Finn, *Bacillus* virus Glittering, *Bacillus* virus Riggi, *Bacillus* virus Taylor, *Gordonia* virus Attis, *Mycobacterium* virus Barnyard, *Mycobacterium* virus Konstantine, *Mycobacterium* virus Predator, *Mycobacterium* virus Bernal13, *Staphylococcus* virus 13, *Staphylococcus* virus 77, *Staphylococcus* virus 108PVL, *Mycobacterium* virus Bron, *Mycobacterium* virus Faith1, *Mycobacterium* virus Joedirt, *Mycobacterium* virus Rumpelstiltskin, *Lactococcus* virus bIL67, *Lactococcus* virus c2, *Lactobacillus* virus c5, *Lactobacillus* virus Ld3, *Lactobacillus* virus Ld17, *Lactobacillus* virus Ld25A, *Lactobacillus* virus LLKu, *Lactobacillus* virus phiLdb, *Cellulophaga* virus Cba121, *Cellulophaga* virus Cba171, *Cellulophaga* virus Cba181, *Cellulophaga* virus ST, *Bacillus* virus 250, *Bacillus* virus IEBH, *Mycobacterium* virus Ardmore, *Mycobacterium* virus Avani, *Mycobacterium* virus Boomer, *Mycobacterium* virus Che8, *Mycobacterium* virus Che9d, *Mycobacterium* virus Deadp, *Mycobacterium* virus Dlane, *Mycobacterium* virus Dorothy, *Mycobacterium* virus Dotproduct, *Mycobacterium* virus Drago, *Mycobacterium* virus Fruitloop, *Mycobacterium* virus Gumbie, *Mycobacterium* virus Ibhubesi, *Mycobacterium* virus LIij, *Mycobacterium* virus Mozy, *Mycobacterium* virus Mutaforma13, *Mycobacterium* virus Pacc40, *Mycobacterium* virus PMC, *Mycobacterium* virus Ramsey, *Mycobacterium* virus Rockyhorror, *Mycobacterium* virus SG4, *Mycobacterium* virus Shauna1, *Mycobacterium* virus Shilan, *Mycobacterium* virus Spartacus, *Mycobacterium* virus Taj, *Mycobacterium* virus Tweety, *Mycobacterium* virus Wee, *Mycobacterium* virus Yoshi, *Salmonella* virus Chi, *Salmonella* virus FSLSP030, *Salmonella* virus FSLSP088, *Salmonella* virus iEPS5, *Salmonella* virus SPN19, *Mycobacterium* virus 244, *Mycobacterium* virus Bask21, *Mycobacterium* virus CJW1, *Mycobacterium* virus Eureka, *Mycobacterium* virus Kostya, *Mycobacterium* virus Porky, *Mycobacterium* virus Pumpkin, *Mycobacterium* virus Sirduracell, *Mycobacterium* virus Toto, *Mycobacterium* virus Corndog, *Mycobacterium* virus Firecracker, *Rhodobacter* virus RcCronus, *Pseudomonas* virus D3112, *Pseudomonas* virus DMS3, *Pseudomonas* virus FHA0480, *Pseudomonas* virus LPB1, *Pseudomonas* virus MP22, *Pseudomonas* virus MP29, *Pseudomonas* virus MP38, *Pseudomonas* virus PA1KOR, *Pseudomonas* virus D3, *Pseudomonas* virus PMG1, *Arthrobacter* virus Decurro, *Gordonia* virus Demosthenes, *Gordonia* virus Katyusha, *Gordonia* virus Kvothe, *Propionibacterium* virus B22, *Propionibacterium* virus Doucette, *Propionibacterium* virus E6, *Propionibacterium* virus G4, *Burkholderia* virus phi6442, *Burkholderia* virus phi1026b, *Burkholderia* virus phiE125, *Edwardsiella* virus eiAU, *Mycobacterium* virus Ff47, *Mycobacterium* virus Muddy, *Mycobacterium* virus Gaia, *Mycobacterium* virus Giles, *Arthrobacter* virus Captnmurica, *Arthrobacter* virus Gordon, *Gordonia* virus GordTnk2, *Paenibacillus* virus Harrison, *Escherichia* virus EK99P1, *Escherichia* virus HK578, *Escherichia* virus JL1, *Escherichia* virus SSL2009a, *Escherichia* virus YD2008s, *Shigella* virus EP23, *Sodalis* virus SO1, *Escherichia* virus HK022, *Escherichia* virus HK75, *Escherichia* virus HK97, *Escherichia* virus HK106, *Escherichia* virus HK446, *Escherichia* virus HK542, *Escherichia* virus HK544, *Escherichia* virus HK633, *Escherichia* virus mEp234, *Escherichia* virus mEp235, *Escherichia* virus mEpX1, *Escherichia* virus mEpX2, *Escherichia* virus mEp043, *Escherichia* virus mEp213, *Escherichia* virus mEp237, *Escherichia* virus mEp390, *Escherichia* virus mEp460, *Escherichia* virus mEp505, *Escherichia* virus mEp506, *Brevibacillus* virus Jenst, *Achromobacter* virus 83-24, *Achromobacter* virus JWX, *Arthrobacter* virus Kellezzio, *Arthrobacter* virus Kitkat, *Arthrobacter* virus Bennie, *Arthrobacter* virus DrRobert, *Arthrobacter* virus Glenn, *Arthrobacter* virus HunterDalle, *Arthrobacter* virus Joann, *Arthrobacter* virus Korra, *Arthrobacter* virus Preamble, *Arthrobacter* virus Pumancara, *Arthrobacter* virus Wayne, *Mycobacterium* virus Alma, *Mycobacterium* virus Arturo, *Mycobacterium* virus Astro, *Mycobacterium* virus Backyardigan, *Mycobacterium* virus BBPiebs31, *Mycobacterium* virus Benedict, *Mycobacterium* virus Bethlehem, *Mycobacterium* virus Billknuckles, *Mycobacterium* virus Bruns, *Mycobacterium* virus Bxb1, *Mycobacterium* virus Bxz2, *Mycobacterium* virus Che12, *Mycobacterium* virus Cuco, *Mycobacterium* virus D29, *Mycobacterium* virus Doom, *Mycobacterium* virus Ericb, *Mycobacterium* virus Euphoria, *Mycobacterium* virus George, *Mycobacterium* virus Gladiator, *Mycobacterium* virus Goose, *Mycobacterium* virus Hammer, *Mycobacterium* virus Heldan, *Mycobacterium* virus Jasper, *Mycobacterium* virus JC27, *Mycobacterium* virus Jeffabunny, *Mycobacterium* virus JHC117, *Mycobacterium* virus KBG, *Mycobacterium* virus Kssjeb, *Mycobacterium* virus Kugel, *Mycobacterium* virus L5, *Mycobacterium* virus Lesedi, *Mycobacterium* virus LHTSCC, *Mycobacterium* virus lockley, *Mycobacterium* virus Marcell, *Mycobacterium* virus Microwolf, *Mycobacterium* virus Mrgordo, *Mycobacterium* virus Museum, *Mycobacterium* virus Nepal, *Mycobacterium* virus Packman, *Mycobacterium* virus Peaches, *Mycobacterium* virus Perseus, *Mycobacterium* virus Pukovnik, *Mycobacterium* virus Rebeuca, *Mycobacterium* virus Redrock, *Mycobacterium* virus Ridgecb, *Mycobacterium* virus Rockstar, *Mycobacterium* virus Saintus, *Mycobacterium* virus Skipole, *Mycobacterium* virus Solon, *Mycobacterium* virus Switzer, *Mycobacterium* virus SWU1, *Mycobacterium* virus Ta17a, *Mycobacterium* virus Tiger, *Mycobacterium* virus Timshel, *Mycobacterium* virus Trixie, *Mycobacterium* virus Turbido, *Mycobacterium* virus Twister, *Mycobacterium* virus U2, *Mycobacterium* virus Violet, *Mycobacterium* virus Wonder, *Escherichia* virus DE3, *Escherichia* virus HK629, *Escherichia* virus HK630, *Escherichia* virus Lambda, *Arthrobacter* virus Laroye, *Mycobacterium* virus Halo, *Mycobacterium* virus Liefie, *Mycobacterium* virus Marvin, *Mycobacterium* virus Mosmoris, *Arthrobacter* virus Circum, *Arthrobacter* virus Mudcat, *Escherichia* virus N15, *Escherichia* virus 9 g, *Escherichia* virus JenK1, *Escherichia* virus JenP1, *Escherichia* virus JenP2, *Pseudomonas* virus NP1, *Pseudomonas* virus PaMx25, *Mycobacterium* virus Baka, *Mycobacterium* virus Courthouse, *Mycobacterium* virus Littlee, *Mycobacterium* virus Omega, *Mycobacterium* virus Optimus, *Mycobacterium* virus Thibault, *Polaribacter* virus P12002L, *Polaribacter* virus P12002S, Nonlabens virus P12024L, Nonlabens virus P12024S, *Thermus* virus P23-45, *Thermus* virus P74-26, *Listeria* virus LP26, *Listeria* virus LP37, *Listeria* virus LP110, *Listeria* virus LP114, *Listeria* virus P70, *Propionibacterium* virus ATCC29399BC, *Propionibacterium* virus ATCC29399BT, *Propionibacterium* virus Attacne, *Propionibacterium* virus Keiki, *Propionibacterium* virus Kubed, *Propionibacterium* virus Lauchelly, *Propionibacterium* virus MrAK, *Propionibacterium* virus Ouroboros, *Propionibacterium* virus P91, *Propionibacterium* virus P105, *Propionibacterium* virus P144, *Propionibacterium* virus P1001, *Propionibacterium* virus P1.1, *Propionibacterium* virus P100A, *Propionibacterium* virus P100D, *Propionibacterium* virus P101A, *Propionibacterium* virus P104A, *Propionibacterium* virus PA6, *Propionibacterium* virus Pacnes201215, *Propionibacterium* virus PAD20, *Propionibacterium* virus PAS50, *Propionibacterium* virus PHL009M11, *Propionibacterium* virus PHL025M00, *Propionibacterium* virus PHL037M02, *Propionibacterium* virus PHL041M10, *Propionibacterium* virus PHL060L00, *Propionibacterium* virus PHL067M01, *Propionibacterium* virus PHL070N00, *Propionibacterium* virus PHL071N05, *Propionibacterium* virus PHL082M03, *Propionibacterium* virus PHL092M00, *Propionibacterium* virus PHL095N00, *Propionibacterium* virus PHL111M01, *Propionibacterium* virus PHL112N00, *Propionibacterium* virus PHL113M01, *Propionibacterium* virus PHL114L00, *Propionibacterium* virus PHL116M00, *Propionibacterium* virus PHL117M00, *Propionibacterium* virus PHL117M01, *Propionibacterium* virus PHL132N00, *Propionibacterium* virus PHL141N00, *Propionibacterium* virus PHL151M00, *Propionibacterium* virus PHL151N00, *Propionibacterium* virus PHL152M00, *Propionibacterium* virus PHL163M00, *Propionibacterium* virus PHL171M01, *Propionibacterium* virus PHL179M00, *Propionibacterium* virus PHL194M00, *Propionibacterium* virus PHL199M00, *Propionibacterium* virus PHL301M00, *Propionibacterium* virus PHL308M00, *Propionibacterium* virus Pirate, *Propionibacterium* virus Procrass1, *Propionibacterium* virus SKKY, *Propionibacterium* virus Solid, *Propionibacterium* virus Stormborn, *Propionibacterium* virus Wizzo, *Pseudomonas* virus PaMx28, *Pseudomonas* virus PaMx74, *Mycobacterium* virus Patience, *Mycobacterium* virus PBI1, *Rhodococcus* virus Pepy6, *Rhodococcus* virus Poco6, *Propionibacterium* virus PFR1, *Streptomyces* virus phiBT1, *Streptomyces* virus phiC31, *Streptomyces* virus TG1, *Caulobacter* virus Karma, *Caulobacter* virus Magneto, *Caulobacter* virus phiCbK, *Caulobacter* virus Rogue, *Caulobacter* virus Swift, *Staphylococcus* virus 11, *Staphylococcus* virus 29, *Staphylococcus* virus 37, *Staphylococcus* virus 53, *Staphylococcus* virus 55, *Staphylococcus* virus 69, *Staphylococcus* virus 71, *Staphylococcus* virus 80, *Staphylococcus* virus 85, *Staphylococcus* virus 88, *Staphylococcus* virus 92, *Staphylococcus* virus 96, *Staphylococcus* virus 187, *Staphylococcus* virus 52a, *Staphylococcus* virus 80alpha, *Staphylococcus* virus CNPH82, *Staphylococcus* virus EW, *Staphylococcus* virus IPLA5, *Staphylococcus* virus IPLA7, *Staphylococcus* virus IPLA88, *Staphylococcus* virus PH15, *Staphylococcus* virus phiETA, *Staphylococcus* virus phiETA2, *Staphylococcus* virus phiETA3, *Staphylococcus* virus phiMR11, *Staphylococcus* virus phiMR25, *Staphylococcus* virus phiNM1, *Staphylococcus* virus phiNM2, *Staphylococcus* virus phiNM4, *Staphylococcus* virus SAP26, *Staphylococcus* virus X2, *Enterococcus* virus FL1, *Enterococcus* virus FL2, *Enterococcus* virus FL3, *Lactobacillus* virus ATCC8014, *Lactobacillus* virus phiJL1, *Pediococcus* virus cIP1, *Aeromonas* virus pIS4A, *Listeria* virus LP302, *Listeria* virus PSA, *Methanobacterium* virus psiM1, *Roseobacter* virus RDJL1, *Roseobacter* virus RDJL2, *Rhodococcus* virus RER2, *Enterococcus* virus BC611, *Enterococcus* virus IMEEF1, *Enterococcus* virus SAP6, *Enterococcus* virus VD13, *Streptococcus* virus SPQS1, *Mycobacterium* virus Papyrus, *Mycobacterium* virus Send513, *Burkholderia* virus KL1, *Pseudomonas* virus 73, *Pseudomonas* virus Ab26, *Pseudomonas* virus Kakheti25, *Escherichia* virus Cajan, *Escherichia* virus Seurat, *Staphylococcus* virus SEP9, *Staphylococcus* virus Sextaec, *Streptococcus* virus 858, *Streptococcus* virus 2972, *Streptococcus* virus ALQ132, *Streptococcus* virus O1205, *Streptococcus* virus Sfi11, *Streptococcus* virus 7201, *Streptococcus* virus DT1, *Streptococcus* virus phiAbc2, *Streptococcus* virus Sfi19, *Streptococcus* virus Sfi21, *Paenibacillus* virus Diva, *Paenibacillus* virus Hb10c2, *Paenibacillus* virus Rani, *Paenibacillus* virus Shelly, *Paenibacillus* virus Sitara, *Paenibacillus* virus Willow, *Lactococcus* virus 712, *Lactococcus* virus ASCC191, *Lactococcus* virus ASCC273, *Lactococcus* virus ASCC281, *Lactococcus* virus ASCC465, *Lactococcus* virus ASCC532, *Lactococcus* virus Bibb29, *Lactococcus* virus bIL170, *Lactococcus* virus CB13, *Lactococcus* virus CB14, *Lactococcus* virus CB19, *Lactococcus* virus CB20, *Lactococcus* virus jj50, *Lactococcus* virus P2, *Lactococcus* virus P008, *Lactococcus* virus sk1, *Lactococcus* virus S14, *Bacillus* virus Slash, *Bacillus* virus Stahl, *Bacillus* virus Staley, *Bacillus* virus Stills, *Gordonia* virus Bachita, *Gordonia* virus ClubL, *Gordonia* virus OneUp, *Gordonia* virus Smoothie, *Gordonia* virus Soups, *Bacillus* virus SPbeta, *Vibrio* virus MAR10, *Vibrio* virus SSP002, *Escherichia* virus AKFV33, *Escherichia* virus BF23, *Escherichia* virus DT57C, *Escherichia* virus EPS7, *Escherichia* virus FFH1, *Escherichia* virus H8, *Escherichia* virus slur09, *Escherichia* virus T5, *Salmonella* virus 118970sal2, *Salmonella* virus Shivani, *Salmonella* virus SPC35, *Salmonella* virus Stitch, *Arthrobacter* virus Tank, *Tsukamurella* virus TIN2, *Tsukamurella* virus TIN3, *Tsukamurella* virus TIN4, *Rhodobacter* virus RcSpartan, *Rhodobacter* virus RcTitan, *Mycobacterium* virus Anaya, *Mycobacterium* virus Angelica, *Mycobacterium* virus Crimd, *Mycobacterium* virus Fionnbarth, *Mycobacterium* virus Jaws, *Mycobacterium* virus Larva, *Mycobacterium* virus Macncheese, *Mycobacterium* virus Pixie, *Mycobacterium* virus TM4, *Bacillus* virus BMBtp2, *Bacillus* virus TP21, *Geobacillus* virus Tp84, *Staphylococcus* virus 47, Staphylococcus virus 3a, Staphylococcus virus 42e, Staphylococcus virus IPLA35, Staphylococcus virus phi12, Staphylococcus virus phiSLT, Mycobacterium virus 32HC, Rhodococcus virus RGL3, Paenibacillus virus Vegas, Gordonia virus Vendetta, Bacillus virus Wbeta, Mycobacterium virus Wildcat, Gordonia virus Twister6, Gordonia virus Wizard, Gordonia virus Hotorobo, Gordonia virus Monty, Gordonia virus Woes, Xanthomonas virus CP1, Xanthomonas virus OP1, Xanthomonas virus phi17, Xanthomonas virus Xop411, Xanthomonas virus Xp10, Streptomyces virus TP1604, Streptomyces virus YDN12, Alphaproteobacteria virus phiJI001, Pseudomonas virus LKO4, Pseudomonas virus M6, Pseudomonas virus MP1412, Pseudomonas virus PAE1, Pseudomonas virus Yua, Pseudoalteromonas virus PM2, Pseudomonas virus phi6, Pseudomonas virus phi8, Pseudomonas virus phi12, Pseudomonas virus phi13, Pseudomonas virus phi2954, Pseudomonas virus phiNN, Pseudomonas virus phiYY, Vibrio virus fs1, Vibrio virus VGJ, Ralstonia virus RS603, Ralstonia virus RSM1, Ralstonia virus RSM3, Escherichia virus M13, Escherichia virus 122, Salmonella virus IKe, Acholeplasma virus L51, Vibrio virus fs2, Vibrio virus VFJ, Escherichia virus If1, Propionibacterium virus B5, Pseudomonas virus Pf1, Pseudomonas virus Pf3, Ralstonia virus PE226, Ralstonia virus RSS1, Spiroplasma virus SVTS2, Stenotrophomonas virus PSH1, Stenotrophomonas virus SMA6, Stenotrophomonas virus SMA7, Stenotrophomonas virus SMA9, Vibrio virus CTXphi, Vibrio virus KSF1, Vibrio virus VCY, Vibrio virus Vf33, Vibrio virus VfO3K6, Xanthomonas virus Cf1c, Spiroplasma virus C74, Spiroplasma virus R8A2B, Spiroplasma virus SkV1CR23x, Escherichia virus FI, Escherichia virus Qbeta, Escherichia virus BZ13, Escherichia virus MS2, Escherichia virus alpha3, Escherichia virus 1D21, Escherichia virus 1D32, Escherichia virus 1D62, Escherichia virus NC28, Escherichia virus NC29, Escherichia virus NC35, Escherichia virus phiK, Escherichia virus St1, Escherichia virus WA45, Escherichia virus G4, Escherichia virus 1D52, Escherichia virus Talmos, Escherichia virus phiX174, Bdellovibrio virus MAC1, Bdellovibrio virus MH2K, Chlamydia virus Chp1, Chlamydia virus Chp2, Chlamydia virus CPAR39, Chlamydia virus CPG1, Spiroplasma virus SpV4, Acholeplasma virus L2, Pseudomonas virus PR4, Pseudomonas virus PRD1, Bacillus virus AP50, Bacillus virus Bam35, Bacillus virus GIL16, Bacillus virus Wip1, Escherichia virus phi80, Escherichia virus RB42, Escherichia virus T2, Escherichia virus T3, Escherichia virus T6, Escherichia virus VT2-Sa, Escherichia virus VT1-Sakai, Escherichia virus VT2-Sakai, Escherichia virus CP-933V, Escherichia virus P27, Escherichia virus Stx2phi-1, Escherichia virus Stx1phi, Escherichia virus Stx2phi-II, Escherichia virus CP-1639, based on the Escherichia virus BP-4795, Escherichia virus 86, Escherichia virus Min27, Escherichia virus 2851, Escherichia virus 1717, Escherichia virus YYZ-2008, Escherichia virus EC026_P06, Escherichia virus ECO103_P15, Escherichia virus ECO103_P12, Escherichia virus ECO111_P16, Escherichia virus ECO111_P11, Escherichia virus VT2phi_272, Escherichia virus TL-2011c, Escherichia virus P13374, Escherichia virus Spy; the first bacteriophage being different from the second bacteriophage.

In one embodiment, the first bacteriophage is selected in the group consisting of BW73, B278, D6, D108, E, EI, E24, E41, FI-2, FI-4, FI-5, HI8A, Ff18B, i, MM, Mu, 025, PhI-5, Pk, PSP3, PI, PID, P2, P4, SI, Wφ, φK13, φI, φ2, φ7, φ92, 7 A, 8φ, 9φ, 18, 28-1, 186, 299, HH-Escherichia (2), AB48, CM, C4, C16, DD-VI, E4, E7, E28, FII, FI3, H, HI, H3, H8, K3, M, N, ND-2, ND-3, ND4, ND-5, ND6, ND-7, Ox-1, Ox-2, Ox-3, Ox-4, Ox-5, Ox-6, PhI-I, RB42, RB43, RB49, RB69, S, Sal-1, Sal-2, Sal-3, Sal-4, Sal-5, Sal-6, TC23, TC45, TuII*-6, TuIP-24, TuII*46, TuIP-60, T2, T4, T6, T35, αI, 1, IA, 3, 3A, 3T+, 5φ, 9266Q, CFO103, HK620, J, K, KIF, m59, no. A, no. E, no. 3, no. 9, N4, sd, T3, T7, WPK, W31, ΔH, φC3888, φK3, φK7, φK12, φV-1, φ04-CF, φ05, φ06, φ07, φI φI.2, φ20, φ95, φ263, φIO92, φI, φII, Ω8, 1, 3, 7, 8, 26, 27, 28-2, 29, 30, 31, 32, 38, 39, 42, 933W, NN-Escherichia (1), Esc-7-11, AC30, CVX-5, CI, DDUP, ECI, EC2, E21, E29, FI, F26S, F27S, Hi, HK022, HK97, HK139, HK253, HK256, K7, ND-I, PA-2, q, S2, TI, ), T3C, T5, UC-I, w, β4, γ2, λ, φD326, φγ, φ06, φ7, φ10, φ80, χ, 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J and 933H.

In a particular embodiment, said first type of bacteriophage is a prophage.

In another particular embodiment, said first type of bacteriophage is a temperate bacteriophage, filamentous phage, or pseudo-lysogenic phage.

By "temperate bacteriophage" or "lysogenic bacteriophage" is meant herein a bacteriophage which infects bacteria or achaea, which can be stably maintained in the genome and/or as episomes of/in a strain, and which replicates with cells without, in their lysogenic state, producing virions. It is well-known from the skilled person which bacteriophages, in the bacteriophages listed above, are temperate phages.

By "filamentous phage" is meant herein a bacteriophage characterized by having a single-stranded DNA genome that is encased by a long protein capsid cylinder. Typically, bacteria infected by filamentous phages are not lysed during the life cycle and replication of the phage, but rather experience a reduced rate of growth. It is well-known from the skilled person which bacteriophages, in the bacteriophages listed above, are filamentous phages.

By "pseudo-lysogenic phage" is meant herein a bacteriophage being at a stage of stalled development in a host cell without either multiplication of the phage genome (as in lytic development) or its replication synchronized with the cell cycle and stable maintenance in the cell line (as in lysogenization), which proceeds with no viral genome degradation, thus allowing the subsequent restart of virus development.

In a preferred embodiment, said first type of bacteriophage is a K. pneumoniae prophage. In another preferred embodiment, said first type of bacteriophage is a C. acnes bacteriophage.

In a preferred embodiment, said second type of bacteriophage is lambda bacteriophage. In another preferred embodiment, said second type of bacteriophage is a P. freudenreichii bacteriophage.

In a preferred embodiment, said first type of bacteriophage is a K. pneumoniae prophage and said second type of bacteriophage is lambda bacteriophage. In another preferred embodiment, said first type of bacteriophage is a C. acnes bacteriophage and said second type of bacteriophage is a P. freudenreichii bacteriophage.

Additional Bacterial Gene

As well-known from the skilled person, some phages use products produced by their bacterial host for folding and/or assembly of their structural elements, and/or for proper packaging of their DNA.

Therefore, in a particular embodiment, said production bacterial cell further comprises at least one bacterial gene, derived from a bacterial species or strain from which the first type of bacteriophage comes, involved in folding and/or assembly of phage structural elements and/or involved in DNA packaging.

As will be understood by the skilled person, bacterial genes involved in folding and/or assembly of phage structural elements depend on the particular bacteriophage from which said phage structural elements are obtained. They typically include bacterial genes encoding chaperones.

Similarly, bacterial genes involved in phage DNA packaging depend on the particular bacteriophage from which the phage DNA packaging genes are obtained. Examples of such bacterial genes include genes encoding IHF proteins.

Payload

In a particular embodiment, said production bacterial cell further comprises a payload to be packaged into said phage particles or phage-derived delivery vehicles.

As used herein, the term "payload" refers to any nucleic acid sequence (DNA and/or RNA) or amino acid sequence, or a combination of both (such as, without limitation, peptide nucleic acid or peptide-oligonucleotide conjugate) transferred into a bacterium with a delivery vehicle. In a particular embodiment, the payload is a nucleic acid payload, more particularly a DNA and/or RNA payload, still particularly a DNA payload.

The term "payload" may also refer to a plasmid, a vector or a cargo.

The payload can be a phagemid or phasmid obtained from a natural, evolved or engineered bacteriophage genome. The payload can also be composed only in part of a phagemid or phasmid obtained from a natural, evolved or engineered bacteriophage genome.

As used herein, the term "phagemid" or "phasmid" are equivalent and refer to a recombinant DNA vector comprising at least one sequence of a bacteriophage genome and is able to permit packaging in a capsid, and which is preferably not able of producing progeny, more particularly a vector that derives from both a plasmid and a bacteriophage genome. A phagemid of the disclosure comprises a phage packaging site and optionally an origin of replication (ori), in particular a bacterial and/or phage origin of replication. In one embodiment, the phagemid does not comprise an origin of replication and thus cannot replicate by itself once injected into a bacterium. Alternatively, the phagemid comprises a plasmid origin of replication, in particular a bacterial and/or phage origin of replication.

In a particular embodiment, said payload is to be packaged in the form of a packaged phagemid.

As used herein, the term "packaged phagemid" refers to a phagemid which is encapsidated in a bacteriophage scaffold, phage-derived delivery particle or capsid. Particularly, it refers to a bacteriophage scaffold, phage delivery particle or capsid devoid of a bacteriophage genome. The packaged phagemid may be produced with a helper phage strategy, well known from the man skilled in the art. The helper phage typically comprises all the genes coding for the structural and functional proteins that are indispensable for the phagemid according to the invention to be encapsidated.

In a particular embodiment, said payload is to be delivered into targeted bacterial cells, as defined below.

In a more particular embodiment, said payload is stably maintained in said targeted bacterial cells. In an alternative embodiment, said payload does not replicate in said targeted bacterial cells.

Sequence of Interest Under the Control of a Promoter

In a particular embodiment, the payload comprises a sequence of interest, in particular under the control of a promoter.

As known by the person skilled in the art, a promoter may be classified as strong or weak according to its affinity for RNA polymerase. The strength of a promoter may depend on whether initiation of transcription occurs at that promoter with high or low frequency. Different promoters with different strengths may be used in the present invention leading to different levels of gene/protein expression (e.g. the level of expression initiated from an mRNA originating from a weak promoter is lower than the level of expression initiated from a strong promoter).

It will be appreciated by those of ordinary skill in the art that a promoter sequence may be selected from a large number of known bacterial genes expressed by various bacterial species. Also, methods of prokaryotic promoter prediction exist, and can be based on DNA stability analysis as described in Kanhere and Bansal (BMC Bioinformatics 2005, 6:1). The choice of promoter on the payload used in the context of the present invention can thus be made based on the bacteria to target.

In some embodiments, the nucleic acid of interest may be positioned under the control of a recombinant or heterologous promoter, which refers to a promoter that is not normally associated with the nucleic acid of interest in its natural environment.

Examples of bacterial promoters for use in accordance with the present invention include, without limitation, positively regulated *E. coli* promoters such as positively regulated a 70 promoters (e.g., inducible pBad/araC promoter, Lux cassette right promoter, modified lambda Prm promote, plac Or2-62 (positive), pBad/AraC with extra REN sites, pBad, P(Las) TetO, P(Las) C10, P(RhI), Pu, FecA, pRE, cadC, hns, pLas, pLux), a "s" promoter (e.g., Pdps), σ 32 promoters (e.g., heat shock) and a 54 promoters (e.g., glnAp2); negatively regulated *E. coli* promoters such as negatively regulated a 70 promoters (e.g., Promoter (PRM+), modified lambda Prm promoter, TetR-TetR-4C P(Las) TetO, P(Las) CIO, P(Lac) IQ, RecA_DIexO_D-Lac01, dapAp, FecA, Pspac-hy, pel, plux-cl, plux-lac, CinR, CinL, glucose controlled, modified Pr, modified Prm+, FecA, Pcya, rec A (SOS), Rec A (SOS), EmrR_regulated, Betl_regulated, pLac_lux, pTet_Lac, pLac/Mnt, pTet/Mnt, LsrA/cl, pLux/cl, LacI, LacIQ, pLacIQI, pLas/cl, pLas/Lux, pLux/Las, pRecA with LexA binding site, reverse BBa_R0011, pLacI/ara-1, pLaclq, rrnB PI, cadC, hns, PfhuA, pBad/araC, nhaA, OmpF, RcnR), σ S promoters (e.g., Lutz-Bujard LacO with alternative sigma factor σ 38), σ 32 promoters (e.g., Lutz-Bujard LacO with alternative sigma factor σ 32), σ 54 promoters (e.g., glnAp2); negatively regulated *B. subtilis* promoters such as repressible *B. subtilis* σA promoters (e.g., Gram-positive IPTG-inducible, Xyl, hyper-spank), σ promoters, and the BioFAB promoters disclosed in Mutalik V K et al (Nature Methods, 2013, 10: 354-360, see in particular the supplementary data) as well as on the BioFAB website (http://biofab.synberc.org/data). Other inducible microbial promoters and/or bacterial promoters may be used in accordance with the present invention. An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Particularly preferred bacterial promoters for use in accordance with the present invention may be selected from constitutive promoters regulated by a 70 such as the promoters of the Anderson collection (http://parts.igem.org/Promoters/Catalog/Anderson): BBa_J23100, BBa_J23101, BBa_J23102, BBa_J23103, BBa_J23104, BBa_J23105, BBa_J23106, BBa_J23107, BBa_J23108, BBa_J23109, BBa_J23110, BBa_J23111, BBa_J23112, BBa_J23113, BBa_J23114, BBa_J23115, BBa_J23116, BBa_J23117, BBa_J23118, and BBa_J23119.

Other preferred bacterial promoters are the promoters disclosed in Stanton et al. (2014) *Nat. Chem. Biol.* 10:99-105, incorporated herein by reference, including in particular TetR, IcaR(A), AmtR, BetI, SrpR, Orf2, BM3R1, ButR, PhlF, PsrA, HlyIIR, AmeR, LmrA, QacR, ScbR, McbR, LitR, HapR, SmcR, TarA and variants thereof. In a particular embodiment, said promoter is SrpR and/or PhlF, or a variant thereof.

In some embodiments of the present invention, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter.

In some embodiments, the payload may comprise a terminator sequence, or terminator. A "terminator," as used herein, is a nucleic acid sequence that causes transcription to stop. A terminator may be unidirectional or bidirectional. It consists of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. A terminator may be necessary in vivo to achieve desirable gene/protein expression levels.

The most commonly used type of terminator is a forward terminator. When placed downstream of a nucleic acid of interest that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only. In prokaryotic systems, terminators usually fall into two categories (1) rho-independent terminators and (2) rho-dependent terminators. Rho-independent terminators are generally composed of a palindromic sequence that forms a stem loop rich in G-C base pairs followed by a string of uracil bases.

Terminators for use in accordance with the present invention include any terminator of transcription described herein or known to one of ordinary skill in the art. Examples of terminators include, without limitation, the termination sequences of genes such as, for example, the bovine growth hormone terminator, and viral termination sequences such as, for example, the TO terminator, the TE terminator, lambda TI and the T1T2 terminator found in bacterial systems. In some embodiments, the termination signal may be a sequence that cannot be transcribed or translated, such as those resulting from a sequence truncation.

Terminators for use in accordance with the present invention also include terminators disclosed in Chen Y J et al (2013, Nature Methods, 10: 659-664), and the BioFAB terminators disclosed in Cambray G et al (Nucl Acids Res, 2013, 41(9): 5139-5148).

In one embodiment, the sequence of interest is a programmable nuclease circuit to be delivered to the targeted bacteria. This programmable nuclease circuit may be able to mediate in vivo sequence-specific elimination of bacteria that contain a target gene of interest (e.g. a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases. Thus, the engineered autonomously distributed circuits provided herein may be used to selectively cleave DNA encoding a gene of interest such as, for example, a toxin gene, a virulence factor gene, an antibiotic resistance gene, a remodeling gene or a modulatory gene (cf. WO2014124226 and US2015/0064138).

Other sequences of interest, preferably programmable, can be added to the payload so as to be delivered to targeted bacteria. Preferably, the sequence of interest added to the payload leads to cell death of the targeted bacteria. For example, the nucleic acid sequence of interest added to the payload may encode holins, endolysins, restriction enzymes or toxins affecting the targeted bacteria.

Alternatively, the sequence of interest added to the payload does not lead to death of targeted bacteria. For example, the sequence of interest may encode reporter genes leading to a luminescence or fluorescence signal. Alternatively, the sequence of interest may comprise proteins and enzymes achieving a useful function such as modifying the metabolism of the targeted bacteria, the composition of its environment or affecting the host subject. More specifically the sequence of interest can be an antigen triggering a host subject's immune response. The specific antigen can be released in the environment after induction of the lysis of the target cell or can be secreted by the target cell. (Costa et al. Nat Rev Microbiol. 2015 June; 13(6):343-59; Anné et al. Curr Top Microbiol Immunol. 2017; 404:267-308)

In a particular embodiment, the nucleic acid sequence of interest is selected from the group consisting of a Cas nuclease, a Cas9 nuclease, a guide RNA, a single guide RNA (sgRNA), a CRISPR locus, a gene expressing an enzyme such as a nuclease or a kinase, a TALEN, a ZFN, a meganuclease, a recombinase, a transposase, a bacterial receptor, a membrane protein, a structural protein, a secreted protein, a gene expressing resistance to an antibiotic or to a drug in general, a gene expressing a toxic protein or a toxic factor and a gene expressing a virulence protein or a virulence factor, a bacterial secretory protein or transporter, a bacterial pore or any of their combination. These proteins can also be modified or engineered to include extra features, like the addition or removal of a function (e.g. dCas9), the addition of a secretion signal to a protein not normally secreted, the addition of an exogenous peptide in a loop as non-limiting examples.

In a particular embodiment, the nucleic acid sequence of interest encodes a guide RNA-assisted targeting (INTEGRATE) system, typically as disclosed in Vo et al. Nat Biotechnol. 2021 April; 39(4):480-489, said INTEGRATE system including for example a Type I-F *V. cholerae* CRISPR-transposon or a Type V-K *S. hofmanii* CRISPR-transposon. In a particular embodiment, said nucleic acid sequence of interest includes a nucleic acid encoding a crRNA, a nucleic acid encoding TniQ cascade, cas8, cas7 and cas6 proteins, a nucleic acid encoding tnsA, tnsB and tnsC proteins, and further including a donor DNA, said donor DNA encoding a protein of interest to be added into the targeted bacteria genome. In a particular embodiment, said nucleic acids encoding TniQ cascade, cas8, cas7 and cas6 proteins, and encoding tnsA, tnsB and tnsC proteins, are in the form of a single polycistronic nucleic acid. In another particular embodiment, said nucleic acid sequence of interest includes a nucleic acid encoding a guide RNA, a nucleic acid encoding cas12k protein, tnsB and tnsC proteins and TniQ cascade, and further including a donor DNA, said donor DNA encoding a protein of interest to be added into the targeted bacteria genome.

In a particular embodiment, the payload used in the context of the invention comprises a sequence of interest that encodes a bacteriocin, which can be a proteinaceous toxin produced by bacteria to kill or inhibit growth of other bacteria. Bacteriocins are categorized in several ways, including producing strain, common resistance mechanisms, and mechanism of killing. Such bacteriocins have been described from gram negative bacteria (e.g. microcins, colicin-like bacteriocins and tailocins) and from gram positive bacteria (e.g. Class I, Class II, Class III or Class IV bacteriocins).

In one embodiment, the payload used in the context of the invention further comprises a sequence of interest encoding a toxin selected in the group consisting of microcins, colicin-like bacteriocins, tailocins, Class I, Class II, Class III and Class IV bacteriocins. The circuit may also encode the transporter needed to secrete the toxin to the extracellular space.

In a particular embodiment, the corresponding immunity polypeptide (i.e. anti-toxin) may be used to protect bacterial cells (see review by Cotter et al., Nature Reviews Microbiology 11: 95, 2013) for payload production and encapsidation purpose but is absent in the pharmaceutical composition and in the targeted bacteria in which the payload used in the context of the invention is delivered.

In a particular embodiment, the payload used in the context of the invention comprises a sequence of interest that encodes a CRISPR-Cas system.

The CRISPR system contains two distinct elements, i.e. i) an endonuclease, in this case the CRISPR associated nuclease (Cas or "CRISPR associated protein") and ii) a guide RNA. Depending on the type of CRISPR system, the guide RNA may be in the form of a chimeric RNA which consists of the combination of a CRISPR (crRNA) bacterial RNA and a tracrRNA (trans-activating RNA CRISPR) (Jinek et al. Science. 2012 Aug. 17; 337(6096):816-21). The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix.

The CRISPR system includes two main classes depending on the nuclease mechanism of action:
Class 1 is made of multi-subunit effector complexes and includes type I, III and IV;
Class 2 is made of single-unit effector modules, like Cas9 nuclease, and includes type II (II-A,II-B,II-C,II-C variant), V (V-A,V-B,V-C,V-D,V-E,V-U1,V-U2,V-U3,V-U4,V-U5) and VI (VI-A,VI-B1,VI-B2,VI-C,VI-D).

The sequence of interest according to the present invention may comprise a nucleic acid sequence encoding Cas protein. A variety of CRISPR enzymes are available for use as a sequence of interest on the payload used in the context of the present invention. In some embodiments, the CRISPR enzyme is a Type II CRISPR enzyme, a Type 11-A or Type 11-B CRISPR enzyme. In another embodiment, the CRISPR enzyme is a Type I CRISPR enzyme or a Type III CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a guide RNA or single guide RNA (sgRNA). In certain embodiments, the guide RNA or sgRNA targets a gene selected from the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general and a gene causing a deleterious effect to the host subject.

The sequence of interest may comprise a nucleic acid sequence encoding a guide RNA or sgRNA to guide the Cas protein endogenous to the targeted bacteria, alone or in combination with a Cas protein and/or a guide RNA encoded by the payload.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, Mad4, Mad7, Cms1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA(s).

The sequence encoding Cas9 (the entire protein or a fragment thereof) as used in the context of the invention can be obtained from any known Cas9 protein (Fonfara et al. Nucleic Acids Res. 2014 February; 42(4):2577-90; Koonin et al. Curr Opin Microbiol. 2017 June; 37:67-78). Examples of Cas9 proteins useful in the present invention include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the invention can be obtained from any known Cpf1 (Cas12a) protein (Koonin et al. Curr Opin Microbiol. 2017 June; 37:67-78). Examples of Cpf1(Cas12a) proteins useful in the present invention include, but are not limited to, Cpf1(Cas12a) proteins of *Acidaminococcus* sp, *Lachnospiraceae bacteriu* and *Francisella novicida*.

The sequence encoding Cas13a (the entire protein or a fragment thereof) as used in the context of the invention can be obtained from any known Cas13a (C2c2) protein (Abudayyeh et al. Nature. 2017 Oct. 12; 550(7675):280-284). Examples of Cas13a (C2c2) proteins useful in the present invention include, but are not limited to, Cas13a (C2c2) proteins of Leptotrichia *wadei* (LwaCas13a).

The sequence encoding Cas13d (the entire protein or a fragment thereof) as used in the context of the invention can be obtained from any known Cas13d protein (Yan et al. Mol Cell. 2018 Apr. 19; 70(2):327-339.e5.). Examples of Cas13d proteins useful in the present invention include, but are not limited to, Cas13d proteins of *Eubacterium siraeum* and *Ruminococcus* sp.

The sequence encoding Mad4 (the entire protein or a fragment thereof) as used in the context of the invention is disclosed in international application WO2018/236548.

The sequence encoding Mad7 (the entire protein or a fragment thereof) as used in the context of the invention is disclosed in international application WO2018/236548.

The sequence encoding Cms1 (the entire protein or a fragment thereof) as used in the context of the invention is disclosed in international patent application WO2017/141173.

In a particular embodiment, the nucleic sequence of interest is a CRISPR/Cas9 system for the reduction of gene expression or inactivation of a gene selected from the group consisting of an antibiotic resistance gene, virulence factor or protein gene, toxin factor or protein gene, a gene expressing a bacterial receptor, a membrane protein, a structural protein, a secreted protein, a gene expressing resistance to a drug in general and a gene causing a deleterious effect to the host subject.

In one embodiment, the CRISPR system is used to target and inactivate a virulence factor. A virulence factor can be any substance produced by a pathogen that alter host subject-pathogen interaction by increasing the degree of damage done to the host subject. Virulence factors are used by pathogens in many ways, including, for example, in cell adhesion or colonization of a niche in the host subject, to evade the host subject's immune response, to facilitate entry to and egress from host subject's cells, to obtain nutrition from the host subject, or to inhibit other physiological processes in the host subject. Virulence factors can include enzymes, endotoxins, adhesion factors, motility factors, factors involved in complement evasion, scavenging factors and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), stx2k, fimA, fimF, fimH, neuC, kpsE, sfa, foc, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCDI) T3SS external needle subunit). For example, such targeted virulence factor gene can be *Francisella tularensis* virulence factor gene such as, without limitation, fslA. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdI, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft. For example, such targeted virulence factor gene can be *Cutibacterium acnes* porphyrins genes, CAMP-factors (CAMP1, CAMP2, CAMP3, CAMP4), Hyaluronate lyase (HYL-IB/II, HYL-IA), Lipases (GehA, GehB), Haemolysins, Sialidases, Endoglycoceramidases, Endo-ß-N-acetylglucosaminidase, Dermatan sulfate adhesin (DsA1, DsA2), Proline-Threonine Repeats (PTRs) or any virulence factors included on the acne associated genomic loci 1, 2, 3(plasmid), 4 such as a tight adhesion locus (tad), Streptolysin S-associated genes (sag), nonribosomal peptide synthetases (NRPS) as described in Tomida et al. mBio. 2013 Apr. 30; 4(3):e00003-13.

In another embodiment, the CRISPR/Cas system is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecI, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FoIP, Tetracycline inactivation enzyme TetX, TetA, TetB, TetC, Tet30, Tet31, TetM, TetO, TetQ, Tet32, Tet36, MacAB-TolC, MsbA, MsrA, VgaB, EmrD, EmrAB-TolC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD https://card.mcmaster.ca/).

In another embodiment, the CRISPR/Cas system is used to target and inactivate a bacterial toxin gene. Bacterial toxins can be classified as either exotoxins or endotoxins. Exotoxins are generated and actively secreted; endotoxins remain part of the bacteria. The response to a bacterial toxin can involve severe inflammation and can lead to sepsis. Such toxin can be for example *Botulinum* neurotoxin, *Tetanus* toxin, *Staphylococus* toxins, *Diphteria* toxin, *Anthrax* toxin, *Alpha* toxin, *Pertussis* toxin, *Shiga* toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

In a particular embodiment, the payload used in the context of the invention comprises a sequence of interest that encodes a base editing system.

Base editing (BE) refers to the ability to substitute a specific nucleotide base pair on a DNA or RNA molecule by another. Until recently, the only way to perform a specific substitution on DNA in vivo was using recombination of a template DNA, carrying the specific base pair change, with the locus of interest. Base editing technology relies on completely different strategies. There is no exchange of DNA, instead an enzymatic reaction converts a nucleotide to another one leading to a mismatch at the level of dsDNA that is then corrected by the cell machinery.

In some embodiments, the base editing system comprises one or more of the following enzymes and systems:

A) Cytosine base editors (CBE) and Adenosine base editors (ABE), as described in Rees, H. A. & Liu, D. R. *Nat Rev Genet* 19, 770-788 (2018).

So far there are seven types of DNA base editors described:
- Cytosine Base Editor (CBE) that convert C:G into T:A (Komor, A et al. Nature 533:420-4. (2016))
- Adenine Base Editor (ABE) that convert A:T into G:C (Gaudelli, N. M. et al. Nature 551(7681) 464-471 (2017))
- Cytosine Guanine Base Editor (CGBE) that convert C:G into G:C (Chen, L et al. Precise and programmable C:G to G:C base editing in genomic DNA. Biorxiv (2020).; Kurt, I et al. CRISPR C-to-G base editors for inducing targeted DNA transversions in human cells. Nature Biotechnology (2020))
- Cytosine Adenine Base Editor (CABE) that convert C:G into A:T (Zhao, D et al. New base editors change C to A in bacteria and C to G in mammalian cells. Nature Biotechnology (2020))
- Adenine Cytosine Base Editor (ACBE) that convert A:T into C:G (WO2020181180)
- Adenine Thymine Base Editor (ATBE) that convert A:T into T:A (WO2020181202)
- Thymine Adenine Base Editor (TABE) that convert T:A into A:T (WO2020181193; WO2020181178; WO2020181195)

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY.

ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA. TadA* include TadA-8a-e and TadA-7.10.

Except from base modification enzyme there has been also modifications implemented to base editor to increase editing efficacy, precision and modularity:
- the addition of one or two uracil DNA glycosylase inhibitor domain (UGI) to prevent base excision repair mechanism to revert base edition
- the addition of Mu-GAM that decrease insertion-deletion rate by inhibiting Non-homologous end joining mechanism in the cell (NHEJ)
- the use of nickase active Cas9 (nCas9 D10A) that, by creating nicks on the non-edited strand favors its repair and consequently the fixation of the edited base.
- the use of diverse Cas proteins from for example different organisms, mutants with different PAM motifs or different fidelity or different family (e.g. Cas12a).

Non-limiting examples of DNA-based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:
- A cytosine deaminase (rAPOBEC) and base excision repair proteins (e.g. rXRCC1) (Chen, L et al. Precise and programmable C:G to G:C base editing in genomic DNA. Biorxiv (2020).; Chen et al. Nature Communications 12:1384 (2021))
- A rat APOBEC1 variant (R33A) protein and an *E. coli*-derived uracil DNA N-glycosylase (eUNG) (Kurt, I et al. CRISPR C-to-G base editors for inducing targeted DNA transversions in human cells. Nature Biotechnology (2020))

Cytosine Adenine Base Editors (CABE) consist of a Cas9 nickase, a cytidine deaminase (e.g. AID), and a uracil-DNA glycosylase (Ung) (Zhao, D et al. New base editors change C to A in bacteria and C to G in mammalian cells. Nature Biotechnology (2020)).

ACBE include a nucleic acid programmable DNA-binding protein and an adenine oxidase (WO2020181180).

ATBE consist of a Cas9 nickase and one or more adenosine deaminase or an oxidase domain (WO2020181202).

TABE consist of a Cas9 nickase and an adenosine methyltransferase, a thymine alkyltransferase, or an adenosine deaminase domain (WO2020181193; WO2020181178; WO2020181195).

Base editor molecules can also consist of two or more of the above listed editor enzymes fused to a Cas protein (e.g. combination of an ABE and CBE). These biomolecules are named dual base editors and enable the editing of two different bases (Grunewald, J et al. A dual-deaminase CRISPR base editor enables concurrent adenine and cytosine editing, Nature Biotechnology (2020); Li, C et al. Targeted, random mutagenesis of plant genes with dual cytosine and adenine base editors, Nature Biotechnology (2020)).

In a particular embodiment, the base editing system comprises a Cytosine base editor (CBE) and/or an Adenosine base editor (ABE) as defined above.

B) Prime editors (PE), as described in Anzalone, A. V. et al. *Nature* 576, 149-157 (2019), consist of a nCas9 fused to a reverse transcriptase used in combination with a prime editing RNA (pegRNA; a guide RNA that includes a template region for reverse transcription).

Prime Editing allows introduction of insertions, deletions (indels), and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:
a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)
a prime editing guide RNA (pegRNA)

To favor editing, the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3inv, PE2, PE3, PE3b.

Cas9 Retron precISe Parallel Editing via homologY ('CRISPEY'), a retron RNA fused to the sgRNA and expressed together with Cas9 and the retron proteins including at least the reverse transcriptase (Sharon, E. et al. *Cell* 175, 544-557.e16 (2018)).

The SCRIBE strategy: a retron system expressed in combination with a recombinase promoting the recombination of single stranded DNA, also known as single stranded annealing proteins (SSAPs) (Farzadfard, F. & Lu, T. K. *Science* 346, 1256272 (2014)). Such recombinases include but are not limited to phage recombinases such as lambda red, recET, Sak, Sak4, and newly described SSAPs described in Wannier, T. M. et al. Improved bacterial recombineering by parallelized protein discovery. *Biorxiv* 2020.01.14.906594 (2020) doi:10.1101/2020.01.14.906594.

The targetron system based on group II introns described in Karberg, M. et al. *Nat Biotechnol* 19, 1162-7 (2001) which has been adapted to many bacterial species.

Other retron based gene targeting approaches are described in Simon, A. J., Ellington, A. D. & Finkelstein, I. J. *Nucleic Acids Res* 47, 11007-11019 (2019).

C) CRISPR/Cas. In various embodiments, the sequence of interest encodes fusion proteins comprising a Cas9 (e.g., a Cas9 nickase) domain and a deaminase domain. In some embodiments, the fusion protein comprises Cas9 and a cytosine deaminase enzyme, such as APOBEC enzymes, or adenosine deaminase enzymes, such as ADAT enzymes, for example as disclosed in U.S. Patent Publ. 2015/0166980. In one embodiment, the deaminase is an ACF1/ASE deaminase.

In various embodiments, the APOBEC deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In various embodiments, the fusion protein comprises a Cas9 domain, a cytosine deaminase domain, and a uracil glycosylase inhibitor (UGI) domain.

In one embodiment, the deaminase is an adenosine deaminase that deaminate adenosine in DNA, for example as disclosed in U.S. Pat. No. 10,113,163. In some embodiments, the fusion proteins further comprise an inhibitor of base repair, such as, a nuclease dead inosine specific nuclease (dISN), for example as disclosed in U.S. Pat. No. 10,113,163. In various embodiments, the nucleic acid of interest encodes fusion proteins comprising a catalytically impaired Cas9 endonuclease fused to an engineered reverse transcriptase, programmed with a prime editing guide RNA (pegRNA) that both specifies the target site and encodes the desired edit, for example as described in Anzalone et al.

In some embodiments, other programmable nucleases can be used. These include an engineered TALEN (Transcription Activator-Like Effector Nuclease) and variants, engineered zinc finger nuclease (ZFN) variants, natural, evolved or engineered meganuclease or recombinase variants, and any combination or hybrids of programmable nucleases. Thus, the programmable nucleases provided herein may be used to selectively modify DNA encoding a DNA sequence or gene of interest such as, for example, a toxin gene, a virulence factor gene, an antibiotic resistance gene, a remodeling gene or a modulatory gene (cf. WO2014124226 and US2015/0064138).

In one embodiment, the base editing system or base editor is used to inactivate the expression of a gene by editing one or several nucleotides involved in transcription or translation. More specifically the base editing system or base editor is targeting one or several nucleotides of a promoter, a RBS, a start codon.

In one embodiment, the base editing system or base editor is used to introduce a premature stop codon.

In one embodiment, the base editing system or base editor is used to introduce one or several rare codons.

In another embodiment, the base editing system or base editor is used to modulate the expression of genes by editing one or several nucleotides involved in transcription or translation. More specifically the base editing system or base editor is targeting one or several nucleotides of a promoter, a RBS, a start codon. leading to an increase or decrease of gene expression.

In another embodiment, the base editing system or base editor is used to revert a mutation that leads to the inactivation, decrease or increase in activity of a gene or pathway.

In another embodiment, the base editing system or base editor is used to revert a mutation that leads to an increase of pathogenicity.

In one embodiment, the base editing system or base editor is used to modify the regulation of a gene by editing one or several nucleotides involved in its regulation such as nucleotides of operator sequence, transcription factor binding site, riboswitch, RNAse recognition site, protease cleavage site, methylation site, post translational modification site (phosphorylation, glycosylation, acetylation, pupylation . . . ).

In some embodiments, the sequence of interest encodes a RNA base editing system. RNA base editing is based on the same principle as DNA base editing: an enzyme catalyzing the conversion of a RNA base into another must be brought close to the target base to perform its conversion locally. In one embodiment, the enzyme used for RNA editing is an adenosine deaminase from ADAR family that converts Adenosine into Inosine in dsRNA structure. Several seminal studies used this specificity for dsRNA and fused the ADAR deaminase domain (ADAR$_{DD}$) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to a hyperactive mutant of ADAR2 deaminase domain (ADAR2$_{DD}$-E488Q for REPAIRv1 and ADAR2$_{DD}$-E488Q-T375G for REPAIRv2), Cox et al improved specificity and efficiency compare to previous RNA editing strategies (Cox, D. B. T. et al. Science 358, 1019-1027 (2017)).

Non-limiting examples of RNA based editor proteins include REPAIRv1 and REPAIRv2.

In one embodiment, the RNA base editor is used to inactivate the expression of a gene by editing one or several nucleotides involved in translation. More specifically the base editor is targeting one or several nucleotides of a 5'UTR, a RBS, a start codon.

In one embodiment, the RNA base editor is used to introduce a premature stop codon.

In one embodiment, the RNA base editor is used to introduce one or several rare codons.

In another embodiment, the RNA base editor is used to modulate the expression of genes by editing one or several nucleotides involved in translation. More specifically the base editor is targeting one or several nucleotides of a 5'UTR, a RBS, a start codon leading to an increase or decrease of gene expression.

In another embodiment, the RNA base editor is used to revert a mutation that leads to the inactivation or a decrease in activity of a gene or pathway.

In another embodiment, the base editor is used to revert a mutation that leads to an increase of pathogenicity.

In a preferred embodiment, said sequence of interest only generates an effect in said targeted bacterial cells. More preferably, said sequence of interest is only expressed in said targeted bacterial cells.

Origins of Replication

In a particular embodiment, the copy number of said payload is controlled, in said production bacterial cell, by said at least one induction mechanism defined above. In an alternative embodiment, another induction mechanism controls the copy number of said payload in said production bacterial cell.

Origins of replication known in the art have been identified from species-specific plasmid DNAs (e.g. ColE1, RI, pT181, pSC101, pMB1, R6K, RK2, p15a and the like), from bacterial virus (e.g. φX174, M13, F1 and P4) and from bacterial chromosomal origins of replication (e.g. oriC).

In one embodiment, the payload used in the context of the invention comprises a bacterial origin of replication that is functional in the targeted bacteria.

Alternatively, the payload used in the context of the invention does not comprise any functional bacterial origin of replication or contains an origin of replication that is inactive in the targeted bacteria. In such embodiment, the payload used in the context of the invention cannot replicate by itself once it has been introduced into a bacterium by the phage particle or phage-derived delivery particle.

In one embodiment, the origin of replication on the payload to be packaged is inactive in the targeted bacteria, meaning that this origin of replication is not functional in the bacteria targeted by the phage particle or phage-derived delivery vehicle, thus preventing unwanted plasmid replication.

In one embodiment, the payload comprises a bacterial origin of replication that is functional in the production bacterial cell of the invention.

Bacteria-Specific Origins of Replication

Plasmid replication depends on host bacteria enzymes and on plasmid-controlled cis and trans determinants. For example, some plasmids have determinants that are recognized in almost all gram-negative bacteria and act correctly in each host bacteria during replication initiation and regulation. Other plasmids possess this ability only in some bacteria (Kues, U and Stahl, U 1989 Microbiol Rev 53:491-516).

Plasmids are replicated by three general mechanisms, namely theta type, strand displacement, and rolling circle (reviewed by Del Solar et al. 1998 Microbio and Molec Biol. Rev 62:434-464) that start at the origin of replication. These replication origins contain sites that are required for interactions of plasmid and/or host encoded proteins.

Origins of replication used on the payload used in the context of the invention may be moderate copy number, such as ColE1 ori from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication is selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

More preferably, the bacterial origin of replication is a *E. coli* origin of replication selected in the group consisting of ColE1, pMB1 and variants (pBR322, pET, pUC, etc), p15a, ColA, ColE2, pOSAK, pSC101, R6K, IncW(pSa etc), IncFII, pT181, P1, F IncP, IncC, IncJ, IncN, IncP1, IncP4, IncQ, IncH11, RSF1010, CloDF13, NTP16, R1, f5, pPS10.

More preferably, the bacterial origin of replication is selected in the group consisting of pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

Even more preferably, the bacterial origin of replication are ColE1 and p15a.

In one embodiment, the bacterial origin of replication is functional in *Propionibacterium* and *Cutibacterium*, more specifically in *Propionibacterium freudenreichii* and *Cuti-*

*bacterium acnes* and is selected from the group consisting of pLME108, pLME106, p545, pRGO1, pZGX01, pPG01, pYS1, FRJS12-3, FRJS25-1, pIMPLE-HL096PA1, A_15_1_R1. In a particular embodiment, the bacterial origin of replication is selected from the bacterial origins of replication disclosed in US applications US2022/135986 and US2022/135987.

Phage Origin of Replication

The payload used in the context of the invention may comprise a phage origin of replication which can initiate, with complementation of a complete phage genome, the replication of the payload for later encapsulation into the different capsids.

A phage origin of replication can also be engineered to act as a bacterial origin of replication without the need to package any phage particles.

A phage origin of replication comprised in the payload used in the context of the invention can be any origin of replication found in a phage.

Preferably, the phage origin of replication can be the wild-type or non-wild type sequence of the M13, f1, φX174, P4, Lambda, P2, 186, Lambda-like, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 PI-like, P2-like, P22, P22-like, N15 and N15-like bacteriophages.

More preferably, the phage origin of replication is selected in the group consisting of phage origins of replication of M13, f1, φX174, P4, and Lambda.

In a particular embodiment, the phage origin of replication is the P4 origin of replication.

In a particular embodiment, the phage origin of replication is from *Propionibacterium* phages: BW-like phages such as Doucette, B22, E6, G4; BV-like phages such as Anatole, E1, B3; BX-like phages such as PFR1 and PFR2; filamentous B5 phage; BU-like phages (*Cutibacterium acnes* phages). In a particular embodiment, the phage origin of replication is selected from the phage origins of replication disclosed in US applications US2022/135986 and US2022/135987.

Conditional Origin of Replication

In a particular embodiment, the payload comprises a conditional origin of replication which is inactive in the targeted bacteria but is active in the production bacterial cell.

In the context of the invention, a "conditional origin of replication" refers to an origin of replication whose functionality may be controlled by the presence of a specific molecule.

In a particular embodiment, the conditional origin of replication is an origin of replication, the replication of which depends upon the presence of one or more given protein, peptid, RNA, nucleic acid, molecule or any combination thereof.

In a particular embodiment, the replication involving said origin of replication may further depend on a process, such as transcription, to activate said replication.

In the context of the invention, said conditional origin of replication is inactive in the targeted bacteria because of the absence of said given protein, peptid, RNA, nucleic acid, molecule or any combination thereof in said targeted bacteria.

In a particular embodiment, said conditional origin of replication is active in said production bacterial cell because said production bacterial cell expresses said given protein, peptid, RNA, nucleic acid, molecule or any combination thereof. In a particular embodiment, said protein, peptid, RNA nucleic acid, molecule or any combination thereof is expressed in trans in said production bacterial cell.

By "in trans" is meant herein that said protein, peptid, RNA, nucleic acid, molecule or any combination thereof is not encoded on the same nucleic acid molecule as the one comprising the origin of replication. In a particular embodiment, said protein, peptid, RNA, nucleic acid, molecule or any combination thereof is encoded on a chromosome or on a vector, in particular a plasmid. In a particular embodiment, said vector comprises an antibiotic resistance marker. In an alternative embodiment, said vector is devoid of antibiotic resistance marker.

Since said conditional origin of replication is inactive in the targeted bacteria because of the absence of said given protein, peptid, RNA, nucleic acid, molecule or any combination thereof in said targeted bacteria, said conditional origin of replication may be selected depending on the specific bacteria to be targeted.

The conditional origin of replication disclosed herein may originate from plasmids, bacteriophages or PICIs which preferably share the following characteristics: they contain in their origin of replication repeat sequences, or iterons, and they code for at least one protein interacting with said origin of replication (i.e. Rep, protein O, protein P, pri) which is specific to them.

By way of example, mention may be made of the conditional replication systems of the following plasmids and bacteriophages: RK2, R1, pSC101, F, Rts1, RSF1010, P1, P4, lambda, phi82, phi80.

In a particular embodiment, said conditional origin of replication is selected from the group consisting of the R6Kλ DNA replication origin and derivatives thereof, the IncPα oriV origin of replication and derivatives thereof, ColE1 origins of replication modified to be under an inducible promoter, and origins of replication from phage-inducible chromosomal islands (PICIs) and derivatives thereof.

In a particular embodiment, said conditional origin of replication is an origin of replication present in less than 50%, or less than 40%, less than 30%, less than 20%, less than 10% or less than 5% of the bacteria of the host subject's microbiome.

In another particular embodiment, said conditional origin of replication comprises or consists of a sequence less than 80% identical, in particular less than 70%, less than 60%, less than 50%, less than 40%, less than 30%, less than 20%, less than 10%, less than 5% or less than 1% identical to the sequences of the origins of replication of the bacteria of the host subject's microbiome, in particular of the bacteria representing more than 50%, more particularly more than 60%, more than 70%, more than 80%, more than 90% or more than 95% of the host subject's microbiome.

As used herein, the term "phage-inducible chromosomal islands" or "PICIs" refers to mobile genetic elements having a conserved gene organization, and encode a pair of divergent regulatory genes, including a PICI master repressor. Typically, in Gram-positive bacteria, left of rpr, and transcribed in the same direction, PICIs encode a small set of genes including an integrase (int) gene; right of rpr, and transcribed in the opposite direction, the PICIs encode an excision function (xis), and a replication module consisting of a primase homolog (pri) and optionally a replication initiator (rep), which are sometimes fused, followed by a replication origin (ori), next to these genes, and also transcribed in the same direction, PICIs encode genes involved in phage interference, and optionally, a terminase small subunit homolog (terS).

In a particular embodiment, said conditional origin of replication is an origin of replication derived from phage-inducible chromosomal islands (PICIs).

A particular conditional origin of replication has indeed been derived from PICIs.

It was shown that it is possible to derive novel conditionally replicative vectors, in particular based on the primase-helicase and origin of replication from PICIs. These origins may be relatively rare in target strains, and more advantageously the primase-ori pair may be unique for each PICI, significantly reducing the possibility of undesired recombination or payload spread events. They can further be modified to further limit recombination chances and remove restriction sites to bypass target bacteria defense systems.

In a particular embodiment, said conditional origin of replication is derived from the origin of replication from the PICI of the *Escherichia coli* strain CFT073, disclosed in Fillol-Salom et al. (2018) *The ISME Journal* 12:2114-2128.

In a particular embodiment, said conditional origin of replication is the primase ori from the PICI of the *Escherichia coli* strain CFT073, typically of sequence SEQ ID NO: 1.

In another particular embodiment, said conditional origin of replication is the primase ori from the PICI of the *Escherichia coli* strain CFT073, devoid of at least 1, at least 2, at least 3, at least 4, at least 5, at least 6, at least 7, at least 8, at least 9, at least 10, at least 11, at least 12, at least 13, at least 14, at least 15 or at least 16 restriction site(s) selected from the group consisting of GAAABCC, GCCGGC, RCCGGY, GCNGC, TWCANNNNNNTGG (SEQ ID NO: 2), TGGCCA, ACCYAC, YGGCCR, AGACC, GCWGC, GGGANGC, GKAGATD, GCCGGYYD, GGCYAC, RGCCGGYYD, and VGCCGGYBD.

In a particular embodiment, said conditional origin of replication is the primase ori from the PICI of the *Escherichia coli* strain CFT073, devoid of the restriction site GAAABCC. Preferably, said conditional origin of replication is of sequence SEQ ID NO: 3.

In another particular embodiment, said conditional origin of replication is the primase ori from the PICI of the *Escherichia coli* strain CFT073 devoid of the restriction sites GAAABCC, GCCGGC, RCCGGY, GCNGC, TWCANNNNNNTGG (SEQ ID NO: 2), TGGCCA, ACCYAC, YGGCCR, AGACC, GCWGC, GGGANGC, GKAGATD, GCCGGYYD, GGCYAC, RGCCGGYYD, and VGCCGGYBD. Preferably, said conditional origin of replication is of sequence SEQ ID NO: 4.

In a particular embodiment, wherein said origin of replication is derived from phage-inducible chromosomal islands (PICIs), said conditional origin of replication is active in said production bacterial cell because said production bacterial cell expresses a rep protein, in particular a primase-helicase, in particular a primase-helicase of sequence SEQ ID NO: 5, typically encoded by a nucleic acid comprising or consisting of the sequence SEQ ID NO: 6.

It was demonstrated that these specific conditional origins of replication were particularly compatible with lambda-based packaging, leading to sufficiently high titers (>$10^{10}$/mL) required for microbiota-related applications.

Preferably, said production bacterial cell stably comprises said payload and is able to replicate said payload.

In a particular embodiment, when the conditional origin of replication of said payload is an origin of replication, the replication of which depends upon the presence of a given protein, peptid, nucleic acid, RNA, molecule or any combination thereof, said donor bacterial cell expresses said protein, peptid, nucleic acid, RNA, molecule or any combination thereof. Preferably, said protein, peptid, nucleic acid, RNA, molecule or any combination thereof is expressed in trans, as defined above.

In a particular embodiment, said production bacterial cell stably comprises a nucleic acid encoding said protein, peptid, nucleic acid, RNA, molecule or any combination thereof.

In a particular embodiment, when said origin of replication is derived from phage-inducible chromosomal islands (PICIs), said conditional origin of replication is active in said donor bacterial cell because said donor bacterial cell expresses a rep protein, in particular a primase-helicase, in particular a primase-helicase of sequence SEQ ID NO: 5.

In a particular embodiment, said production bacterial cell stably comprises a nucleic acid encoding said rep protein, in particular said primase-helicase, said nucleic acid typically comprising or consisting of the sequence SEQ ID NO: 6.

Packaging Site

In a particular embodiment, said payload is a nucleic acid payload comprising a packaging site derived from said first type of bacteriophage.

By "packaging site" is meant herein the DNA sequence on the phage genome that is required for genome packaging into the virion. Host-specific bacteriophages (and their packaging sites) include but are not limited to SPP1 (SPP1 pac site), P1 (P1 pac site), T1 (T1 pac site), T7 (T7 concatamer junction), lambda (cos site), mu (mu pac site), P22 (P22 pac site), φ8 (φ8 pac site), Sf6 (Sf6 pac site), 149 (149 pac site), and A1122 (A1122-concatamer junction). For most bacteriophages, the packaging site is termed the pac site. In some cases, the packaging site is referred to as a concatamer junction (e.g. T7 concatamer junction). In every case, the packaging site is substantially in isolation from sequences naturally occurring adjacent thereto in the bacteriophage genome.

For some bacteriophages, the packaging site may be unknown. In these cases, pac sites can be determined by taking advantage of the property that plasmids containing a functional bacteriophage pac site are packaged. For example, the DNA sequences necessary for packaging of bacteriophage λ were determined by incorporating small restriction fragments of the λ phage genomic DNA into a plasmid (Hohn 1983 PNAS USA 80:7456-7460). Following introduction into an in vivo packaging strain, the efficiency of packaging/transduction was quantitatively assessed. Using a similar strategy, the pac sites for a number of bacteriophages have been determined: A (Miwa 1982 Gene 20:267-279); Mu (Croenen et al. 1985 Virology 144:520-522); filamentous bacteriophages including f1, fd, M13, and Ike (Russel et al. 1989 J Virol 1989 63:3284-3295); P22 (Petri et al. 1990 Gene 88:47-55; Wu et al. 2002 Molec Microbiol 45:1631-1646); T7 (Chung et al. 1990 J Mol Biol 216:927-938), and T3 (Hashimoto et al. 1992 Virology 187:788-795).

In a particular embodiment, said packaging site is as disclosed in US applications US2022/135986 and US2022/135987, incorporated herein by reference.

Other Components of the Payload

The payload used in the context of the invention is preferably devoid of antibiotic resistance marker.

Antibiotic resistance genes are well known in the art and include but are not limited to ampicillin resistance (Amp), chloramphenicol resistance (Cm), tetracycline resistance (Tet), kanamycin resistance (Kan), hygromycin resistance (Qiyg or hph genes), and zeomycin resistance (Zeo).

In a particular embodiment, the payload used in the context of the invention comprises an auxotrophic marker.

Auxotrophic markers in bacteria have previously been described, for example, in U.S. Pat. Nos. 4,920,048, 5,691, 185, 6,291,245, 6,413,768, and 6,752,994; U.S. Patent Publication No. 20050186666; Struhl et al. (1976) PNAS USA 73; 1471-1475; MacCormick et al., (1995) FEMS Microbiol. Lett. 127:105-109; Dickely et al. (1995) Mol. Microbiol. 15:839-847; Sorensen et al. (2000) Appl. Environ. Microbiol 66:1253-1258; and Fiedler & Skerra (2001) Gene 274: 111 118, and typically include DapA and ThyA. In a particular embodiment, said auxotrophic marker is ThyA.

In a particular embodiment, said payload does not comprise any restriction site recognized by restriction enzymes which are frequently encoded by said targeted bacterial cell. In another particular embodiment, said payload comprises no more than 40, 30, 20, 10, 9, 8, 7, 6, 5, 4, 3, 2 or 1 restriction site(s) recognized by restriction enzymes which are frequently encoded by said targeted bacterial cell or a population or a group of targeted bacterial cell(s).

As used herein, the terms "restriction site" and "restriction enzyme site" are equivalent and refer to locations on a nucleic acid containing specific sequences of nucleotides, which are recognized by restriction enzymes. In particular, the nucleic acid comprises specific sequences which are bound and cleaved by restriction enzymes. Restriction sites are generally palindromic sequences of 4-8 base pairs in length. More precisely, the restriction site refers to a particular sequence and a modification state, so as to be bound and cleaved by restriction enzymes. In particular, it refers to a particular unmodified sequence, so as to be bound and cleaved by restriction enzymes. Especially the sequence is not methylated, hydroxymethylated and glucosyl-hydroxymethylated. In this context, the restriction enzyme is of type I, II or III. Alternatively, it may refer to a particular modified sequence, so as to be bound and cleaved by restriction enzymes, for instance a methylated, hydroxymethylated and glucosyl-hydroxymethylated DNA. In this context, the restriction enzyme is of type IV.

As used herein, "recognized by" with respect to a restriction site and a restriction enzyme means that the restriction site is cleaved by the restriction enzyme.

In a restriction site sequence N means that the nucleotide can be A, C, G or T; B means that the nucleotide can be C, G or T; Y means that the nucleotide can be C or T; W means that the nucleotide can be A or T; R means that the nucleotide can be A or G; and D means A, G or T.

As used herein, the terms "restriction enzyme" and "restriction endonuclease" are equivalent and refer to an enzyme that cuts nucleic acids at or near restriction sites. Restriction enzymes are commonly classified into four types (types I to type IV). The REBASE database allow to list the restriction sites that a given bacterium can recognize according to the restriction enzymes that it expresses.

By "frequent" or "frequently" in a group of bacteria of interest is meant that at least 10, 20, 30, 40, 50, 60, 70, 75, 80, 85, 90, 95 or 99% of the bacteria of the group encode the restriction enzyme.

The payload according to the invention preferably comprises no more than 100 restriction sites. In a preferred embodiment, the payload according to the invention comprises no more than 10 restriction sites. In a most preferred embodiment, the payload according to the invention does not comprise any restriction site.

Targeted Bacteria

The bacteria targeted by the phage particles or phage-derived delivery particles of the invention can be any bacteria present in a mammal organism, a plant or in the environment. It can be any commensal, symbiotic or pathogenic bacteria of the microbiota or microbiome.

A microbiome may comprise a variety of endogenous bacterial species, any of which may be targeted in accordance with the present disclosure. In some embodiments, the genus and/or species of targeted endogenous bacterial cells may depend on the first type of bacteriophage as defined in the section "Bacteriophage and gene derived from a bacteriophage" above. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells include, without limitation, cells from bacteria of the genus *Yersinia* spp., *Escherichia* spp., *Klebsiella* spp., *Acinetobacter* spp., *Bordetella* spp., *Neisseria* spp., *Aeromonas* spp., *Francisella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., *Erysipelothrix* spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Brucella* spp., *Campylobacter* spp., *Chlamydophila* spp., *Cutibacterium* spp., *Propionibacterium* spp., *Gardnerella* spp., *Ehrlichia* spp., *Haemophilus* spp., *Leptospira* spp., *Listeria* spp., *Mycoplasma* spp., *Nocardia* spp., *Rickettsia* spp., *Ureaplasma* spp., *Lactobacillus* spp., *Faecalibacterium* spp., Ruminococcus spp. and a mixture thereof.

Thus, phage particles, phage delivery particles and/or phages may target (e.g., specifically target) a bacterial cell from any one or more of the foregoing genus of bacteria in particular to specifically deliver the payload according to the invention.

Preferably, the targeted bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., *Listeria* spp., *Cutibacterium* spp., *Propionibacterium* spp., *Fusobacterium* spp., *Porphyromonas* spp. and *Gardnerella* spp.

In some embodiments, the targeted bacteria are anaerobic bacterial cells (e.g., cells that do not require oxygen for growth). Anaerobic bacterial cells include facultative anaerobic cells such as but not limited to *Escherichia coli*, *Shewanella oneidensi*, *Gardnerella vaginalis* and *Listeria*. Anaerobic bacterial cells also include obligate anaerobic cells such as, for example, *Bacteroides*, *Clostridium*, *Cutibacterium*, *Propionibacterium*, *Fusobacterium* and *Porphyromonas* species. In humans, anaerobic bacteria are most commonly found in the gastrointestinal tract. In some particular embodiments, the targeted bacteria are thus bacteria most commonly found in the gastrointestinal tract. Bacteriophages used for preparing the hybrid helper phage, and then the phage particles, phage delivery vehicles and/or phages, may target (e.g., to specifically target) anaerobic bacterial cells according to their specific spectra known by the person skilled in the art to specifically deliver the plasmid.

In some embodiments, the targeted bacterial cells are, without limitation, *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Streptomyces phaechromogenes, Streptomyces ghanaenis, Klebsiella pneumoniae, Enterobacter cloacae, Enterobacter aerogenes, Serratia marcescens, Morganella morganii, Citrobacter freundii, Propionibacterium freudenreichii, Pseudomonas aeruginosa, Parvimonas micra, Prevotella intermedia, Fusobacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes* (formerly *Propionibacterium acnes*), *Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexneri, Shigella dysenteriae, Staphylococcus saprophyticus, Streptococcus pneumoniae, Streptococcus pyogenes, Gardnerella vaginalis, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas aeruginosa*, and a mixture thereof, preferably the bacteria of interest are selected from the group consisting of *Escherichia coli, Enterococcus faecium, Staphylococcus aureus, Klebsiella pneumoniae, Acinetobacter baumanii, Pseudomonas aeruginosa, Enterobacter cloacae*, and *Enterobacter aerogenes*, and a mixture thereof.

In some embodiments, the targeted bacterial cells are, without limitation, *Anaerotruncus, Acetanaerobacterium, Acetitomaculum, Acetivibrio, Anaerococcus, Anaerofilum, Anaerosinus, Anaerostipes, Anaerovorax, Butyrivibrio, Clostridium, Capracoccus, Dehalobacter, Dialister, Dorea, Enterococcus, Ethanoligenens, Faecalibacterium, Fusobacterium, Gracilibacter, Guggenheimella, Hespellia, Lachnobacterium, Lachnospira, Lactobacillus, Leuconostoc, Megamonas, Moryella, Mitsuokella, Oribacterium, Oxobacter, Papillibacter, Proprionispira, Pseudobutyrivibrio, Pseudoramibacter, Roseburia, Ruminococcus, Sarcina, Seinonella, Shuttleworthia, Sporobacter, Sporobacterium, Streptococcus, Subdoligranulum, Syntrophococcus, Thermobacillus, Turibacter, Weisella, Clostridium, Bacteroides, Ruminococcus, Faecalibacterium, Treponema, Phascolarctobacterium, Megasphaera, Faecalibacterium, Bifidobacterium, Lactobacillus, Sutterella*, and/or *Prevotella*.

In other embodiments, the targeted bacteria cells are, without limitation, *Achromobacter xylosoxidans, Acidaminococcus fermentans, Acidaminococcus intestini, Acidaminococcus* sp., *Acinetobacter baumannii, Acinetobacter junii, Acinetobacter lwoffii, Actinobacillus capsulatus, Actinomyces naeslundii, Actinomyces neuii, Actinomyces odontolyticus, Actinomyces radingae, Adlercreutzia equolifaciens, Aeromicrobium massiliense, Aggregatibacter actinomycetemcomitans, Akkermansia muciniphila, Aliagarivorans marinus, Alistipes finegoldii, Alistipes indistinctus, Alistipes inops, Alistipes onderdonkii, Alistipes putredinis, Alistipes senegalensis, Alistipes shahii, Alistipes timonensis, Alloscardovia omnicolens, Anaerobacter polyendosporus, Anaerobaculum hydrogeniformans, Anaerococcus hydrogenalis, Anaerococcus prevotii, Anaerococcus senegalensis, Anaerofustis stercorihominis, Anaerostipes caccae, Anaerostipes hadrus, Anaerotruncus colihominis, Aneurinibacillus aneurinilyticus, Bacillus licheniformis, Bacillus massilioanorexius, Bacillus massiliosenegalensis, Bacillus simplex, Bacillus smithii, Bacillus subtilis, Bacillus thuringiensis, Bacillus timonensis, Bacteroides xylanisolvens, Bacteroides acidifaciens, Bacteroides caccae, Bacteroides capillosus, Bacteroides cellulosilyticus, Bacteroides clarus, Bacteroides coprocola, Bacteroides coprophilus, Bacteroides dorei, Bacteroides eggerthii, Bacteroides faecis, Bacteroides finegoldii, Bacteroides fluxus, Bacteroides fragilis, Bacteroides gallinarum, Bacteroides intestinalis, Bacteroides nordii, Bacteroides oleiciplenus, Bacteroides ovatus, Bacteroides pectinophilus, Bacteroides plebeius, Bacteroides salanitronis, Bacteroides salyersiae, Bacteroides* sp., *Bacteroides stercoris, Bacteroides thetaiotaomicron, Bacteroides uniformis, Bacteroides vulgatus, Bacteroides xylanisolvens, Bacteroides pectinophilus* ATCC, *Barnesiella intestinihominis, Bavariicoccus seileri, Bifidobacterium adolescentis, Bifidobacterium angulatum, Bifidobacterium animalis, Bifidobacterium bifidum, Bifidobacterium breve, Bifidobacterium catenulatum, Bifidobacterium dentium, Bifidobacterium gallicum, Bifidobacterium longum, Bifidobacterium pseudocatenulatum, Bifidobacterium stercoris, Bilophila wadsworthia, Blautia faecis, Blautia hansenii, Blautia hydrogenotrophica, Blautia luti, Blautia obeum, Blautia producta, Blautia wexlerae, Brachymonas chironomi, Brevibacterium senegalense, Bryantella formatexigens*, butyrate-producing *bacterium, Butyricicoccus pullicaecorum, Butyricimonas virosa, Butyrivibrio crossotus, Butyrivibrio fibrisolvens, Caldicoprobacter faecalis, Campylobacter concisus, Campylobacter jejuni, Campylobacter upsaliensis, Catenibacterium mitsuokai, Cedecea davisae, Cellulomonas massiliensis, Cetobacterium somerae, Citrobacter braakii, Citrobacter freundii, Citrobacter pasteurii, Citrobacter* sp., *Citrobacter youngae, Cloacibacillus evryensis, Clostridiales bacterium, Clostridioides difficile, Clostridium asparagiforme, Clostridium bartlettii, Clostridium boliviensis, Clostridium bolteae, Clostridium hathewayi, Clostridium hiranonis, Clostridium*

*hylemonae, Clostridium leptum, Clostridium methylpentosum, Clostridium nexile, Clostridium orbiscindens, Clostridium ramosum, Clostridium scindens, Clostridium sp, Clostridium sp., Clostridium spiroforme, Clostridium sporogenes, Clostridium symbiosum, Collinsella aerofaciens, Collinsella intestinalis, Collinsella stercoris, Collinsella tanakaei, Coprobacillus cateniformis, Coprobacter fastidiosus, Coprococcus catus, Coprococcus comes, Coprococcus eutactus, Corynebacterium ammoniagenes, Corynebacterium amycolatum, Corynebacterium pseudodiphtheriticum, Cutibacterium acnes, Dermabacter hominis, Desulfitobacterium hafniense, Desulfovibrio fairfieldensis, Desulfovibrio piger, Dialister succinatiphilus, Dielma fastidiosa, Dorea formicigenerans, Dorea longicatena, Dysgonomonas capnocytophagoides, Dysgonomonas gadei, Dysgonomonas mossii, Edwardsiella tarda, Eggerthella lenta, Eisenbergiella tayi, Enorma massiliensis, Enterobacter aerogenes, Enterobacter asburiae, Enterobacter cancerogenus, Enterobacter cloacae, Enterobacter massiliensis, Enterococcus casseliflavus, Enterococcus durans, Enterococcus faecalis, Enterococcus faecium, Enterococcus flavescens, Enterococcus gallinarum, Enterococcus sp., Enterovibrio nigricans, Erysipelatoclostridium ramosum, Escherichia coli, Escherichia sp., Eubacterium biforme, Eubacterium dolichum, Eubacterium hallii, Eubacterium limosum, Eubacterium ramulus, Eubacterium rectale, Eubacterium siraeum, Eubacterium ventriosum, Exiguobacterium marinum, Exiguobacterium undae, Faecalibacterium* cf, *Faecalibacterium prausnitzii, Faecalitalea cylindroides, Ferrimonas balearica, Finegoldia magna, Flavobacterium daejeonense, Flavonifractor plautii, Fusicatenibacter saccharivorans, Fusobacterium gonidiaformans, Fusobacterium mortiferum, Fusobacterium necrophorum, Fusobacterium nucleatum, Fusobacterium periodonticum, Fusobacterium sp., Fusobacterium ulcerans, Fusobacterium varium, Gallibacterium anatis, Gemmiger formicilis, Gordonibacter pamelaeae, Hafnia alvei, Helicobacter bilis, Helicobacter bills, Helicobacter canadensis, Helicobacter canis, Helicobacter cinaedi, Helicobacter macacae, Helicobacter pametensis, Helicobacter pullorum, Helicobacter pylori, Helicobacter rodentium, Helicobacter winghamensis, Herbaspirillum massiliense, Holdemanella biformis, Holdemania fdiformis, Holdemania filiformis, Holdemania massiliensis, Holdemania filiformis, Hungatella hathewayi, Intestinibacter bartlettii, Intestinimonas butyriciproducens, Klebsiella oxytoca, Klebsiella pneumoniae, Kurthia massiliensis, Lachnospira pectinoschiza, Lactobacillus acidophilus, Lactobacillus amylolyticus, Lactobacillus animalis, Lactobacillus antri, Lactobacillus brevis, Lactobacillus buchneri, Lactobacillus casei, Lactobacillus curvatus, Lactobacillus delbrueckii, Lactobacillus fermentum, Lactobacillus gasseri, Lactobacillus helveticus, Lactobacillus hilgardii, Lactobacillus iners, Lactobacillus intestinalis, Lactobacillus johnsonii, Lactobacillus murinus, Lactobacillus paracasei, Lactobacillus plantarum, Lactobacillus reuteri, Lactobacillus rhamnosus, Lactobacillus ruminis, Lactobacillus sakei, Lactobacillus salivarius, Lactobacillus ultunensis, Lactobacillus vaginalis, Lactobacillus plantarum* subsp., *Leuconostoc mesenteroides, Leuconostoc pseudomesenteroides, Listeria grayi, Listeria innocua, Mannheimia granulomatis, Marvinbryantia formatexigens, Megamonas funiformis, Megamonas hypermegale, Methanobrevibacter smithii, Methanobrevibacter smithiiFI, Micrococcus luteus, Microvirgula aerodenitrificans, Mitsuokella jalaludinii, Mitsuokella multacida, Mollicutes bacterium, Murimonas intestini, Neisseria macacae, Nitriliruptor alkaliphilus, Oceanobacillus massiliensis, Odoribacter laneus, Odoribacter splanchnicus, Ornithobacterium rhinotracheale, Oxalobacter formigenes, Paenibacillus barengoltzii, Paenibacillus chitinolyticus, Paenibacillus lautus, Paenibacillus motobuensis, Paenibacillus senegalensis, Paenisporosarcina quisquiliarum, Parabacteroides distasonis, Parabacteroides goldsteinii, Parabacteroides gordonii, Parabacteroides johnsonii, Parabacteroides merdae, Paraprevotella xylaniphila, Parasutterella excrementihominis, Parvimonas micra, Pediococcus acidilactici, Peptoclostridium difficile, Peptoniphilus harei, Peptoniphilus obesi, Peptoniphilus senegalensis, Peptoniphilus timonensis, Phascolarctobacterium succinatutens, Porphyromonas asaccharolytica, Porphyromonas uenonis, Prevotella baroniae, Prevotella bivia, Prevotella copri, Prevotella dentalis, Prevotella micans, Prevotella multisaccharivorax, Prevotella oralis, Prevotella salivae, Prevotella stercorea, Prevotella veroralis, Propionibacterium acnes, Propionibacterium avidum, Propionibacterium freudenreichii, Propionimicrobium lymphophilum, Proteus mirabilis, Proteus penneri* ATCC, *Providencia alcalifaciens, Providencia rettgeri, Providencia rustigianii, Providencia stuartii, Pseudoflavonifractor capillosus, Pseudomonas aeruginosa, Pseudomonas luteola, Ralstonia pickettii, Rheinheimera perlucida, Rheinheimera texasensis, Riemerella columbina, Romboutsia lituseburensis, Roseburia faecis, Roseburia intestinalis, Roseburia inulinivorans, Ruminococcus bicirculans, Ruminococcus bromii, Ruminococcus callidus, Ruminococcus champanellensis, Ruminococcus faecis, Ruminococcus gnavus, Ruminococcus lactaris, Ruminococcus obeum, Ruminococcus sp, Ruminococcus sp., Ruminococcus torques, Sarcina ventriculi, Sellimonas intestinalis, Senegalimassilia anaerobia, Shigella sonnei, Slackia piriformis, Staphylococcus epidermidis, Staphylococcus lentus, Staphylococcus nepalensis, Staphylococcus pseudintermedius, Staphylococcus xylosus, Stenotrophomonas maltophilia, Streptococcus agalactiae, Streptococcus anginosus, Streptococcus australis, Streptococcus caballi, Streptococcus castoreus, Streptococcus didelphis, Streptococcus equinus, Streptococcus gordonii, Streptococcus henryi, Streptococcus hyovaginalis, Streptococcus infantarius, Streptococcus infantis, Streptococcus lutetiensis, Streptococcus merionis, Streptococcus mitis, Streptococcus mutans, Streptococcus oralis, Streptococcus ovis, Streptococcus parasanguinis, Streptococcus plurextorum, Streptococcus porci, Streptococcus pyogenes, Streptococcus salivarius, Streptococcus sobrinus, Streptococcus thermophilus, Streptococcus thoraltensis, Streptomyces albus, Subdoligranulum variabile, Succinatimonas hippei, Sutterella parvirubra, Sutterella wadsworthensis, Terrisporobacter glycolicus, Terrisporobacter mayombei, Thalassobacillus devorans, Timonella senegalensis, Turicibacter sanguinis,* unknown sp., unknown sp., *Varibaculum cambriense, Veillonella atypica, Veillonella dispar, Veillonella parvula, Vibrio cincinnatiensis, Virgibacillus salexigens* and/or *Weissella paramesenteroides.*

In other embodiments, the targeted bacteria cells are those commonly found on the skin microbiota and are without limitation *Acetobacter farinalis, Acetobacter malorum, Acetobacter orleanensis, Acetobacter sicerae, Achromobacter anxifer, Achromobacter denitrificans, Achromobacter marplatensis, Achromobacter spanius, Achromobacter xylosoxidans* subsp. *xylosoxidans, Acidovorax konjaci, Acidovorax radicis, Acinetobacter johnsonii, Actinomadura citrea, Actinomadura coerulea, Actinomadura fibrosa, Actinomadura fulvescens, Actinomadura jiaoheensis, Actinomadura luteofluorescens, Actinomadura mexicana, Actinomadura nitritigenes, Actinomadura verrucosospora,*

*Actinomadura yumaensis, Actinomyces odontolyticus, Actinomycetospora atypica, Actinomycetospora corticicola, Actinomycetospora rhizophila, Actinomycetospora rishiriensis, Aeromonas australiensis, Aeromonas bestiarum, Aeromonas bivalvium, Aeromonas encheleia, Aeromonas eucrenophila, Aeromonas hydrophila* subsp. *hydrophila, Aeromonas piscicola, Aeromonas popoffii, Aeromonas rivuli, Aeromonas salmonicida* subsp. *pectinolytica, Aeromonas salmonicida* subsp. *smithia, Amaricoccus kaplicensis, Amaricoccus veronensis, Aminobacter aganoensis, Aminobacter ciceronei, Aminobacter lissarensis, Aminobacter niigataensis, Ancylobacter polymorphus, Anoxybacillus flavithermus* subsp. *yunnanensis, Aquamicrobium aerolatum, Archangium gephyra, Archangium gephyra, Archangium minus, Archangium violaceum, Arthrobacter viscosus, Bacillus anthracis, Bacillus australimaris, Bacillus drentensis, Bacillus mycoides, Bacillus pseudomycoides, Bacillus pumilus, Bacillus safensis, Bacillus vallismortis, Bosea thiooxidans, Bradyrhizobium huanghuaihaiense, Bradyrhizobium japonicum, Brevundimonas aurantiaca, Brevundimonas intermedia, Burkholderia aspalathi, Burkholderia choica, Burkholderia cordobensis, Burkholderia diffusa, Burkholderia insulsa, Burkholderia rhynchosiae, Burkholderia terrestris, Burkholderia udeis, Buttiauxella gaviniae, Caenimonas terrae, Capnocytophaga gingivalis, Chitinophaga dinghuensis, Chryseobacterium gleum, Chryseobacterium greenlandense, Chryseobacterium jejuense, Chryseobacterium piscium, Chryseobacterium sediminis, Chryseobacterium tructae, Chryseobacterium ureilyticum, Chryseobacterium vietnamense, Corynebacterium accolens, Corynebacterium afermentans* subsp. *lipophilum, Corynebacterium minutissimum, Corynebacterium sundsvallense, Cupriavidus metallidurans, Cupriavidus nantongensis, Cupriavidus necator, Cupriavidus pampae, Cupriavidus yeoncheonensis, Curtobacterium flaccumfaciens, Devosia epidermidihirudinis, Devosia riboflavina, Devosia riboflavina, Diaphorobacter oryzae, Dietzia psychralcaliphila, Ensifer adhaerens, Ensifer americanus, Enterococcus malodoratus, Enterococcus pseudoavium, Enterococcus viikkiensis, Enterococcus xiangfangensis, Erwinia rhapontici, Falsirhodobacter halotolerans, Flavobacterium araucananum, Flavobacterium frigidimaris, Gluconobacter frateurii, Gluconobacter thailandicus, Gordonia alkanivorans, Halomonas aquamarina, Halomonas axialensis, Halomonas meridiana, Halomonas olivaria, Halomonas songnenensis, Halomonas variabilis, Herbaspirillum chlorophenolicum, Herbaspirillum frisingense, Herbaspirillum hiltneri, Herbaspirillum huttiense* subsp. *putei, Herbaspirillum lusitanum, Herminiimonas fonticola, Hydrogenophaga intermedia, Hydrogenophaga pseudoflava, Klebsiella oxytoca, Kosakonia sacchari, Lactobacillus delbrueckii* subsp. *bulgaricus, Lactobacillus modestisalitolerans, Lactobacillus plantarum* subsp. *argentoratensis, Lactobacillus xiangfangensis, Lechevalieria roselyniae, Lentzea albida, Lentzea californiensis, Leuconostoc carnosum, Leuconostoc citreum, Leuconostoc gelidum* subsp. *gasicomitatum, Leuconostoc mesenteroides* subsp. *suionicum, Luteimonas aestuarii, Lysobacter antibioticus, Lysobacter koreensis, Lysobacter oryzae, Magnetospirillum moscoviense, Marinomonas alcarazii, Marinomonas primoryensis, Massilia aurea, Massilia jejuensis, Massilia kyonggiensis, Massilia timonae, Mesorhizobium acaciae, Mesorhizobium qingshengii, Mesorhizobium shonense, Methylobacterium haplocladii, Methylobacterium platani, Methylobacterium pseudosasicola, Methylobacterium zatmanii, Microbacterium oxydan, Micromonospora chaiyaphumensis, Micromonospora chalcea, Micromonospora citrea, Micromonospora coxensis, Micromonospora echinofusca, Micromonospora halophytica, Micromonospora kangleipakensis, Micromonospora maritima, Micromonospora nigra, Micromonospora purpureochromogene, Micromonospora rhizosphaerae, Micromonospora saelicesensis, Microvirga subterranea, Microvirga zambiensis, Mycobacterium alvei, Mycobacterium avium* subsp. *silvaticum, Mycobacterium colombiense, Mycobacterium conceptionense, Mycobacterium conceptionense, Mycobacterium farcinogenes, Mycobacterium fortuitum* subsp. *fortuitum, Mycobacterium goodii, Mycobacterium insubricum, Mycobacterium llatzerense, Mycobacterium neoaurum, Mycobacterium neworleansense, Mycobacterium obuense, Mycobacterium peregrinum, Mycobacterium saopaulense, Mycobacterium septicum, Mycobacterium setense, Mycobacterium smegmatis, Neisseria subflava, Nocardia lijiangensis, Nocardia thailandica, Novosphingobium barchaimii, Novosphingobium lindaniclasticum, Novosphingobium lindaniclasticum, Novosphingobium mathurense, Ochrobactrum pseudogrignonense, Oxalicibacterium solurbis, Paraburkholderia glathei, Paraburkholderia humi, Paraburkholderia phenazinium, Paraburkholderia phytofirmans, Paraburkholderia sordidicola, Paraburkholderia terricola, Paraburkholderia xenovorans, Paracoccus laeviglucosivorans, Patulibacter ginsengiterrae, Polymorphospora rubra, Porphyrobacter colymbi, Prevotella jejuni, Prevotella melaninogenica, Propionibacterium acnes* subsp. *elongatum, Proteus vulgaris, Providencia rustigianii, Pseudoalteromonas agarivorans, Pseudoalteromonas atlantica, Pseudoalteromonas paragorgicola, Pseudomonas asplenii, Pseudomonas asuensis, Pseudomonas benzenivorans, Pseudomonas cannabina, Pseudomonas cissicola, Pseudomonas congelans, Pseudomonas costantinii, Pseudomonas ficuserectae, Pseudomonas frederiksbergensis, Pseudomonas graminis, Pseudomonas jessenii, Pseudomonas koreensis, Pseudomonas koreensis, Pseudomonas kunmingensis, Pseudomonas marginalis, Pseudomonas mucidolens, Pseudomonas panacis, Pseudomonas plecoglossicida, Pseudomonas poae, Pseudomonas pseudoalcaligenes, Pseudomonas putida, Pseudomonas reinekei, Pseudomonas rhizosphaerae, Pseudomonas seleniipraecipitans, Pseudomonas umsongensis, Pseudomonas zhaodongensis, Pseudonocardia alaniniphila, Pseudonocardia ammonioxydans, Pseudonocardia autotrophica, Pseudonocardia kongjuensis, Pseudonocardia yunnanensis, Pseudorhodoferax soli, Pseudoxanthomonas daejeonensis, Pseudoxanthomonas indica, Pseudoxanthomonas kaohsiungensis, Psychrobacter aquaticus, Psychrobacter arcticus, Psychrobacter celer, Psychrobacter marincola, Psychrobacter nivimaris, Psychrobacter okhotskensis, Psychrobacter okhotskensis, Psychrobacter piscatorii, Psychrobacter pulmonis, Ramlibacterginsenosidimutans, Rheinheimera japonica, Rheinheimera muenzenbergensis, Rheinheimera soli, Rheinheimera tangshanensis, Rheinheimera texasensis, Rheinheimera tilapiae, Rhizobium alamii, Rhizobium azibense, Rhizobium binae, Rhizobium daejeonense, Rhizobium endophyticum, Rhizobium etli, Rhizobium fabae, Rhizobium freirei, Rhizobium gallicum, Rhizobium loessense, Rhizobium sophoriradicis, Rhizobium taibaishanense, Rhizobium yarns, Rhizobium vignae, Rhizobium vignae, Rhizobium yanglingense, Rhodococcus baikonurensis, Rhodococcus enclensis, Rhodoferax saidenbachensis, Rickettsia canadensis, Rickettsia heilongjiangensis, Rickettsia honei, Rickettsia raoultii, Roseateles aquatilis, Roseateles aquatilis, Salmonella enterica* subsp. *salamae, Serratia ficaria, Serratia myotis, Serratia vespertilionis, Shewanella aestuarii, Shewanella decolorationis, Sphingobium amiense, Sphingobium baderi,*

Sphingobium barthaii, Sphingobium chlorophenolicum, Sphingobium cupriresistens, Sphingobium czechense, Sphingobium fuliginis, Sphingobium indicum, Sphingobium indicum, Sphingobium japonicum, Sphingobium lactosutens, Sphingomonas dokdonensis, Sphingomonas pseudosanguinis, Sphingopyxis chilensis, Sphingopyxis fribergensis, Sphingopyxis granuli, Sphingopyxis indica, Sphingopyxis witflariensis, Staphylococcus agnetis, Staphylococcus aureus subsp. aureus, Staphylococcus epidermidis, Staphylococcus hominis subsp. novobiosepticus, Staphylococcus nepalensis, Staphylococcus saprophyticus subsp. bovis, Staphylococcus sciuri subsp. carnaticus, Streptomyces caeruleatus, Streptomyces canarius, Streptomyces capoamus, Streptomyces ciscaucasicus, Streptomyces griseorubiginosus, Streptomyces olivaceoviridis, Streptomyces panaciradicis, Streptomyces phaeopurpureus, Streptomyces pseudovenezuelae, Streptomyces resistomycificus, Tianweitania sediminis, Tsukamurella paurometabola, Variovorax guangxiensis, Vogesella alkaliphila, Xanthomonas arboricola, Xanthomonas axonopodis, Xanthomonas cassavae, Xanthomonas cucurbitae, Xanthomonas cynarae, Xanthomonas euvesicatoria, Xanthomonas fragariae, Xanthomonas gardneri, Xanthomonas perforans, Xanthomonas pisi, Xanthomonas populi, Xanthomonas vasicola, Xenophilus aerolatus, Yersinia nurmii, Abiotrophia defectiva, Acidocella aminolytica, Acinetobacter guangdongensis, Acinetobacter parvus, Acinetobacter radioresistens, Acinetobacter soli, Acinetobacter variabilis, Actinomyces cardiffensis, Actinomyces dentalis, Actinomyces europaeus, Actinomyces gerencseriae, Actinomyces graevenitzii, Actinomyces haliotis, Actinomyces johnsonii, Actinomyces massiliensis, Actinomyces meyeri, Actinomyces meyeri, Actinomyces naeslundii, Actinomyces neuii subsp. anitratus, Actinomyces odontolyticus, Actinomyces oris, Actinomyces turicensis, Actinomycetospora corticicola, Actinotignum schaalii, Aerococcus christensenii, Aerococcus urinae, Aeromicrobium flavum, Aeromicrobium massiliense, Aeromicrobium tamlense, Aeromonas sharmana, Aggregatibacter aphrophilus, Aggregatibacter segnis, Agrococcus baldri, Albibacter methylovorans, Alcaligenes faecalis subsp. faecalis, Algoriphagus ratkowskyi, Alkalibacterium olivapovliticus, Alkalibacterium pelagium, Alkalibacterium pelagium, Alloprevotella rava, Alsobacter metallidurans, Amaricoccus kaplicensis, Amaricoccus veronensis, Anaerococcus hydrogenalis, Anaerococcus lactolyticus, Anaerococcus murdochii, Anaerococcus octavius, Anaerococcus prevotii, Anaerococcus vaginalis, Aquabacterium citratiphilum, Aquabacterium olei, Aquabacterium olei, Aquabacterium parvum, Aquincola tertiaricarbonis, Arcobacter venerupis, Arsenicicoccus bolidensis, Arthrobacter russicus, Asticcacaulis excentricus, Atopobium deltae, Atopobium parvulum, Atopobium rimae, Atopobium vaginae, Aureimonas altamirensis, Aureimonas rubiginis, Azospira oryzae, Azospirillum oryzae, Bacillus circulans, Bacillus drentensis, Bacillus fastidiosus, Bacillus lehensis, Bacillus oceanisediminis, Bacillus rhizosphaerae, Bacteriovorax stolpii, Bacteroides coagulans, Bacteroides dorei, Bacteroides fragilis, Bacteroides ovatus, Bacteroides stercoris, Bacteroides uniformis, Bacteroides vulgatus, Bdellovibrio bacteriovorus, Bdellovibrio exovorus, Belnapia moabensis, Belnapia soli, Blautia hansenii, Blautia obeum, Blautia wexlerae, Bosea lathyri, Brachybacterium fresconis, Brachybacterium muris, Brevibacterium ammoniilyticum, Brevibacterium casei, Brevibacterium epidermidis, Brevibacterium iodinum, Brevibacterium luteolum, Brevibacterium paucivorans, Brevibacterium pityocampae, Brevibacterium sanguinis, Brevundimonas albigilva, Brevundimonas diminuta, Brevundimonas vancanneytii, Caenimonas terrae, Calidifontibacter indicus, Campylobacter concisus, Campylobacter gracilis, Campylobacter hominis, Campylobacter rectus, Campylobacter showae, Campylobacter ureolyticus, Capnocytophaga gingivalis, Capnocytophaga leadbetteri, Capnocytophaga ochracea, Capnocytophaga sputigena, Cardiobacterium hominis, Cardiobacterium valvarum, Carnobacterium divergens, Catonella morbi, Caulobacter henricii, Cavicella subterranea, Cellulomonas xylanilytica, Cellvibrio vulgaris, Chitinimonas taiwanensis, Chryseobacterium arachidis, Chryseobacterium daecheongense, Chryseobacterium formosense, Chryseobacterium formosense, Chryseobacterium greenlandense, Chryseobacterium indologenes, Chryseobacterium piscium, Chryseobacterium rigui, Chryseobacterium solani, Chryseobacterium taklimakanense, Chryseobacterium ureilyticum, Chryseobacterium ureilyticum, Chryseobacterium zeae, Chryseomicrobium aureum, Cloacibacterium haliotis, Cloacibacterium normanense, Cloacibacterium normanense, Collinsella aerofaciens, Comamonas denitrificans, Comamonas terrigena, Corynebacterium accolens, Corynebacterium afermentans subsp. lipophilum, Corynebacterium ammoniagenes, Corynebacterium amycolatum, Corynebacterium aurimucosum, Corynebacterium aurimucosum, Corynebacterium coyleae, Corynebacterium durum, Corynebacterium freiburgense, Corynebacterium glaucum, Corynebacterium glyciniphilum, Corynebacterium imitans, Corynebacterium jeikeium, Corynebacterium jeikeium, Corynebacterium kroppenstedtii, Corynebacterium lipophiloflavum, Corynebacterium massiliense, Corynebacterium mastitidis, Corynebacterium matruchotii, Corynebacterium minutissimum, Corynebacterium mucifaciens, Corynebacterium mustelae, Corynebacterium mycetoides, Corynebacterium pyruviciproducens, Corynebacterium simulans, Corynebacterium singulare, Corynebacterium sputi, Corynebacterium suicordis, Corynebacterium tuberculostearicum, Corynebacterium tuberculostearicum, Corynebacterium ureicelerivorans, Corynebacterium variabile, Couchioplanes caeruleus subsp. caeruleus, Cupriavidus metallidurans, Curtobacterium herbarum, Dechloromonas agitata, Deinococcus actinosclerus, Deinococcus antarcticus, Deinococcus caeni, Deinococcus ficus, Deinococcus geothermalis, Deinococcus radiodurans, Deinococcus wulumuqiensis, Deinococcus xinjiangensis, Dermabacter hominis, Dermabacter vaginalis, Dermacoccus nishinomiyaensis, Desemzia incerta, Desertibacter roseus, Dialister invisus, Dialister micraerophilus, Dialister propionicifaciens, Dietzia aurantiaca, Dietzia cercidiphylli, Dietzia timorensis, Dietzia timorensis, Dokdonella koreensis, Dokdonella koreensis, Dolosigranulum pigrum, Eikenella corrodens, Elizabethkingia miricola, Elstera litoralis, Empedobacter brevis, Enhydrobacter aerosaccus, Enterobacter xiangfangensis, Enterococcus aquimarinus, Enterococcus faecalis, Enterococcus olivae, Erwinia rhapontici, Eubacterium eligens, Eubacterium infirmum, Eubacterium rectale, Eubacterium saphenum, Eubacterium sulci, Exiguobacterium mexicanum, Facklamia tabacinasalis, Falsirhodobacter halotolerans, Finegoldia magna, Flavobacterium cutihirudinis, Flavobacterium lindanitolerans, Flavobacterium resistens, Friedmanniella capsulata, Fusobacterium nucleatum subsp. polymorphum, Gemella haemolysans, Gemella morbillorum, Gemella palaticanis, Gemella sanguinis, Gemmobacter aquaticus, Gemmobacter caeni, Gordonia jinhuaensis, Gordonia kroppenstedtii, Gordonia polyisoprenivorans, Gordonia polyisoprenivorans, Granulicatella adiacens, Granulicatella elegans, Haemophilus parainfluenzae, Haemophilus sputorum, Halomonas suffidaeris, Herpetosiphon aurantiacus, Hydrocarboniphaga effusa, Idiomarina marls, Janibacter anophelis, Janibacter hoylei, Janibacter indicus, Janibacter limosus, Janibacter melonis, Jeotgalicoccus halophilus, Jonquetella anthropi, Kaistia geumhonensis, Kingella denitrificans, Kingella oralis, Klebsiella oxytoca, Knoellia aerolata, Knoellia locipacati, Kocuria atrinae, Kocuria carniphila, Kocuria kristinae, Kocuria palustris, Kocuria turfanensis, Lachnoanaerobaculum saburreum, Lachnoanaerobaculum saburreum, Lactobacillus crispatus, Lactobacillus iners, Lactococcus lactis subsp. lactis, Lactococcus lactis subsp. lactis, Lactococcus piscium, Lapillicoccus jejuensis, Lautropia mirabilis, Legionella beliardensis, Leptotrichia buccalis, Leptotrichia goodfellowii, Leptotrichia hofstadii, Leptotrichia hongkongensis, Leptotrichia shahii, Leptotrichia trevisanii, Leptotrichia wadei, Luteimonas terricola, Lysinibacillus fusiformis, Lysobacter spongiicola, Lysobacter xinjiangensis, Macrococcus caseolyticus, Marmoricola pocheonensis, Marmoricola scoriae, Massilia alkalitolerans, Massilia alkalitolerans, Massilia aurea, Massilia plicata, Massilia timonae, Megamonas rupellensis, Meiothermus silvanus, Methylobacterium dankookense, Methylobacterium goesingense, Methylobacterium goesingense, Methylobacterium isbiliense, Methylobacterium jeotgali, Methylobacterium oxalidis, Methylobacterium platani, Methylobacterium pseudosasicola, Methyloversatilis universalis, Microbacterium foliorum, Microbacterium hydrothermale, Microbacterium hydrothermale, Microbacterium lacticum, Microbacterium lacticum, Microbacterium laevaniformans, Microbacterium paludicola, Microbacterium petrolearium, Microbacterium phyllosphaerae, Microbacterium resistens, Micrococcus antarcticus, Micrococcus cohnii, Micrococcus flavus, Micrococcus lylae, Micrococcus terreus, Microlunatus aurantiacus, Micropruina glycogenica, Microvirga aerilata, Microvirga aerilata, Microvirga subterranea, Microvirga vignae, Microvirga zambiensis, Microvirgula aerodenitrificans, Mogibacterium timidum, Moraxella atlantae, Moraxella catarrhalis, Morganella morganii subsp. morganii, Morganella psychrotolerans, Murdochiella asaccharolytica, Mycobacterium asiaticum, Mycobacterium chubuense, Mycobacterium crocinum, Mycobacterium gadium, Mycobacterium holsaticum, Mycobacterium iranicum, Mycobacterium longobardum, Mycobacterium neoaurum, Mycobacterium neoaurum, Mycobacterium obuense, Negativicoccus succinicivorans, Neisseria bacilliformis, Neisseria oralis, Neisseria sicca, Neisseria subflava, Nesterenkonia lacusekhoensis, Nesterenkonia rhizosphaerae, Nevskia persephonica, Nevskia ramosa, Niabella yanshanensis, Niveibacterium umoris, Nocardia niwae, Nocardia thailandica, Nocardioides agariphilus, Nocardioides dilutus, Nocardioides ganghwensis, Nocardioides hwasunensis, Nocardioides nanhaiensis, Nocardioides sediminis, Nosocomiicoccus ampullae, Noviherbaspirillum malthae, Novosphingobium lindaniclasticum, Novosphingobium rosa, Ochrobactrum rhizosphaerae, Olsenella uli, Ornithinimicrobium murale, Ornithinimicrobium tianjinense, Oryzobacter terrae, Ottowia beijingensis, Paenalcaligenes suwonensis, Paenibacillus agaridevorans, Paenibacillus phoenicis, Paenibacillus xylanexedens, Paludibacterium yongneupense, Pantoea cypripedii, Parabacteroides distasonis, Paraburkholderia andropogonis, Paracoccus alcaliphilus, Paracoccus angustae, Paracoccus kocurii, Paracoccus laeviglucosivorans, Paracoccus sediminis, Paracoccus sphaerophysae, Paracoccus yeei, Parvimonas micra, Parviterribacter multiflagellatus, Patulibacter ginsengiterrae, Pedobacter aquatilis, Pedobacter ginsengisoli, Pedobacter xixiisoli, Peptococcus niger, Peptoniphilus coxii, Peptoniphilus gorbachii, Peptoniphilus harei, Peptoniphilus koenoeneniae, Peptoniphilus lacrimalis, Peptostreptococcus anaerobius, Peptostreptococcus stomatis, Phascolarctobacterium faecium, Phenylobacterium haematophilum, Phenylobacterium kunshanense, Pluralibacter gergoviae, Polymorphobacter multimanifer, Porphyromonas bennonis, Porphyromonas endodontalis, Porphyromonas gingivalis, Porphyromonas gingivicanis, Porphyromonas pasteri, Porphyromonas pogonae, Porphyromonas somerae, Povalibacter uvarum, Prevotella aurantiaca, Prevotella baroniae, Prevotella bivia, Prevotella buccae, Prevotella buccalis, Prevotella copri, Prevotella corporis, Prevotella denticola, Prevotella enoeca, Prevotella histicola, Prevotella intermedia, Prevotella jejuni, Prevotella jejuni, Prevotella maculosa, Prevotella melaninogenica, Prevotella melaninogenica, Prevotella micans, Prevotella multiformis, Prevotella nanceiensis, Prevotella nigrescens, Prevotella oris, Prevotella oulorum, Prevotella pallens, Prevotella pleuritidis, Prevotella saccharolytica, Prevotella salivae, Prevotella shahii, Prevotella timonensis, Prevotella veroralis, Propionibacterium acidifaciens, Propionibacterium acnes subsp. acnes, Propionibacterium acnes subsp. acnes, Propionibacterium acnes subsp. elongatum, Propionibacterium granulosum, Propionimicrobium lymphophilum, Propionispira arcuata, Pseudokineococcus lusitanus, Pseudomonas aeruginosa, Pseudomonas chengduensis, Pseudonocardia benzenivorans, Pseudorhodoplanes sinuspersici, Psychrobacter sanguinis, Ramlibacter ginsenosidimutans, Rheinheimera aquimaris, Rhizobium alvei, Rhizobium daejeonense, Rhizobium larrymoorei, Rhizobium rhizoryzae, Rhizobium soli, Rhizobium taibaishanense, Rhizobium vignae, Rhodanobacter glycinis, Rhodobacter veldkampii, Rhodococcus enclensis, Rhodococcus fascians, Rhodococcus fascians, Rhodovarius lipocyclicus, Rivicola pingtungensis, Roseburia inulinivorans, Rosenbergiella nectarea, Roseomonas aerilata, Roseomonas aquatica, Roseomonas mucosa, Roseomonas rosea, Roseomonas vinacea, Rothia aeria, Rothia amarae, Rothia dentocariosa, Rothia endophytica, Rothia mucilaginosa, Rothia nasimurium, Rubellimicrobium mesophilum, Rubellimicrobium roseum, Rubrobacter bracarensis, Rudaea cellulosilytica, Ruminococcus gnavus, Runella zeae, Saccharopolyspora rectivirgula, Salinicoccus qingdaonensis, Scardovia wiggsiae, Sediminibacterium ginsengisoli, Selenomonas artemidis, Selenomonas infelix, Selenomonas noxia, Selenomonas sputigena, Shewanella aestuarii, Shuttleworthia satelles, Simonsiella muelleri, Skermanella aerolata, Skermanella stibiiresistens, Slackia exigua, Smaragdicoccus niigatensis, Sneathia sanguinegens, Solirubrobacter soli, Sphingobacterium caeni, Sphingobacterium daejeonense, Sphingobacterium hotanense, Sphingobacterium kyonggiense, Sphingobacterium multivorum, Sphingobacterium nematocida, Sphingobacterium spiritivorum, Sphingobium amiense, Sphingobium indicum, Sphingobium lactosutens, Sphingobium subterraneum, Sphingomonas abaci, Sphingomonas aestuarii, Sphingomonas canadensis, Sphingomonas daechungensis, Sphingomonas dokdonensis, Sphingomonas echinoides, Sphingomonas fonticola, Sphingomonas fonticola, Sphingomonas formosensis, Sphingomonas gei, Sphingomonas hankookensis, Sphingomonas hankookensis, Sphingomonas koreensis, Sphingomonas kyeonggiensis, Sphingomonas laterariae, Sphingomonas mucosissima, Sphingomonas oligophenolica, Sphingomonas pseudosanguinis, Sphingomonas sediminicola, Sphingomonas yantingensis, Sphingomonas yunnanensis, Sphingopyxis indica, Spirosoma rigui, Sporacetigenium mesophilum, Sporocytophaga myxococcoides,

*Staphylococcus auricularis, Staphylococcus epidermidis, Staphylococcus epidermidis, Staphylococcus hominis* subsp. *novobiosepticus, Staphylococcus lugdunensis, Staphylococcus pettenkoferi, Stenotrophomonas koreensis, Stenotrophomonas rhizophila, Stenotrophomonas rhizophila, Streptococcus agalactiae, Streptococcus canis, Streptococcus cristatus, Streptococcus gordonii, Streptococcus infantis, Streptococcus intermedius, Streptococcus mutans, Streptococcus oligofermentans, Streptococcus oralis, Streptococcus sanguinis, Streptomyces iconiensis, Streptomyces yanglinensis, Tabrizicola aquatica, Tahibacter caeni, Tannerella forsythia, Tepidicella xavieri, Tepidimonas fonticaldi, Terracoccus luteus, Tessaracoccus flavescens, Thermus thermophilus, Tianweitania sediminis, Tianweitania sediminis, Treponema amylovorum, Treponema denticola, Treponema lecithinolyticum, Treponema medium, Turicella otitidis, Turicibacter sanguinis, Undibacterium oligocarboniphilum, Undibacterium squillarum, Vagococcus salmoninarum, Varibaculum cambriense, Vibrio metschnikovii, Xanthobacter tagetidis, Xenophilus aerolatus, Xenophilus arseniciresistens, Yimella lutea, Zimmermannella alba, Zimmermannella bifida* and/or *Zoogloea caeni.*

In other embodiments, the targeted bacteria cells are those commonly found in the vaginal microbiota and are, without limitation, *Acinetobacter antiviralis, Acinetobacter baumannii, Acinetobacter calcoaceticus, Acinetobacter johnsonii, Actinobaculum massiliense, Actinobaculum schaalii, Actinomyces europaeus, Actinomyces graevenitzii, Actinomyces israelii, Actinomyces meyeri, Actinomyces naeslundii, Actinomyces neuii, Actinomyces odontolyticus, Actinomyces turicensis, Actinomyces urogenitalis, Actinomyces viscosus, Aerococcus christensenii, Aerococcus urinae, Aerococcus viridans, Aeromonas encheleia, Aeromonas salmonicida, Afipia massiliensis, Agrobacterium tumefaciens, Algoriphagus aquatilis, Aliivibrio wodanis, Alistipes finegoldii, Alloiococcus otitis, Alloprevotella tannerae, Alloscardovia omnicolens, Altererythrobacter epoxidivorans, Ammoniphilus oxalaticus, Amnibacterium kyonggiense, Anaerococcus hydrogenalis, Anaerococcus lactolyticus, Anaerococcus murdochii, Anaerococcus obesiensis, Anaerococcus prevotii, Anaerococcus tetradius, Anaerococcus vaginalis, Anaeroglobus geminatus, Anoxybacillus pushchinoensis, Aquabacterium parvum, Arcanobacterium phocae, Arthrobacter aurescens, Asticcacaulis excentricus, Atopobium minutum, Atopobium parvulum, Atopobium rimae, Atopobium vaginae, Avibacterium gallinarum, Bacillus acidicola, Bacillus atrophaeus, Bacillus cereus, Bacillus cibi, Bacillus coahuilensis, Bacillus gaemokensis, Bacillus methanolicus, Bacillus oleronius, Bacillus pumilus, Bacillus shackletonii, Bacillus sporothermodurans, Bacillus subtilis, Bacillus wakoensis, Bacillus weihenstephanensis, Bacteroides barnesiae, Bacteroides coagulans, Bacteroides dorei, Bacteroides faecis, Bacteroides forsythus, Bacteroides fragilis, Bacteroides nordii, Bacteroides ovatus, Bacteroides salyersiae, Bacteroides stercoris, Bacteroides uniformis, Bacteroides vulgatus, Bacteroides xylanisolvens, Bacteroides zoogleoformans, Barnesiella viscericola, Bhargavaea cecembensis, Bifidobacterium adolescentis, Bifidobacterium bifidum, Bifidobacterium breve, Bifidobacterium dentium, Bifidobacterium logum* subsp. *infantis, Bifidobacterium longum, Bifidobacterium pseudocatenulatum, Bifidobacterium scardovii, Bilophila wadsworthia, Blautia hydrogenotrophica, Blautia obeum, Blautia producta, Brachybacterium faecium, Bradyrhizobium japonicum, Brevibacterium mcbrellneri, Brevibacterium otitidis, Brevibacterium paucivorans, Bulleidia extructa, Burkholderia fungorum, Burkholderia phenoliruptix, Caldicellulosiruptor saccharolyticus, Caldimonas taiwanensis, Campylobacter gracilis, Campylobacter hominis, Campylobacter sputorum, Campylobacter ureolyticus, Capnocytophaga ochracea, Cardiobacterium hominis, Catonella morbi, Chlamydia trachomatis, Chlamydophila abortus, Chondromyces robustus, Chryseobacterium aquaticum, Citrobacter youngae, Cloacibacterium normanense, Clostridium cavendishii, Clostridium colicanis, Clostridium jejuense, Clostridium perfringens, Clostridium ramosum, Clostridium sordellii, Clostridium viride, Comamonas terrigena, Corynebacterium accolens, Corynebacterium appendicis, Corynebacterium coyleae, Corynebacterium glucuronolyticum, Corynebacterium glutamicum, Corynebacterium jeikeium, Corynebacterium kroppenstedtii, Corynebacterium lipophiloflavum, Corynebacterium minutissimum, Corynebacterium mucifaciens, Corynebacterium nuruki, Corynebacterium pseudo genitalium, Corynebacterium pyruviciproducens, Corynebacterium singulare, Corynebacterium striatum, Corynebacterium tube rculostearicum, Corynebacterium xerosis, Cryobacterium psychrophilum, Curtobacterium flaccumfaciens, Cutibacterium acnes, Cutibacterium avidum, Cytophaga xylanolytica, Deinococcus radiophilus, Delftia tsuruhatensis, Desulfovibrio desulfuricans, Dialister invisus, Dialister micraerophilus, Dialister pneumosintes, Dialister pro pionicifaciens, Dickeya chrysanthemi, Dorea longicatena, Eggerthella lenta, Eggerthia catenaformis, Eikenella corrodens, Enhydrobacter aerosaccus, Enterobacter asburiae, Enterobacter cloacae, Enterococcus avium, Enterococcus durans, Enterococcus faecalis, Enterococcus faecium, Enterococcus hirae, Erwinia persicina, Erwinia rhapontici, Erwinia toletana, Escherichia coli, Escherichia fergusonii, Eubacterium brachy, Eubacterium eligens, Eubacterium nodatum, Eubacterium rectale, Eubacterium saphenum, Eubacterium siraeum, Eubacterium sulci, Eubacterium yurii, Exiguobacterium acetylicum, Facklamia ignava, Faecalibacterium prausnitzii, Filifactor alocis, Finegoldia magna, Fusobacterium gonidiaformans, Fusobacterium nucleatum, Fusobacterium periodonticum, Gardnerella vaginalis, Gemella asaccharolytica, Gemella bergeri, Gemella haemolysans, Gemella sanguinis, Geobacillus stearothermophilus, Geobacillus thermocatenulatus, Geobacillus thermoglucosidasius, Geobacter grbiciae, Granulicatella elegans, Haemophilus ducreyi, Haemophilus haemolyticus, Haemophilus parahaemolyticus, Haemophilus parainfluenzae, Hafnia alvei, Halomonas meridiana, Halomonas phoceae, Halomonas venusta, Herbaspirillum seropedicae, Janthinobacterium lividum, Jonquetella anthropi, Klebsiella granulomatis, Klebsiella oxytoca, Klebsiella pneumoniae, Lactobacillus acidophilus, Lactobacillus amylovorus, Lactobacillus brevis, Lactobacillus coleohominis, Lactobacillus crispatus, Lactobacillus curvatus, Lactobacillus delbrueckii, Lactobacillus fermentum, Lactobacillus gasseri, Lactobacillus helveticus, Lactobacillus iners, Lactobacillus jensenii, Lactobacillus johnsonii, Lactobacillus kalixensis, Lactobacillus kefiranofaciens, Lactobacillus kimchicus, Lactobacillus kitasatonis, Lactobacillus mucosae, Lactobacillus panis, Lactobacillus paracasei, Lactobacillus plantarum, Lactobacillus pontis, Lactobacillus reuteri, Lactobacillus rhamnosus, Lactobacillus salivarius, Lactobacillus ultunensis, Lactobacillus vaginalis, Lactococcus lactis, Leptotrichia buccalis, Leuconostoc carnosum, Leuconostoc citreum, Leuconostoc garlicum, Leuconostoc lactis, Leuconostoc mesenteroides, Lysinimonas kribbensis, Mageeibacillus indolicus, Maribacter orientalis, Marinomonas protea, Marinospirillum insulare, Massilia timonae, Megasphaera elsdenii, Megasphaera micronuciformis, Mesorhizobium amorphae, Methylobacterium radiotoler-* ans, *Methylotenera versatilis, Microbacterium halophilum, Micrococcus luteus, Microterricola viridarii, Mobiluncus curtisii, Mobiluncus mulieris, Mogibacterium timidum, Moorella glycerini, Moraxella osloensis, Morganella morganii, Moryella indoligenes, Murdochiella asaccharolytica, Mycoplasma alvi, Mycoplasma genitalium, Mycoplasma hominis, Mycoplasma muris, Mycoplasma salivarium, Negativicoccus succinicivorans, Neisseria flava, Neisseria gonorrhoeae, Neisseria mucosa, Neisseria subflava, Nevskia ramosa, Nevskia soli, Nitriliruptor alkaliphilus, Odoribacter splanchnicus, Oligella urethralis, Olsenella uli, Paenibacillus amylolyticus, Paenibacillus humicus, Paenibacillus pabuli, Paenibacillus pasadenensis, Paenibacillus pini, Paenibacillus validus, Pantoea agglomerans, Parabacteroides merdae, Paraburkholderia caryophylli, Paracoccus yeei, Parastreptomyces abscessus, Parvimonas micra, Pectobacterium betavasculorum, Pectobacterium carotovorum, Pediococcus acidilactici, Pediococcus ethanolidurans, Pedobacter alluvionis, Pedobacter wanjuense, Pelomonas aquatica, Peptococcus niger, Peptoniphilus asaccharolyticus, Peptoniphilus gorbachii, Peptoniphilus harei, Peptoniphilus indolicus, Peptoniphilus lacrimalis, Peptoniphilus massiliensis, Peptostreptococcus anaerobius, Peptostreptococcus massiliae, Peptostreptococcus stomatis, Photobacterium angustum, Photobacterium frigidiphilum, Photobacterium phosphoreum, Porphyromonas asaccharolytica, Porphyromonas bennonis, Porphyromonas catoniae, Porphyromonas endodontalis, Porphyromonas gingivalis, Porphyromonas somerae, Porphyromonas uenonis, Prevotella amnii, Prevotella baroniae, Prevotella bergensis, Prevotella bivia, Prevotella buccae, Prevotella buccalis, Prevotella colorans, Prevotella copri, Prevotella corporis, Prevotella dentalis, Prevotella denticola, Prevotella disiens, Prevotella intermedia, Prevotella loescheii, Prevotella marshii, Prevotella melaninogenica, Prevotella micans, Prevotella nigrescens, Prevotella oris, Prevotella pleuritidis, Prevotella ruminicola, Prevotella shahii, Prevotella stercorea, Prevotella timonensis, Prevotella veroralis, Propionimicrobium lymphophilum, Proteus mirabilis, Pseudomonas abietaniphila, Pseudomonas aeruginosa, Pseudomonas amygdali, Pseudomonas azotoformans, Pseudomonas chlororaphis, Pseudomonas cuatrocienegasensis, Pseudomonas fluorescens, Pseudomonas fulva, Pseudomonas lutea, Pseudomonas mucidolens, Pseudomonas oleovorans, Pseudomonas orientalis, Pseudomonas pseudoalcaligenes, Pseudomonas psychrophila, Pseudomonas putida, Pseudomonas synxantha, Pseudomonas syringae, Pseudomonas tolaasii, Pseudo propionibacterium propionicum, Rahnella aquatilis, Ralstonia pickettii, Ralstonia solanacearum, Raoultella planticola, Rhizobacter dauci, Rhizobium etli, Rhodococcus fascians, Rhodopseudomonas palustris, Roseburia intestinalis, Roseburia inulinivorans, Rothia mucilaginosa, Ruminococcus bromii, Ruminococcus gnavus, Ruminococcus torques, Sanguibacter keddieii, Sediminibacterium salmoneum, Selenomonas bovis, Serratia fonticola, Serratia liquefaciens, Serratia marcescens, Shewanella algae, Shewanella amazonensis, Shigella boydii, Shigella sonnei, Slackia exigua, Sneathia Sneathia sanguinegens, Solobacterium moorei, Sorangium cellulosum, Sphingobium amiense, Sphingobium japonicum, Sphingobium yanoikuyae, Sphingomonas wittichii, Sporosarcina aquimarina, Staphylococcus aureus, Staphylococcus auricularis, Staphylococcus capitis, Staphylococcus epidermidis, Staphylococcus haemolyticus, Staphylococcus hominis, Staphylococcus lugdunensis, Staphylococcus saprophyticus, Staphylococcus schleiferi, Staphylococcus simiae, Staphylococcus simulans, Staphylococcus warneri, Stenotrophomonas maltophilia, Stenoxybacter acetivorans, Streptococcus agalactiae, Streptococcus anginosus, Streptococcus australis, Streptococcus equinus, Streptococcus gallolyticus, Streptococcus infantis, Streptococcus intermedius, Streptococcus lutetiensis, Streptococcus marimammalium, Streptococcus mitis, Streptococcus mutans, Streptococcus oralis, Streptococcus parasanguinis, Streptococcus phocae, Streptococcus pseudopneumoniae, Streptococcus salivarius, Streptococcus sanguinis, Streptococcus thermophilus, Sutterella wadsworthensis, Tannerella forsythia, Terrahaemophilus aromaticivorans, Treponema denticola, Treponema maltophilum, Treponema parvum, Treponema vincentii, Trueperella bernardiae, Turicella otitidis, Ureaplasma parvum, Ureaplasma urealyticum, Varibaculum cambriense, Variovorax paradoxus, Veillonella atypica, Veillonella dispar, Veillonella montpellierensis, Veillonella parvula, Virgibacillus proomii, Viridibacillus arenosi, Viridibacillus arvi, Weissella cibaria, Weissella soli, Xanthomonas campestris, Xanthomonas vesicatoria, Zobellia laminariae* and/or *Zoogloea ramigera*.

In one embodiment, the targeted bacteria are *Escherichia coli*.

In one embodiment, the targeted bacteria are *Cutibacterium acnes* more specifically the acne related *Cutibacterium acnes* from the phylogroup IA1 or RT4, RT5, RT8, RT9, RT10 or Clonal Complex(CC) CC1, CC3, CC4, more specifically the ST1, ST3, ST4.

Thus, the first type of bacteriophage disclosed herein, and therefore the phage particles or phage-derived delivery particles of the invention, may target (e.g., specifically target) a bacterial cell from any one or more of the foregoing genus and/or species of bacteria in particular to specifically deliver the payload.

In one embodiment, the targeted bacteria are pathogenic bacteria. The targeted bacteria can be virulent bacteria.

The targeted bacteria can be antibacterial resistance bacteria, preferably selected from the group consisting of extended-spectrum beta-lactamase-producing (ESBL) *Escherichia coli*, ESBL *Klebsiella pneumoniae*, vancomycin-resistant *Enterococcus* (VRE), methicillin-resistant *Staphylococcus aureus* (MRSA), multidrug-resistant (MDR) *Acinetobacter baumannii*, MDR *Enterobacter* spp., and a combination thereof. Preferably, the targeted bacteria can be selected from the group consisting of extended-spectrum beta-lactamase-producing (ESBL) *Escherichia coli* strains.

Alternatively, the targeted bacterium can be a bacterium of the microbiome of a given species, preferably a bacterium of the human microbiota.

In a particular embodiment, said targeted bacterial cells are from a species or strain different from the production bacterial cell.

Hybrid Helper Phage System and Hybrid Helper Phage

The present invention also concerns a hybrid helper phage system comprising:
 (i) at least one phage DNA packaging gene(s), as defined in the section "Production bacterial cell" above, derived from a first type of bacteriophage, as defined in the section "Bacteriophage and gene derived from a bacteriophage" above,
 (i') at least one phage structural gene(s), as defined in the section "Production bacterial cell" above, derived from said first type of bacteriophage, and (ii) at least one gene, derived from a second type of bacteriophage, as defined in the section "Bacteriophage and gene derived from a bacteriophage" above, involved in phage excision/insertion, phage DNA replication, and/or phage regulation, as defined in the section "Production bacterial cell" above, wherein said genes (i), (i') and (ii) are comprised in a unique nucleic acid molecule or in separate nucleic acid molecules, wherein said first type of bacteriophage comes from and/or target bacterial species or strain different from the bacterial species or strain from which said second type of bacteriophage comes and/or that said second type of bacteriophage targets, and wherein said hybrid helper phage system does not comprise any expressed phage structural gene, as defined in the section "Production bacterial cell" above, derived from said second type of bacteriophage.

In the context of the invention, the term "hybrid helper phage system" is meant a group of at least one nucleic acid molecule, preferably of at least two separate nucleic acid molecules, comprising the genes (i), (i') and (ii) defined above, which enables the production of phage particles and/or phage-derived delivery vehicles by the production bacterial cell system, wherein when the system comprises at least two separate nucleic acid molecules, said genes (i), (i') and (ii) are distributed on said at least two separate nucleic acid molecules.

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Weigele et al. Chem Rev. 2016 Oct. 26; 116(20):12655-12687. The term "nucleic acid" also encompasses any nucleic acid analogs which may contain other backbones comprising, without limitation, phosphoramide, phosphorothioate, phosphorodithioate, O-methylphophoroamidite linkage and/or deoxyribonucleotides and ribonucleotides nucleic acids. Any combination of the above features of a nucleic acid is also encompassed by the present invention.

In a particular embodiment, said genes (i), (i') and (ii) are comprised in a bacterial chromosome, in particular in a production bacterial cell chromosome. In a more particular embodiment, said genes (i), (i') and (ii) are comprised in a bacterial chromosome in a same region. In an alternative embodiment, said genes (i), (i') and (ii) are comprised in a bacterial chromosome in distinct regions.

In an alternative embodiment, said genes (i), (i') and (ii) are comprised in separate plasmids. In another particular embodiment, said genes (i), (i') and (ii) are all comprised in a same plasmid.

In another particular embodiment, said genes (i), (i') and (ii) are each independently comprised in a bacterial chromosome or in a plasmid.

In a more particular embodiment, said genes (i), (i') and (ii) are comprised in a hybrid helper phage.

Therefore, in a particular embodiment, said hybrid helper phage system consists of a hybrid helper phage comprising:

(i) at least one phage DNA packaging gene(s) and at least one phage structural gene(s), as defined in the section "Production bacterial cell" above, derived from a first type of bacteriophage, as defined in the section "Bacteriophage and gene derived from a bacteriophage" above, and (ii) at least one gene, derived from a second type of bacteriophage, as defined in the section "Bacteriophage and gene derived from a bacteriophage" above, involved in phage excision/insertion, phage DNA replication, and/or phage regulation, as defined in the section "Production bacterial cell" above, wherein said first type of bacteriophage comes from and/or target bacterial species or strain different from the bacterial species or strain from which said second type of bacteriophage comes and/or that said second type of bacteriophage targets, and wherein said hybrid helper phage does not comprise any phage structural gene, as defined in the section "Production bacterial cell" above, derived from said second type of bacteriophage.

By "helper phage" is meant herein an engineered phage providing all the necessary gene products for particle formation when using phagemid vectors. Helper phages typically have a defective origin of replication or packaging signal, and hence, are inefficient in self-packaging.

By "hybrid helper phage" is meant herein an engineered helper phage which is constituted of elements derived from at least two different types of bacteriophage.

In a particular embodiment, the hybrid helper phage of the invention is integrated in the genome of the production bacterial cell as a prophage.

Production Method

The present invention further concerns a method for producing phage particles or phage-derived delivery vehicles, comprising:

(a) providing the production bacterial cell of the invention, and (b) inducing, in said production bacterial cell, expression of said at least one of said phage structural gene(s) and at least one of said phage DNA packaging gene(s), and assembly of the products expressed by said at least one phage structural gene(s) and said at least one phage DNA packaging gene(s), thereby producing phage particles or phage-derived delivery vehicles.

The inducing step (b) can be carried out by any technique well-known from the skilled person. In particular, as will be understood by the skilled person, said inducing step will depend on the particular induction mechanism controlling the expression of said at least one of said phage structural genes and phage DNA packaging genes, in said production bacterial cell.

More particularly, it will be understood by the skilled person that, when said induction mechanism comprises at least one gene, derived from a second type of bacteriophage, involved in phage excision/insertion, phage DNA replication, and/or phage regulation, said inducing step will depend on the bacteriophage from which said sequences are derived. Typically, said inducing step can be a thermal induction (for phages that are naturally triggered by this signal or engineered repressors such as lambda cI), small molecule inducers (depending on the phage), any signal triggering SOS response (for instance addition of mitomycin), etc.

Production of Tailocin and/or Pyocin

The approach disclosed above can also be applied to the production of tailocins and/or pyocins, enabling the safe and efficient production of such bacteriocins in manipulable production cells.

The present invention thus also concerns a production bacterial cell for producing tailocin and/or pyocin, said production bacterial cell stably comprising at least one tailocin and/or pyocin structural gene(s) derived from a bacterial species or strain containing tailocin and/or pyocin genes, wherein the expression of at least one of said tailocin and/or pyocin structural gene(s) in said production bacterial cell is controlled by at least one induction mechanism, and wherein said production bacterial cell is from a bacterial species or strain different from the bacterial species or strain containing tailocin and/or pyocin genes from which said tailocin and/or pyocin structural gene(s) is derived.

By "tailocin" is meant herein a multisubunit bacteriocin that resembles bacteriophage tails. There are two classes of tailocin particles, the flexible noncontractile F-tailocins and the rigid contractile R-tailocins, which resemble and are evolutionarily related to Siphoviridae and Myoviridae phage tails, respectively. Examples of tailocins typically include F-type and R-type pyocins, carotovoricin, xenorhabdicin, and maltocin.

By "pyocin" is meant herein a bacteriocin formed by *Pseudomonas aeruginosa*. They can be produced spontaneously or induced by certain chemicals, such as mitomycin C. Three different types of pyocins have been identified: R-type, S-type, and F-type (Nakayama et al., (2000) *Mol. Microbiol.* 38:213-231). They differ by their morphology and mode of killing. Their bactericidal activities are strain specific. R-type pyocins resemble inflexible and contractile tails of bacteriophages, belong to the tailocins disclosed above, and are further classified into five groups: R1, R2, R3, R4, and R5. F-type pyocins also resemble phage tails, flexible but noncontractile rod-like structure, with distal filaments, and also belong to the tailocins disclosed above. They are similar in structure and serological properties, but they are different in receptor specificities. Three subtypes of F-type pyocins were reported: F1, F2, and F3. In a particular embodiment, said pyocin is a R-type or F-type pyocin.

By "tailocin and/or pyocin structural gene" is meant herein genes from a tailocin and/or pyocin producing bacteria which are involved in the building of the tailocin and/or pyocin. Tailocin and/or pyocin structural genes include genes encoding the subunits and/or components of said tailocin and/or pyocin, as disclosed above, and genes encoding bacterial proteins involved in the assembly of the tailocin and/or pyocin subunits and/or components.

In a particular embodiment, said tailocin and/or pyocin structural genes are pyocin structural genes as defined above. In that embodiment, said bacterial species or strain containing tailocin and/or pyocin genes from which said pyocin structural genes are derived, is preferably a *Pseudomonas aeruginosa* bacteria.

In a particular embodiment, said tailocin and/or pyocin structural genes are tailocin structural genes as defined above. In that embodiment, said bacterial species or strain containing tailocin and/or pyocin genes from which said tailocin structural genes are derived, is preferably selected from the bacteria, defined in the section "Targeted bacteria" above, which naturally contain said tailocin structural genes, and preferably produce tailocins.

In a particular embodiment, said tailocin and/or pyocin structural gene(s) are comprised in at least one plasmid, chromosome, and/or helper phage.

In the context of the invention, said induction mechanism is as defined in the section "Production bacterial cell" above.

More particularly, in an embodiment, the at least one induction mechanism controls the expression of all said tailocin and/or pyocin structural gene(s).

In a particular embodiment, said at least one induction mechanism further controls the copy number of said at least one of said tailocin and/or pyocin structural gene(s).

In a particular embodiment, said at least one induction mechanism comprises at least one gene involved in tailocin and/or pyocin regulation, said gene involved in tailocin and/or pyocin regulation being derived from a bacterial species or strain containing tailocin and/or pyocin genes which are different from those from which said tailocin and/or pyocin structural genes are derived.

Therefore in a particular embodiment, said production bacterial cell further comprises at least one gene involved in tailocin and/or pyocin regulation, said gene involved in tailocin and/or pyocin regulation being derived from a bacterial species or strain containing tailocin and/or pyocin genes which are different from those from which said tailocin and/or pyocin structural genes are derived.

By "gene involved in tailocin and/or pyocin regulation" is meant herein genes encoding regulatory elements controlling induction and/or expression of tailocin and/or pyocin in a natural tailocin and/or producing bacterial cell.

Alternatively, said at least one induction mechanism comprises at least one gene, derived from a bacteriophage, as defined in the section "Bacteriophage and gene derived from a bacteriophage" above, involved in phage excision/insertion, phage DNA replication, and/or phage regulation, as defined in the section "Production bacterial cell" above, said bacteriophage coming from and/or targeting bacterial species or strain different from the bacterial species or strain from which said tailocin and/or pyocin structural gene(s) is derived.

Therefore, in a particular embodiment, said production bacterial cell further comprises at least one gene, derived from a bacteriophage, as defined in the section "Bacteriophage and gene derived from a bacteriophage" above, involved in phage excision/insertion, phage DNA replication, and/or phage regulation, as defined in the section "Production bacterial cell" above, said bacteriophage coming from and/or targeting bacterial species or strain different from the bacterial species or strain from which said tailocin and/or pyocin structural gene(s) is derived.

In a particular embodiment, said tailocin and/or pyocin is intended to lyse targeted bacterial cells, as defined in the section "Targeted bacterial cells" above.

In a particular embodiment, said targeted bacterial cells are from a species or strain different from the production bacterial cell.

In a particular embodiment, said production bacterial cell is from the same bacterial species or strain as the bacterial species or strain from which said bacteriophage comes and/or that said bacteriophage targets.

In a particular embodiment, said production bacterial cell is an *E. coli* bacterial cell.

The present invention further concerns a method for producing tailocin and/or pyocin, comprising:

(a) providing the tailocin and/or pyocin production bacterial cell defined above, and
(b) inducing, as defined in the section "Producing method" above, in said production bacterial cell, expression of said at least one of said tailocin and/or pyocin structural gene(s), as defined above, and assembly of the products expressed by said at least one tailocin and/or pyocin structural gene(s), thereby producing tailocin and/or pyocin.

The present invention also concerns a hybrid production system comprising:
(i') at least one tailocin and/or pyocin structural gene(s), as defined above, derived from a bacterial species or strain containing tailocin and/or pyocin genes, as defined above, and
(ii) at least one gene, derived from a bacteriophage, as defined in the section "Bacteriophage and gene derived from a bacteriophage" above, involved in phage excision/insertion, phage DNA replication, and/or phage regulation, as defined in the section "Production bacterial cell" above; or at least one gene involved in tailocin and/or pyocin regulation, said gene involved in tailocin and/or pyocin regulation being derived from a bacterial species or strain containing tailocin and/or pyocin genes which are different from those from which said tailocin and/or pyocin structural genes are derived,
wherein said genes (i') and (ii) are comprised in a unique nucleic acid molecule or in separate nucleic acid molecules, as defined in the section "Hybrid helper phage system and hybrid helper phage" above,
wherein said bacteriophage comes from and/or targets bacterial species or strain different from the bacterial species or strain from which said tailocin and/or pyocin structural gene(s) is derived, and
wherein said hybrid production system does not comprise any expressed phage structural gene, as defined in the section "Production bacterial cell" above, derived from said bacteriophage.

By "hybrid production system" is meant herein a group of at least one nucleic acid molecule, preferably of at least two separate nucleic acid molecules, comprising the genes (i') and (ii) defined above, which enables the production of tailocins and/or pyocins by the production bacterial cell comprising said system, wherein when the system comprises at least two separate nucleic acid molecules, said genes (i') and (ii) are distributed on said at least two separate nucleic acid molecules.

In a particular embodiment, wherein said genes (i') and (ii) are comprised in a bacterial chromosome.

In an alternative embodiment, said genes (i') and (ii) are comprised in separate plasmids.

In still an alternative embodiment, said hybrid production system consists of a hybrid helper phage comprising:
(i') at least one tailocin and/or pyocin structural gene(s), as defined above, derived from a bacterial species or strain containing tailocin and/or pyocin genes, and
(ii) at least one gene, derived from a bacteriophage, as defined in the section "Bacteriophage and gene derived from a bacteriophage" above, involved in phage excision/insertion, phage DNA replication, and/or phage regulation, as defined in the section "Production bacterial cell" above,
wherein said bacteriophage comes from and/or targets bacterial species or strain different from the bacterial species or strain from which said tailocin and/or pyocin structural gene(s) is derived, and
wherein said hybrid helper phage does not comprise any expressed phage structural gene, as defined in the section "Production bacterial cell" above, derived from said bacteriophage.

Unless defined otherwise, all technical and scientific terms used herein have the same meaning as commonly understood by one of ordinary skills in the art to which this invention belongs.

It must be noted that as used herein, the singular forms "a", "an" and "the" include plural referents unless the context clearly dictates otherwise. Thus, for example, reference to "a cell" includes a plurality of such cells (e.g., a population of such cells). Similarly, reference to "a nucleic acid" includes one or more of such nucleic acids.

Although the invention has been described in conjunction with specific embodiments thereof, many alternatives, modifications and variations will be apparent to those skilled in the art. Accordingly, it is intended to embrace all such alternatives, modifications and variations to fall within the spirit and broad scope of the appended claims.

All publications, patents and patent applications mentioned in this specification are herein incorporated in their entirety by reference into the specification, to the same extent as if such individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The following examples are given for the purpose of illustrating various embodiments of the invention and are not meant to limit the present invention in any fashion.

| | Sequences | |
|---|---|---|
| SEQ ID NO: | Description | Type |
| 1 | primase ori from the PICI of the *Escherichia coli* strain CFT073 | DNA |
| 2 | Restriction site | DNA |
| 3 | Primase ori deltaGAAABCC | DNA |
| 4 | Primase ori devoid of restriction sites | DNA |
| 5 | PICI primase-helicase | Protein |
| 6 | PICI primase-helicase | DNA |
| 7 | Kappa structural operon region | DNA |
| 8 | Sequence upstream of small terminase gene of Kappa prophage | DNA |
| 9 | p1866 payload | DNA |
| 10 | Candidate HNH protein ORF | DNA |
| 11 | Candidate HNH protein | Protein |
| 12 | p1869 plasmid | DNA |
| 13 | Larger region upstream of Kappa prophage terminase | DNA |
| 14 | p1867 plasmid | DNA |
| 15 | Predicted ORF | DNA |
| 16 | Predicted protein with 2 Zn fingers | Protein |
| 17 | Short cos site | DNA |
| 18 | p1868 payload | DNA |
| 19 | p1872 plasmid | DNA |
| 20 | AD1334 primer | DNA |
| 21 | AD1335 primer | DNA |
| 22 | AD1336 primer | DNA |
| 23 | AD1337 primer | DNA |
| 24 | AD1322 primer | DNA |
| 25 | AD1323 primer | DNA |
| 26 | BW4 genome | DNA |
| 27 | PAC7 genome | DNA |
| 28 | pANS514 plasmid | DNA |

-continued

| SEQ ID NO: | Description | Type |
|---|---|---|
| 29 | PAC7 cos of pAN594 | DNA |
| 30 | operon of gp15-gp19 + gp45 | DNA |
| 31 | pAN241 vector | DNA |

EXAMPLES

Figure 1:
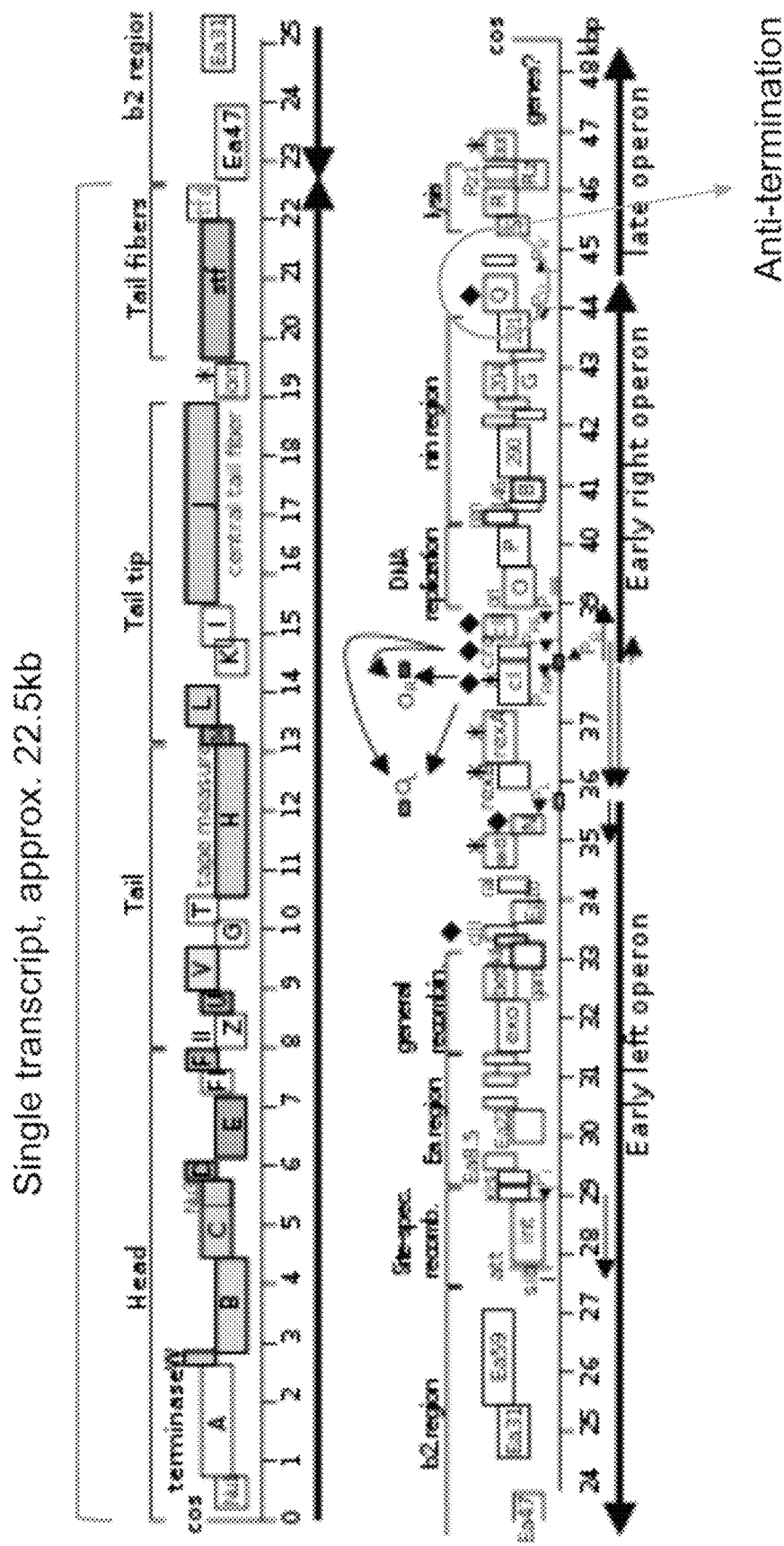
FIG. 1: Lambda genome organization (Lambda packaged phagemid variant). The structural operon is marked with a red line as well as the antitermination protein Q that allows transcription of the late structural operon. Figure adapted from Rajagopala et al. BMC Microbiol 11, 213 (2011).

Example 1: Exchange of the Structural Operon of Lambda with that of a Phage from a Different Species The inventors considered that phages can be viewed as more or less large genetic circuits whose final output is the generation of more phage particles. To do this, no matter if the phage is lytic, temperate or chronic (for instance filamentous phages such as M13), the information encoded in their genomes can be roughly categorized depending on the function it performs:

Genes devoted to insertion/excision (for temperate phages).

Genes devoted to DNA replication, RNA transcription, etc. . . . Some lytic phages encode their own RNA or DNA polymerases, for instance. Some genes modify the host's RNA polymerases to be able to work past terminators, and some other genes are involved in the segregation of the prophage sequence if it exists in a plasmid or linear plasmid form.

Genes related to defense from host's anti-phage mechanisms, degradation/modification of host's elements to complete the lytic cycle, super-exclusion mechanisms or genes that are advantageous for the host.

Genes devoted to DNA packaging: terminases and accessory proteins, ligases, etc.

Structural genes devoted to building a protein capsid for the DNA: apart from strictly structural genes, such as capsid genes, tape measure, fibers, baseplate etc, many other genes are needed to assemble the components (chaperones, proteases) as well as proteins that can be packaged inside the capsid, be it as scaffold or as pilot proteins injected into the cell (for instance, the RNA polymerase of phage N4 or some minor pilot proteins in other phages).

The last two categories (DNA packaging and structural genes) are deeply connected, since the packaging machinery recognizes the pre-assembled heads and the DNA to be packaged, initiates and terminates DNA packaging.

The inventors hypothesized that by abstracting and differentiating all the modules defined above, in principle a system could be built that contains all excision/insertion, replication and regulation elements from one phage and encodes the packaging/structural elements from another one, since, in principle, they could be viewed as independent genetic modules.

In the present example, it is referred to "structural elements" for proteins needed for DNA packaging and structural proteins needed to assemble a mature virion.

Such a system could be very advantageous for different approaches, because:

the structural module from a phage that is not easily amplified or induced could be transferred to another one (i.e. prophages with unknown inducers; prophages found in strains with PICI/SaPI systems; phages for which the host is not known, etc.);

a species which is more amenable for laboratory work/large scale production/safer could be used to produce such particles where the structural genes come from another species;

pure phagemid producing strains could be constructed using the regulatory elements of a well-characterized phage (for instance, Lambda) driving the production of capsids of a different phage, etc.

Figure 2:
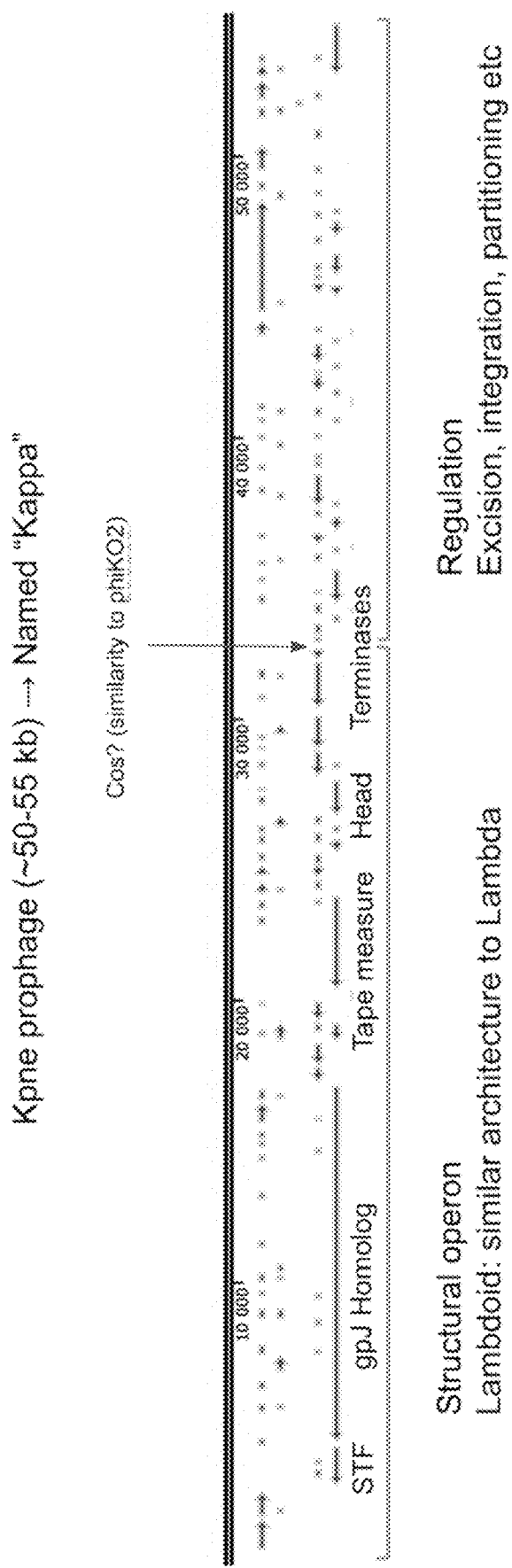
FIG. 2: Klebsiella pneumoniae prophage genome organization (prophage variant). The structural and regulatory operons are marked with a red line and some structural elements labeled.
Figure 3:
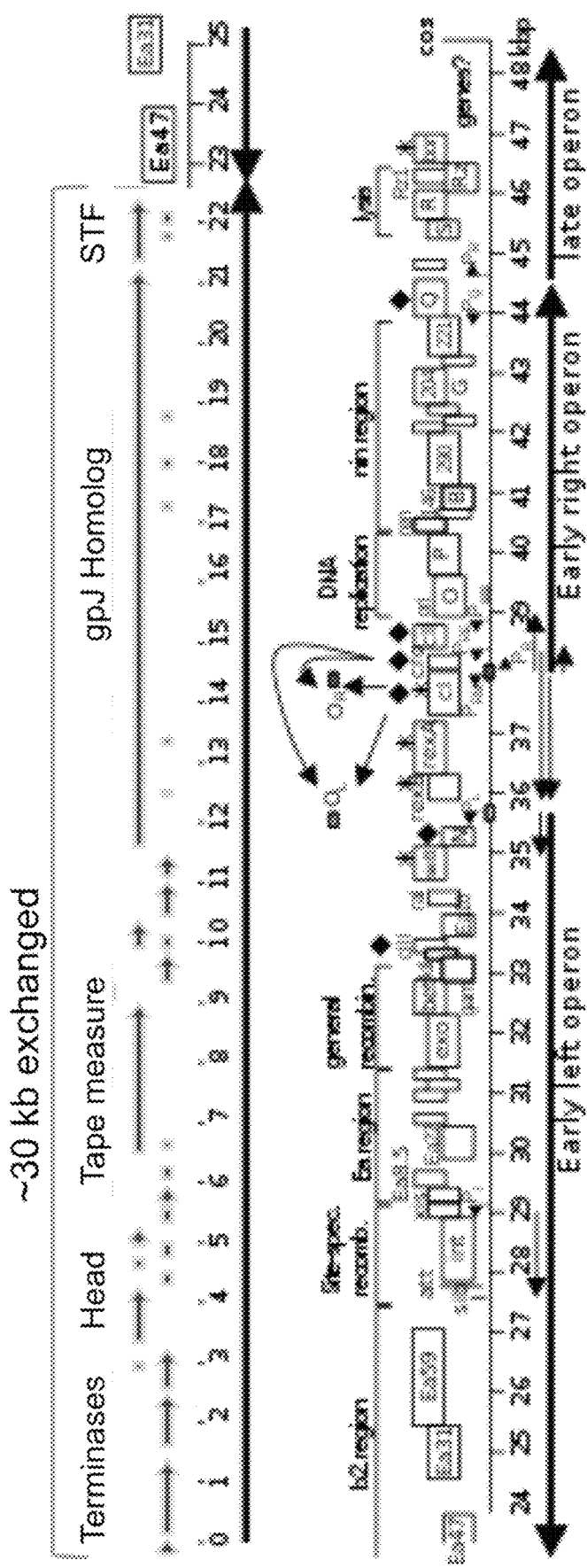
FIG. 3: Lambda-K. pneumoniae prophage hybrid. The complete structural operon from the K. pneumoniae prophage (marked with a red line) now occupies the place of the lambda late structural operon. The rest of the Lambda prophage regulating all other functions is intact.

This is the approach that was developed herein. Using a production strain encoding a system to generate pure Lambda phagemids, its structural operon has been exchanged (from the small terminase to the STF gene, about 23 kb) with the structural operon of a prophage coming from a different species (*Klebsiella pneumoniae*). A schematic diagram shows the changes made for the *Klebsiella pneumoniae* hybrid variant (FIGS. 1-3).

In this system, the thermolabile version of the prophage Lambda contains all regulatory elements needed to excise the prophage, replicate the circularized excised genome and drive the expression of the long, late operon, including the presence of the antitermination protein Q. This should drive the assembly and packaging of pure phagemid particles completely based on other phages when supplemented with a plasmid containing the correct packaging signals (cos site for the *Klebsiella pneumoniae* phage).

Analysis of the *Klebsiella pneumoniae* Prophage

The Kpne strain LMR_3612 (s17699) was analyzed with PHAST to extract prophage regions. One of them contains a predicted lambdoid prophage with some similarities to HK97. This prophage was called Kappa. Of note, a similar *Klebsiella oxytoca* prophage has been described in the literature and named phiKO2 (Casjens et al. J Bacteriol. 2004 March; 186(6):1818-32). The structural operon was found to span a continuous region encoding terminases, structural genes (capsid, tail, fibers, etc), assembly proteases and chaperones. This region is about 30 kb in length (SEQ ID NO: 7).

Construction of the Hybrid

The Lambda prophage structural operon was exchanged with the Kappa one using the lambda red recombineering system, starting from a production strain containing a Lambda prophage without the cos site (s1965). Of note, some codons were recoded to be efficiently recognized by *E. coli*.

Production and Titrations

The produced strain containing a completely exchanged structural operon was labeled Kappa. Next, a payload suitable to be packaged by this phagemid was constructed. To do this, a 350-bp long sequence (SEQ ID NO: 8) right upstream of the small terminase gene of the Kappa prophage, a candidate to encode the cos signal recognized by the Kappa terminases, was inserted in a payload containing a chloramphenicol marker and a sfGFP gene. This payload was labeled pTEST (p1866, SEQ ID NO: 9). Of note, several restriction sites found in the *Klebsiella pneumoniae* REBASE database were removed, where possible. The strain Kappa harboring the p1866 plasmid was grown overnight in LB+chloramphenicol and the next day a production following the protocol below was performed.

Overnight cultures were diluted 1:6 in a final volume of LB+5 mM $CaCl_2$) supplemented with chloramphenicol and grown for 30 min at 30° C. with shaking. After that, a 45-minute-long heat shock at 42° C. was performed. Finally the cultures were grown at 37° C. for 3 hours with shaking. After this period, cells were recovered by centrifugation and lysed using 3 mL of B-PER protein extraction reagent, 600 mg of detergent removal bio-beads were added and an incubation at room temperature with mild shaking performed for 1 hour. After that, the lysates were centrifuged for 10 min at 10,000 g and the supernatants filtered through a 0.2 micron pore-size membrane.

Two collections of *Klebsiella pneumoniae* strains belonging to different ST types (192 strains in total) were used to verify if phagemid particles were produced. Overnight cultures of *Klebsiella pneumoniae* strains were diluted 1:100 in LB+$CaCl_2$), grown for 2 hours at 37° C. and diluted 1:20 before the transductions. 10 μL of phagemid lysate was added to 90 μL of each of the *Klebsiella pneumoniae* dilutions and incubated for 30 min at 37° C. Finally, 10 μL of each transduction were plated on LB agar supplemented with chloramphenicol and incubated overnight at 37° C. Additionally, *Klebsiella pneumoniae* strain F3 (s19091), MG1655 (s003), MG1656-Omp00157 (s14269) and MG1656-dOmpC-dLamB harboring 6 different *Klebsiella pneumoniae* OmpC variants in trans were used to verify the titers of the productions.

Figure 4:
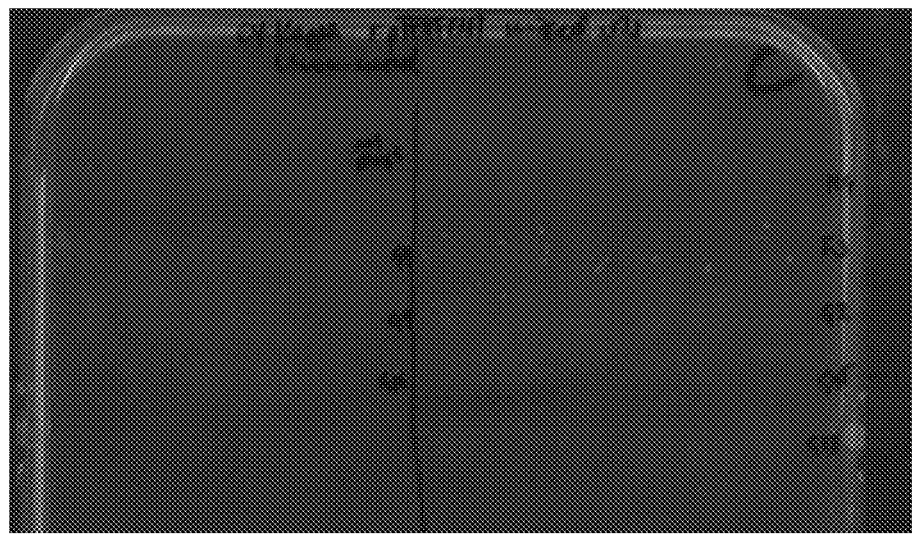
FIG. 4: Titrations of Kappa packaged phagemids with payload pTEST. From top to bottom and left to right, MG1656-OmpCO157, MG1655, MG-Kpne OmpC G1, Kpne F3, MG-Kpne OmpC 7, MG-Kpne OmpC G2, MG-Kpne OmpC G16, MG-Kpne OmpC G15, MG-Kpne OmpC G18. No hits were observed
Figure 5:
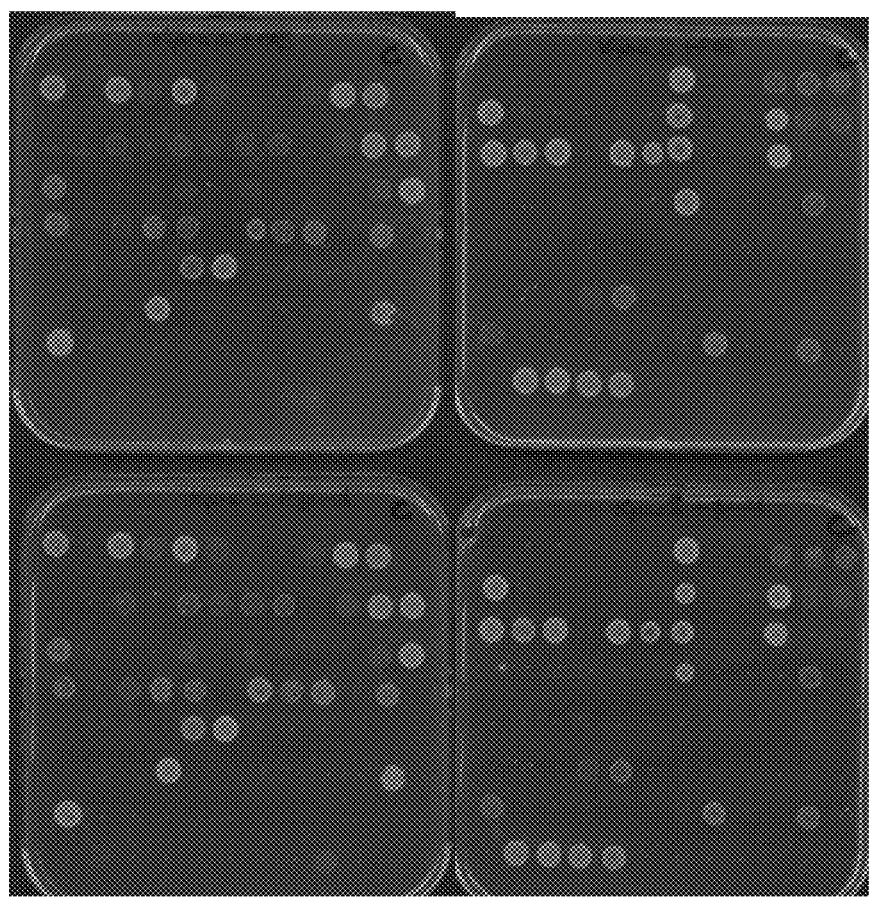
FIG. 5: Titrations of Kappa packaged phagemids on Klebsiella pneumoniae collections with payload pTEST. Top panels: Kpne collections treated with PBS only and plated on chloramphenicol to see background Cm resistance (left Kpne plate 1; right, Kpne plate 2). Bottom panels: Kpne collections treated with a lysate from Kappa+pTEST. No hits were observed.

In this first assay, absolutely no hits were observed, either in the 192 *Klebsiella pneumoniae* strains or in any of the other 9 strains used for titrations (FIGS. 4-5).

After these results, a more detailed analysis of the Kappa prophage was performed to see if some structural or packaging element had been missed. Since this prophage seems to belong to the same family as HK97, a literature search was conducted in order to find any missing elements, and it was identified that HK97 (and in general, many other phages but not Lambda) need a small protein containing an HNH nuclease domain that assists in the processivity of the cos site cutting by the terminase complex (Moodley et al. Protein Sci. (2012) 21(6):809-818 and Kala et al. Proceedings of the National Academy of Sciences April 2014, 111 (16) 6022-6027). An analysis of the Kappa prophage region right upstream of the terminase genes (and the putative cos site) revealed the presence of an operon containing an HNH protein, some other small ORFs with unknown functions and a Zn-finger domain-containing protein right upstream of the putative cos site.

To test the hypothesis that the HNH protein was the element missing in the production strain, this ORF (SEQ ID NO: 10 and SEQ ID NO: 11) was cloned in a plasmid under the control of the inducible repressor PhIF (p1869, SEQ ID NO: 12) and used to complement the productions. Additionally, a second payload was built that contained a larger region upstream of the terminases (SEQ ID NO: 13), in case the cos site present in pTEST was not complete. This second plasmid was labeled pTEST-2 (p1867, SEQ ID NO: 14).

Phagemids were produced as for the initial experiment, but DAPG was added to the productions when the cultures were shifted to 42° C. in order to induce expression of the HNH protein. Screening of the collections was done as described above.

Figure 6:
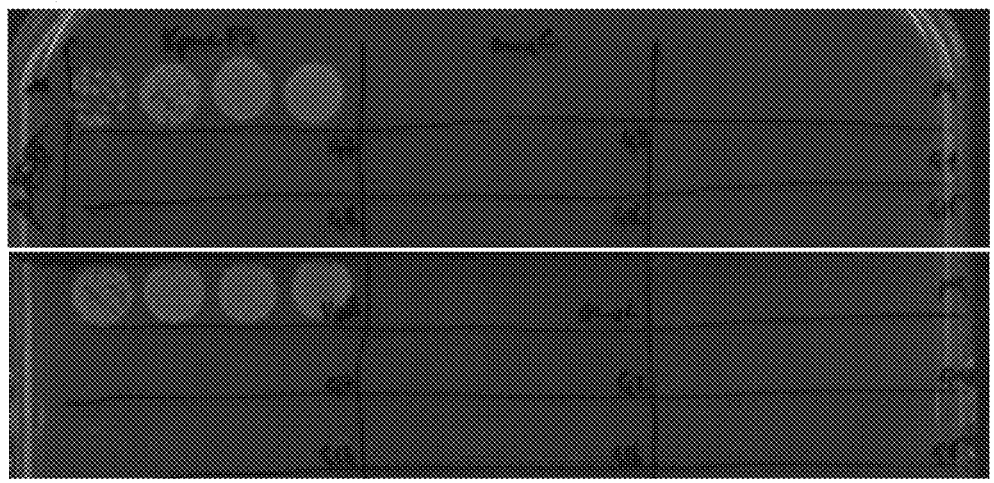
FIG. 6: Titrations of Kappa packaged phagemids with payloads pTEST or pTEST-2 in the presence of the HNH protein. Top panel, pTEST+HNH in trans. Bottom panel, pTEST-2+HNH in trans. From top to bottom and left to right, Kpne F3, MG1656-OmpCO157, MG1655, MG-Kpne OmpC G7, MG-Kpne OmpC G2, MG-Kpne OmpC G1, MG-Kpne OmpC G18, MG-Kpne OmpC G16, MG-Kpne OmpC G15.

The results showed that in the presence of the HNH protein, phagemids are readily produced (FIG. 6). In this case, the titration in single MG1655 or *Klebsiella pneumoniae* F3 strains revealed that the phagemid is specific to *Klebsiella* and that it does not recognize *E. coli* at all. This is proof that the phagemids being produced are structurally based on Kappa, but regulated and maintained in the lysogenic state by the Lambda prophage.

Figure 7:
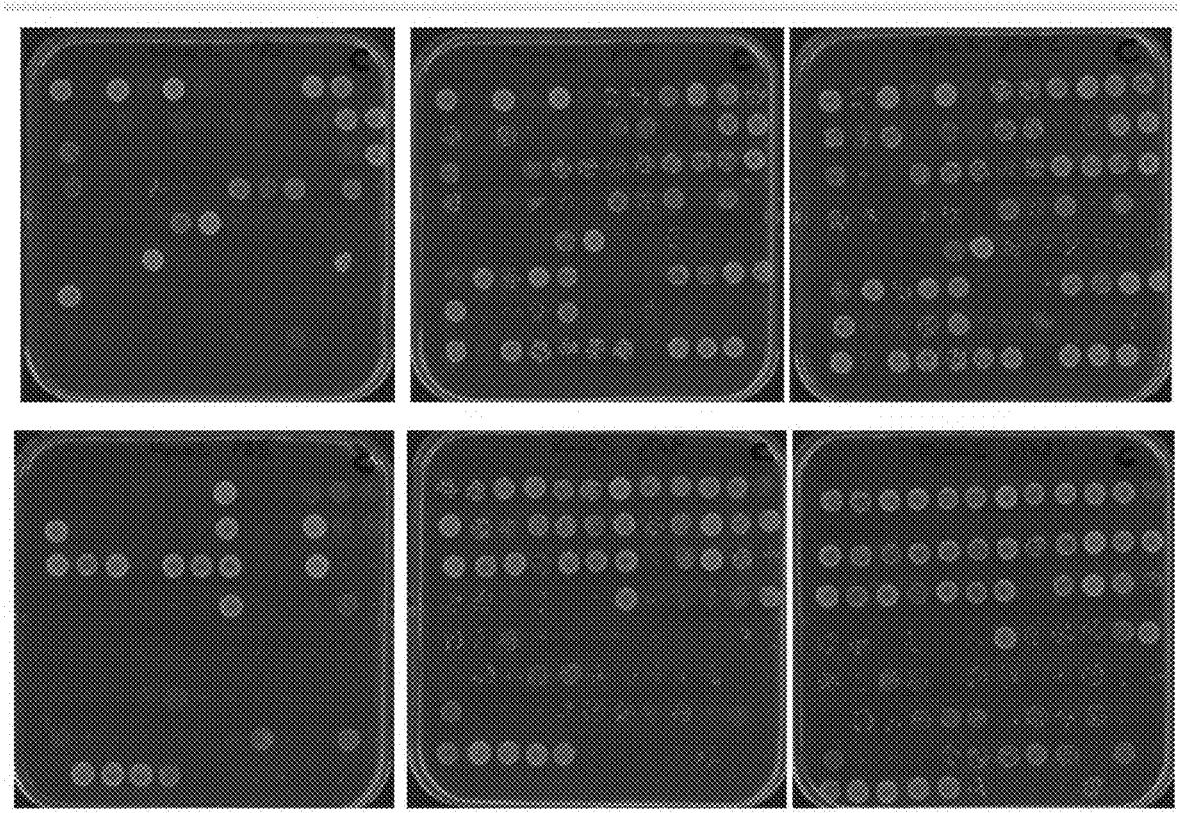
FIG. 7: Titrations of Kappa packaged phagemids with payloads pTEST or pTEST-2 in the presence of the HNH protein on Klebsiella pneumoniae collections. Top panels: Kpne collection 1 treated with: left) PBS; middle) pTEST+HNH in trans; right) pTEST-2+HNH in trans. Bottom panels, Kpne collection 2 treated with: left) PBS; middle) pTEST+HNH in trans; right) pTEST-2+HNH in trans.

Similarly, when titrated on both Kpne collections, this time many hits were observed (FIG. 7).

Two observations can be made from this experiment:
Titers are different when produced with pTEST or pTEST-2 payloads, both carrying the HNH protein in trans (estimated $5 \times 10^5$ TU/mL for pTEST and $5 \times 10^6$ TU/mL for pTEST-2).
Even at low titers, spots in the *Klebsiella pneumoniae* collection are dense, indicating that the delivery efficiency must be high.

Concerning the difference in titers for the payloads tested, the only change between both productions is that the putative cos site present in pTEST-2 is longer than pTEST; but also, pTEST-2 encodes a small ORF (which is part of the longer cos region) with two Zn fingers predicted (SEQ ID NO: 15 and SEQ ID NO: 16). If this protein is involved in packaging, it may be the reason why titers are higher in lysates containing pTEST-2 than in those containing pTEST, and not because of the length per se. For this reason, a third system was built in which a payload encoding a short cos site (to avoid encoding any proteins in that region) (SEQ ID NO: 17) was used, labeled pTEST-3 (p1868, SEQ ID NO: 18). To complement the putative packaging proteins in trans, the so-called "HNH-Operon" plasmid was built (p1872, SEQ ID NO: 19), encoding the HNH protein (SEQ ID NO: 10 and SEQ ID NO: 11) and the putative Zn-finger containing protein (SEQ ID NO: 15 and SEQ ID NO: 16). Productions were made the same way as described above.

Figure 8:
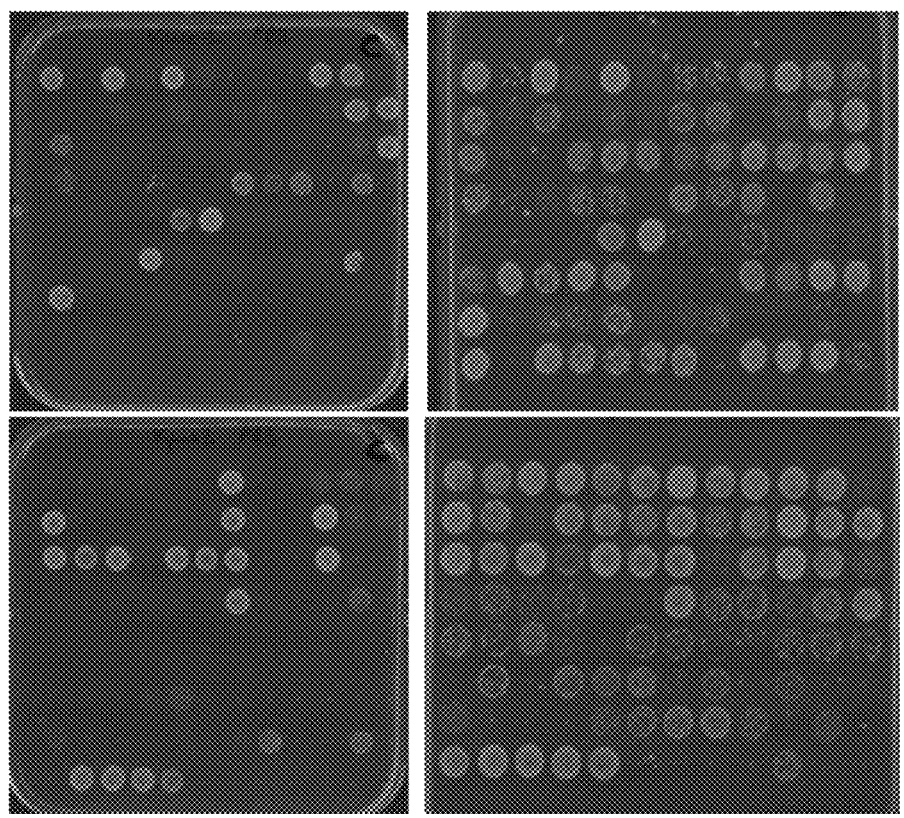
FIG. 8: Titrations of packaged phagemids on Kpne collections. Top panels: Klebsiella pneumoniae collection 1 treated with left, PBS; right, pTEST-3+HNH-Operon in trans. Bottom panels, Klebsiella pneumoniae collection 2 treated with: left, PBS; right, pTEST-3+HNH-Operon in trans.

In this third case, a similar behavior as for pTEST-2 was observed: many hits in the Kpne collections, confirming successful productions of phagemids and titers of about $5 \times 10^6$ TU/mL (FIG. 8). The titers were obtained by analyzing dense spots on the *Klebsiella pneumoniae* plates and using those strains to titrate the lysates. These results show that the minimal cos site is encoded in a shorter region than pTEST and pTEST-2 and that the HNH-Operon machinery is necessary and improves the packaging reaction.

These results show that an *E. coli* production strain is able to produce *Klebsiella*-specific pure phagemid particles. The specificity does not come solely from the addition of a single structural element, such as a tail fiber. The complete protein composition of the phagemids produced is from *K. pneumoniae* origin, proving that phagemid particles for other species can be assembled using *E. coli* as a production strain.

Example 2: Production of *Cutibacterium acnes* Phage-Derived Particles

*Cutibacterium acnes* is one of the most prevalent and abundant species of the skin (Kashaf et al. *Nat Microbiol* 7, 169-179 (2022)) where it colonizes the pilosebaceous unit (PSU). Unlike on the stratum corneum, bacteria present in the PSU are surrounded by living cells notably keratinocytes, sebocytes and different immune cells (Kabashima et al. *Nat Rev Immunol* 19, 19-30 (2019)). Close contact between *C. acnes* and these cells might lead to either beneficial or detrimental interactions. (Bruggemann et al. *Front Microbiol* 12, 673845 (2021)). Being able to genetically modify *C. acnes* was notoriously challenging before the applicant's new tools disclosed in US applications US2022/135986 and US2022/135987. In these patent applications, the inventors described, for the first time, the production of *C. acnes* phage-derived particles using *C. acnes* as a production strain.

In the present example, the inventors used *P. freudenreichii* strain to produce *C. acnes* phage-derived particles by swapping the structural genes from a *P. freudenreichii* prophage for the structural genes of a *C. acnes* phage.

Results

Isolation of BW4 Phage

*P. freudenreichii* and associated bacteriophages are known to be present in some dairy products (Gautier et al. (1995) *Lait* 75:427-434; Gautier et al. (1995) *Appl. Environ. Microbiol.* 61:2572-2576; Cheng et al. (2018) *BMC Microbiology* 18:19). The inventors therefore screened for the presence of both *Propionibacterium* phages or *P. freudenreichii* lysogens in cheese samples.

Different types of cheese samples were grinded, resuspended in Reinforced Clostridial Medium (RCM) and incubated at 30° C. in anaerobic conditions for 2 days. After incubation, a dilution of the culture was performed in lithium glycerol broth, a media selective for Propionibacteria (WO1994017201), and incubated for 6 days at 30° C. A final dilution in RCM+mitomycin C was incubated for 1 day at 30° C. in order to induce potential prophages. The induced cultures were filtered (0.2 µm) and spotted on different indicator strains. One of the samples led to turbid plaque formation on top agar of the *P. freudenreichii* strain Pf0s2841. Three individual plaques were isolated by two successive picking and streaking on Pf0s2841 and amplification was performed on top agar of Pf0s2841. For the three different plaques, amplification led to phage suspension ~$10^{10}$ PFU/mL.

Two clusters of temperate dsDNA *P. freudenreichii* phages (BW and BV) have been previously identified (Cheng et al. (2018) BMC Microbiology 18:19). Using PCRs designed on BW genome from Doucette phage (KX620751) two different fragments were extracted:
ORF3 with AD1334 (SEQ ID NO: 20)/AD1335 (SEQ ID NO: 21)
ORF5 with AD1336 (SEQ ID NO: 22)/AD1337 (SEQ ID NO: 23).

Figure 9:
FIG. 9: Identification of P. freudenreichii phages with PCR. PCR on ORF3 and ORF5 was performed on all phage suspensions. BW4 from plaques 1-3 give a band at the expected size for both orf3 and orf5. Ladder is GeneRuler 1 kb plus.
Figure 9:
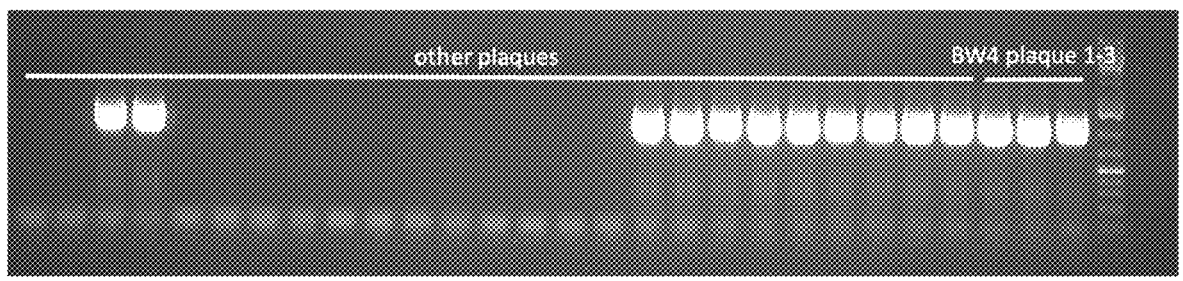

The inventors could classify the isolated phages as BW-like (FIG. 9). Sequencing of ORF5 revealed that all phages were most probably identical and therefore were coming from the same BW-like phage that was named BW4.

Isolation of Pf0s2841 Lysogen Carrying the BW4 Phage

The inventors then isolated *P. freudenreichii* lysogen carrying the BW4 phage as a prophage. For that, BW4 phage suspension was spotted on strain Pf0s2841 and incubated for 3 days. Turbid plaques were picked, resuspended and streaked. After 5 days, single colonies were obtained, several colonies were streaked and incubated a second and third time and presence of the phage genes was checked, at each streaking, by PCR, after DNAse treatment, across the cohesive ends (AD1322 (SEQ ID NO: 24)/AD1323 (SEQ ID NO: 25)) to ensure presence of the phage but absence of phage particles.

Figure 10:
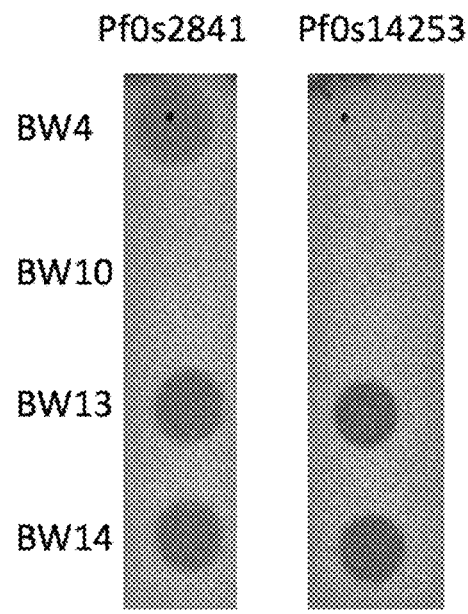
FIG. 10: Immunity to superinfection of lysogen Pf0s14253. Left panel: Top agar of Pf0s2841 with spots of 4 different BW-like phage suspensions. Right panel: Top agar of Pf0s14253 with spots of 4 different BW-like phage suspensions.

After the third streak, colonies were grown as a top agar and a spot of non diluted BW-like phages suspensions were spotted on the putative lysogene strain (Pf0s14253) and on the ancestor strain (Pf0s2841). After incubation, clearance was observed for both strains for BW13 and BW14 spots whereas clearance was only observed for Pf0s2841 in the case of BW4 spot (FIG. 10). This indicates that the strain Pf0s14253 is immune to BW4 phage superinfection and carries the BW4 prophage. The absence of immunity for BW14 and BW13 indicates that these phages have likely a different immunity repressor.

BW4 Prophage Induction

Figure 11:
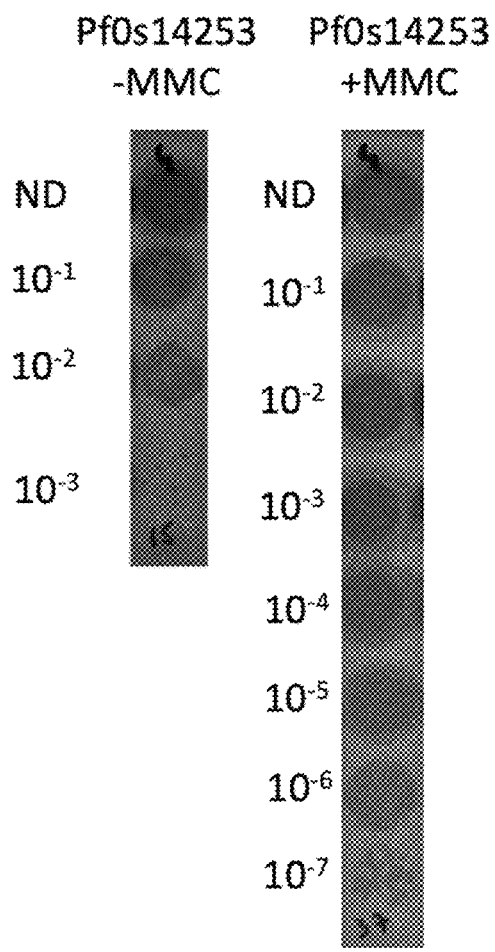
FIG. 11: High induction of BW4 phage after mitomycin C treatment. Left panel: Top agar of Pf0s2841 with spots of culture supernatant from Pf0s14253 without mitomycin C (MMC) induction (ND: non diluted to dilution $10^{-3}$). Right panel: Top agar of Pf0s2841 with spots of culture supernatant from Pf0s14253 with 0.5 μg/ml of mitomycin C induction (ND: non diluted to dilution $10^{-7}$).

In order to use the BW4 lysogen strain as a production strain for phage-derived particles the inventors first had to test the ability to produce high concentration of the BW4 phage upon induction of the lytic cycle. To do so, Pf0s14253 was grown in absence or presence of mitomycin C (MMC), an antibiotic known to induce prophages, and the culture supernatant was titered for the presence of BW4 phage particles on the indicator strain Pf0s2841. A high amount of BW4 phage particles was observed in the condition supplemented with mitomycin C (FIG. 11) with $7.4 \times 10^7$ PFU/µL against $3.0 \times 10^3$ PFU/µL for the condition without mitomycin C. This indicates a high dynamic range between lytic and lysogenic cycle for BW4 prophage under such conditions and confirmed the potential of BW4 for the production of phage-derived particles.

Sequencing and Annotation of BW4 Phage

To engineer the BW4 prophage towards production of *C. acnes* phage-derived particles, the BW4 phage was sequenced. DNA isolation (Promega Wizard DNA Clean-Up System) followed by Illumina sequencing was performed on BW4 phage suspension. Raw reads were assembled into a single contig using Spades and termini were corrected by sanger sequencing (SEQ ID NO: 26). Annotation was performed using Phaster and manually curated based on homologies with other BW-like phages (Cheng et al. (2018) *BMC Microbiology* 18:19).

As described in Cheng et al. (2018) *BMC Microbiology* 18:19, BW-like phages have typical genomic architecture of other temperate phages with a large putative structural operon (also called lytic operon) organized in different functional modules with, in order of transcription: packaging, head, tail, and lysis module. Surprisingly, the first gene of the putative operon (gp1) appears to be related to DNA replication based on HHpred as it contains a domain similar to bifunctional primase and polymerase proteins. Other parts of the BW4 phage genome contain the genes necessary for prophage integration/excision, DNA replication, DNA recombination, regulation of the lytic/lysogenic cycle and other accessory proteins. This modular architecture confirms the possibility to swap the genes necessary for the production of BW4 phage capsid and the packaging of the phage genome by their equivalent from a *C. acnes* phage genome.

Isolation of *C. acnes* PAC7 Phage

*C. acnes* phages were isolated from skin of healthy volunteers. Briefly a patch (Biore) was applied to the nose allowing to extract comedones that were resuspended in RCM, plated on MRS and incubated at 37° C. in anaerobic conditions. For some of the plates, plaques could be observed in the dense lawn of *C. acnes*. DPBS (Dulbecco's Phosphate Buffered Saline) was poured on the plate to resuspend potential phages and filtered to remove bacteria. This phage suspension was streaked on plate and a top agar of strain Ca0s2345 was added. Plates were incubated for 2 days and plaques were reisolated by three successive picking, streaking and top agar plating. Finally a plaque was amplified on top agar with Ca0s2345 strain and the resulting phage suspension was PEG precipitated. High titer ($>10^6$ PFU/µL) phage suspension was obtained when titered on Ca0s2345.

Sequencing and Annotation of PAC7 Phage

Figure 12:
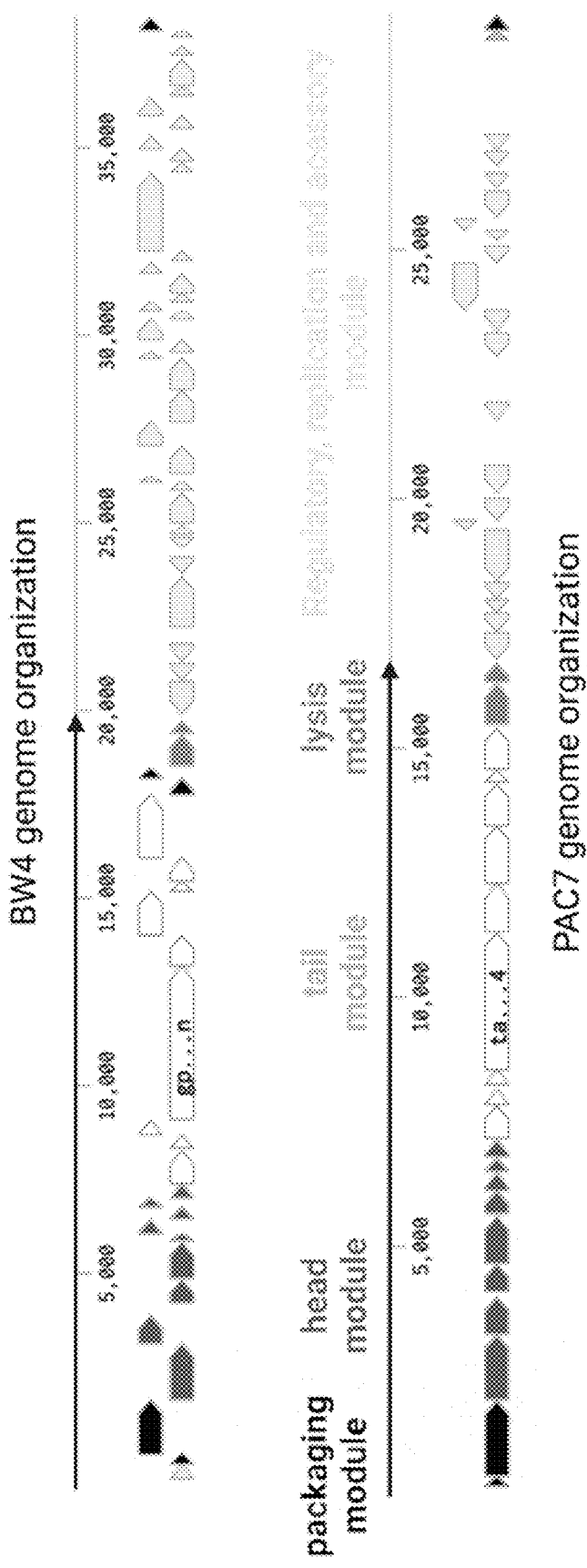
FIG. 12: Genome organization of BW4 and PAC7 bacteriophages. BW4 and PAC7 genome organization is similar with both putative structural operons (represented by the arrows) containing the packaging, head, tail and lysis modules.

DNA isolation (Promega Wizard DNA Clean-Up System) followed by Illumina sequencing was performed on PAC7 phage suspension. Raw reads were assembled into a single contig using Spades and termini were corrected by sanger sequencing (SEQ ID NO: 27). Annotation was performed using Phaster and manually curated based on homologies with other *C. acnes* phages (Marinelli et al. (2012) *mBio* 3:e00279-12). Similar to the *P. freudenreichii* BW4 phage, a structural operon comprising modules for packaging, head and tail assembly and cell lysis was identified (FIG. 12). An HNH endonuclease was identified as the last gene of the phage (gp45). Such endonuclease has already been shown to be essential for efficient packaging (Quiles-Puchalt et al. (2014) *Proc Nat. Acad. Sci.* 111:6016-6021).

Construction of Lysogen Strain with a Chimeric BW4-PAC7 Prophage

Figure 13:
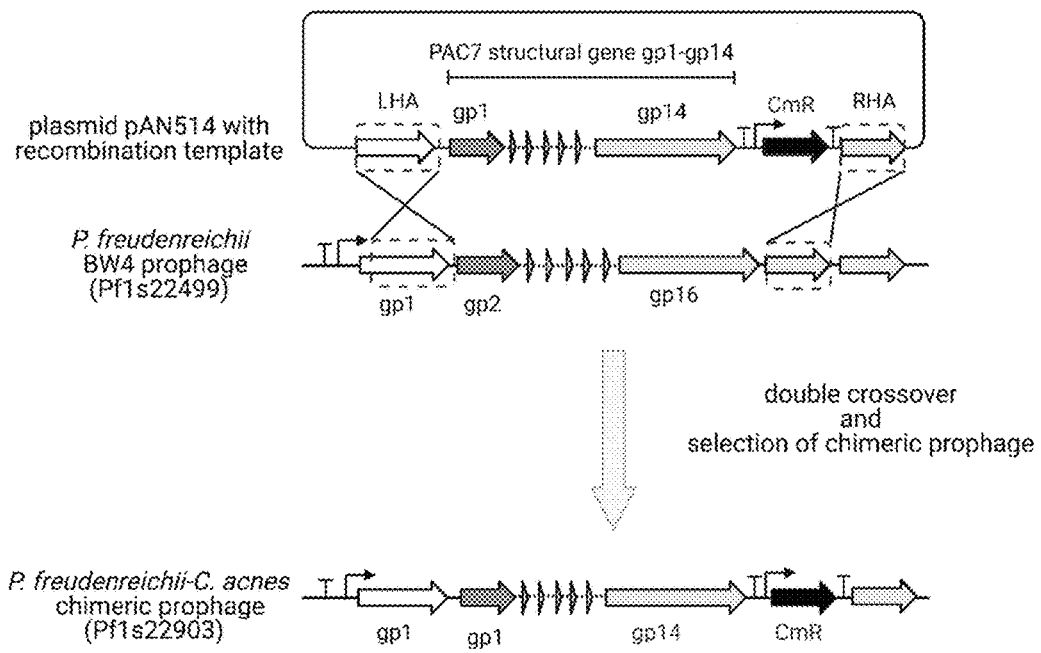
FIG. 13: Construction of chimeric BW4-PAC7 prophage. Transformation of the pAN514 suicide plasmid into strain Pf1s22499 containing the BW4 prophage. Selection on chloramphenicol was used to select for double crossover at the Left Homology Arm (LHA) and Right Homology Arm (RHA). The prophage obtained is a chimer containing a structural operon with first BW4 gp1 followed by gp1-gp14 of PAC7 and after the chloramphenicol selection cassette (CmR) the leftover of BW4 structural genes (gp15-gp25).

The genes in the structural operon of BW4 prophage, from the small terminase gp2 to the tape-measure protein gp16 included, were replaced by the structural PAC7 genes from gp1 to gp14 (FIG. 13). This was performed by homologous recombination using plasmid pAN514 (SEQ ID NO: 28), a *P. freudenreichii* suicide vector that was cloned in *E. coli* DH10B. After transformation of the vector, a double crossing over event was selected in *P. freudenreichii* (Pf1s22499) by selection on chloramphenicol. The chimeric BW4-PAC7 structural operon integrity was globally confirmed by PCR and sanger sequencing of the entire chimeric structural operon.

Figure 14:
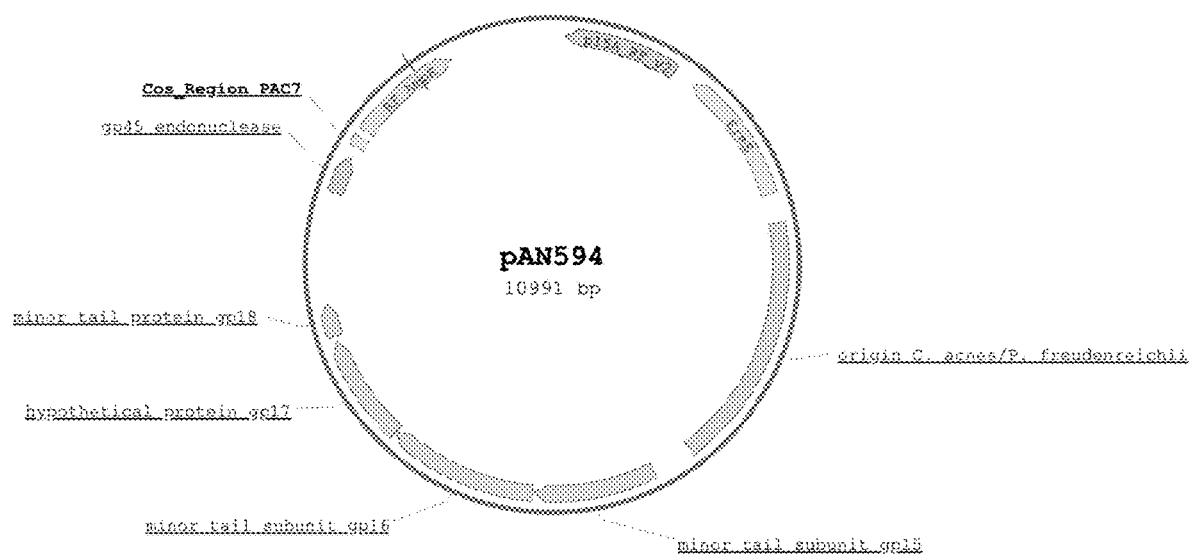
FIG. 14: Plasmid map of cosmid pAN594.

Production and Titration of PAC7 Derived Particles from a Lysogen Strain Carrying a Chimeric BW4-PAC7 Prophage In order to produce *C. acnes* phage-derived particles from a *P. freudenreichii* BW4-PAC7 chimeric lysogen, the pAN594 cosmid (FIG. 14) containing the packaging signal of the PAC7 phage (SEQ ID NO: 29), an operon expressing five genes of the PAC7 tail module (gp15-gp19) and the gp45 endonuclease (SEQ ID NO: 30) and an origin of replication functional in *P. freudenreichii* and *C. acnes* (as disclosed in US2022/135986 and US2022/135987) were transformed into Pf1s22903. Transformants were streaked and grown in presence of both chloramphenicol (1 µg/mL) to select for the presence of the prophage and erythromycin (2.5 µg/mL) to select for the presence of pAN594. At $OD_{600\ nm}$~0.4, culture was supplemented with 0.5 µg/ml of mitomycin C and grown overnight at 30° C. in anaerobic conditions. After incubation, cells were collected by centrifugation, lysed by bead beating (2×20 min at 30 Hz with 0.1 mm glass beads), supernatant was filtered and the presence of phage derived particles was titered on *C. acnes* Ca0s2258.

Figure 15:
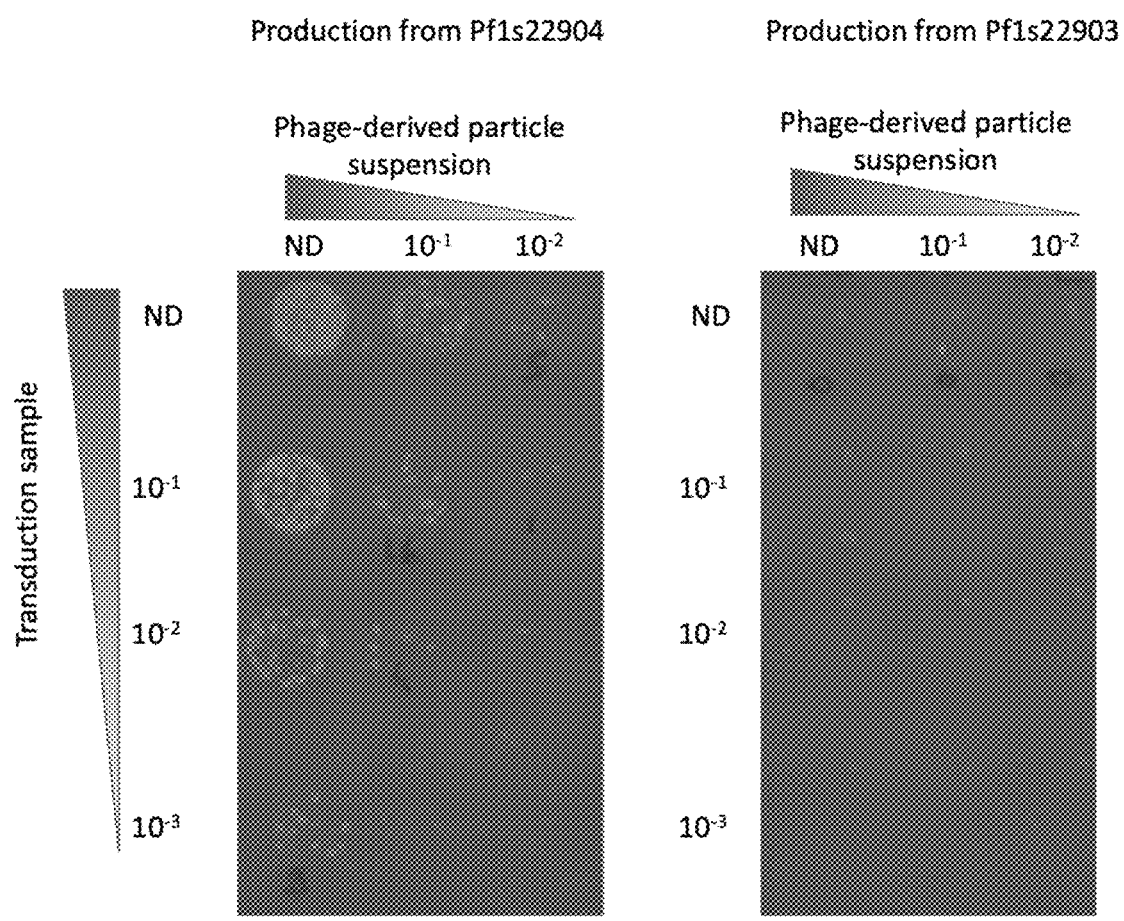
FIG. 15: Titration of PAC7 phage-derived particles. Left Panel: Titration from Pf1s22904 plated on erythromycin. Right Panel: Titration from control suspension of strain Pf1s22903 that does not carry any cosmid plated on erythromycin.
Figure 16:
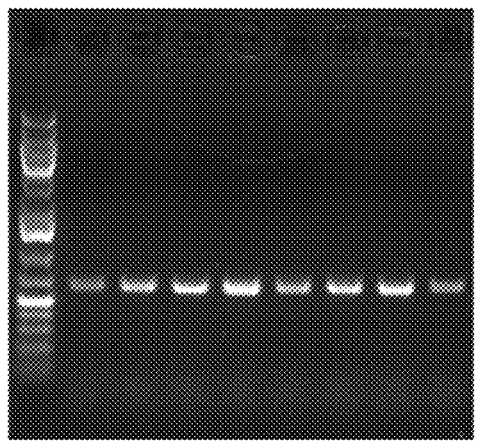
FIG. 16: Confirmation for 8 colonies streaked from phage-derived particles titration of Pf1s22904 production by PCR. Top Panel: SLTS PCR (Scholz 2014) on 8 colonies streaked from the phage derived titration assay. Expected size is 612 bp. Bottom Panel: pAN594 specific PCR on 8 colonies. Expected size is 769 bp. Ladder is generuler 1 kb plus.
Figure 16:
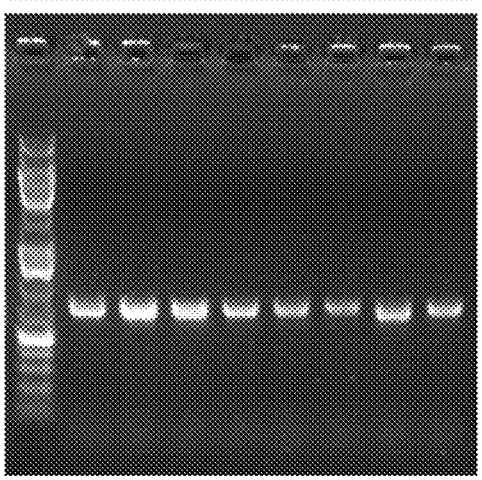

Up to ~$10^2$ potential transductants per μL were obtained (FIG. 15). 8 colonies were streaked on Brain Heart Infusion (BHI) erythromycin (5 μg/mL) and confirmed to be *C. acnes* and transductants carrying pAN594 using PCR (FIG. 16).

The inventors thus demonstrated for the first time that *C. acnes* phage-derived particles able to deliver DNA into *Cutibacterium acnes* can be produced by swapping structural genes of a *P. freudenreichii* prophage for the structural genes of a *Cutibacterium acnes* phage.

Material and Methods:
Strain Used and Generated

TABLE 1

Strains used and generated

| Eligo ID | Description |
| --- | --- |
| Pf0s2841 | Indicator strain for *P. freudenreichii* BW4 phage (CIRM-BIA 509, TL110 belonging to INRAE) |
| Pf0s14253 | Strain Pf0s2841 with a BW4 prophage |
| Pf1s22499 | Strain Pf0s14253 with the packaging signal of BW4 deleted |
| Pf1s22903 | Strain Pf1s22499 with the BW4 genes gp2-gp16 replaced by PAC7 gp1-gp14 |
| Pf1s22904 | Strain Pf1s22903 with pAN594 |
| Ca0s2345 | Indicator strain for *C. acnes* PAC7 phage |
| Ca0s2258 | *Cutibacterium acnes* ATCC 11828 |

Culture Conditions

All incubations of *P. freudenreichii* strains were performed at 30° C. in anaerobic conditions (Thermo Scientific™ Sachet Oxoid™ AnaeroGen).

All incubations of *C. acnes* strains were performed at 37° C. in anaerobic chamber.

Construction of Strain Pf1s22499

Deletion of the packaging signal from BW4 prophage was performed by homologous recombination and CRISPR-Cas selection of the recombinant using the pAN241 *P. freudenreichii* vector that was cloned in *E. coli* and then transformed into Pf0s14253 strain. The pAN241 vector contains a template for homologous recombination (SEQ ID NO: 31) and a FnCpf1 transcriptional cassette with a crRNA targeting the cos of the BW4 prophage.

Transformation Protocol for *P. freudenreichii*

Transformation of *P. freudenreichii* was adapted from Brede, D. A. et al. *Appl Environ Microb* 71, 8077-8084 (2005), replacing SLB (sodium lactate broth) media for BHI.

Phage-Derived Particles Titration

Strain Ca0s2258 was streaked on BHI agar plate. Once dense growth on plate was obtained, a liquid culture was set up in BHI. After overnight incubation, the turbid culture was concentrated 10× in BHI. 90 μl of cells were mixed with pure, diluted 1/10 and diluted 1/100 solutions of 10 μL of phage-derived particles produced from either Pf1s22904 or Pf1s22903 as negative control. Samples were incubated 2 hours at room temperature and then 1/10 serial dilutions were performed in BHI, samples were incubated 2 h at 37° C. in anaerobic conditions before spotting 4 μL on BHI+5 μg/mL erythromycin. Plates were incubated for 7 days at 37° C. in anaerobic conditions.

The invention claimed is:

1. Production bacterial cell for producing phage particles or phage-derived delivery vehicles, said production bacterial cell stably comprising phage structural genes and phage DNA packaging genes of a first type of bacteriophage,
wherein the expression of said phage structural genes and phage DNA packaging genes in said production bacterial cell is controlled by an induction mechanism comprising phage excision/insertion genes, phage DNA replication genes, and phage regulation genes of a second, different type of bacteriophage, wherein said phage excision/insertion genes, phage DNA replication genes and phage regulation genes are neither phage DNA packaging genes nor phage structural genes,
wherein said production bacterial cell does not comprise phage excision/insertion genes and/or phage replication genes of the first type of bacteriophage,
wherein said production bacterial cell is from a bacterial species or strain different from the bacterial species or strain from which said first type of bacteriophage comes from and/or that said first type of bacteriophage targets and wherein said production bacterial cell is from the same bacterial species or strain as the bacterial species or strain from which said second type of bacteriophage comes from and/or that said second type of bacteriophage targets,
wherein said production bacterial cell is a *P. freudenreichii* bacterial cell,
wherein the first type of bacteriophage is a *C. acnes* phage and
wherein the second type of bacteriophage is a *P. freudenreichii* phage.

2. The production bacterial cell according to claim 1, wherein said bacterial cell further comprises a payload to be packaged into said phage particles or phage-derived delivery vehicles.

3. The production bacterial cell according to claim 2, wherein said payload is a nucleic acid payload comprising a packaging site derived from said first type of bacteriophage.

4. The production bacterial cell according to claim 2, wherein said payload is to be delivered into targeted bacterial cells.

5. The production bacterial cell according to claim 4, wherein said payload comprises a sequence of interest.

6. The production bacterial cell according to claim 5, wherein said sequence of interest only generates an effect in said targeted bacterial cells.

7. The production bacterial cell according to claim 6, wherein said targeted bacterial cells are from a species or strain different from the production bacterial cell.

8. The production bacterial cell of claim 1, wherein said phage structural genes and phage DNA packaging genes of said first type of bacteriophage are comprised in at least one plasmid, chromosome and/or helper phage.

9. The production bacterial cell according to claim 1, comprising the entire structural operon of the first type of bacteriophage.

* * * * *